US012516039B2

(12) United States Patent
Fuller et al.

(10) Patent No.: US 12,516,039 B2
(45) Date of Patent: Jan. 6, 2026

(54) N-LINKED ISOQUINOLINE AMIDES AS LRRK2 INHIBITORS, PHARMACEUTICAL COMPOSITIONS, AND USES THEREOF

(71) Applicant: Merck Sharp & Dohme LLC, Rahway, NJ (US)

(72) Inventors: Peter H. Fuller, Ashland, MA (US); Anmol Gulati, Watertown, MA (US); Solomon D. Kattar, Wakefield, MA (US); Mitchell H. Keylor, Malden, MA (US); Kaila A. Margrey, Cambridge, MA (US); Xin Yan, Newton Highlands, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 404 days.

(21) Appl. No.: 18/248,407

(22) PCT Filed: Oct. 27, 2021

(86) PCT No.: PCT/US2021/056734
§ 371 (c)(1),
(2) Date: Apr. 10, 2023

(87) PCT Pub. No.: WO2022/093881
PCT Pub. Date: May 5, 2022

(65) Prior Publication Data

US 2023/0406844 A1 Dec. 21, 2023

Related U.S. Application Data

(60) Provisional application No. 63/106,974, filed on Oct. 29, 2020.

(51) Int. Cl.

| | |
|---|---|
| ***C07D 405/12*** | (2006.01) |
| ***C07D 217/22*** | (2006.01) |
| ***C07D 401/04*** | (2006.01) |
| ***C07D 401/14*** | (2006.01) |
| ***C07D 405/14*** | (2006.01) |
| ***C07D 409/14*** | (2006.01) |
| ***C07D 413/04*** | (2006.01) |
| ***C07D 471/04*** | (2006.01) |
| ***C07D 471/08*** | (2006.01) |

(52) U.S. Cl.
CPC ......... *C07D 405/12* (2013.01); *C07D 217/22* (2013.01); *C07D 401/04* (2013.01); *C07D 401/14* (2013.01); *C07D 405/14* (2013.01); *C07D 409/14* (2013.01); *C07D 413/04* (2013.01); *C07D 471/04* (2013.01); *C07D 471/08* (2013.01)

(58) Field of Classification Search
CPC .. C07D 405/12; C07D 217/22; C07D 401/04; C07D 401/14; C07D 405/14; C07D 409/14; C07D 413/04; C07D 471/04; C07D 471/08
See application file for complete search history.

(56) References Cited

U.S. PATENT DOCUMENTS

| | | | |
|---|---|---|---|
| 4,166,452 | A | 9/1979 | Generales, Jr. |
| 4,256,108 | A | 3/1981 | Theeuwes |
| 4,265,874 | A | 5/1981 | Bonsen et al. |
| 9,433,614 | B2 | 9/2016 | Luithle et al. |
| 10,039,753 | B2 | 8/2018 | Coffman et al. |
| 2017/0002000 | A1 | 1/2017 | Galatsis |
| 2018/0208580 | A1 | 7/2018 | Kc et al. |

(Continued)

FOREIGN PATENT DOCUMENTS

| | | | |
|---|---|---|---|
| WO | 2007149798 | A2 | 12/2007 |
| WO | 2008064054 | A2 | 5/2008 |

(Continued)

OTHER PUBLICATIONS

Aasly, J.O. et al., Clinical Features of LRRK2-Associated Parkinson's Disease in Central Norway, Ann Neurol, 2005, 762-765, 57(5).

Adams, J.R. et al., PET in LRRK2 mutations: comparison to sporadic Parkinson's disease and evidence for presymptomatic compensation, Brain, 2005, 2777-2785, 128.

Bailey, R.M. et al., LRRK2 phosphorylates novel tau epitopes and promotes tauopathy, Acta Neuropathol, 2013, 809-827, 126.

Bingham, A.L., et al.,, "Over One Hundred Solvates of sulfathiazole", Chem. Commun., 2001, pp. 603-604.

Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.

(Continued)

*Primary Examiner* — Timothy R Rozof
(74) *Attorney, Agent, or Firm* — Sylvia A. Ayler; Catherine D. Fitch

(57) ABSTRACT

The present invention is directed to certain 2-aminoquinzaoline derivatives of Formula (I) and pharmaceutically acceptable salts thereof, wherein $R^1$, $R^2$, and $R^3$ are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of such diseases in which LRRK-2 kinase is involved.

(I)

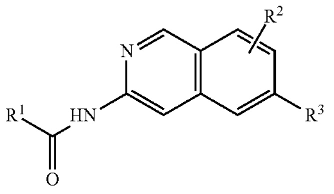

20 Claims, No Drawings

(56) References Cited

U.S. PATENT DOCUMENTS

| | | | | |
|---|---|---|---|---|
| 2018/0282282 | A1* | 10/2018 | Chan | A61K 31/506 |
| 2021/0363144 | A1 | 11/2021 | Kim et al. | |

FOREIGN PATENT DOCUMENTS

| | | | |
|---|---|---|---|
| WO | 2012062783 | A1 | 5/2012 |
| WO | 2012080284 | A2 | 6/2012 |
| WO | 2013079494 | A1 | 6/2013 |
| WO | 2013164321 | A1 | 11/2013 |
| WO | 2015113452 | A1 | 8/2015 |
| WO | 2016036586 | A1 | 3/2016 |
| WO | 2017087905 | A1 | 5/2017 |
| WO | 2017156493 | A1 | 9/2017 |
| WO | 2017189829 | A1 | 11/2017 |
| WO | 2017218843 | A1 | 12/2017 |
| WO | 2018163030 | A1 | 9/2018 |
| WO | 2018163066 | A1 | 9/2018 |
| WO | 2018170167 | A1 | 9/2018 |
| WO | 2018183964 | A1 | 10/2018 |
| WO | 2019012093 | A1 | 1/2019 |
| WO | 2019104086 | A1 | 5/2019 |
| WO | 2019112269 | A1 | 6/2019 |
| WO | 2020170205 | A1 | 8/2020 |

OTHER PUBLICATIONS

Daher, J.P. et al., Leucine-rich Repeat Kinase 2 (LRRK2) Pharmacological Inhibition Abates alpha-Synuclein Gene-induced Neurodegeneration, The Journal of Biological Chemistry, 2015, 19433-19444, 290(32).

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Danoy, P. et al., Association of Variants at 1932 and STAT3 with Ankylosing Spondylitis Suggests Genetic Overlap with Crohn's Disease, PLoS Genetics, 2010, 1-5, 6(12):e1001195.

Engel, P. et al., Therapeutic Targeting of B Cells for Rheumatic Autoimmune Diseases, Pharmacological Reviews, 2011, 127-156, 63(1).

Gilks, W.P. et al., A common LRRK2 mutation in idiopathic Parkinson's disease, Lancet, 2005, 415-416, 365.

Guo, L. et al., The Parkinson's disease-associated protein, leucine-rich repeat kinase 2 (LRRK2), is an authentic GTPase that stimulates kinase activity, Experimental Cell Research, 2007, 3658-3670, 313.

Kawakami, F. et al., LRRK2 Phosphorylates Tubulin-Associated Tau but Not the Free Molecule: LRRK2-Mediated Regulation of the Tau-Tubulin Association and Neurite Outgrowth, PLoS ONE, 2012, 1-9, 7(1):e30834.

Kumari, U. et al., LRRK2 in Parkinson's disease: genetic and clinical studies from patients, The FEBS Journal, 2009, 6455-6463, 276.

Lee, B.D. et al., Inhibitors of leucine-rich repeat kinase-2 protect against models of Parkinson's disease, Nature Medicine, 2010, 998-1000, 16.

Li, Y. et al., Mutant LRRK2R1441G BAC transgenic mice recapitulate cardinal features of Parkinson's disease, Nature Neuroscience, 2009, 826-828, 12(7).

Looyenda, B.D. et al., Chromosomal amplification of leucine-rich repeat kinase-2 (LRRK2) is required for oncogenic MET signaling in papillary renal and thyroid carcinomas, Proc Natl Acad Sci USA, 2011, 1439-1444, 108(4).

Moehle, M.S. et al., LRRK2 Inhibition Attenuates Microglial Inflammatory Responses, The Journal of Neuroscience, 2012, 1602-1611, 32(5).

Nichols, W. C. et al., Genetic screening for a single common LRRK2 mutation in familial Parkinson's disease, Lancet, 2005, 410-412, 365.

Saunders-Pullman, R. et al., LRRK2 G2019S Mutations are Associated with an Increased Cancer Risk in Parkinson Disease, Movement Disorders, 2010, 2536-22541, 25(15).

Showell, Graham, A. et al., (R)-Sila-venlafaxine: A selective noradrenaline reuptake inhibitor for the treatment of emesis, Bioorganic & Medicinal Chemistry Letters, 2006, pp. 2555-2558, vol. 16.

Shtilbans, A. et al., Differential gene expression in patients with amyotrophic lateral sclerosis, Amyotrophic Lateral Sclerosis, 2011, 250-256, 12(4).

Umeno, J. et al., Meta-analysis of Published Studies Identified Eight Additional Common Susceptibility Loci for Crohn's Disease and Ulcerative Colitis, Inflammatory Bowel Disease, 2011, 2407-2415, 17(12).

Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. 1, Article 12, US.

Volpicelli-Daley, L.A. et al., G2019S-LRRK2 Expression Augments alpha-Synuclein Sequestration into Inclusions in Neurons, The Journal of Neuroscience, 2016, 7415-7427, 36(28).

Zhang, Fu-Ren et al., Genomewide Association Study of Leprosy, The New England Journal of Medicine, 2009, 2609-2618, 361.

Zhao, Yi et al., LRRK2 variant associated with Alzheimer's disease, Neurobiology of Aging, 2011, 1990-1993, 32.

Zhu, X. et al., LRRK2 in Parkinson's disease and dementia with Lewy bodies, Molecular Neurodegeneration, 2006, 1-9, 1:17.

Zimprich, A. et al., Mutations in LRRK2 Cause Autosomal-Dominant Parkinsonism with Pleomorphic Pathology, Neuron, 2004, 601-607, 44(4).

Agalliu, I. et al., Higher Frequency of Certain Cancers in LRRK2 G2019S Mutation Carriers With Parkinson Disease, JAMA Neurology, 72(1), 58-65, 2015.

* cited by examiner

N-LINKED ISOQUINOLINE AMIDES AS LRRK2 INHIBITORS, PHARMACEUTICAL COMPOSITIONS, AND USES THEREOF

CROSS REFERENCE TO RELATED APPLICATIONS

This application is a U.S. National Phase application under 35 U.S.C. § 371 of PCT Application No. PCT/US2021/056734 filed Oct. 27, 2021, which claims priority from U.S. 63/106,974, filed Oct. 29, 2020.

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7 (1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5): 1602-11). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6). LRRK2 inhibitors have been disclosed in the art, e.g., WO2016036586.

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscluar disease, 2010) and ankylosing spondylitis (Danoy et al., PLoS Genet. 2010 Dec. 2; 6 (12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Journal of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain N-linked isoquinoline amide derivatives, which are collectively or individually referred to herein as "compound(s) of the invention" or "compounds of Formula (I)", as described herein. Applicant has found, surprisingly and advantageously, that the compounds of Formula (I), each of which possess a N-substituted isoquinoline amide moiety, the amino substituent attached to a carbon atom of a $C_{3-8}$ carbocyclic, exhibit excellent LRRK2 inhibitory activity. In some embodiments, the compounds of the invention exhibit unexpectedly superior potency as inhibitors of LRRK2 kinase, as evidenced by the data reported herein. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I):

I

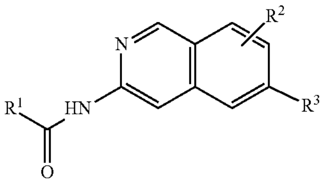

or a pharmaceutically acceptable salt thereof, wherein:

$R^1$ is selected from monocyclic or bicyclic $C_{3-8}$ carbocycle, said carbocycle optionally interrupted by oxygen atom and optionally substituted with 1 to 3 groups selected from $C_{1-6}$ alkyl, $(CH_2)_nOC_{1-6}$alkyl, CN, $C_{1-3}$haloalkyl, $C_{3-10}$ heteroaryl, $C_{3-10}$ heterocyclyl, and halogen, said heteroaryl and heterocyclyl optionally substituted with 1 to 3 groups selected from $C_{1-6}$ alkyl, $CF_3$, and CN;

$R^2$ is selected from hydrogen, $C_{1-6}$ alkyl, $OC_{1-6}$alky, $C_{3-6}$ cycloalkyl, and halogen;

$R^3$ is selected from N-linked oxo-oxazolidinyl, oxoazabicycloheptanyl, azabicycloheptanyl, piperidinyl, tetrahydropyrazolopyridinyl, azaspiroheptanyl, and piperazinyl said N-linked oxazolidinyl, oxazolidinonyl, oxoazabicycloheptanyl, piperidinyl, tetrahydropyrazolopyridinyl, azaspiroheptanyl, and piperazinyl unsubstituted or substituted with 1 to 3 groups independently selected from $C_{1-6}$ alkyl, $OC_{1-6}$ alkyl, OH, halogen, CN, azetidinyl, wherein said piperazinyl is further substituted at available nitrogen atom with a group independently selected from $C_{1-6}$ alkyl, oxetanyl, azetidinyl, and tetrahydrofuranyl, said oxetanyl, azetidinyl, and tetrahydrofuranyl unsubstituted or substituted with 1 to 2 groups independently selected from $C_{1-6}$ alkyl, $OC_{1-6}$ alkyl, halogen, CN, and OH and n is selected from 0 to 3.

In one embodiment, the compounds of the invention have the structural Formula (I"):

I"

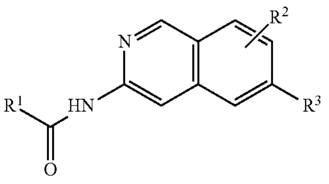

or a pharmaceutically acceptable salt thereof, wherein:

$R^1$ is selected from monocyclic or bicyclic $C_{3-8}$ carbocycle, said carbocycle optionally interrupted by oxygen atom and optionally substituted with 1 to 3 groups selected from $C_{1-6}$ alkyl, $(CH_2)_nOC_{1-6}$alkyl, and halogen;

$R^2$ is selected from hydrogen, $C_{1-6}$ alkyl, $OC_{1-6}$alky, $C_{3-6}$ cycloalkyl, and halogen;

$R^3$ is selected from N-linked oxo-oxazolidinyl, oxoazabicycloheptanyl, azabicycloheptanyl, piperidinyl, tetrahydropyrazolopyridinyl, azaspiroheptanyl, and piperazinyl said oxazolidinyl, oxazolidinonyl, oxoazabicycloheptanyl, piperidinyl, tetrahydropyrazolopyridinyl, azaspiroheptanyl, and piperazinyl unsubstituted or substituted with 1 to 3 groups independently selected from $C_{1-6}$ alkyl, $OC_{1-6}$ alkyl, OH, halogen, azetidinyl, wherein said piperazinyl is further substituted at available nitrogen atom with a group independently selected from $C_{1-6}$ alkyl, oxetanyl, azetidinyl, and tetrahydrofuranyl, said oxetanyl, azetidinyl, and tetrahydrofuranyl unsubstituted or substituted with 1 to 2 groups independently selected from $C_{1-6}$ alkyl, $OC_{1-6}$ alkyl, halogen, and OH and n is selected from 0 to 3.

In another embodiment of this invention is realized when $R^1$ is a monocyclic or bicyclic $C_{3-8}$ carbocycle optionally interrupted with an oxygen atom, said carbocycle selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of this invention is realized when $R^1$ is selected from substituted or unsubstituted cyclopropyl, cyclobutyl, cyclopentyl, cyclohexyl, heptanyl, octanyl, tetrahydrofuranyl, and tetrahydropyranyl. Another subembodiment of this invention is realized when $R^1$ is selected from substituted or unsubstituted spirohexanyl, spiropentanyl, and bicyclopentanyl. Still another subembodiment of this invention is realized when $R^1$ is selected from substituted or unsubstituted oxabicyclohexanyl, oxabicycloheptanyl, oxaspiroheptanyl, oxaspirooctanyl, and oxaspirononanyl. Unlimiting examples of said spirohexanyl, spiropentanyl, bicyclopentanyl oxabicyclohexanyl, oxabicycloheptanyl, oxaspiroheptanyl, oxaspirooctanyl, and oxaspirononanyl moieties are oxaspiro[2.5]octanyl, oxaspiro[2.5]nonanyl, oxaspiro[2.4]heptanyl, spiro[2.3]hexanyl, spiro[2.2]pentanyl, azaspiro[3.3]heptanyl, oxabicyclo[3.1.0]hexanyl, oxabicyclo[2.1.1]hexanyl, and bicyclo[1.1.1]pentanyl. A subembodiment of this aspect of the invention is realized when $R^1$ is substituted or unsubstituted cyclopropyl. Another subembodiment of this aspect of the invention is realized when $R^1$ is substituted or unsubstituted cyclobutyl. Another subembodiment of this aspect of the invention is realized when $R^1$ is substituted or unsubstituted cyclopentyl. Another subembodiment of this aspect of the invention is realized when $R^1$ is substituted or unsubstituted cyclohexyl. Another subembodiment of this aspect of the invention is realized when $R^1$ is substituted or unsubstituted heptanyl. Another subembodiment of this aspect of the invention is realized when $R^1$ is substituted or unsubstituted octanyl. Another subembodiment of this aspect of the invention is realized when $R^1$ is substituted or unsubstituted tetrahydrofuranyl. Another subembodiment of this aspect of the invention is realized when $R^1$ is substituted or unsubstituted tetrahydropyranyl. Another subembodiment of this aspect of the invention is realized when $R^1$ is substituted or unsubstituted spirohexanyl. Another subembodiment of this aspect of the invention is realized when $R^1$ is substituted or unsubstituted spiropentanyl. Another subembodiment of this aspect of the invention is realized when $R^1$ is substituted or unsubstituted bicyclopentanyl. Another subembodiment of this aspect of the invention is realized when $R^1$ is substituted or unsubstituted oxabicyclohexanyl. Another subembodiment of this aspect of the invention is realized when $R^1$ is substituted or unsubstituted oxabicycloheptanyl. Another subembodiment of this aspect of the invention is realized when $R^1$ is substituted or unsubstituted oxaspiroheptanyl. Another subembodiment of this aspect of the invention is realized when $R^1$ is substituted or unsubstituted oxaspirooctanyl. Another subembodiment of this aspect of the invention is realized when $R^1$ is substituted or unsubstituted oxaspirononanyl. Another subembodiment of this aspect of the invention is realized when $R^1$ is unsubstituted. Another subembodiment of this aspect of the invention is realized when $R^1$ is substituted with 1 to 3 groups independently selected from $C_{1-6}$ alkyl, $(CH_2)_nOC_{1-6}$alkyl, halogen and optionally substituted pyridyl, pyrimidinyl, pyrazolyl, triazolyl, thienyl, furanyl, tetrahydropyranyl, tetrahydrofuranyl, and oxabicycloheptanyl. Still another subembodiment of this aspect of the invention is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN.

Another embodiment of this invention is realized when $R^2$ is hydrogen. Still another embodiment of this invention is realized when $R^2$ is halogen. A subembodiment of this aspect of the invention is realized when the halogen is chlorine. Another subembodiment of this aspect of the invention is realized when the halogen is fluorine. Another subembodiment of this aspect of the invention is realized when $R^2$ is $C_{3-6}$ cycloalkyl. A further subembodiment of this aspect of the invention is realized when $R^2$ is cyclopropyl. Another subembodiment of this aspect of the invention is realized when $R^2$ is methyl. Another subembodiment of this aspect of the invention is realized when $R^2$ is selected from methyl and chloro.

Another embodiment of this invention is realized when $R^3$ is selected from N-linked oxo-oxazolidinyl, oxoazabicycloheptanyl, azabicycloheptanyl, piperidinyl, tetrahydropyrazolopyridinyl, azaspiroheptanyl, and piperazinyl, said N-linked oxo-oxazolidinyl, oxoazabicycloheptanyl, azabicycloheptanyl, piperidinyl, tetrahydropyrazolopyridinyl, azaspiroheptanyl, and piperazinyl (on a carbon atom) optionally substituted with 1 to 3 groups selected from $C_{1-6}$ alkyl, $OC_{1-6}$ alkyl, OH, halogen, CN and azetidinyl, wherein said piperazinyl is further substituted at available nitrogen atom with a group independently selected from $C_{1-6}$ alkyl, oxetanyl, azetidinyl, and tetrahydrofuranyl, said oxetanyl, azetidinyl, and tetrahydrofuranyl unsubstituted or substituted with 1 to 2 groups independently selected from $C_{1-6}$ alkyl, $OC_{1-6}$ alkyl, halogen, and OH.

Another embodiment of the invention is realized when $R^3$ is substituted or unsubstituted N-linked oxo-oxazolidinyl. An aspect of this invention is realized when $R^3$ is substituted or unsubstituted oxo-oxazolidinyl, represented by structural formula Ia:

Ia

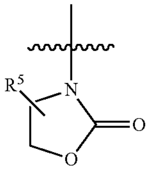

wherein ∿∿ line represents the point of attachment for $R^3$ to the isoquinoline and $R^5$ is selected from hydrogen, $C_{1-6}$ alkyl, $OC_{1-6}$ alkyl, OH, CN, and halogen.

Another embodiment of the invention is realized when $R^3$ is substituted or unsubstituted N-linked oxoazabicycloheptanyl or azabicyloheptanyl. An aspect of this invention is realized when $R^3$ is N-linked oxoazabicycloheptanyl or azabicycloheptanyl represented by structural formula Ib and Ib', respectively:

Ib

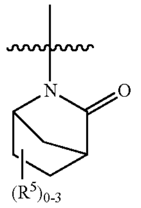

or

Ib'

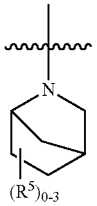

wherein ∿∿∿ line represents the point of attachment for $R^3$ to the isoquinoline structure and $R^5$ is selected from hydrogen, $C_{1-6}$ alkyl, $OC_{1-6}$ alkyl, OH, CN, and halogen. An embodiment of this invention is realized when $R^3$ is Ib. An embodiment of this invention is realized when $R^3$ is Ib'.

Another embodiment of the invention is realized when $R^3$ is substituted or unsubstituted N-linked piperidinyl. An aspect of this invention is realized when $R^3$ is piperidinyl represented by structural formula Ic:

Ic

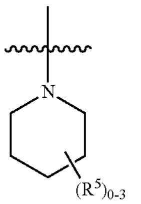

wherein ∿∿∿ line represents the point of attachment for $R^3$ to the isoquinoline structure and $R^5$ is selected from hydrogen, $C_{1-6}$ alkyl, $OC_{1-6}$ alkyl, OH, CN, and halogen.

Another embodiment of the invention is realized when $R^3$ is substituted or unsubstituted N-linked tetrahydropyrazolopyridinyl. An aspect of this invention is realized when $R^3$ is tetrahydropyrazolopyridinyl represented by structural formula Id:

Id

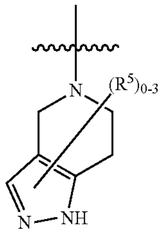

wherein ∿∿∿ line represents the point of attachment for $R^3$ to the isoquinoline structure and $R^5$ is selected from hydrogen, $C_{1-6}$ alkyl, $OC_{1-6}$ alkyl, OH, CN, and halogen.

Another embodiment of the invention is realized when $R^3$ is substituted or unsubstituted N-linked azaspiroheptanyl. An aspect of this invention is realized when $R^3$ is azaspiroheptanyl represented by structural formula Ie:

Ie

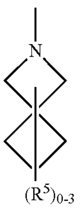

wherein ∿∿∿ line represents the point of attachment for $R^3$ to the isoquinoline structure and $R^5$ is selected from hydrogen, $C_{1-6}$ alkyl, $OC_{1-6}$ alkyl, OH, CN, and halogen.

Another embodiment of the invention is realized when $R^3$ is substituted or unsubstituted N-linked piperazinyl. A further subembodiment of this aspect of the invention is realized when the available nitrogen of piperazinyl is substituted with a group selected from methyl, ethyl, propyl, butyl, oxetanyl, azetidinyl, and tetrahydrofuranyl, said oxetanyl, azetidinyl, and tetrahydrofuranyl unsubstituted or substituted with 1 to 2 groups independently selected from $C_{1-6}$ alkyl $OC_{1-6}$ alkyl, halogen, and OH. An aspect of this invention is realized when $R^3$ is piperazinyl represented by structural formula If:

If

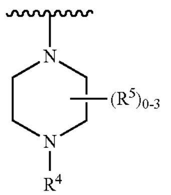

wherein ∿∿∿ line represents the point of attachment for $R^3$ to the isoquinoline structure, $R^5$ is selected from hydrogen, $C_{1-6}$ alkyl, $OC_{1-6}$ alkyl, OH, CN, and halogen, and $R^4$ is selected from $C_{1-6}$ alkyl, oxetanyl and tetrahydrofuranyl, said oxetanyl and tetrahydrofuranyl unsubstituted or substituted with 1 to 2 groups independently selected from $C_{1-6}$ alkyl $OC_{1-6}$ alkyl, halogen, and OH.

Another embodiment of this invention is represented by structural Formula II:

II

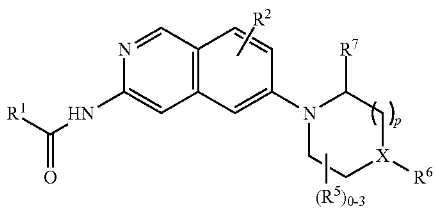

or a pharmaceutically acceptable salt thereof, wherein $R^1$, $R^2$, and $R^5$ are as described herein, p is 0 or 1, X is N, O, or CH, $R^7$ is selected from the group consisting of hydrogen, $C_{1-6}$ alkyl and =O, and $R^6$ is selected from the group consisting of 1) $R^4$, when X is N, p is 1 and $R^7$ is hydrogen or $C_{1-6}$ alkyl,
2) absent, when X is O, p is 0, and $R^7$ is =O, and
3) hydrogen, $C_{1-6}$ alkyl, or OH, when X is CH, p is 1, and $R^7$ is hydrogen or $C_{1-6}$ alkyl, wherein when p is 0 (or absent) a five membered ring is present and when p is 1 a six membered ring is present, and $R^4$ is selected from $C_{1-6}$ alkyl, oxetanyl and tetrahydrofuranyl said oxetanyl and tetrahydrofuranyl unsubstituted or substituted with 1 to 2 groups independently selected from $C_{1-6}$ alkyl, $OC_{1-6}$ alkyl and OH.

A subembodiment of Formula II is realized when p is 1 and X is N or CH. Another subembodiment of Formula II is realized when p is 0 resulting in a five membered ring and X is O.

Another subembodiment of Formula II is realized when $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. Another subembodiment of Formula II is realized when $R^1$ is selected from substituted or unsubstituted cyclopropyl, cyclobutyl, cyclopentyl, cyclohexyl, heptanyl, octanyl, spirohexanyl, spiropentanyl, and bicyclopentanyl. Another subembodiment of Formula II is realized when $R^1$ is cyclopropyl substituted with 1 to 3 groups selected from $C_{1-6}$ alkyl and optionally substituted pyrazolyl. Another subembodiment of Formula II is realized when $R^1$ is selected from substituted or unsubstituted tetrahydrofuranyl, and tetrahydropyranyl. Another subembodiment of Formula II is realized when $R^1$ is selected from substituted or unsubstituted oxabicyclohexanyl, oxabicycloheptanyl, oxaspiroheptanyl, oxaspirooctanyl, and oxaspirononanyl. Another subembodiment of Formula II is realized when $R^1$ is substituted or unsubstituted oxabicyclohexanyl. Another subembodiment of Formula II is realized when $R^1$ is substituted or unsubstituted oxabicycloheptanyl. Another subembodiment of Formula II is realized when $R^1$ is substituted or unsubstituted oxaspiroheptanyl. Another subembodiment of Formula II is realized when $R^1$ is substituted or unsubstituted oxaspirooctanyl. Another subembodiment of Formula II is realized when $R^1$ is substituted or unsubstituted oxaspirononanyl. Still another subembodiment of the invention of Formula II is realized when $R^1$ is unsubstituted. Another subembodiment of the invention of Formula II is realized when $R^1$ is substituted with 1 to 3 groups independently selected from $C_{1-6}$ alkyl, $(CH_2)_nOC_{1-6}$alkyl, halogen and optionally substituted pyridyl, pyrimidinyl, pyrazolyl, thienyl, furanyl, tetrahydropyranyl, tetrahydrofuranyl and oxabicycloheptanyl. Still another subembodiment of Formula II is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, triazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN.

Another embodiment of this invention is represented by structural Formula III:

III

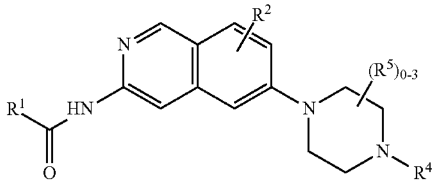

or a pharmaceutically acceptable salt thereof, wherein $R^1$, $R^2$, $R^4$, and $R^5$ are as described herein. A subembodiment of the invention of Formula III is realized when $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula III is realized when $R^1$ is substituted or unsubstituted cyclopropyl. A subembodiment of Formula III is realized when $R^1$ is substituted cyclopropyl substituted with 1 to 3 groups selected from $C_{1-6}$ alkyl and optionally substituted pyrazolyl. Another subembodiment Formula III is realized when $R^1$ is substituted or unsubstituted cyclobutyl. Another subembodiment of Formula III is realized when $R^1$ is substituted or unsubstituted cyclopentyl. Another subembodiment of Formula III is realized when $R^1$ is substituted or unsubstituted cyclohexyl. Another subembodiment of Formula III is realized when $R^1$ is substituted or unsubstituted heptanyl. Another subembodiment of Formula III is realized when $R^1$ is substituted or unsubstituted octanyl. Another subembodiment of Formula III is realized when $R^1$ is substituted or unsubstituted tetrahydrofuranyl. Another subembodiment of Formula III is realized when $R^1$ is substituted or unsubstituted tetrahydropyranyl. Another subembodiment of Formula III is realized when $R^1$ is substituted or unsubstituted spirohexanyl. Another subembodiment of Formula III is realized when $R^1$ is substituted or unsubstituted spiropentanyl. Another subembodiment of Formula III is realized when $R^1$ is substituted or unsubstituted bicyclopentanyl. Another subembodiment of Formula III is realized when $R^1$ is substituted or unsubstituted oxabicyclohexanyl. Another subembodiment of Formula III is realized when $R^1$ is substituted or unsubstituted oxabicycloheptanyl. Another subembodiment of Formula III is realized when $R^1$ is substituted or unsubstituted oxaspiroheptanyl. Another subembodiment of Formula III is realized when $R^1$ is substituted or unsubstituted oxaspirooctanyl. Another subembodiment of Formula III is realized when $R^1$ is substituted or unsubstituted oxaspirononanyl. Another subembodiment of Formula III is realized when $R^1$ is unsubstituted. Another subembodiment of Formula III is realized when $R^1$ is substituted with 1 to 3 groups independently selected from $C_{1-6}$ alkyl, $(CH_2)_nOC_{1-6}$alkyl, halogen, and optionally substituted pyridyl, pyrimidinyl, pyrazolyl, triazolyl, thienyl, furanyl, tetrahydropyranyl, tetrahydrofuranyl, and oxabicycloheptanyl. Still another subembodiment of Formula III is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN.

Yet another subembodiment of Formula III is realized when $R^2$ is hydrogen. Another subembodiment of Formula III is realized when $R^2$ is chlorine or fluorine. Another subembodiment of Formula III is realized when $R^2$ is cyclopropyl.

Still another subembodiment of Formula III is realized when $R^4$ is selected from methyl, ethyl, propyl, oxetanyl, tetrahydrofuranyl, said oxetanyl and tetrahydrofuranyl substituted or unsubstituted with 1 to 2 groups selected from $C_{1-6}$ alkyl, $OC_{1-6}$ alkyl, and OH. Still another subembodiment of Formula III is realized when $R^4$ is selected from methyl, ethyl, propyl, oxetanyl, tetrahydrofuranyl, said oxetanyl and tetrahydrofuranyl substituted with 1 to 2 groups selected from $C_{1-6}$ alkyl, $OC_{1-6}$ alkyl, and OH, wherein the substituent(s) is in a cis position relative to each other and/or the piperazinyl nitrogen. Another subembodiment of Formula III is realized when $R^4$ is selected from methyl. Another subembodiment of Formula III is realized when $R^4$ is selected from ethyl. Another subembodiment of Formula III is realized when $R^4$ is selected from propyl. Another subembodiment of Formula III is realized when $R^4$ is oxetanyl, unsubstituted or substituted with 1 to 2 groups selected from $C_{1-6}$ alkyl, $OC_{1-6}$ alkyl and OH. Still another subembodiment of Formula III is realized when $R^4$ is oxetanyl substituted with 1 to 2 groups selected from $C_{1-6}$ alkyl, $OC_{1-6}$ alkyl, and OH. Another subembodiment of Formula III is realized when $R^4$ is oxetanyl substituted with 2 groups selected from $C_{1-6}$ alkyl, $OC_{1-6}$ alkyl, and OH, wherein both substituents are in a cis position relative to each other and/or the piperazinyl nitrogen. Still another subembodiment of Formula III is realized when $R^4$ is oxetanyl substituted with 2 groups selected from methyl, $OCH_3$, and OH, wherein the methyl, $OCH_3$ and OH are substituted in a cis position relative to each other and/or the piperazinyl nitrogen. Another subembodiment of Formula III is realized when $R^4$ is tetrahydrofuranyl, unsubstituted or substituted with 1 to 2 groups selected from $C_{1-6}$ alkyl, $OC_{1-6}$ alkyl and OH. Still another subembodiment of Formula III is realized when $R^4$ is tetrahydrofuranyl substituted with 1 to 2 groups selected from $C_{1-6}$ alkyl, $OC_{1-6}$ alkyl and OH. Another subembodiment of Formula III is realized when $R^4$ is tetrahydrofuranyl substituted with 2 groups selected from $C_{1-6}$ alkyl, $OC_{1-6}$ alkyl and OH, wherein both substituents are in a cis position relative to each other and/or the piperazinyl nitrogen. Still another subembodiment of Formula III is realized when $R^4$ is tetrahydrofuranyl substituted with 2 groups selected from methyl, $OCH_3$ and OH, wherein the methyl, $OCH_3$ and OH are substituted in a cis position relative to each other and/or the piperazinyl nitrogen.

Yet another subembodiment of Formula III is realized when $R^1$ is substituted or unsubstituted cyclopropyl, $R^2$ is hydrogen, chlorine, or fluorine and $R^4$ is substituted or unsubstituted tetrahydrofuranyl. Another subembodiment of Formula III is realized when $R^1$ is substituted or unsubstituted cyclobutyl, $R^2$ is hydrogen, chlorine, or fluorine and $R^4$ is substituted or unsubstituted tetrahydrofuranyl. Another subembodiment of Formula III is realized when $R^1$ is substituted or unsubstituted cyclopentanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted cyclohexyl, $R^2$ is hydrogen, chlorine, or fluorine and $R^4$ is substituted or unsubstituted tetrahydrofuranyl. Another subembodiment of Formula III is realized when $R^1$ is substituted or unsubstituted heptanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted octanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted tetrahydrofuranyl, $R^2$ is hydrogen, chlorine, or fluorine and $R^4$ is substituted or unsubstituted tetrahydrofuranyl. Another subembodiment of Formula III is realized when R is substituted or unsubstituted tetrahydropyranyl, $R^2$ is hydrogen, chlorine, or fluorine and $R^4$ is substituted or unsubstituted tetrahydrofuranyl. Another subembodiment of Formula III is realized when $R^1$ is substituted or unsubstituted bicyclopentanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted oxabicyclohexanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted oxabicycloheptanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted spiropentanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted spirohexanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted oxaspiroheptanyl, $R^2$ is hydrogen, chlorine, or fluorine and $R^4$ is substituted or unsubstituted tetrahydrofuranyl. Another subembodiment of Formula III is realized when $R^1$ is substituted or unsubstituted oxaspirooctanyl, $R^2$ is hydrogen, chlorine, or fluorine and $R^4$ is substituted or unsubstituted tetrahydrofuranyl. Yet another subembodiment of Formula III is realized when the $R^4$ tetrahydrofuranyl is substituted with 1 to 2 group selected from $C_{1-6}$ alkyl and OH. Still another subembodiment of Formula III is realized when the $R^4$ tetrahydrofuranyl is substituted with $C_{1-6}$ alkyl and OH Yet another subembodiment of Formula III is realized when $R^1$ is substituted or unsubstituted cyclopropyl, $R^2$ is hydrogen, chlorine, or fluorine and $R^4$ is substituted or unsubstituted oxetanyl. Another subembodiment of Formula III is realized when $R^1$ is substituted or unsubstituted cyclobutyl, $R^2$ is hydrogen, chlorine, or fluorine and $R^4$ is substituted or unsubstituted oxetanyl. Another subembodiment of Formula III is realized when $R^1$ is substituted or unsubstituted cyclopentanyl, $R^2$ is hydrogen, chlorine, or fluorine and $R^4$ is substituted or unsubstituted oxetanyl. Another subembodiment of Formula III is realized when $R^1$ is substituted or unsubstituted cyclohexyl, $R^2$ is hydrogen, chlorine, or fluorine and $R^4$ is substituted or unsubstituted oxetanyl. Another subembodiment of Formula III is realized when $R^1$ is substituted or unsubstituted heptanyl, $R^2$ is hydrogen, chlorine, or fluorine and $R^4$ is substituted or unsubstituted oxetanyl. Another subembodiment of Formula III is realized when $R^1$ is substituted or unsubstituted octanyl, $R^2$ is hydrogen, chlorine, or fluorine and $R^4$ is substituted or unsubstituted oxetanyl. Another subembodiment of Formula III is realized when $R^1$ is substituted or unsubstituted tetrahydrofuranyl, $R^2$ is hydrogen, chlorine, or fluorine and $R^4$ is substituted or unsubstituted oxetanyl. Another subembodiment of Formula III is realized when $R^1$ is substituted or unsubstituted tetrahydropyranyl, $R^2$ is hydrogen, chlorine, or fluorine and $R^4$ is substituted or unsubstituted oxetanyl. Another subembodiment of Formula III is realized when $R^1$ is substituted or unsubstituted bicyclopentanyl, $R^2$ is hydrogen, chlorine, or fluorine and $R^4$ is substituted or unsubstituted oxetanyl. Another subembodiment of Formula III is realized when $R^1$ is substituted or unsubstituted oxabicyclohexanyl, $R^2$ is hydrogen, chlorine, or fluorine and $R^4$ is substituted or unsubstituted oxetanyl. Another subembodiment of Formula III is realized when $R^1$ is substituted or unsubstituted oxabicycloheptanyl, $R^2$ is hydrogen, chlorine, or fluorine and $R^4$ is substituted or unsubstituted oxetanyl. Another subembodiment of Formula III is realized when $R^1$ is substituted or unsubstituted spiropentanyl, $R^2$ is hydrogen, chlorine, or fluorine and $R^4$ is substituted or unsubstituted oxetanyl. Another subembodiment of Formula III is realized when $R^1$ is substituted or unsubstituted spirohexanyl, $R^2$ is hydrogen, chlorine, or fluorine and $R^4$ is substituted or unsubstituted oxetanyl. Another subembodiment of Formula III is realized when $R^1$ is substituted or unsubstituted oxaspiroheptanyl, $R^2$ is hydrogen, chlorine, or fluorine and $R^4$ is substituted or unsubstituted oxetanyl. Another subembodiment of Formula III is realized when $R^1$ is substituted or unsubstituted oxaspirooctanyl, $R^2$ is hydrogen, chlorine, or fluorine and $R^4$ is substituted or unsubstituted oxetanyl. Yet another subembodiment of Formula III is realized when $R^4$ oxetanyl is unsubstituted. Yet another subembodiment of Formula III is realized when $R^4$ oxetanyl is substituted with 1 to 2 group selected from $C_{1-6}$ alkyl and OH.

Another embodiment of this invention is represented by structural Formula IV:

IV

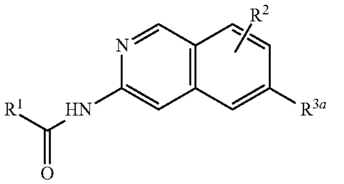

or a pharmaceutically acceptable salt thereof, wherein $R^1$ and $R^2$ are as described herein and $R^{3a}$ is selected from the group consisting of:

Ia

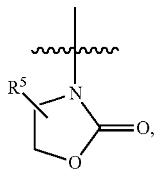

Ib

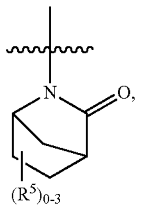

Ib'

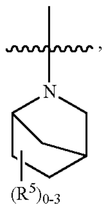

Ic

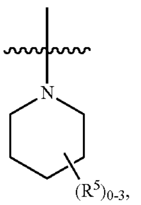

Id

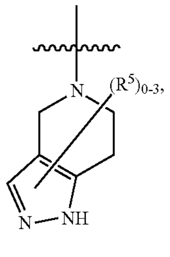

and

-continued

Ie

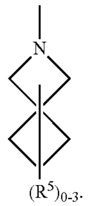

wherein $R^5$ are as described herein.

A subembodiment of Formula IV is realized when $R^{3a}$ is Ia and $R^1$ and $R^2$ are as described herein. An aspect of this subembodiment of Formula IV is realized when $R^{3a}$ is Ia and $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula IV when $R^{3a}$ is Ia is realized when $R^1$ is substituted or unsubstituted cyclopropyl. Another subembodiment Formula IV when $R^{3a}$ is Ia is realized when $R^1$ is substituted or unsubstituted cyclobutyl. Another subembodiment of Formula IV when $R^{3a}$ is Ia is realized when $R^1$ is substituted or unsubstituted cyclopentyl. Another subembodiment of Formula IV when $R^{3a}$ is Ia is realized when $R^1$ is substituted or unsubstituted cyclohexyl. Another subembodiment of Formula IV when $R^{3a}$ is Ia is realized when $R^1$ is substituted or unsubstituted heptanyl. Another subembodiment of Formula IV when $R^{3a}$ is Ia is realized when $R^1$ is substituted or unsubstituted octanyl. Another subembodiment of Formula IV when $R^{3a}$ is Ia is realized when $R^1$ is substituted or unsubstituted tetrahydrofuranyl. Another subembodiment of Formula IV when $R^{3a}$ is Ia is realized when $R^1$ is substituted or unsubstituted tetrahydropyranyl. Another subembodiment of Formula IV when $R^{3a}$ is Ia is realized when $R^1$ is substituted or unsubstituted spirohexanyl. Another subembodiment of Formula IV when $R^{3a}$ is Ia is realized when $R^1$ is substituted or unsubstituted spiropentanyl. Another subembodiment of Formula IV when $R^{3a}$ is Ia is realized when $R^1$ is substituted or unsubstituted bicyclopentanyl. Another subembodiment of Formula IV when $R^{3a}$ is Ia is realized when $R^1$ is substituted or unsubstituted oxabicyclohexanyl. Another subembodiment of Formula IV when $R^{3a}$ is Ia is realized when $R^1$ is substituted or unsubstituted oxabicycloheptanyl. Another subembodiment of Formula IV when $R^{3a}$ is Ia is realized when $R^1$ is substituted or unsubstituted oxaspiroheptanyl. Another subembodiment of Formula IV when $R^{3a}$ is Ia is realized when $R^1$ is substituted or unsubstituted oxaspirooctanyl. Another subembodiment of Formula IV when $R^{3a}$ is Ia is realized when $R^1$ is substituted or unsubstituted oxaspirononanyl. Another subembodiment of Formula IV when $R^{3a}$ is Ia is realized when $R^1$ is unsubstituted. Another subembodiment of Formula IV when $R^{3a}$ is Ia is realized when $R^1$ is substituted with 1 to 3 groups independently selected from $C_{1-6}$ alkyl, $(CH_2)_nOC_{1-6}$alkyl, halogen pyridyl, pyrimidinyl, pyrazolyl, triazolyl, thienyl, furanyl, tetrahydropyranyl, tetrahydrofuranyl, and oxabicycloheptanyl. Still another subembodiment of Formula IV when $R^{3a}$ is Ia is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN. Another aspect of this subembodiment of Formula IV when $R^{3a}$ is Ia is realized when $R^2$ is hydrogen. Another aspect of this subembodiment of Formula IV when $R^{3a}$ is Ia is realized when $R^2$ is chlorine or fluorine.

A subembodiment of Formula IV is realized when $R^{3a}$ is Ib or Ib' and $R^1$ and $R^2$ are as described herein. An aspect of this subembodiment is realized when $R^{3a}$ is Ib or Ib' and $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula IV when $R^{3a}$ is Ib or Ib' is realized when $R^1$ is substituted or unsubstituted cyclopropyl. Another subembodiment Formula IV when $R^{3a}$ is Ib or Ib' is realized when $R^1$ is substituted or unsubstituted cyclobutyl. Another subembodiment of Formula IV when $R^{3a}$ is Ib or Ib' is realized when $R^1$ is substituted or unsubstituted cyclopentyl. Another subembodiment of Formula IV when $R^{3a}$ is Ib or Ib' is realized when $R^1$ is substituted or unsubstituted cyclohexyl. Another subembodiment of Formula IV when $R^{3a}$ is Ib or Ib' is realized when $R^1$ is substituted or unsubstituted heptanyl. Another subembodiment of Formula IV when $R^{3a}$ is Ib or Ib' is realized when $R^1$ is substituted or unsubstituted octanyl. Another subembodiment of Formula IV when $R^{3a}$ is Ib or Ib' is realized when $R^1$ is substituted or unsubstituted tetrahydrofuranyl. Another subembodiment of Formula IV when $R^{3a}$ is Ib or Ib' is realized when $R^1$ is substituted or unsubstituted tetrahydropyranyl. Another subembodiment of Formula IV when $R^{3a}$ is Ib or Ib' is realized when $R^1$ is substituted or unsubstituted spirohexanyl. Another subembodiment of Formula IV when $R^{3a}$ is Ib or Ib' is realized when $R^1$ is substituted or unsubstituted spiropentanyl. Another subembodiment of Formula IV when $R^{3a}$ is Ib or Ib' is realized when $R^1$ is substituted or unsubstituted bicyclopentanyl. Another subembodiment of Formula IV when $R^{3a}$ is Ib or Ib' is realized when $R^1$ is substituted or unsubstituted oxabicyclohexanyl. Another subembodiment of Formula IV when $R^{3a}$ is Ia is realized when $R^1$ is substituted or unsubstituted oxabicycloheptanyl. Another subembodiment of Formula IV when $R^{3a}$ is Ib or Ib' is realized when $R^1$ is substituted or unsubstituted oxaspiroheptanyl. Another subembodiment of Formula IV when $R^{3a}$ is Ib or Ib' is realized when $R^1$ is substituted or unsubstituted oxaspirooctanyl. Another subembodiment of Formula IV when $R^{3a}$ is Ib or Ib' is realized when $R^1$ is substituted or unsubstituted oxaspirononanyl. Another subembodiment of Formula IV when $R^{3a}$ is Ib or Ib' is realized when $R^1$ is unsubstituted. Another subembodiment of Formula IV when $R^{3a}$ is Ib or Ib' is realized when $R^1$ is substituted with 1 to 3 groups independently selected from $C_{1-6}$ alkyl, $(CH_2)_nOC_{1-6}$alkyl, halogen, and optionally substituted pyridyl, pyrimidinyl, pyrazolyl, triazolyl, thienyl, furanyl, tetrahydropyranyl, tetrahydrofuranyl, and oxabicycloheptanyl. Still another subembodiment of Formula IV when $R^{3a}$ is Ib or Ib' is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN. Another aspect of this subembodiment of Formula IV when $R^{3a}$ is Ib or Ib' is realized when $R^2$ is hydrogen. Another aspect of this subembodiment of Formula IV when $R^{3a}$ is Ib or Ib' is realized when $R^2$ is chlorine or fluorine.

A subembodiment of Formula IV is realized when $R^{3a}$ is Ic and $R^1$ and $R^2$ are as described herein. An aspect of this subembodiment is realized when $R^{3a}$ is Ic and $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula IV when $R^{3a}$ is Ic is realized when $R^1$ is substituted or unsubstituted cyclopropyl. Another subembodiment Formula IV when $R^{3a}$ is Ic is realized when $R^1$ is substituted or unsubstituted cyclobutyl. Another subembodiment of Formula IV when $R^{3a}$ is Ic is realized when $R^1$ is substituted or unsubstituted cyclopentyl. Another subembodiment of Formula IV when $R^{3a}$ is Ic is realized when $R^1$ is substituted or unsubstituted cyclohexyl. Another subembodiment of Formula IV when $R^{3a}$ is Ic is realized when $R^1$ is substituted or unsubstituted heptanyl. Another subembodiment of Formula IV when $R^{3a}$ is Ic is realized when $R^1$ is substituted or unsubstituted octanyl. Another subembodiment of Formula IV when $R^{3a}$ is Ic is realized when $R^1$ is substituted or unsubstituted tetrahydrofuranyl. Another subembodiment of Formula IV when $R^{3a}$ is Ic or is realized when $R^1$ is substituted or unsubstituted tetrahydropyranyl. Another subembodiment of Formula IV when $R^{3a}$ is Ic is realized when $R^1$ is substituted or unsubstituted spirohexanyl. Another subembodiment of Formula IV when $R^{3a}$ is Ic is realized when $R^1$ is substituted or unsubstituted spiropentanyl. Another subembodiment of Formula IV when $R^{3a}$ is Ic is realized when $R^1$ is substituted or unsubstituted bicyclopentanyl. Another subembodiment of Formula IV when $R^{3a}$ is Ic is realized when $R^1$ is substituted or unsubstituted oxabicyclohexanyl. Another subembodiment of Formula IV when $R^{3a}$ is Ia is realized when $R^1$ is substituted or unsubstituted oxabicycloheptanyl. Another subembodiment of Formula IV when $R^{3a}$ is Ic is realized when $R^1$ is substituted or unsubstituted oxaspiroheptanyl. Another subembodiment of Formula IV when $R^{3a}$ is Ic is realized when $R^1$ is substituted or unsubstituted oxaspirooctanyl. Another subembodiment of Formula IV when $R^{3a}$ is Ic is realized when $R^1$ is substituted or unsubstituted oxaspirononanyl. Another subembodiment of Formula IV when $R^{3a}$ is Ic is realized when $R^1$ is unsubstituted. Another subembodiment of Formula IV when $R^{3a}$ is Ic is realized when $R^1$ is substituted with 1 to 3 groups independently selected from $C_{1-6}$ alkyl, $(CH_2)_nOC_{1-6}$alkyl, halogen and optionally substituted pyridyl, pyrimidinyl, pyrazolyl, thienyl, furanyl, tetrahydropyranyl, tetrahydrofuranyl, and oxabicycloheptanyl. Still another subembodiment of Formula IV when $R^{3a}$ is Ic is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, triazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN. Another aspect of this subembodiment of Formula IV when $R^{3a}$ is Ic is realized when $R^2$ is hydrogen. Another aspect of this subembodiment of Formula IV when $R^{3a}$ is Ic is realized when $R^2$ is chlorine or fluorine.

A subembodiment of Formula IV is realized when $R^{3a}$ is Id and $R^1$ and $R^2$ are as described herein. An aspect of this subembodiment is realized when $R^{3a}$ is Id and $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula IV when $R^{3a}$ is Id is realized when $R^1$ is substituted or unsubstituted cyclopropyl. Another subembodiment Formula IV when $R^{3a}$ is Id is realized when $R^1$ is substituted or unsubstituted cyclobutyl. Another subembodiment of Formula IV when $R^{3a}$ is Id is realized when $R^1$ is substituted or unsubstituted cyclopentyl. Another subembodiment of Formula IV when $R^{3a}$ is Id is realized when $R^1$ is substituted or unsubstituted cyclohexyl. Another subembodiment of Formula IV when $R^{3a}$ is Id is realized when $R^1$ is substituted or unsubstituted heptanyl. Another subembodiment of Formula IV when $R^{3a}$ is Id is realized when $R^1$ is substituted or unsubstituted octanyl. Another subembodiment of Formula IV when $R^{3a}$ is Id is realized when $R^1$ is substituted or unsubstituted tetrahydrofuranyl. Another subembodiment of Formula IV when $R^{3a}$ is Id is realized when $R^1$ is substituted or unsubstituted tetrahydropyranyl. Another subembodiment of Formula IV when $R^{3a}$ is Id is realized when $R^1$ is substituted or unsubstituted spirohexanyl. Another subembodiment of Formula IV when $R^{3a}$ is Id is realized when $R^1$ is substituted or unsubstituted spiropentanyl. Another subembodiment of Formula IV when $R^{3a}$ is Id is realized when $R^1$ is substituted or unsubstituted bicyclopentanyl. Another subembodiment of Formula IV when $R^{3a}$ is Id is realized when $R^1$ is substituted or unsubstituted oxabicyclohexanyl. Another subembodiment of Formula IV when $R^{3a}$ is Id is realized when $R^1$ is substituted or unsubstituted oxabicycloheptanyl. Another subembodiment of Formula IV when $R^{3a}$ is Id is realized when $R^1$ is substituted or unsubstituted oxaspiroheptanyl. Another subembodiment of Formula IV when $R^{3a}$ is Id is realized when $R^1$ is substituted or unsubstituted oxaspirooctanyl. Another subembodiment of Formula IV when $R^{3a}$ is Id is realized when $R^1$ is substituted or unsubstituted oxaspirononanyl. Another subembodiment of Formula IV when $R^{3a}$ is Id is realized when $R^1$ is unsubstituted. Another subembodiment of Formula IV when $R^{3a}$ is Id is realized when $R^1$ is substituted with 1 to 3 groups independently selected from $C_{1-6}$ alkyl, $(CH_2)_nOC_{1-6}$alkyl, halogen, and optionally substituted pyridyl, pyrimidinyl, pyrazolyl, triazolyl, thienyl, furanyl, tetrahydropyranyl, tetrahydrofuranyl, and oxabicycloheptanyl. Still another subembodiment of Formula IV when $R^{3a}$ is Id is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, thienyl, furanyl, tetrahydropyranyl, tetrahydrofuranyl, and oxabicycloheptanyl, said pyridyl, pyrimidinyl, pyrazolyl, triazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN. Another aspect of this subembodiment of Formula IV when $R^{3a}$ is Id is realized when $R^2$ is hydrogen. Another aspect of this subembodiment of Formula IV when $R^{3a}$ is Id is realized when $R^2$ is chlorine or fluorine.

A subembodiment of the invention of Formula IV is realized when $R^{3a}$ is Ie and $R^1$ and $R^2$ are as described herein. An aspect of this subembodiment is realized when $R^{3a}$ is Ie and $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl. A subembodiment of Formula IV when $R^{3a}$ is Ie is realized when $R^1$ is substituted or unsubstituted cyclopropyl. Another subembodiment Formula IV when $R^{3a}$ is Ie is realized when $R^1$ is substituted or unsubstituted cyclobutyl. Another subembodiment of Formula IV when $R^{3a}$ is Ie is realized when $R^1$ is substituted or unsubstituted cyclopentyl. Another subembodiment of Formula IV when $R^{3a}$ is Ie is realized when $R^1$ is substituted or unsubstituted cyclohexyl. Another subembodiment of Formula IV when $R^{3a}$ is Ie is realized when $R^1$ is substituted or unsubstituted heptanyl. Another subembodiment of Formula IV when $R^{3a}$ is Ie is realized when $R^1$ is substituted or unsubstituted octanyl. Another subembodiment of Formula IV when $R^{3a}$ is Ie is realized when $R^1$ is substituted or unsubstituted tetrahydrofuranyl. Another subembodiment of Formula IV when $R^{3a}$ is Ie is realized when $R^1$ is substituted or unsubstituted tetrahydropyranyl. Another subembodiment of Formula IV when $R^{3a}$ is Ie is realized when $R^1$ is substituted or unsubstituted spirohexanyl. Another subembodiment of Formula IV when $R^{3a}$ is Ie is realized when $R^1$ is substituted or unsubstituted spiropentanyl. Another subembodiment of Formula IV when $R^{3a}$ is Ie is realized when $R^1$ is substituted or unsubstituted bicyclopentanyl. Another subembodiment of Formula IV when $R^{3a}$ is Ie is realized when $R^1$ is substituted or unsubstituted oxabicyclohexanyl. Another subembodiment of Formula IV when $R^{3a}$ is Ie is realized when $R^1$ is substituted or unsubstituted oxabicycloheptanyl. Another subembodiment of Formula IV when $R^{3a}$ is Ie is realized when $R^1$ is substituted or unsubstituted oxaspiroheptanyl. Another subembodiment of Formula IV when $R^{3a}$ is Ie is realized when $R^1$ is substituted or unsubstituted oxaspirooctanyl. Another subembodiment of Formula IV when $R^{3a}$ is Ie is realized when $R^1$ is substituted or unsubstituted oxaspirononanyl. Another subembodiment of Formula IV when $R^{3a}$ is Ie is realized when $R^1$ is unsubstituted. Another subembodiment of Formula IV when $R^{3a}$ is Ie is realized when $R^1$ is substituted with 1 to 3 groups independently selected from $C_{1-6}$ alkyl, $(CH_2)_nOC_{1-6}$alkyl, halogen and optionally substituted pyridyl, pyrimidinyl, pyrazolyl, thienyl, furanyl, tetrahydropyranyl, tetrahydrofuranyl, and oxabicycloheptanyl. Still another subembodiment of Formula IV when $R^{3a}$ is Ie is realized when $R^1$ is substituted with 1 to 3 groups independently selected from $CH_3$, $CH_2CH_3$, $(CH_2)_nOCH_3$, chlorine, fluorine, pyridyl, pyrimidinyl, pyrazolyl, triazolyl, thienyl, furanyl, tetrahydropyranyl, tetrahydrofuranyl, and oxabicycloheptanyl, said pyridyl, pyrimidinyl, pyrazolyl, triazolyl, thienyl, furanyl, tetrahydropyranyl, tetrahydrofuranyl, and oxabicycloheptanyl optionally substituted with 1 to 3 group selected from $C_{1-6}$ alkyl, $CF_3$ and CN. Another aspect of this subembodiment of Formula IV when $R^{3a}$ is Ie is realized when $R^2$ is hydrogen. Another aspect of this subembodiment of Formula IV when $R^{3a}$ is Ie is realized when $R^2$ is chlorine or fluorine.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

DETAILED DESCRIPTION OF THE INVENTION

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formulae I, II, III, and IV the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulae I, II, III, and IV. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulae I, II, III, and IV can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $—CH_2C(O)—$ groups (keto forms) may undergo tautomerism to form hydroxyl $—CH{=}C(OH)—$ groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the methyl group is emerging from the plane of the paper and the ethyl group is descending into the plane of the paper with the cyclohexene ring in the plane of the paper.

Illus-I

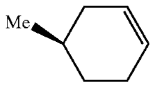

Illus-2

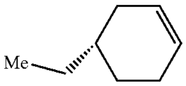

Illus-3

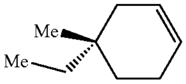

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents appended to a compound substrate, for example, a halogen or a moiety appended to a portion of a structure replacing a hydrogen, means that one substituent of the group of substituents specified is present, and more than one of said substituents may be bonded to any of the defined or chemically accessible bonding points of the substrate.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"optionally interrupted" means that the carbon atom can be replaced by a heteroatom selected oxygen and/or nitrogen.

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula I, Formula II, Formula III, or Formula IV that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula I through Formula IV to a compound of Formula I, Formula II, Formula III, or Formula IV or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

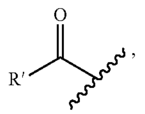

equally, with no differentiation implied using any or all of these representations;

The term "alkyl" (including the alkyl portions of other moieties, such as trifluoromethyl-alkyl- and alkoxy-) means a straight or branched aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "cycloalkyl" means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term "cycloalkyl" also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamantly; and the like;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

Where a structural formula represents bonding between a moiety and a substrate using a bonding line that terminates in the middle of the structure, for example the following representations:

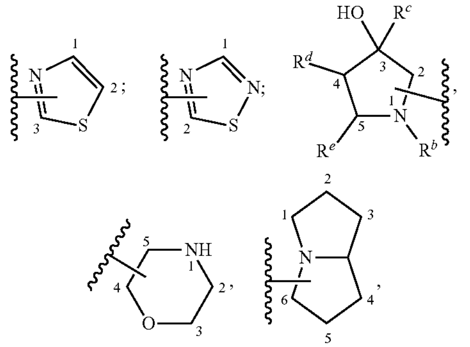

whether or not numbered the structure indicates that unless otherwise defined the moiety may be bonded to the substrate through any of available ring atom, for example, the numbered atoms of the example moieties;

The term "heterocyclyl" (or heterocycloalkyl) means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiophenyl and tetrahydrothiopyranyl); and wherein the heteroatoms can be alone or in combination provided that the moiety does not contain adjacent oxygen and/or sulfur atoms present in the ring system; preferred heterocyclyl moieties contain 5 to 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected substituents;

The nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl—

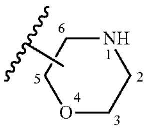

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

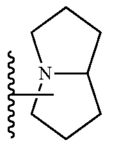 and 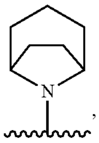, and the like.

The term "halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$;

The term "hydroxyl" and "hydroxy" means an CO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and The bonding sequence is indicated by hyphens where moieties are represented in text, for example—alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

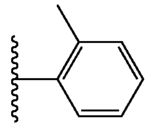, indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

The line -, as a bond generally indicates a mixture of, or either of, the possible isomers, e.g., containing (R)- and (S)-stereochemical configuration. For example:

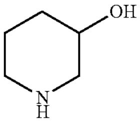 encompasses 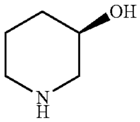 and/or 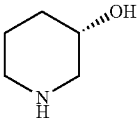

Furthermore, unwedged-bolded or unwedged-hashed lines are used in structures containing multiple stereocenters in order to depict relative configuration where it is known. For example:

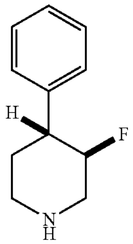

means that the fluorine and hydrogen atoms are on the same face of the piperidine ring, but represents a mixture of, or one of, the possible isomers at right

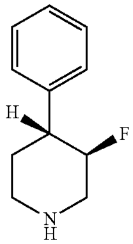 and/or 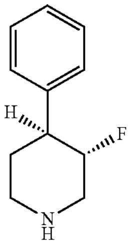

whereas:

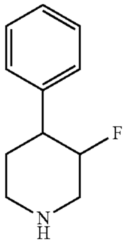 [SMILES: FC1CNCCC1c1ccccc1]

represents a mixture of, or one of, the possible isomers at right

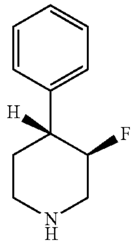 and/or 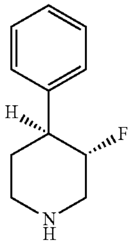 and/or

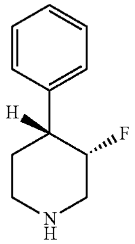 and/or 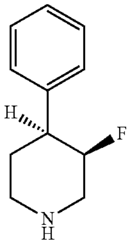

In all cases, compound name(s) accompany the structure drawn and are intended to capture each of the stereochemical permutations that are possible for a given structural isomer based on the synthetic operations employed in its preparation. Lists of discrete stereoisomers that are conjoined using or indicate that the presented compound (e.g. 'Example number') was isolated as a single stereoisomer, and that the identity of that stereoisomer corresponds to one of the possible configurations listed. Lists of discrete stereoisomers that are conjoined using and indicate that the presented compound was isolated as a racemic mixture or diastereomeric mixture.

A specific absolute configuration is indicated by use of a wedged-bolded or wedged-hashed line. Unless a specific absolute configuration is indicated, the present invention is meant to encompass all such stereoisomeric forms of these compounds.

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

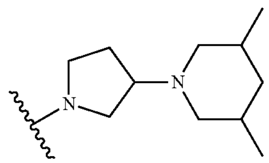

represents

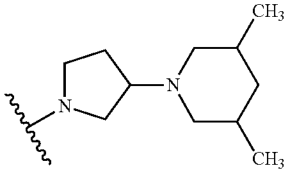

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.,* 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

This invention also includes the compounds of this invention in isolated and purified form obtained by routine techniques. Polymorphic forms of the compounds of Formula I, Formula II, Formula III, and Formula IV and of the salts, solvates and prodrugs of the compounds of Formula I, Formula II, Formula III, and Formula IV are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

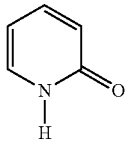

and

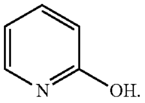

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of Formula I, Formula II, Formula III, and Formula IV, or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I, Formula II, Formula III, and Formula IV is used contemporaneously with one or more other drugs, a pharmaceutical composition in unit dosage form containing such other drugs and the compound of Formula I, Formula II, Formula III, or Formula IV is preferred. However, the combination therapy may also include therapies in which the compound of Formula I, Formula II, Formula III, or Formula IV, and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I, Formula II, Formula III, or Formula IV.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or acetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above-mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the present invention can be prepared according to the following schemes and specific examples, or modifications thereof, using readily available starting materials, reagents and conventional synthesis procedures. It is also possible to make use of variants which are themselves known to those of ordinary skill in this art but are not mentioned in detail. The general procedures for making the compounds claimed in this invention can be readily understood by one skilled in the art from viewing the following schemes and descriptions. Abbreviations used in the experimentals may include, but are not limited to the following: Abbreviations used in the experimentals may include, but are not limited to the following:

| | |
|---|---|
| 2-MeTHF | 2-Methyltetrahydrofuran |
| AcOH | Acetic Acid |
| aq | Aqueous |
| BHT | 3,5-Di-tert-4-butylhydroxytoluene |
| BINAP | (2,2'-bis(diphenylphosphino)-1,1'-binaphthyl) |
| $C_2Cl_6$ | Hexachloroethane |
| CPME | Cyclopentyl methyl ether |
| DAST | Diethylaminosulfur trifluoride |
| DCE | Dichloroethane |
| DCM | Dichloromethane |
| DIPEA | N,N-Diisopropylethylamine |
| DMA | Dimethylacetamide |
| DMAP | 4-Dimethylaminopyridine |
| DMCDA | trans-N,N'-dimethylcyclohexane-1,2-diamine |
| DMF | Dimethylformamide |
| DMSO | Dimethyl sulfoxide |
| EtOAc | Ethyl acetate |
| $Et_3N$ | Triethylamine |
| ESI | Electrospray ionization |
| h | Hours |
| $^1$H-NMR | Proton nuclear magnetic resonance |
| HPLC | High performance liquid chromatography |
| IPA | Isopropyl alcohol |
| Josiphos-SL-J009-1-Pd-G3 | {(R)-1-[(Sp)-2-(Dicyclohexylphosphino)ferrocenyl]ethyldi-tert-butylphosphine}[2-(2'-amino-1,1'-biphenyl)]palladium(II) methanesulfonate (MFCD27978424)<br>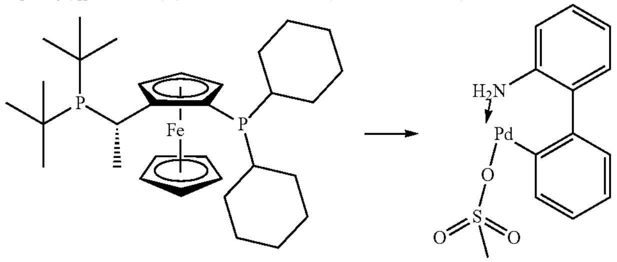<br>Josiphos-SL-J009-1-Pd-G3 |
| LCMS | Liquid chromatography-mass spectrometry |
| LiHMDS | Lithium bis(trimethylsilyl)amide |
| MeCN | Acetonitrile |
| MeOH | Methanol |
| MS | Mass spectrometry |
| m/z | Mass to charge ratio |
| NBS | N-bromosuccinimide |
| NMP | N-Methyl-2-pyrrolidone |
| Pd/C | Palladium on Carbon |
| PE | Petroleum ether |
| psi | Pounds per square inch |
| RT | Room temperature |
| SFC | Supercritical Fluid Chromatography |
| TFA | Trifluoroacetic acid |
| THF | Tetrahydrofuran |
| TLC | Thin Layer Chromatography |
| $t_R$ | Retention time |

-continued

| | |
|---|---|
| TBAF | Tetra-n-butylammonium fluoride |
| TBDPS | Tert-butyldiphenylsilyl |
| Tf2O | Trifluoromethanesulfonic anhydride |
| TEA | triethylamine |
| MeONa | Sodium methanolate methanol |
| TBDPSCl | tert-Butyl(chloro)diphenylsilane |
| DEA | diethanolamine |
| DMP | Dess-Martin periodinane |
| TMS/TMS-CN | Trimethylsilyl/trimethylsilyl-cyanide |
| 2-MeTHF | 2-methyltetrahydrofuran |
| Celite | Trademark for diatomaceous earth |
| HATU | 1-[Bis(dimethylamino)methylene]-1H-1,2,3-triazolo[4,5-b]pyridinium3-oxidehexafluorophosphate |
| PCC | Pyridinium chlorochromate |
| RuPhos PdG3 | (2-Dicyclohexylphosphino-2',6'-diisopropoxy-1,1'-biphenyl)[2-(2'-amino-1,1'-biphenyl)]palladium(II) methanesulfonate 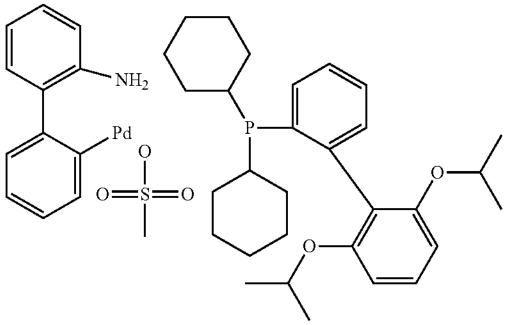 |
| RuPhos | 2-Dicyclohexylphosphino-2',6'-diisopropoxy-1,1'-biphenyl |
| Xantphos Pd G3 | [(4,5-Bis(diphenylphosphino)-9,9-dimethylxanthene)-2-(2'-amino-1,1'-biphenyl)]palladium(II) methanesulfonate 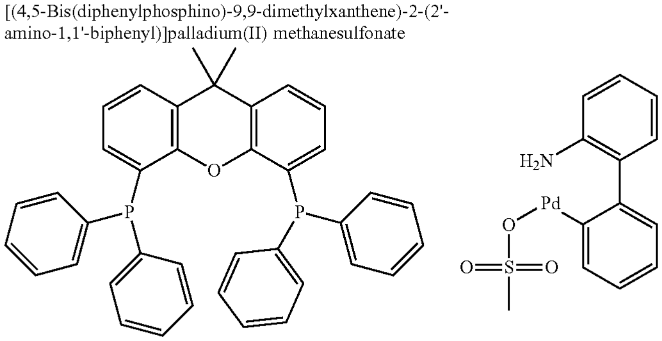 |
| Cataxium Pd G3 | Mesylate[(di(1-adamantyl)-n-butylphosphine)-2-(2'-amino-1,1'-biphenyl)]palladium(II),[(Di(1-adamantyl)-butylphosphine)-2-(2'-amino-1,1'-biphenyl)]palladium(II) methanesulfonate |
| RuPhos Pd G4 | Methansulfonato(2-dicyclohexylphosphino-2',6'-di-i-propoxy-1,1'-biphenyl)(2'-methylamino-1,1-biphenyl-2-yl) Palladium (II) |
| DIEA | N,N-Diisopropylethylamine |
| XPhos PD G3 | (2-Dicyclohexylphosphino-2',4',6'-triisopropyl-1,1'-biphenyl)[2-(2'-amino-1,1'-biphenyl)]palladium(II) methanesulfonate |
| RockPhos Pd G3 | [(2-Di-tert-butylphosphino-3-methoxy-6-methyl-2',4,6'-triisopropyl-1,1'-biphenyl)-2-(2-aminobiphenyl)]palladium(II) methanesulfonate |
| Si-DMT | Si-N,N-Dimethyltryptamine |
| HTP | hydroxytryptophan |
| Rac-BINAP Pd G3 | Racemic methanesulfonato[2,2'-bis(diphenylphosphino)-1,1'-binaphthyl](2'-amino-1,1'-biphenyl-2-yl)palladium(II) |
| Rac or Rac | racemate |

General Experimental Information

Unless otherwise noted, all reactions are magnetically stirred. Unless otherwise noted, when diethyl ether is used in the experiments described below, it is Fisher ACS certified material and is stabilized with BHT. Unless otherwise noted, "concentrated" and/or "solvent removed under reduced pressure" means evaporating the solvent from a solution or mixture using a rotary evaporator or vacuum pump. Unless otherwise noted, flash chromatography is carried out on a Teledyne Isco (Lincoln, NE), Analogix (Burlington, WI), or Biotage (Stockholm, SWE) automated chromatography system using a commercially available cartridge as the column. Columns may be purchased from Teledyne Isco, Analogix, Biotage, Varian (Palo Alto, CA), or Supelco (Bellefonte, PA) and are usually filled with silica gel as the stationary phase. Reverse phase prep-HPLC conditions, where used, can be found at the end of each experimental section. Aqueous solutions were concentrated on a Genevac (Ipswich, ENG) or by freeze-drying/lyophilization. Unless otherwise noted, all LRRK2 $pIC_{50}$ data presented in tables refers to the LRRK2 G2019S $K_m$ ATP LanthaScreen™ assay (Life Technologies Corp., Carlsbad, CA) that is described in the Biological Assay section.

Synthesis of Common Intermediates

Scheme 1. Synthesis of N-6-bromo-7-chloroisoquinolin-3-amine and 6-bromo-5-chloroisoquinolin-3-amine (3)

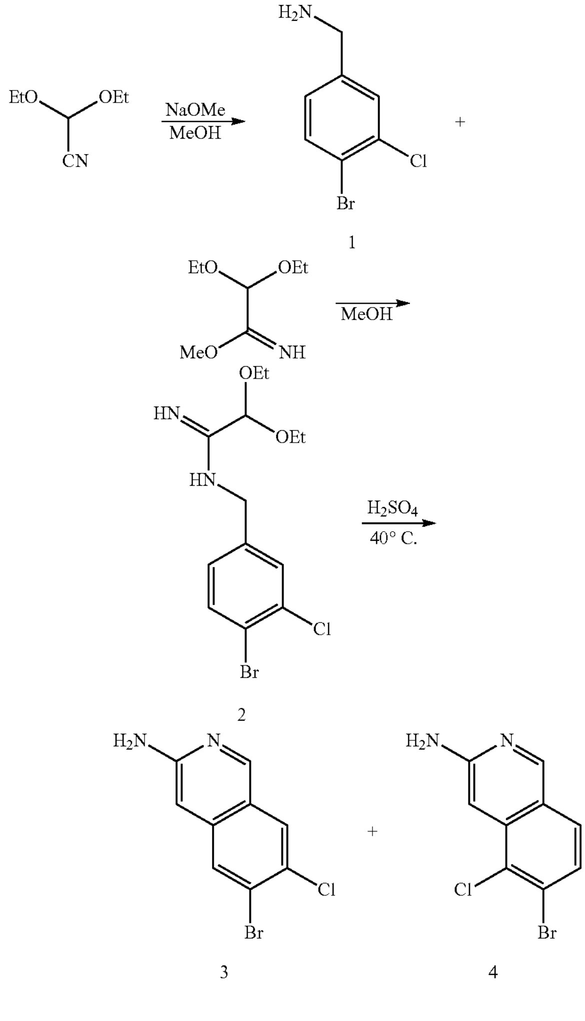

N-(4-bromo-3-chlorobenzyl)-2,2-diethoxyacetimidamide (1)

A 5 L round-bottom flask was charged with 2,2-diethoxyacetonitrile (250 g, 1.94 mol, 1.00 eq.), and MeOH (1.50 L). Sodium methoxide (24.4 g, 135 mmol, 30% purity) was added to the mixture dropwise. The flask was evacuated and purged with $N_2$ three times. The resulting mixture was allowed to stir for 6 hours at 25° C. The crude reaction mixture was adjusted to a pH of 8-9 using dry $CO_2$. The reaction was concentrated and then diluted with water (100 mL). The organic material was extracted out of the aqueous solution using EtOAc (250 mL×2). Four reactions of the same scale were combined for the following workup. The organic layers were combined and washed with water, dried over sodium sulfate. The solution was then concentrated in vacuo, to afford the title compound 1.

N-(4-bromo-3-chlorobenzyl)-2,2-diethoxyacetimidamide (2)

A 500 mL round-bottom flask was charged with (4-bromo-3-chlorophenyl)methanamine 1 (1.00 kg, 4.56 mol) into MeOH (150 mL). Methyl 2,2-diethoxyacetimidate (918 g, 5.69 mol) was added to the mixture and stirred at 15° C. for 16 hours. The crude material concentrated in vacuo to afford the title compound 2 which was used directly in a subsequent reaction without further purification.

6-bromo-7-chloroisoquinolin-3-amine (3) and 6-bromo-5-chloroisoquinolin-3-amine (4)

A 5 L round-bottom flask was charged with N-(4-bromo-3-chlorobenzyl)-2,2-diethoxyacetimidamide 2 (280 g, 800 mmol). Sulfuric acid (1.4 L) was added, and the reaction was stirred overnight at 40° C. The pH of the mixture was adjusted to pH 9 with ammonium hydroxide (3.50 L) to precipitate out the product. The precipitate was collected by filtration and washed with water, affording a mixture of two isomers (1.3 kg, crude). The crude product was purified by pre-HPLC (column: phenomenex luna C18 250 mm*100 mm*10 mm; mobile phase: [water(0.1% TFA)-ACN]; b %: 10%-40%, 30 min).

Ammonium hydroxide was used to adjust to a pH=7-8. The solution was filtered and washed with water (100 ml). The organic layer was concentrated in vacuo to afford the title compound 3. MS (ESI): m/z calc'd for $C_9H_7BrClN_2$ $[M+H]^+$: 257, found 257. $^1H$ NMR (400 MHz, DMSO-$d_6$, 25° C.) δ 8.79 (s, 1H), 8.06 (s, 1H), 8.02 (s, 1H), 6.55 (s, 1H), 6.23 (s, 2H).

Scheme 2. Synthesis of N,N-bis(tert-butyloxycarbonyl)-6-bromo-7-chloroisoquinolin-3-amine (5)

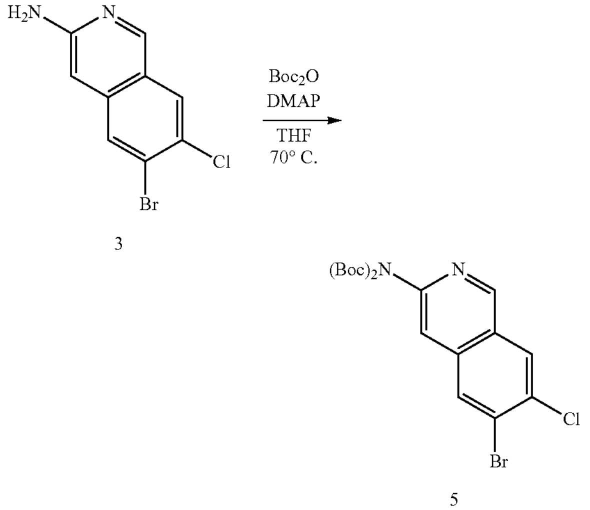

A 5 L round-bottom flask was charged with 6-bromo-7-chloroisoquinolin-3-amine 3 (54.0 g, 209 mmol) and THF (1.00 L) at 25° C. The mixture was heated to 70° C. for 30 minutes after which the solution turns clear. Di-tert-butyl dicarbonate (160 g, 733 mmol) and DMAP (2.56 g, 20.9 mmol) were added to the solution. The reaction was stirred at 70° C. for 1 hour. Solvent was removed under reduced pressure and the crude residue was purified by flash chromatography on silica gel PE/DCM/EtOAc (5:1:0-0:1:1). The mixture was filtered with IPA, and the filtrate was concentrated in vacuo. The crude product was recrystallized from n-heptane (150 mL, 25° C.) to afford the title compound 5. MS (ESI): m/z calc'd for $C_{19}H_{23}BrClN_2O_2$ $[M+H]^+$: 457, found 457. $^1H$ NMR (400 MHz, DMSO-$d_6$, 25° C.) δ 9.24 (s, 1H), 8.58 (s, 1H), 8.52 (s, 1H), 7.85 (s, 1H), 1.39 (s, 18H).

Scheme 3. Synthesis of 7-chloro-6-fluoroisoquinolin-3-yl trifluoromethanesulfonate (8)

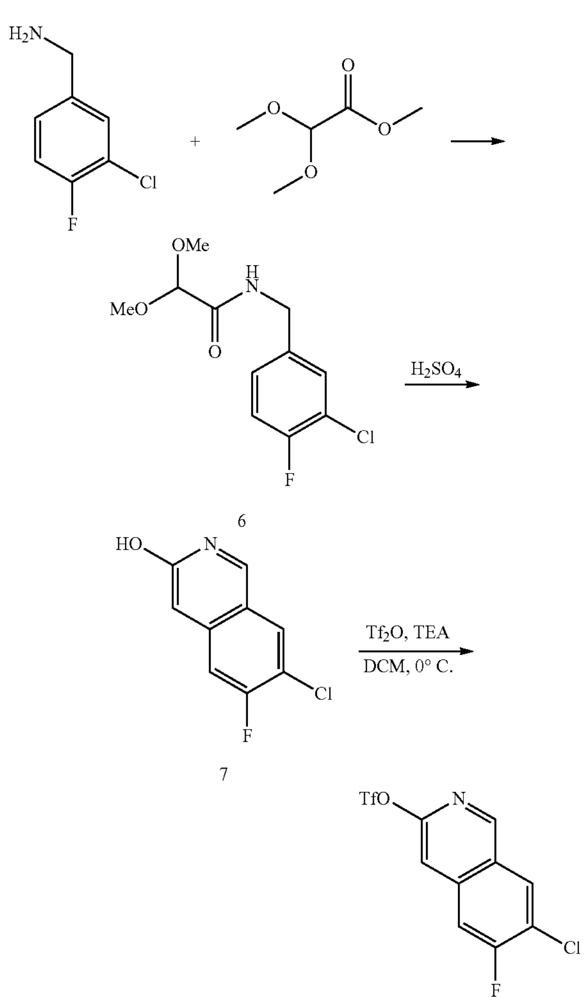

6

7

8

N-(3-chloro-4-fluorobenzyl)-2,2-dimethoxyacetamide (6)

A 20 mL microwave vial was charged with a solution of (3-chloro-4-fluorophenyl)methanamine (3 g, 18.80 mmol) in methyl 2,2-dimethoxyacetate (2.55 g, 19.0 mmol) at 25° C. The reaction was stirred for 1 h at 140° C. in microwave. After the reaction was filtered, the filtrate was concentrated under reduced pressure to afford the title compound 6. MS (ESI): m/z calc'd for $C_{11}H_{14}ClFNO_3$ $[M+H]^+$: 262; found 262.

7-chloro-6-fluoroisoquinolin-3-ol (7)

A 100 mL round bottom flask was charged with a solution of N-(3-chloro-4-fluorobenzyl)-2,2-dimethoxyacetamide 6 (500 mg, 1.91 mmol) in $H_2SO_4$ (5 ml, 94 mmol) at 25° C. The reaction was stirred for 2.2 h at 25° C. The mixture was poured into the saturated $NaHCO_3$ solution (40 mL), extracted with EtOAc (30 mL×3). The combined organic layers were dried by anhydrous $Na_2SO_4$, filtered and the filtrate was concentrated under reduced pressure, which was purified by Pre-TLC($SiO_2$, PE/EtOAc=1:1) to afford the title compound 7. MS (ESI): m/z calc'd for $C_9H_6ClFNO$ $[M+H]^+$: 198; found 198.

7-chloro-6-fluoroisoquinolin-3-yl trifluoromethanesulfonate (8)

A 100 mL round bottom flask was charged with a mixture of 7-chloro-6-fluoroisoquinolin-3-ol 7 (1 g, 5.06 mmol), $Tf_2O$ (1.3 ml, 7.69 mmol) and TEA (1.5 ml, 10.8 mmol) in DCM (25 ml) was stirred at 0° C. for 2 h and at 10° C. for another 10 h. The reaction mixture was concentrated under reduced pressure. The residue was partitioned between EtOAc (20 mL) and sat. $NH_4Cl$ (30 mL). The aqueous phase was extracted with EtOAc (10 mL×3). The combined organic phases were washed with brine (50 mL), dried over anhydrous $Na_2SO_4$, filtered and concentrated under reduced pressure. The residue was purified by flash silica gel chromatography (ISCO®; 12 g SepaFlash® Silica Flash Column, eluent of 0-10% EtOAc/PE gradient @ 30 mL/min) to afford the title compound 8. MS (ESI): m/z calc'd for $C_{10}H_5ClF_4NO_3S$ $[M+H]^+$: 330; found 330. $^1H$ NMR (500 MHz, chloroform-d) δ=9.02 (s, 1H), 8.18 (m, 1H), 7.65 (m, 1H), 7.55 (s, 1H).

Scheme 4. 6-bromo-7-fluoro-isoquinolin-3-amine (9)

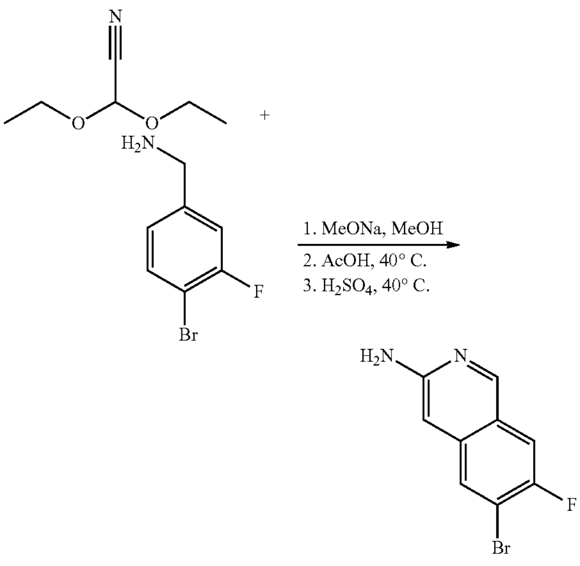

9

6-bromo-7-fluoro-isoquinolin-3-amine (9)

A solution of MeONa/MeOH (0.18 mL, 0.77 mmol) was added dropwise to a solution of 2,2-diethoxyacetonitrile (1.0 g, 7.74 mmol) in MeOH (7.74 mL). The resulting mixture was allowed to stir for 20 hours at room temperature. AcOH (44.3 μL, 0.77 mmol) was added to adjust the pH to 7-8 (using pH strips). 4-Bromo-3-fluoro-phenyl)methanamine hydrochloride (1.86 g, 7.74 mmol) was added and the resulting mixture was stirred at 40° C. for 4 hours. The reaction mixture was concentrated under reduced pressure. Sulfuric acid (12.6 mL, 232.3 mmol) was added and the resulting mixture was stirred at 40° C. for 16 hours. $NH_4OH$ (30.8 mL, 240.0 mmol) was added dropwise at 0° C. The solvent was removed under reduced pressure and the residue was purified by C18 silica gel [0-50% H2O/MeCN (0.1% Formic acid)] to afford the title compound 9. MS (ESI): m/z calc'd for $C_9H_7BrFN_2$ $[M+H]^+$: 241, found 241. $^1H$ NMR (499 MHz, DMSO-d6) δ ppm 6.07 (s, 2H), 6.61 (s, 1H), 7.76 (m, 1H), 8.01 (m, 1H), 8.80 (1H, s).

Scheme 5. Synthesis of 1-(3-methyloxetan-3-yl)piperazine (11)

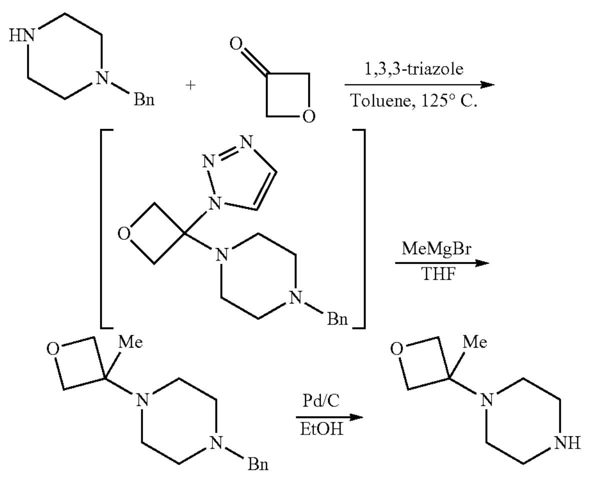

10

11

1-benzyl-4-(3-methyloxetan-3-yl)piperazine (10)

A 1-L 3-necked round-bottom flask was charged with benzylpiperazine (50 g, 284 mmol) under inert atmosphere. Toluene (500 mL) was added, followed by 3-oxetanone (22.5 g, 312 mmol), and finally 1,2,3-triazole (23.5 g, 340 mmol). The resultant solution was warmed to 125° C. and stirred for 2 hr. The solution was allowed to cool to room temperature and the putative triazole adduct used directly in the subsequent step (vide infra). A 1-L 3-necked round-bottom flask was charged with bromo(methyl)magnesium (250 mL, 3M) and THF (250 mL) under inert atmosphere, and the solution was cooled to 10° C. The toluene solution from step 1 was then added dropwise to the stirring mixture at this temperature. The resultant solution was stirred for 30 min at 20° C., at which point it was quenched by the addition of ice water. This mixture was extracted with toluene, and the combined organic layers were dried over anhydrous $Na_2SO_4$. The solution was filtered and solvent was removed under reduced pressure to afford the title compound 10.

1-(3-methyloxetan-3-yl)piperazine (11)

A 500-mL round-bottom flask was charged with 1-benzyl-4-(3-methyloxetan-3-yl)piperazine 10 (18 g, 73 mmol), and Pd/C (11 g, 103 mmol) under inert atmosphere. After purging the headspace, EtOH (240 mL) was added. The inert atmosphere was then carefully exchanged for $H_2$ atmosphere (1 atm), and the resultant mixture was stirred for 5 h at room temperature. Solids were removed by filtration and the filter cake was quenched with water. Solvent was removed from the filtrate under reduced pressure to afford the title compound 11. MS (ESI): m/z calc'd for $C_8H_{17}N_2O$ $[M+H]^+$: 157, found 157. $^1H$ NMR (400 MHz, DMSO-$d_6$, 25° C.) δ 4.38 (d, J=5.5 Hz, 2H), 4.09 (d, J=5.5 Hz, 2H), 2.74-2.65 (m, 4H), 2.23-2.14 (m, 4H), 1.25 (s, 3H).

Scheme 6. Synthesis of 4-((tert-butyldiphenylsilyl)oxy)dihydrofuran-3(2H)-one (14)

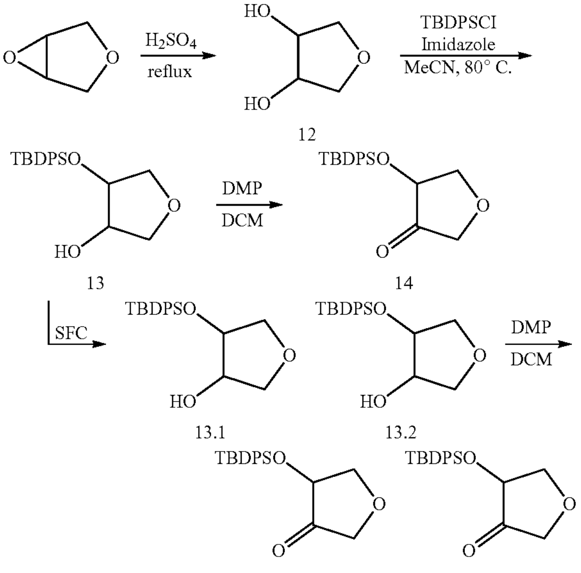

12

13

14

13.1

13.2

14.1

14.2

Oxolane-3,4-diol (12)

A 10-L 4-necked round-bottom flask was charged with 3,6-dioxabicyclo[3.1.0]hexane (409 g, 4750 mmol, 1.00 eq.), $H_2SO_4$ (4 L, 1.5 mol/L). The resulting solution was stirred for 6 h at reflux. The reaction mixture was cooled to room temperature. The pH value of the solution was adjusted to 8 with $Na_2CO_3$. The resulting mixture was concentrated under vacuum. The resulting mixture was washed with 5 L of THF. The resulting mixture was concentrated under vacuum, affording the title compound 12.

4-[(tert-butyldiphenylsilyl)oxy]oxolan-3-ol (13)

A 3-L 4-necked round-bottom flask was purged and maintained with an inert atmosphere of nitrogen, and charged with oxolane-3,4-diol 12 (52.0 g, 499 mmol, 1.00 eq.), ACN (1.5 L), imidazole (51.0 g, 749 mmol, 1.50 eq.), TBDPSCl (137 g, 498 mmol, 1.00 eq.). The resulting solution was stirred for 4 h at 80° C., concentrated under vacuum, diluted with 1 L of EtOAc, washed with water (500 mL×2), dried over anhydrous sodium sulfate and concentrated under vacuum. The residue was purified on a silica gel column with EtOAc/PE (1:100-1:30), affording the title compound 13.

(3S,4R)-4-[(tert-butyldiphenylsilyl)oxy]oxolan-3-ol or (3R,4S)-4-[(tert-butyldiphenylsilyl)oxy]oxolan-3-ol (13.1) and (13.2)

Crude product 13 was purified by Prep-SFC using (Prep SFC350-2): Column, CHIRALPAK AS-H, 5*25 cm, 5 um; mobile phase, $CO_2$ (46%) and IPA (0.2% DEA) (54%); Detector, UV, affording title compounds 13.1 (tR=0.92 min) and 13.2 (tR=1.63 min).

4-[(tert-butyldiphenylsilyl)oxy]oxolan-3-one (14)

A 2-L 3-necked round-bottom flask was purged and maintained with an inert atmosphere of nitrogen, and charged with DMP (93 g, 219 mmol, 1.06 eq.), DCM (1.1 L), 4-[(tert-butyldiphenylsilyl) oxy]oxolan-3-ol 13 (71 g, 207 mmol, 1.00 eq.). The resulting solution was stirred for 3 h at 25-30° C. The resulting solution was diluted with 2 L of PE. The resulting mixture was washed with 2×1 L of aq. $NaHCO_3$ and 1 L of brine. The mixture was dried over anhydrous sodium sulfate and concentrated under vacuum. The residue was applied onto a silica gel column with EtOAc/PE (1:100-1:30), affording the title compound 14. $^1H$ NMR (400 MHz, $CDCl_3$) δ: 7.85-7.76 (m, 2H), 7.72-7.64 (m, 2H), 7.53-7.38 (m, 6H), 4.30 (m, 1H), 4.11-4.02 (m, 2H), 3.93 (d, J=17.5 Hz, 1H), 3.80-3.70 (m, 1H), 1.12 (s, 9H).

(R)-4-[(tert-butyldiphenylsilyl)oxy]oxolan-3-one or (S)-4-[(tert-butyldiphenylsilyl)oxy]oxolan-3-one (14.1)

Into a 5000-mL 4-necked round-bottom flask purged and maintained with an inert atmosphere of nitrogen, was placed (3S,4R or 3R, 4S)-4-[(tert-butyldiphenylsilyl)oxy]oxolan-3-ol 13.1 (85 g, 249 mmol, 1.00 equiv), DCM (1.700 L). This was followed by the addition of Dess-Martin periodinane (116 g, 274 mmol, 1.1 equiv), in portions at room temperature. The resulting solution was stirred for 3 h at 30° C. The reaction was then quenched by the addition of 1500 mL of $NaHCO_3/Na_2S_2O_3$ (1:1). The resulting solution was stirred for 30 min. The resulting solution was extracted with 3×500 mL of DCM. The organic phase was washed with 1×500 mL of NaCl. The organic phase was dried over anhydrous sodium sulfate and concentrated under vacuum. The residue was applied onto a silica gel column with ethyl acetate/petroleum ether (1:100) affording the title compound 14.1. MS (ESI): m/z calc'd for $C_{20}H_{25}O_3Si$ $[M+H]^+$: 341, found 341. $^1H$ NMR (300 MHz, DMSO-$d_6$, 25° C.) δ 7.66 (m, 4H), 7.56-7.36 (m, 6H), 4.35 (m, 1H), 4.18-3.85 (m, 3H), 3.71 (t, 1H), 1.03 (s, 9H).

(R)-4-[(tert-butyldiphenylsilyl)oxy]oxolan-3-one or (S)-4-[(tert-butyldiphenylsilyl)oxy]oxolan-3-one (14.2)

Into a 5000-mL 4-necked round-bottom flask purged and maintained with an inert atmosphere of nitrogen, was placed (3S,4R or 3R, 4S)-4-[(tert-butyldiphenylsilyl)oxy]oxolan-3-ol 13.2 (85 g, 249 mmol, 1.00 equiv), DCM (1.700 L). This was followed by the addition of Dess-Martin periodinane (116 g, 274 mmol, 1.1 equiv), in portions at room temperature. The resulting solution was stirred for 3 h at 30° C. The reaction was then quenched by the addition of 1500 mL of $NaHCO_3/Na_2S_2O_3$ (1:1). The resulting solution was stirred for 30 min. The resulting solution was extracted with 3×500 mL of DCM. The organic phase was washed with 1×500 mL of NaCl. The organic phase was dried over anhydrous sodium sulfate and concentrated under vacuum. The residue was applied onto a silica gel column with ethyl acetate/petroleum ether (1:100) affording the title compound 14.2. MS (ESI): m/z calc'd for $C_{20}H_{25}O_3Si$ $[M+H]^+$: 341, found 341. $^1H$ NMR (300 MHz, DMSO-$d_6$, 25° C.) δ 7.66 (m, 4H), 7.56-7.36 (m, 6H), 4.35 (m, 1H), 4.18-3.85 (m, 3H), 3.71 (t, 1H), 1.03 (s, 9H).

Scheme 7. Synthesis of Rac-1-(4-((tert-butyldiphenylsilyl)oxy)-3-methyltetrahydrofuran-3-yl)piperazine (17)

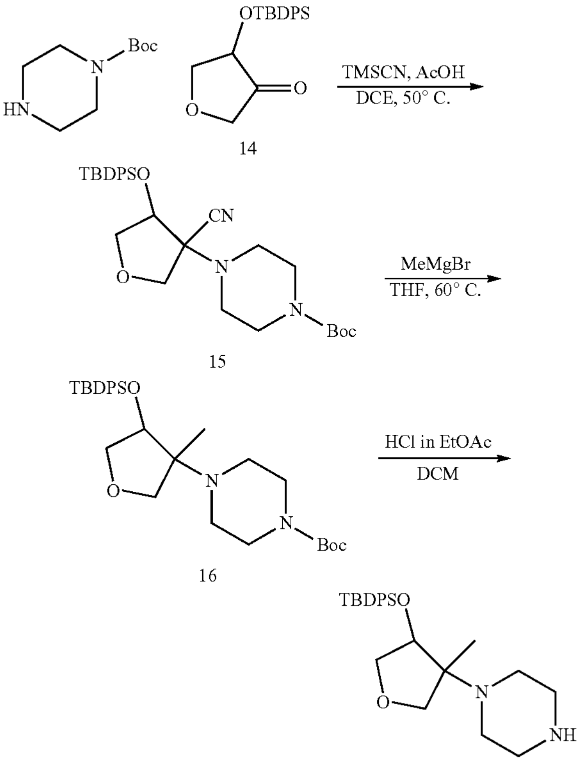

17 tert-butyl4-(4-((tert-butyldiphenylsilyl)oxy)-3-cyanotetrahydrofuran-3-yl)piperazine-1-carboxylate (15)

A 3 L 3-necked round-bottom flask was charged with tert-butyl piperazine-1-carboxylate (50 g, 268 mmol) and 4-((tert-butyldiphenylsilyl)oxy)dihydrofuran-3(2H)-one 14 (119 g, 349 mmol), and dissolved in DCE (2.500 L) followed by acetic acid (24.2 g, 403 mmol) dropwise at 25° C. The reaction was heated to 50° C. After 30 minutes, trimethylsilylcyanide (39.9 g, 403 mmol) was added to the mixture. The mixture was stirred at 50° C. for 12 h. After completion of the reaction, the reaction was quenched by the addition of a saturated aqueous solution of $NaHCO_3$. The resulting solution was extracted with 3×2500 mL of DCM and the organic layers combined and dried over $Na_2SO_4$ and concentrated. The residue was applied onto a silica gel column with PE:EtOAc (30:1) to afford the title compound 15.

tert-butyl 4-(4-((tert-butyldiphenylsilyl)oxy)-3-methyltetrahydrofuran-3-yl) piperazine-1-carboxylate (16)

A 5 L 3-necked round-bottom flask was charged with tert-butyl 4-(4-((tert-butyldiphenylsilyl)oxy)-3-cyanotetrahydrofuran-3-yl) piperazine-1-carboxylate 15 (73 g, 136 mmol). THF (3.65 L) was added and the solution chilled to 0° C. To the flask was added methylmagnesium bromide (227 ml, 681 mmol) at 0° C. under $N_2$. The resulting solution was stirred at 60° C. for 5 h. The reaction was quenched by the addition of a saturated aqueous solution of $NaHCO_3$. The resulting solution was extracted with 3×3000 mL of EtOAc and the organic layers combined and dried over $Na_2SO_4$ and concentrated. The residue was applied onto a silica gel column with pet ether:EtOAc (20:1) to afford the title compound 16.

Rac-1-(4-((tert-butyldiphenylsilyl)oxy)-3-methyltetrahydrofuran-3-yl)piperazine (17)

A 500 mL 3-necked round-bottom flask was charged with tert-butyl 4-(4-((tert-butyldiphenylsilyl)oxy)-3-methyltetrahydrofuran-3-yl)piperazine-1-carboxylate 16 (32.1 g, 61.2 mmol) and was dissolved in DCM (321 ml) and hydrogen chloride (45.9 ml, 184 mmol) at 0° C. under $N_2$. The resulting solution was stirred at 25° C. for 16 h. The solvent was evaporated under reduced pressure and water (300 mL) was added. The solution mixture was added saturated aqueous of $NaHCO_3$ with solution the pH of 7-8. The resulting solution was extracted with 3×300 mL of EtOAc and the organic layers combined and dried over $Na_2SO_4$ and concentrated to afford the title compound 17. MS (ESI): m/z calc'd for $C_{25}H_{37}N_2O_2Si$ $[M+H]^+$: 425, found 425. $^1H$ NMR (400 MHz, DMSO-$d_6$, 25° C.) δ 9.49 (s, 1H), 7.73-7.71 (m, 2H), 7.71-7.62 (m, 2H), 7.49-7.36 (m, 6H), 4.00-3.97 (m, 2H), 3.89-3.83 (m, 2H), 3.61 (d, J=6.8 Hz, 1H), 3.02 (s, 4H), 2.72-2.58 (m, 4H), 1.03 (s, 9H), 0.94 (s, 3H).

Scheme 8. Synthesis of (3R, 4R)-1-(4-((tert-butyldiphenylsilyl)oxy)-3-methyltetrahydrofuran-3-yl)piperazine or (3S, 4S)-1-(4-(tert-butyldiphenylsilyl)oxy)-3-methyltetrahydrofuran-3-yl)piperazine (17.1) and (17.2)

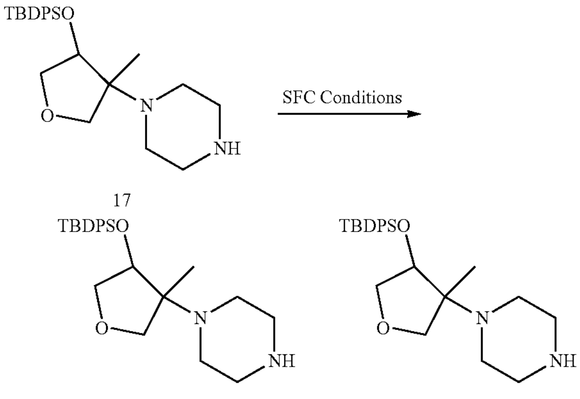

17

17.1

17.2

1-(4-((tert-butyldiphenylsilyl)oxy)-3-methyltetrahydrofuran-3-yl)piperazine 17 was synthesized according to Scheme 7 shown above. The crude product (166 g) was purified by Prep-SFC with the following conditions (Prep SFC-350-4): Column, CHIRAL ART Amylose-SC, 5 cm*25 cm (5 um); mobile phase, $CO_2$ (60%) and MeOH (8 mmol/L $NH_3$·MeOH)-(40%); Detector, UV to afford title compounds 17.1 (tR=1.25 min) and 17.2 (tR=2.7 min). 17.1: MS (ESI): m/z calc'd for $C_{25}H_{37}N_2O_2Si$ $[M+H]^+$: 425, found 425. $^1H$ NMR (400 MHz, DMSO-$d_6$, 25° C.) δ 7.83-7.75 (m, 2H), 7.75-7.67 (m, 2H), 7.50-7.39 (m, 4H), 7.43-7.36 (m, 2H), 4.07 (m, 1H), 4.01 (m, 1H), 3.82 (m, 2H), 3.65 (m, 1H), 2.84 (m, 4H), 2.51 (m, 2H), 2.35 (m, 2H), 2.21 (s, 1H), 1.13 (m, 1H), 1.11 (s, 8H), 0.97-0.92 (m, 3H). 17.2: MS (ESI): m/z calc'd for $C_{25}H_{37}N_2O_2Si$ $[M+H]^+$: 425, found 425. $^1H$ NMR (400 MHz, DMSO-$d_6$, 25° C.) δ 7.78 (m, 2H), 7.70 (m, 2H), 7.51-7.36 (m, 6H), 4.06 (m, 1H), 4.03-3.97 (m, 1H), 3.82 (m, 2H), 3.64 (m, 1H), 2.87 (m, 3H), 2.53 (m, 2H), 2.38 (m, 2H), 1.10 (s, 8H), 0.95 (s, 3H).

Scheme 9. Preparation of (S)-1-((3R,4R)-4-((tert-butyldiphenylsilyl)oxy)-3-methyltetrahydrofuran-3-yl)-2-methylpiperazine or (S)-1-((3S,4S)-4-((tert-butyldiphenylsilyl)oxy)-3-methyltetrahydrofuran-3-yl)-2-methylpiperazine (20)

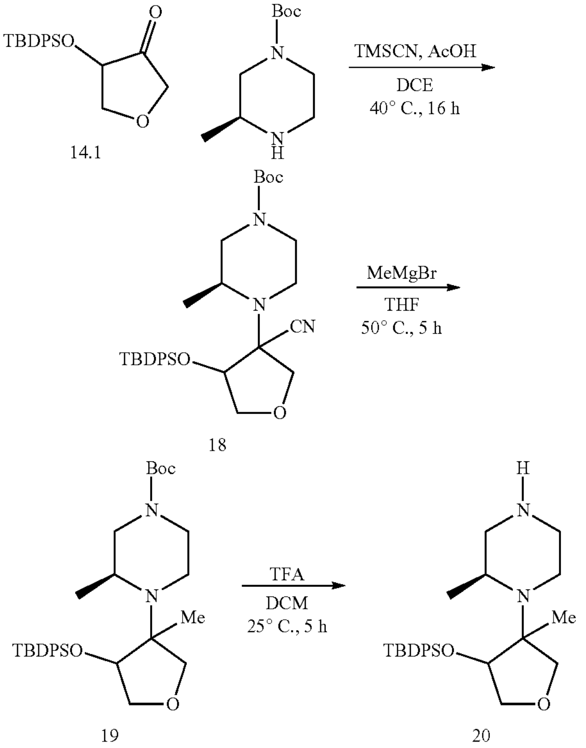

14.1

18

19

20 tert-butyl-(S)-4-((3R,4R)-4-((tert-butyldiphenylsilyl)oxy)-3-cyanotetrahydrofuran-3-yl)-3-methylpiperazine-1-carboxylate or tert-butyl-(S)-4-((3S,4S)-4-((tert-butyldiphenylsilyl)oxy)-3-cyanotetrahydrofuran-3-yl)-3-methylpiperazine-1-carboxylate (18)

A 50 mL round bottom flask was charged with tert-butyl-(S)-3-methylpiperazine-1-carboxylate (1.5 g, 7.5 mmol) and (R)-4-((tert-butyldiphenylsilyl)oxy)dihydrofuran-3(2H)-one or (S)-4-((tert-butyldiphenylsilyl)oxy)dihydrofuran-3(2H)- one 14.1 (5.1 g, 15 mmol). DCE (19 ml) was added, and to the stirring mixture at RT was added acetic acid (0.64 mL, 11 mmol). The resultant mixture was stirred at RT for 15 min after which TMS-CN (1.5 mL, 11 mmol) was added. The reaction mixture was stirred at 40° C. for 16 hrs. The reaction was diluted with DCM and extracted with 1M sodium hydroxide solution. The phases were separated, and the aqueous phase extracted with DCM (3×50 mL). The combined organic phases were washed with $H_2O$ (50 mL), dried over $Na_2SO_4$, and the solvent removed under reduced pressure. The resultant crude residue was subjected to purification by silica gel chromatography (Hexanes in EtOAc, 0-50%) to afford the title compound 18. MS (ESI) m/z calc'd for $C_{31}H_{43}N_3O_4Si$ $[M+H]^+$: 550, found 550.

tert-butyl-(S)-4-((3R,4R)-4-((tert-butyldiphenylsilyl)oxy)-3-methyltetrahydrofuran-3-yl)-3-methylpiperazine-1-carboxylate or tert-butyl-(S)-4-((3S,4S)-4-((tert-butyldiphenylsilyl)oxy)-3-methyltetrahydrofuran-3-yl)-3-methylpiperazine-1-carboxylate (19)

A 50 mL round bottom flask was charged with tert-butyl-(S)-4-((3R,4R)-4-((tert-butyldiphenylsilyl)oxy)-3-cyanotetrahydrofuran-3-yl)-3-methylpiperazine-1-carboxylate or tert-butyl-(S)-4-((3S,4S)-4-((tert-butyldiphenylsilyl)oxy)-3-cyanotetrahydrofuran-3-yl)-3-methylpiperazine-1-carboxylate 18 (1.1 g, 1.8 mmol). THF (9 ml) was added, and to the stirring mixture at RT was added methylmagnesium bromide (0.6 ml, 1.8 mmol). The resultant mixture was stirred at 50° C. for 5 hrs. The reaction was diluted with DCM (25 mL) and quenched by dropwise addition of saturated sodium bicarbonate (25 mL). The phases were separated, and the aqueous phase extracted with DCM (3×50 mL). The combined organic phases were washed with $H_2O$ (50 mL), dried over $Na_2SO_4$, and the solvent removed under reduced pressure. The resultant crude residue was subjected to purification by silica gel chromatography (Hexanes in EtOAc, 0-50%) to afford the title compound 19. MS (ESI) m/z calc'd for $C_{31}H_{46}N_2O_4Si$ $[M+H]^+$: 539, found 539.

(S)-1-((3R,4R)-4-((tert-butyldiphenylsilyl)oxy)-3-methyltetrahydrofuran-3-yl)-2-methylpiperazine or (S)-1-((3S,4S)-4-((tert-butyldiphenylsilyl)oxy)-3-methyltetrahydrofuran-3-yl)-2-methylpiperazine (20)

A 50 mL round bottom flask was charged with tert-butyl-(S)-4-((3R,4R)-4-((tert-butyldiphenylsilyl)oxy)-3-methyltetrahydrofuran-3-yl)-3-methylpiperazine-1-carboxylate or tert-butyl-(S)-4-((3S,4S)-4-((tert-butyldiphenylsilyl)oxy)-3-methyltetrahydrofuran-3-yl)-3-methylpiperazine-1-carboxylate 19 (380 mg, 0.70 mmol). DCM (3.5 ml) was added, and to the stirring mixture at RT was added TFA (0.2, 2.8 mmol). The resultant mixture was stirred at RT for 5 hrs. The reaction was diluted with DCM (25 mL) and quenched by dropwise addition of saturated sodium bicarbonate (25 mL). The phases were separated, and the aqueous phase extracted with DCM (3×50 mL). The combined organic phases were washed with $H_2O$ (50 mL), dried over $Na_2SO_4$, and the solvent removed under reduced pressure to afford the title compound 20. MS (ESI) m/z calc'd for $C_{26}H_{38}N_2O_2Si$ $[M+H]^+$: 439, found 439.

Scheme 10. Synthesis of ((S)-1-((3R,4R)-4-((tert-butyldiphenylsilyl)oxy)-3-ethyltetrahydrofuran-3-yl)-2-methylpiperazine or (S)-1-((3S,4S)-4-((tert-butyldiphenylsilyl)oxy)-3-ethyltetrahydrofuran-3-yl)-2-methylpiperazine (22)

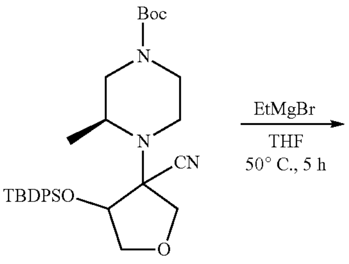

18

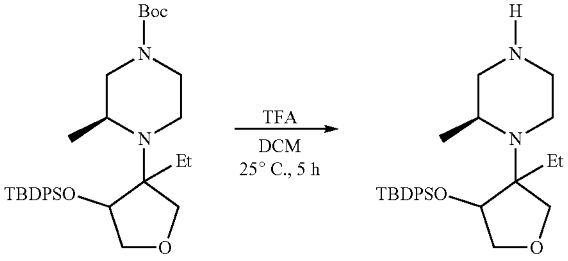

21

22 tert-butyl (S)-4-((3R,4R)-4-((tert-butyldiphenylsilyl)oxy)-3-ethyltetrahydrofuran-3-yl)-3-methylpiperazine-1-carboxylate or tert-butyl (S)-4-((3S,4S)-4-((tert-butyldiphenylsilyl)oxy)-3-ethyltetrahydrofuran-3-yl)-3-methylpiperazine-1-carboxylate (21)

Tert-butyl (S)-4-((3R,4R)-4-((tert-butyldiphenylsilyl)oxy)-3-cyanotetrahydrofuran-3-yl)-3-methylpiperazine-1-carboxylate or tert-butyl (S)-4-((3S,4S)-4-((tert-butyldiphenylsilyl)oxy)-3-cyanotetrahydrofuran-3-yl)-3-methylpiperazine-1-carboxylate 18 (400 mg, 0.728 mmol) was taken up in THF (3638 μl) and the vial was purged with nitrogen. Ethyl magnesium bromide (243 μl, 0.728 mmol) was added and the mixture was stirred overnight at 65° C. The reaction mixture was quenched with saturated ammonium chloride and extracted with EtOAc. Organic layers were combined, dried, and concentrated in vacuo. The crude reaction mixture was diluted in DCM and purified by column chromatography using 0-30% hexanes in ethyl acetate to afford the title compound 21.

((S)-1-((3R,4R)-4-((tert-butyldiphenylsilyl)oxy)-3-ethyltetrahydrofuran-3-yl)-2-methylpiperazine or (S)-1-((3S,4S)-4-((tert-butyldiphenylsilyl)oxy)-3-ethyltetrahydrofuran-3-yl)-2-methylpiperazine (22)

Tert-butyl (S)-4-((3R,4R)-4-((tert-butyldiphenylsilyl)oxy)-3-ethyltetrahydrofuran-3-yl)-3-methylpiperazine-1-carboxylate or tert-butyl (S)-4-((3S,4S)-4-((tert-butyldiphenylsilyl)oxy)-3-ethyltetrahydrofuran-3-yl)-3-methylpiperazine-1-carboxylate 21 (333 mg, 0.602 mmol) was taken up in DCM (3012 μl) and TFA (232 μl, 3.01 mmol) was added. The reaction mixture was stirred at rt overnight. The mixture was extracted with saturated sodium bicarbonate and DCM. Organic layers were combined, dried, and concentrated in vacuo to afford the title compound 22. MS (ESI) m/z calc'd for $C_{27}H_{41}N_2O_2Si[M+H]^+$: 453, found 453.

Scheme 11. Synthesis of 1-((3R,4R)-4-((tert-butyldiphenylsilyl)oxy)-3-ethyltetrahydrofuran-3-yl)piperazine or 1-((3S,4S)-4-((tert-butyldiphenylsilyl)oxy)-3-ethyltetrahydrofuran-3-yl)piperazine (24)

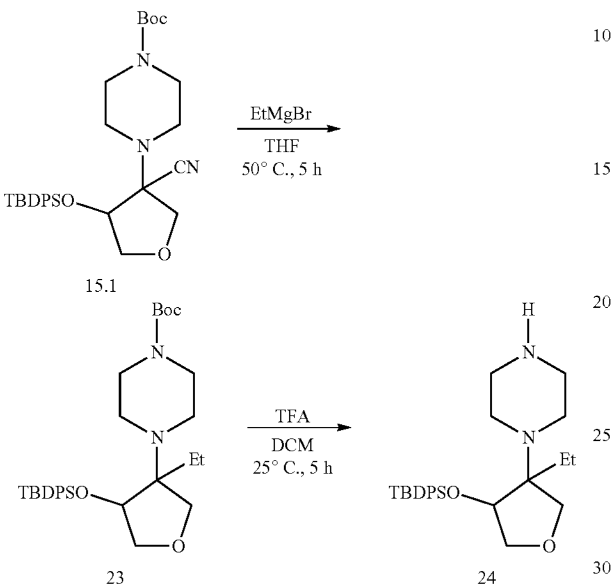

15.1

23

24 tert-butyl 4-((3R,4R)-4-((tert-butyldiphenylsilyl)oxy)-3-ethyltetrahydrofuran-3-yl)piperazine-1-carboxylate or tert-butyl 4-((3S,4S)-4-((tert-butyldiphenylsilyl)oxy)-3-ethyltetrahydrofuran-3-yl)piperazine-1-carboxylate (23)

Tert-butyl 4-((3R,4R)-4-((tert-butyldiphenylsilyl)oxy)-3-cyanotetrahydrofuran-3-yl)piperazine-1-carboxylate or tert-butyl 4-((3S,4S)-4-((tert-butyldiphenylsilyl)oxy)-3-cyanotetrahydrofuran-3-yl)piperazine-1-carboxylate 15.1 (1 g, 1.867 mmol) was taken up in THF (9.33 ml) and the vial was purged with nitrogen. Under positive flow of nitrogen, ethyl magnesium bromide (0.622 ml, 1.867 mmol) was added. The mixture was stirred overnight at 65° C. The reaction mixture was quenched with saturated ammonium chloride and extracted with EtOAc. Organic layers were combined, dried, and concentrated in vacuo. The crude reaction mixture was purified by column chromatography using 0-30% hexanes and ethyl acetate to afford the title compound 23.

1-((3R,4R)-4-((tert-butyldiphenylsilyl)oxy)-3-ethyltetrahydrofuran-3-yl)piperazine or 1-((3S,4S)-4-((tert-butyldiphenylsilyl)oxy)-3-ethyltetrahydrofuran-3-yl)piperazine (24)

Tert-butyl 4-((3R,4R)-4-((tert-butyldiphenylsilyl)oxy)-3-ethyltetrahydrofuran-3-yl)piperazine-1-carboxylate or tert-butyl 4-((3S,4S)-4-((tert-butyldiphenylsilyl)oxy)-3-ethyltetrahydrofuran-3-yl)piperazine-1-carboxylate 23 (680 mg, 1.262 mmol) was taken up in DCM (6.3 ml) and TFA (97 μl, 1.262 mmol) was added. The reaction mixture was stirred at rt overnight. The reaction mixture was quenched with saturated sodium bicarbonate and extracted with DCM. Organic layers were combined, dried, and concentrated in vacuo to afford the title compound 24. MS (ESI) m/z calc'd for $C_{26}H_{39}N_2O_2Si[M+H]^+$: 439, found 439.

Scheme 12. Synthesis of 1-(3-methyltetrahydrofuran-3-yl)piperazine hydrochloride (27)

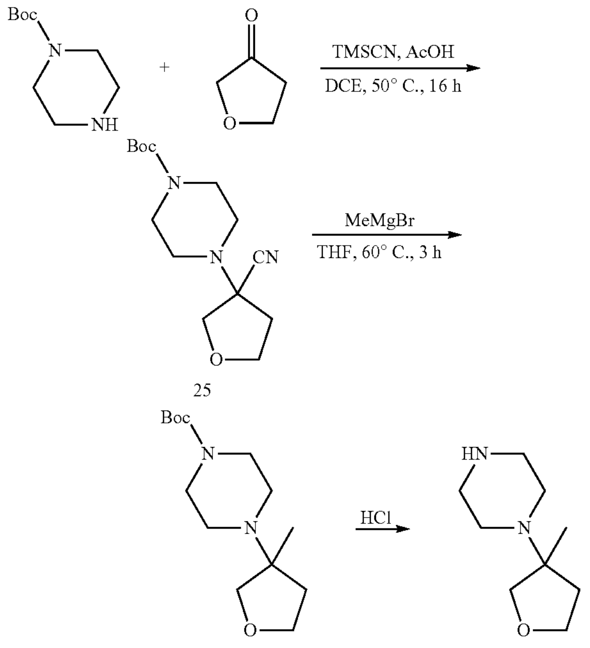

25

26

27

Tert-butyl 4-(3-cyanotetrahydrofuran-3-yl)piperazine-1-carboxylate (25)

Tert-butyl piperazine-1-carboxylate (1 g, 5.37 mmol), dihydrofuran-3(2H)-one (0.924 g, 10.74 mmol) and AcOH (1.537 mL, 26.8 mmol) were stirred in a round bottom and anhydrous DCE (10 mL) was added and stirred at 60° C. for 30 min under $N_2$ protection. Trimethylsilyl cyanide (3.37 mL, 26.8 mmol) was added into the mixture. The final mixture was stirred at 60° C. for 16 hours. The reaction mixture was concentrated to give the crude product which was purified by column chromatography (silica gel, Pet.ether:EtOAc=1:1) to afford the title compound 25. MS (ESI) m/z calc'd for $C_{14}H_{24}N_3O_3[M+H]^+$: 282, found 282.

Tert-butyl 4-(3-methyltetrahydrofuran-3-yl)piperazine-1-carboxylate (26)

To a solution of tert-butyl 4-(3-cyanotetrahydrofuran-3-yl) piperazine-1-carboxylate 25 (500 mg, 1.777 mmol) in THF (8 mL) was added methylmagnesium bromide (2.96 mL, 8.89 mmol) at 0° C. under $N_2$ protection. The resulting solution was stirred at 60° C. for 4 hours. The reaction quenched with saturated aq $NH_4Cl$, and extracted with EtOAc (30 mL×3). The organic layer was washed with water (30 mL), dried over $Na_2SO_4$ and concentrated in vacuo. The crude product was purified by column chromatography (silica gel, EtOAc) to afford the title compound 26. MS (ESI) m/z calc'd for $C_{14}H_{27}N_2O_3[M+H]^+$: 271, found 271.

1-(3-methyltetrahydrofuran-3-yl) piperazine hydrochloride (27)

The mixture of tert-butyl 4-(3-methyltetrahydrofuran-3-yl) piperazine-1-carboxylate 26 (213 mg, 0.788 mmol) in 1,4-dioxane hydrochloride (2M, 2 mL) was stirred at 20° C. for 0.5 hour. The reaction mixture was concentrated in vacuo to afford the title compound 27 which was used in the next step without purification. MS (ESI) m/z calc'd for $C_9H_{19}N_2O[M+H]^+$: 171, found 171.

Scheme 13. Synthesis of 1-((3R,4R)-4-((tert-butyldiphenylsilyl)oxy)tetrahydrofuran-3-yl)piperazine or 1-((3S,4S)-4-((tert-butyldiphenylsilyl)oxy)tetrahydrofuran-3-yl)piperazine (29.1) and (29.2)

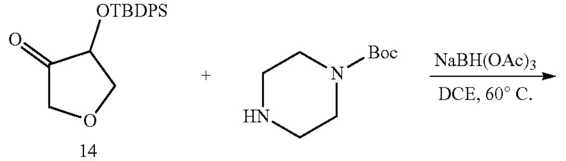

14

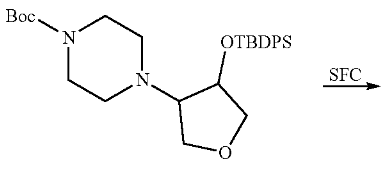

28

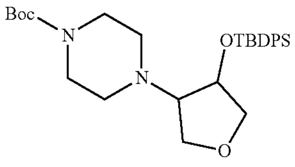

28.1

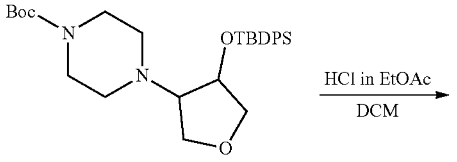

28.2

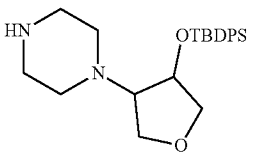

29.1

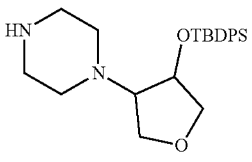

29.2 tert-butyl 4-((3R,4R)-4-((tert-butyldiphenylsilyl)oxy)tetrahydrofuran-3-yl)piperazine-1-carboxylate or tert-butyl 4-((3R,4R)-4-((tert-butyldiphenylsilyl)oxy)tetrahydrofuran-3-yl)piperazine-1-carboxylate (28.1) and (28.2)

A 5 L flask was charged with 4-((tert-butyldiphenylsilyl)oxy)dihydrofuran-3(2H)-one 14 (262 g, 0.77 mol, 1.0 eq) and was dissolved in DCE (2.0 L). Tert-butyl piperazine-1-carboxylate (215 g, 1.15 mol, 1.15 eq) and $NaBH(OAc)_3$ (326 g, 1.54 mol, 2.0 eq) were added to the reaction mixture at room temperature. Acetic acid (92.4 g, 1.54 mol, 2.0 eq) was added dropwise to the reaction mixture at 20° C. The reaction was heated to 60° C. and stirred for 2.5 hours. Several reactions were combined (590 g total of crude material) for the workup. The mixture was poured into 6.0 L of vigorously stirring aqueous saturated sodium bicarbonate. The product was extracted out using DCM (1.0 L×3) and concentrated under reduced pressure. The crude product was purified by column chromatography ($SiO_2$, PE:EtOAc=1:0 to 0:1) to afford the title compound, which was separated by SFC (DAICEL CHIRALCEL OJ (250 mm*50 mm, 10 um); mobile phase: [0.1% $NH_4OH$: EtOH]; B %: 30%-30%, 3.5 min) to afford the title compounds 28.1 (tR=0.59 min) and 28.2 (tR=1.2 min).

1-((3R,4R)-4-((tert-butyldiphenylsilyl)oxy)tetrahydrofuran-3-yl)piperazine or 1-((3S,4S)-4-((tert-butyldiphenylsilyl)oxy)tetrahydrofuran-3-yl)piperazine (29.1) and (29.2)

A 5 L flask was charged with tert-butyl 4-((3R,4R)-4-((tert-butyldiphenylsilyl)oxy)tetrahydrofuran-3-yl)piperazine-1-carboxylate or tert-butyl 4-((3R,4R)-4-((tert-butyldiphenylsilyl)oxy)tetrahydrofuran-3-yl)piperazine-1-carboxylate 28.1 or 28.2 (110 g, 0.22 mol, 1.0 eq) dissolved in EtOAc (2.0 L). Hydrochloric acid in EtOAc (0.35 L, 4M) was added dropwise to the reaction mixture at 0° C. The reaction was warmed to 20° C. for 36 hours. The reaction mixture was concentrated under reduced pressure to a give a residue. The residue was dissolved in EtOAc (0.3 L) and filtered. The filter cake was dissolved in water (500 mL) and the pH was adjusted to a pH of 8 with saturated aqueous sodium bicarbonate. The aqueous solution was extracted with EtOAc (1.0 L×2). The organic layers were combined and washed with brine, dried over sodium sulfate and concentrated under reduced pressure. The residue was washed with MTBE (500 mL) and concentrated under reduced pressure to afford the title compounds 29.1 and 29.2. 29.1: MS (ESI): m/z calc'd for $C_{24}H_{34}N_2O_4Si$ $[M+H]^+$: 411, found 411. $^1H$ NMR (400 MHz, DMSO-$d_6$, 25° C.) δ 7.73 (d, J=6.8 Hz, 2H), 7.64 (d, J=6.8 Hz, 2H), 7.39-7.46 (m, 6H), 4.29 (s, 1H), 3.97-4.00 (m, 1H), 3.91-3.93 (m, 1H), 3.84 (m, 1H), 3.70-3.74 (m, 1H), 3.05 (s, 4H), 2.66-2.73 (m, 5H), 1.08 (s, 9H). 29.2: MS (ESI): m/z calc'd for $C_{24}H_{34}N_2O_4Si$ $[M+H]^+$: 411, found 411. $^1H$ NMR (400 MHz, DMSO-$d_6$, 25° C.) δ 7.74 (m, 2H), 7.72 (m, 2H), 7.27-7.45 (m, 6H), 4.29 (m, 1H), 3.98-4.00 (m, 1H), 3.91-3.93 (m, 1H), 3.82-3.85 (m, 1H), 3.73-3.74 (m, 1H), 3.03-3.04 (m, 4H), 2.64-2.69 (m, 5H), 1.08 (s, 9H).

Scheme 14. (S)-1-((3R,4R)-4-((tert-butyldiphenylsilyl)oxy)tetrahydrofuran-3-yl)-2-methylpiperazine or (S)-1-((3S,4S)-4-((tert-butyldiphenylsilyl)oxy)tetrahydrofuran-3-yl)-2-methylpiperazine (31.1) and (31.2)

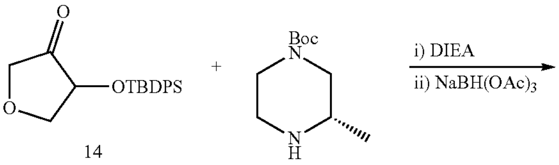

14

-continued

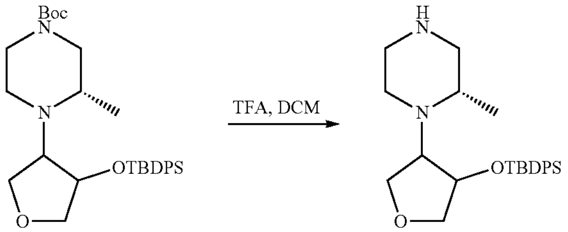

30.1 31.1

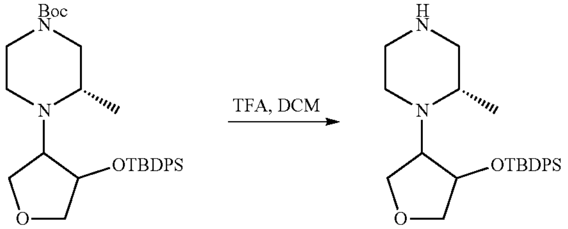

30.2 31.2 tert-butyl (S)-4-((3R,4R)-4-((tert-butyldiphenylsilyl)oxy)tetrahydrofuran-3-yl)-3-methylpiperazine-1-carboxylate or tert-butyl (S)-4-((3S,4S)-4-((tert-butyldiphenylsilyl)oxy)tetrahydrofuran-3-yl)-3-methylpiperazine-1-carboxylate (30.1) and (30.2)

A vial was charged with tert-butyl (S)-3-methylpiperazine-1-carboxylate (750 mg, 3.74 mmol), and 4-((tert-butyldiphenylsilyl)oxy)dihydrofuran-3(2H)-one 14 (2550 mg, 7.49 mmol). DCM (19 ml) was added along with DIEA (1962 μl, 11.23 mmol), and the resulting mixture was stirred for 1 hour. Acetic acid (643 μl, 11.23 mmol) and sodium triacetoxyborohydride (2381 mg, 11.23 mmol) were added and stirred overnight. The residue was purified by column chromatography on silica gel, eluting with 0-60% hexanes/3:1 EtOAc:EtOH to give the title compounds 30.1 and 30.2.

(S)-1-((3R,4R)-4-((tert-butyldiphenylsilyl)oxy)tetrahydrofuran-3-yl)-2-methylpiperazine or (S)-1-((3S,4S)-4-((tert-butyldiphenylsilyl)oxy)tetrahydrofuran-3-yl)-2-methylpiperazine (31.1) and (31.2)

TFA (1715 μl) was added to a solution of tert-butyl (S)-4-((3R,4R)-4-((tert-butyldiphenylsilyl)oxy)tetrahydrofuran-3-yl)-3-methylpiperazine-1-carboxylate or tert-butyl (S)-4-((3S,4S)-4-((tert-butyldiphenylsilyl)oxy)tetrahydrofuran-3-yl)-3-methylpiperazine-1-carboxylate 30.1 and 30.2 (720 mg, 1.372 mmol) in DCM (5145 μl). The resulting mixture was allowed to stir for 1 hour at room temperature. The mixture was concentrated under reduced to pressure to afford the title compounds 31.1 and 31.2. 31.1: MS (ESI): m/z calc'd for $C_{25}H_{37}N_2O_2Si$ $[M+H]^+$: 425, found 425. 31.2: MS (ESI): m/z calc'd for $C_{25}H_{37}N_2O_2Si$ $[M+H]^+$: 425, found 425.

Scheme 15. 1-((3R,4R)-4-methoxytetrahydrofuran-3-yl)piperazine and 1-((3S,4S)-4-methoxytetrahydrofuran-3-yl)piperazine (34)

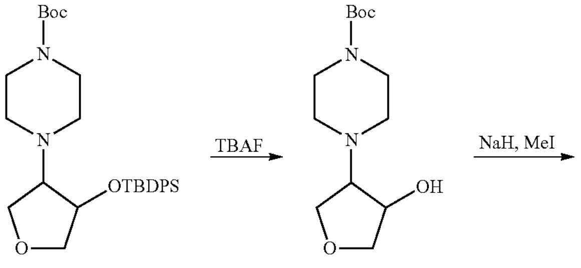

28 32

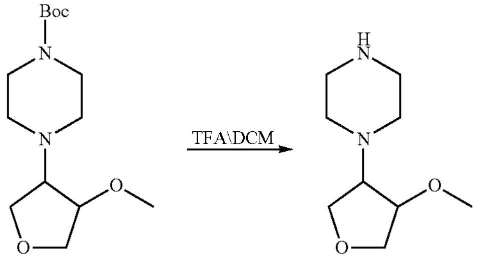

33 34 tert-butyl 4-((3R,4R)-4-hydroxytetrahydrofuran-3-yl)piperazine-1-carboxylate and tert-butyl 4-((3S,4S)-4-hydroxytetrahydrofuran-3-yl)piperazine-1-carboxylate (32)

To a solution of tert-butyl 4-((3R,4R)-4-((tert-butyldiphenylsilyl)oxy)tetrahydrofuran-3-yl)piperazine-1-carboxylate and tert-butyl 4-((3R,4R)-4-((tert-butyldiphenylsilyl)oxy)tetrahydrofuran-3-yl)piperazine-1-carboxylate 28 (1 g, 1.958 mmol) in THF (6 mL) was add TBAF (3.92 mL, 3.92 mmol) and the mixture was stirred at 50° C. for 1 h then concentrated in vacuo to afford the crude product which was purified by column chromatography ($SiO_2$, EtOAc) to afford the title compound 32. MS (ESI) m/z calc'd for $C_{13}H_{25}N_2O_4$ $[M+H]^+$: 273, found 273.

tert-butyl 4-((3R,4R)-4-methoxytetrahydrofuran-3-yl) piperazine-1-carboxylate and tert-butyl 4-((3S,4S)-4-methoxytetrahydrofuran-3-yl) piperazine-1-carboxylate (33)

To a solution of tert-butyl 4-((3R,4R)-4-hydroxytetrahydrofuran-3-yl)piperazine-1-carboxylate and tert-butyl 4-((3S,4S)-4-hydroxytetrahydrofuran-3-yl)piperazine-1-carboxylate 32 (440 mg, 1.616 mmol) in anhydrous DMF (5 mL) was added NaH (129 mg, 3.23 mmol) at 0° C., the resulting mixture was stirred for 0.5 h at 0° C., then added iodomethane (344 mg, 2.423 mmol), the mixture was stirred for 1.5 hours at 20° C. The mixture was quenched with $H_2O$ (40 mL). EtOAc (40 mL) was added into the mixture. The organic layer was separated. The aqueous was extracted with EtOAc (40 mL×3). The mixture was dried by anhydrous $Na_2SO_4$. After filtration and concentration, the reaction mixture was purified by column chromatography (silica gel, EtOAc) to afford the title compound 33. MS (ESI) m/z calc'd for $C_{14}H_{27}N_2O_4$$[M+H]^+$: 287, found 287.

1-((3R,4R)-4-methoxytetrahydrofuran-3-yl)piperazine and 1-((3S,4S)-4-methoxytetrahydrofuran-3-yl) piperazine (34)

To a solution of tert-butyl 4-((3R,4R)-4-methoxytetrahydrofuran-3-yl) piperazine-1-carboxylate and tert-butyl 4-((3S,4S)-4-methoxytetrahydrofuran-3-yl) piperazine-1-carboxylate 33 (400 mg, 1.397 mmol) in DCM (2 mL) was added TFA (0.4 mL) at 25° C., and the mixture was stirred at 25° C. for 2 hours. The mixture concentrated in vacuo to give the crude product which was purified by pre-HPLC (TFA) to afford the title compound 34. MS (ESI) m/z calc'd for $C_9H_{19}N_2O_2[M+H]^+$: 187, found 187.

Scheme 16. Synthesis of (3R,4R)-4-(4-(3-amino-7-chloroisoquinolin-6-yl)piperazin-1-yl-4-methyltetrahydrofuran-3-ol, 2HCl or (3S,4S)-4-(4-(3-amino-7-chloroisoquinolin-6-yl)piperazin-1-yl)-4-methyltetrahydrofuran-3-ol, 2HCl (37)

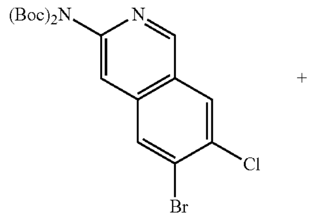

5

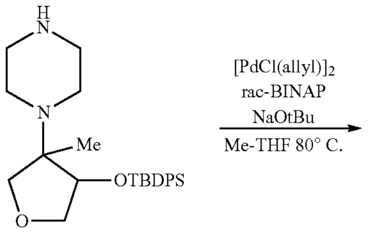

17.1

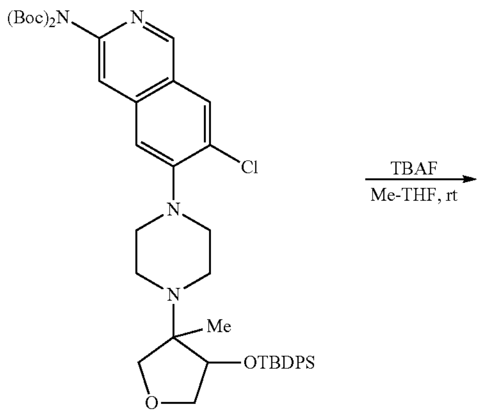

35

-continued

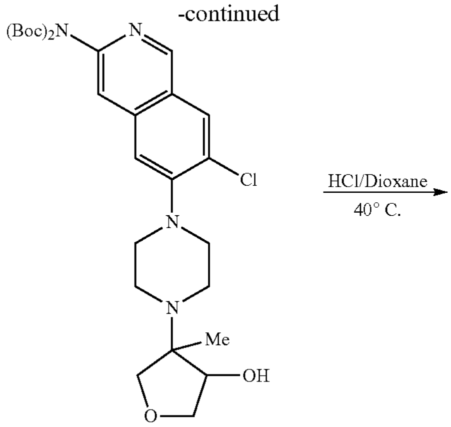

36

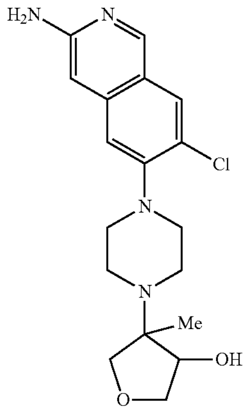

37 tert-butyl (tert-butoxycarbonyl)(6-((3R,4R)-4-(4-((tertbutyldiphenylsilyl)oxy)-3-methyltetrahydrofuran-3-yl)piperazin-1-yl)-7-chloroisoquinolin-3-yl) carbamate or tert-butyl (tert-butoxycarbonyl)(6-((3S,4S)-4-(4-((tertbutyldiphenylsilyl)oxy)-3-methyltetrahydrofuran-3-yl)piperazin-1-yl)-7-chloroisoquinolin-3-yl)carbamate (35)

A 30-ml microwave vial was charged with tert-butyl (6-bromo-7-chloroisoquinolin-3-yl)(tertbutoxycarbonyl) carbamate 5 (0.915 g, 1.999 mmol), -(4-(3R,4R)-((tert-butyldiphenylsilyl)oxy)-3-methyltetrahydrofuran-3-yl)piperazine or 1-(4-(3S,4S)-((tert-butyldiphenylsilyl)oxy)-3-methyltetrahydrofuran-3-yl)piperazine 17.1 (1.019 g, 2.399 mmol) and a stir bar. A solution of 2,2'-bis(diphenylphosphaneyl)-1,1'-binaphthalene (0.149 g, 0.240 mmol) and allyl palladium chloride dimer (0.037 g, 0.100 mmol) in 2-MeTHF (9.99 ml) was prepared separately and then added to the substrates, followed by addition of a freshly prepared solution of sodium 2-methylpropan-2-olate (5.00 ml, 9.99 mmol) in dioxane. The reaction was sealed, removed from the glovebox and heated to 80° C. for 18 h and the reaction was cooled. Reaction was quenched with water and diluted with 2-MeTHF, extracted 2-MeTHF×2, washed with brine, dried, filtered through a pad of silica on top of celite and concentrated in vacuo. Solid was slurried in 40 mL MeOH (heat to 40° C. and gradually cool) for 4 h, then filtered and dried to afford the title compound 35. MS (ESI): m/z calc'd for $C_{44}H_{58}ClN_4O_6Si$ $[M+H-C_5H_9O_2]^+$: 701, found 701.

tert-butyl (tert-butoxycarbonyl)(7-chloro-6-((3R,4R)-4-(4-hydroxy-3-methyltetrahydrofuran-3-yl)piperazin-1-yl)isoquinolin-3-yl)carbamate or tert-butyl (tert-butoxycarbonyl)(7-chloro-6-((3S,4S)-4-(4-hydroxy-3-methyltetrahydrofuran-3-yl)piperazin-1-yl)isoquinolin-3-yl)carbamate (36)

tert-butyl (tert-butoxycarbonyl)(6-((3R,4R)-4-(4-((tert-butyldiphenylsilyl)oxy)-3-methyltetrahydrofuran-3-yl)piperazin-1-yl)-7-chloroisoquinolin-3-yl)carbamate or tert-butyl (tert-butoxycarbonyl)(6-((3S,4S)-4-(4-((tertbutyldiphenylsilyl)oxy)-3-methyltetrahydrofuran-3-yl)piperazin-1-yl)-7-chloroisoquinolin-3-yl)carbamate 35 (0.58 g, 0.724 mmol) was diluted in 2-MeTHF (3.62 ml), then TBAF (3.62 ml, 3.62 mmol) was added and the resulting solution stirred at rt overnight. After, reaction shows full conversion, it is diluted with water, extracted 3× with 2-MeTHF, dried, filtered through a plug of Celite then concentrate in vacuo. Title compound 36 was carried on crude to next step. MS (ESI): m/z calc'd for $C_{28}H_{40}ClN_4O_6$ $[M+H-C_5H^9O_2]^+$: 463, found 463

(3R,4R)-4-(4-(3-amino-7-chloroisoquinolin-6-yl)piperazin-1-yl)-4-methyltetrahydrofuran-3-ol, 2HCl or (3S,4S)-4-(4-(3-amino-7-chloroisoquinolin-6-yl)piperazin-1-yl)-4-methyltetrahydrofuran-3-ol, 2HCl (37)

Tert-butyl (tert-butoxycarbonyl)(7-chloro-6-((3R,4R)-4-(4-hydroxy-3-methyltetrahydrofuran-3-yl)piperazin-1-yl)isoquinolin-3-yl)carbamate or tert-butyl (tert-butoxycarbonyl)(7-chloro-6-((3S,4S)-4-(4-hydroxy-3-methyltetrahydrofuran-3-yl)piperazin-1-yl)isoquinolin-3-yl)carbamate 36 (408 mg, 0.724 mmol) was diluted in dioxane (3620 µl), then HCl (3.6 ml, 14.5 mmol) added and the resulting solution was stirred at 40° C. overnight. The reaction was heated to 50° C. for an additional 6 h. The reaction was cooled and the resulting suspension was filtered, then washed with dioxane followed by 2-MeTHF and then dried under vacuum overnight to afford the title compound 37. MS (ESI): m/z calc'd for $C_{18}H_{26}ClN_4O_2$ $[M+H]^+$: 363, found 363.

Scheme 17. Synthesis of 7-chloro-6-(4-(4-fluoro-3-methyltetrahydrofuran-3-yl)piperazin-1-yl)isoquinolin-3-amine (41.1) and (41.2)

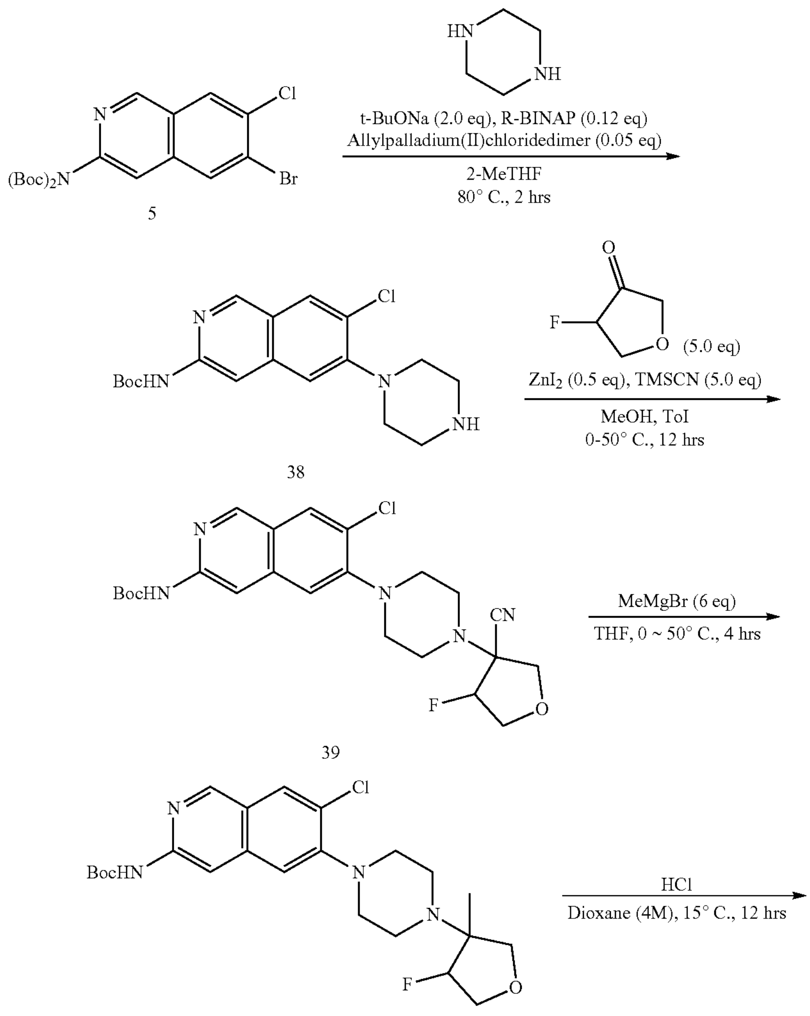

5

38

39

40

-continued

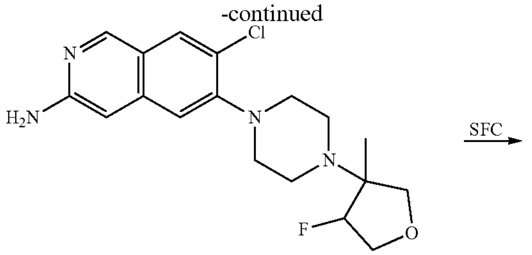

41

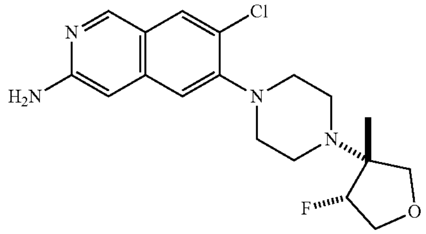

41.1

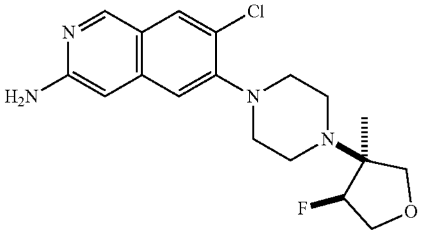

41.2 tert-butyl (7-chloro-6-(piperazin-1-yl)isoquinolin-3-yl)carbamate (38)

A round bottom flask was charged with ditert-butyl (6-bromo-7-chloroisoquinolin-3-yl)carbamate (100 g, 0.11 mol, 1.00 eq), piperazine (28.2 g, 0.16 mol, 1.50 eq) and t-BuONa (42.0 g, 0.22 mmol, 2.00 eq), [1-(2-diphenylphosphanyl-1-naphthyl)-2-naphthyl]-diphenyl-phosphane (16.3 g, 0.013 mmol, 0.12 eq) and allyl(chloro)palladium (2.00 g, 5.46 mmol, 0.05 eq). The vial was sealed, and its contents were placed under an inert atmosphere by performing 3 vacuum/nitrogen cycles. Under positive flow of nitrogen 2-MeTHF (1.00 L) was added and the reaction mixture was stirred at 80° C. for 2 hrs. At 2 hrs, MeOH (4.00 L) was added to quench the reaction. The precipitate was filtered and the filter cake was washed with additional MeOH (4.00 L) to the title compound. MS (ESI) m/z calc'd for $C_{18}H_{23}ClN_4O_2$ $[M+H]^+$: 363, found 363.

tert-butyl (7-chloro-6-(4-(3-cyano-4-fluorotetrahydrofuran-3-yl)piperazin-1-yl)isoquinolin-3-yl)carbamate (39)

A round bottom flask was charged with tert-butyl (7-chloro-6-(piperazin-1-yl)isoquinolin-3-yl)carbamate (60.0 g, 0.13 mol, 1.00 eq), 4-fluorodihydrofuran-3(2H)-one (1.2 kg, 0.69 mol, 6% impurity in DCE, 5.0 eq), toluene (240 mL) and MeOH (240 mL). The vial was sealed, and its contents were placed under an inert atmosphere by performing 3 vacuum/nitrogen cycles. Under positive flow of nitrogen, $ZnI_2$ (22.0 g, 0.68 mmol, 0.50 eq) and TMSCN (68.4 g, 0.68 mol, 86.2 mL, 5.00 eq) were to the mixture at 0° C. The reaction mixture was stirred at 15° C. for 1 hr under $N_2$ followed by additional 7 hrs of stirring at 50° C. At 8 hrs, the reaction mixture was concentrated under reduced pressure. The crude product was diluted with ethyl acetate (500 mL) and extracted with $H_2O$ (200 mL×2). The combined organic phases were washed with H2O (50 mL), dried over Na2SO4, and the solvent removed under reduced pressure. The resultant crude residue was subjected to purification by silica gel chromatography (petroleum ether:ethyl acetate=100/1 to 1/1) to afford the title compound. MS (ESI) m/z calc'd for $C_{23}H_{27}ClFN_5O_3$ $[M+H]^+$: 476, found 476.

tert-butyl (7-chloro-6-(4-(4-fluoro-3-methyltetrahydrofuran-3-yl)piperazin-1-yl)isoquinolin-3-yl)carbamate (40)

A round bottom flask was charged with tert-butyl (7-chloro-6-(4-(3-cyano-4-fluorotetrahydrofuran-3-yl)piperazin-1-yl)isoquinolin-3-yl)carbamate (35.0 g, 0.07 mol, 1.00 eq) and THF (350 mL). The vial was sealed, and its contents were placed under an inert atmosphere by performing 3 vacuum/nitrogen cycles. Under positive flow of nitrogen, MeMgBr (147 mL, 0.44 mol, 6.00 eq) was added drop-wise into the mixture at 0° C. The reaction mixture was stirred at 50° C. for 4 hrs. At 4 hrs, the reaction mixture was diluted with DCM (500 mL) and extracted with saturated ammonium chloride (500 mL). The combined organic phases were washed with H2O (50 mL), dried over Na2SO4, and the solvent removed under reduced pressure. The resultant crude residue was subjected to purification by silica gel chromatography (petroleum ether:ethyl acetate=100/1 to 1/1) to afford the title compound. MS (ESI) m/z calc'd for $C_{23}H_{30}ClFN_4O_3$ $[M+H]^+$: 465, found 465.

7-chloro-6-(4-(4-fluoro-3-methyltetrahydrofuran-3-yl)piperazin-1-yl)isoquinolin-3-amine (41.1) and (41.2)

A round bottom flask was charged with tert-butyl (7-chloro-6-(4-(4-fluoro-3-methyltetrahydrofuran-3-yl)piperazin-1-yl)isoquinolin-3-yl)carbamate (25.0 g, 0.05 mol, 1.00 eq) and dioxane (100 mL). The vial was sealed, and its contents were placed under an inert atmosphere by performing 3 vacuum/nitrogen cycles. Under positive flow of nitrogen, HCl/dioxane (250 mL, 1.0 mol, 18.6 eq) was added. The reaction mixture was stirred at room temperature for 12 hrs. At 12 hrs, the reaction mixture was concentrated under reduced pressure. The crude residue was subject to purification by reversed phase HPLC (column: Phenomenex luna c18 250 mm×100 mm×10 um; mobile phase: [water (0.05% HCl)-ACN]; B %: 0%-20%, 20 min) to give the solution of the desired compound as a racemate. The racemic material could be resolved to its component enantiomers by chiral preparative SFC (column: daicel chiralcel OJ (250 mm×50 mm, 10 um); mobile phase: [0.1% $NH_3H_2O$ IPA]; B %:

45%-45%, 5.5 min) to afford the title compound (Ex-x.x) and (Ex-x.x). MS (ESI) m/z calc'd for $C_{18}H_{22}ClFN_4O$ $[M+H]^+$: 365, found 365. $^1H$ NMR (400 MHz, d-DMSO, 25° C.) δ: 8.64 (s, 1H), 7.85 (s, 1H), 7.06 (s, 1H), 6.52 (s, 1H), 5.95 (s, 2H), 4.85-4.99 (dd, J=3.2 Hz, 54.8 Hz, 1H), 4.07-4.20 (m, 1H), 3.82-3.93 (dd, J=11.6 Hz, 31.6 Hz, 1H), 3.66-3.73 (q, J=7.2 Hz, 2H), 3.25 (s, 4H), 2.75-2.77 (m, 2H), 2.51-2.54 (m, 2H), 1.02 (s, 3H). MS (ESI) m/z calc'd for C18H22ClFN4O $[M+H]^+$: 365, found 365. $^1H$ NMR (400 MHz, d-DMSO, 25° C.) δ: δ: 8.64 (s, 1H), 7.85 (s, 1H), 7.06 (s, 1H), 6.52 (s, 1H), 5.95 (s, 2H), 4.85-4.99 (dd, J=3.2 Hz, 54.8 Hz, 1H), 4.07-4.20 (m, 1H), 3.82-3.93 (dd, J=11.6 Hz, 31.6 Hz, 1H), 3.66-3.73 (q, J=7.2 Hz, 2H), 3.25 (s, 4H), 2.75-2.77 (m, 2H), 2.51-2.54 (m, 2H), 1.02 (s, 3H).

Scheme 18. Synthesis of 6-(4-(4-fluoro-3-methyltetrahydrofuran-3-yl)piperazin-1-yl)methylisoquinolin-3-amine (42.1) and (42.2)

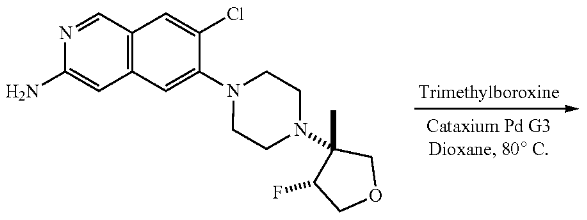

41.1 or 41.2

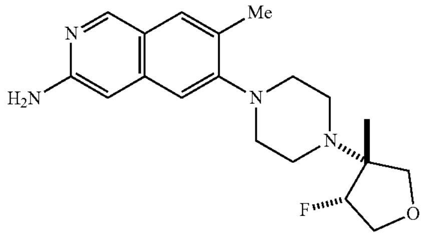

42.1 or 42.2

7-chloro-6-(4-(4-fluoro-3-methyltetrahydrofuran-3-yl)piperazin-1-yl)isoquinolin-3-amine (500 mg, 1.370 mmol), Methansulfonato(diadamantyl-N-butylphosphino)-2'-amino-1,1'-biphenyl-2-yl)palladium(II) dichloromethane adduct (223 mg, 0.274 mmol), cesium carbonate (1786 mg, 5.48 mmol), trimethylboroxine (1916 μl, 13.70 mmol), and dioxane (6167 μl) and water (685 μl) were taken up in a vial. The vial was purged with nitrogen and the reaction mixture was stirred at 80° C. overnight. Crude mixture was filtered, concentrated. The crude reaction mixture was diluted in DCM and purified by column chromatography using 0-100% Hexanes in 3:1 Ethyl Acetate Ethanol to afford the title compound. MS (ESI) m/z calc'd for $C_{19}H_{25}FN_4O$ $[M+H]^+$: 345, found 345.

Scheme 19. Synthesis of (R) or (S)-7-chloro-6-(4-(3-methyltetrahydrofuran-3-yl)piperazin-1-yl)isoquinolin-3-amine dihydrochloride (44.1) and (44.2)

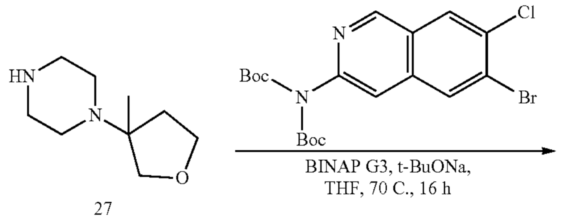

27

-continued

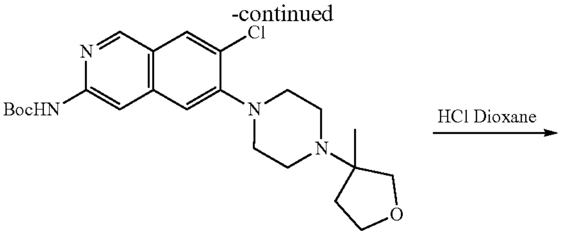

43

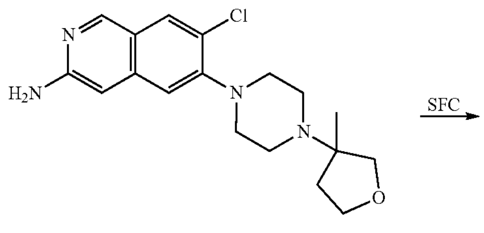

44

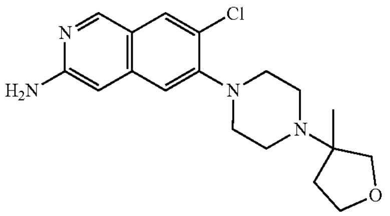

44.1

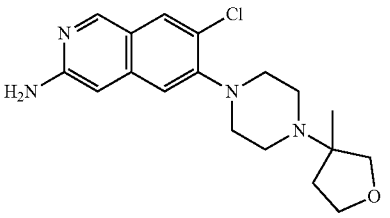

44.2 tert-butyl (7-chloro-6-(4-(3-methyltetrahydrofuran-3-yl)piperazin-1-yl)isoquinolin-3-yl)carbamate (43)

To a solution of tert-butyl (6-bromo-7-chloroisoquinolin-3-yl)(tert-butoxycarbonyl)carbamate (6.8 g, 16.4 mmol), 1-(3-methyltetrahydrofuran-3-yl)piperazine, 27, (2.78 g, 16.34 mmol) and sodium tert-butoxide (4.28 g, 44.6 mmol) in THF (105 mL) was added rac-BINAP-Pd-G3 (1.474 g, 1.486 mmol) in glove box. The reaction was stirred for 16 h at 70° C. The mixture was added to a mixture of EtOAc (200 mL) and HCl (500 mL, 2 N). The mixture was separated, and the aqueous phase was extracted with EtOAc (200 mL×2). The aqueous phase was adjusted with $K_2CO_3$ to pH ~11 and extracted with EtOAc (200 mL×3). The combined organic layers were dried over anhydrous $Na_2SO_4$ and filtered. The filtrate was concentrated in vacuo to give the crude product, which was used directly for the next step. MS (ESI) m/z calc'd for $C_{23}$H31ClN$_4$O$_3$ $[M+H]^+$: 447, found 447.

7-chloro-6-(4-(3-methyltetrahydrofuran-3-yl)piperazin-1-yl)isoquinolin-3-amine dihydrochloride (44)

A solution of tert-butyl (7-chloro-6-(4-(3-methyltetrahydrofuran-3-yl)piperazin-1-yl)isoquinolin-3-yl)carbamate (2.0 g, 4.47 mmol) in HCl (20 mL, 80 mmol) in dioxane, which was used directly for the next step without further purification. MS (ESI) m/z calc'd for $C_{18}H_{23}ClN_4O$ $[M+H]^+$: 347, found 347.

(R) or (S)-7-chloro-6-(4-(3-methyltetrahydrofuran-3-yl)piperazin-1-yl)isoquinolin-3-amine dihydrochloride (44.1) and (44.2)

7-chloro-6-(4-(3-methyltetrahydrofuran-3-yl)piperazin-1-yl)isoquinolin-3-amine dihydrochloride (1.8 g, 4.29 mmol) was send for SFC separation to give 44.1 (Rt=0.806) and 44.2 (Rt=1.148).

Column: Chiralpak AD-3 50×4.6 mm I.D., 3 um Mobile phase: A: CO2 B:ethanol (0.05% DEA)

Isocratic: 40% B Flow rate: 4 mL/minColumn temp.: 35° C. ABPR: 1500 psi 44.1: MS (ESI) m/z calc'd for $C_{18}H_{23}ClN_4O$ $[M+H]^+$: 347, found 347

44.2: MS (ESI) m/z calc'd for $C_{18}H_{23}ClN_4O$ $[M+H]^+$: 347, found 347.

Scheme 20. Synthesis of (R) or (S)-7-methyl-6-(4-(3-methyltetrahydrofuran-3-yl)piperazin-1-yl)isoquinolin-3-amine (47.1) and (47.2)

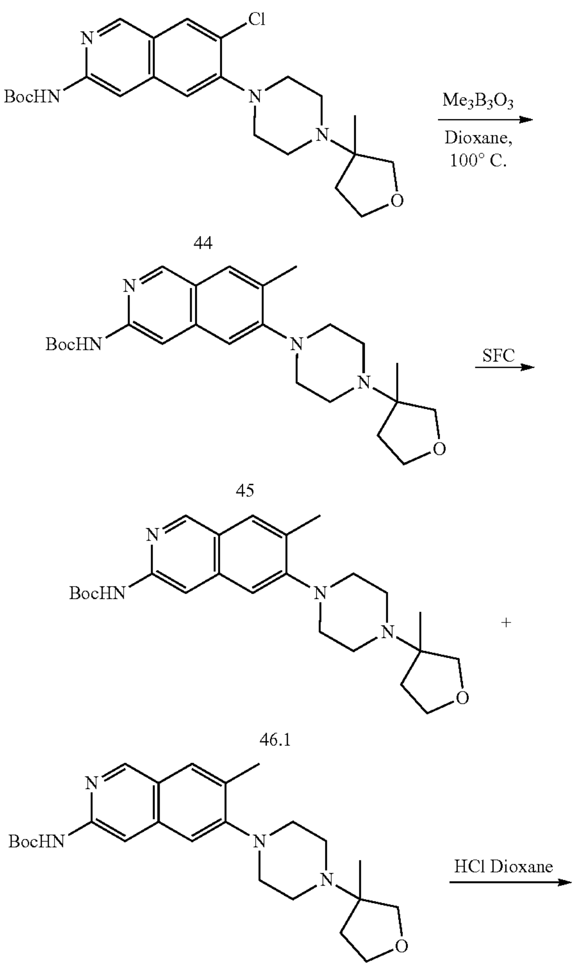

46.2

-continued

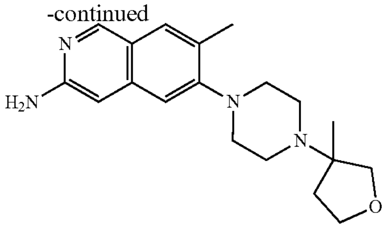

47.1 or 47.2 tert-butyl (7-methyl-6-(4-(3-methyltetrahydrofuran-3-yl)piperazin-1-yl)isoquinolin-3-yl)carbamate (45)

To a solution of tert-butyl (7-chloro-6-(4-(3-methyltetrahydrofuran-3-yl)piperazin-1-yl)isoquinolin-3-yl)carbamate (3 g, 6.71 mmol), trimethylboroxine (2.81 mL, 20.13 mmol) and potassium carbonate (2.78 g, 20.13 mmol) in dioxane (30 mL) was added [1,3-bis(2,6-diisopropylphenyl)imidazol-2-ylidene](3-chloropyridyl)palladium(ii) dichloride (0.473 g, 0.671 mmol) under $N_2$ protection at 18° C. The mixture was stirred at 100° C. for 16 h. The mixture was added into water (100 mL) slowly. EtOAc (100 mL) was added into the mixture.

The organic layer was separated. The aqueous was extracted with EtOAc (100 mL×3). The combined organic layer was dried over anhydrous $Na_2SO_4$, filtered and concentrated in vacuo to give the crude product, which was purified by flash silica gel chromatography (ISCO; 20 g Agela Silica Flash Column, Eluent of 0~50% EtOAc: Pet. ether gradient @ 30 mL/min) to afford the title compound. MS (ESI) m/z calc'd for $C_{24}H_{34}N_4O_3$ $[M+H]^+$: 427, found 427.

Tert-butyl(7-methyl-6-(4-(3-methyltetrahydrofuran-3-yl)piperazin-1-yl)isoquinolin-3-yl)carbamate (46.1) and (46.2)

Tert-butyl(7-methyl-6-(4-(3-methyltetrahydrofuran-3-yl)piperazin-1-yl)isoquinolin-3-yl)carbamate (1.8 g, 4.22 mmol) was send for SFC separation to afford 46.1 (Rt=3.329) and 46.2 (Rt=4.260). Column: Chiralpak IG-3 50×4.6 mm I.D., 3 um Mobile phase: A: $CO_2$ B:ethanol (0.05% DEA) Isocratic: 40% B Flow rate: 4 mL/min Column temp: 35° C. ABPR: 1500 psi 46.1: MS (ESI) m/z calc'd for $C_{24}H_{34}N_4O_3$ $[M+H]^+$: 427, found 427.

46.2: MS (ESI) m/z calc'd for $C_{24}H_{34}N_4O_3$ $[M+H]^+$: 427, found 427.

7-methyl-6-(4-(3-methyltetrahydrofuran-3-yl)piperazin-1-yl)isoquinolin-3-amine (47.1 or 47.2)

The solution of tert-butyl (7-methyl-6-(4-(3-methyltetrahydrofuran-3-yl)piperazin-1-yl)isoquinolin-3-yl)carbamate (790 mg, 1.85 mmol) in HCl dioxane (20 ml) was stirred at 50° C. for 2 h. The mixture was concentrated in vacuo to give the residue. The residue was resolved with MeOH (10 mL), and the suspension was adjusted with $K_2CO_3$ (400 mg) to pH-8, the suspension was concentrated in vacuo to give the mixture. Water (10 mL) was added to the mixture and the mixture was extracted with DCM (10 mL×3). The combined organic layers were dried over $Na_2SO_4$ and filtered. The filtrate was concentrated in vacuo to afford the title compound, which was used directly for the next step without further purification. MS (ESI) m/z calc'd for $C_{19}H_{26}N_4O$ $[M+H]^+$: 327, found 327.

Scheme 21. Synthesis of N-(6-bromo-7-chloroisoquinolin-3-yl)cyclopropanecarboxamide (48)

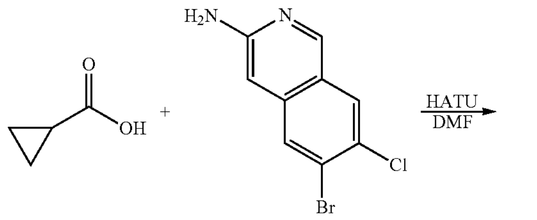

3

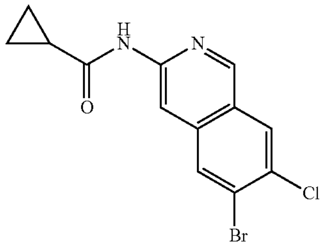

48

A 20 mL vial was charged with 6-bromo-7-chloroisoquinolin-3-amine 3 (400 mg, 1.553 mmol), cyclopropanecarboxylic acid (247 μl, 3.11 mmol), HATU (1181 mg, 3.11 mmol), DMF (4000 μl), and DIEA (1356 μl, 7.77 mmol). The mixture was allowed to stir overnight at room temperature, diluted with EtOAc and washed twice with water and once with brine. The combined organic fractions were dried over anhydrous sodium sulfate, filtered and concentrated under reduced pressure. The residue was purified by column chromatography on silica (0-100% EtOAc/hexanes). The desired fractions were pooled and concentrated under reduced pressure to afford the title compound 48. MS (ESI): m/z calc'd for $C_{13}H_{11}BrClN_2O$ $[M+H]^+$: 327, found 327.

Scheme 22. Synthesis of N-(6-bromo-7-chloroisoquinolin-3-yl)spiro[2.3]hexane-5-carboxamide (49)

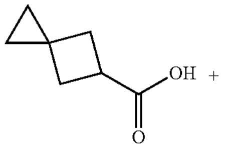

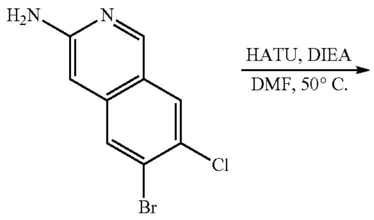

3

-continued

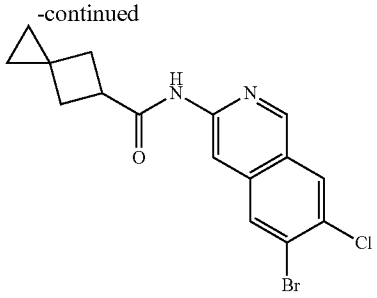

49

A vial was charged with spiro[2.3]hexane-5-carboxylic acid (294 mg, 2.330 mmol), 6-bromo-7-chloroisoquinolin-3-amine 3 (500 mg, 1.942 mmol) and HATU (1477 mg, 3.88 mmol). DMF (6472 μl) and DIPEA (678 μl, 3.88 mmol) were added and the reaction was heated to 50° C. overnight. The reaction was cooled to room temperature and diluted with 30 mL of water. The aqueous solution was extracted with DCM (3×25 mL) and the organic layers were combined and concentrated. The residue was purified by column chromatography on silica gel, eluting with 0-100% 3:1 EtOAc:EtOH/hexanes to give the title compound 49. MS (ESI): m/z calc'd for $C_{16}H_{15}BrClN_2O$ $[M+H]^+$: 365, found 365.

Scheme 23. Synthesis of Rac-N-(6-bromo-7-chloroisoquinolin-3-yl)spiro[2.3]hexane-1-carboxamide (50)

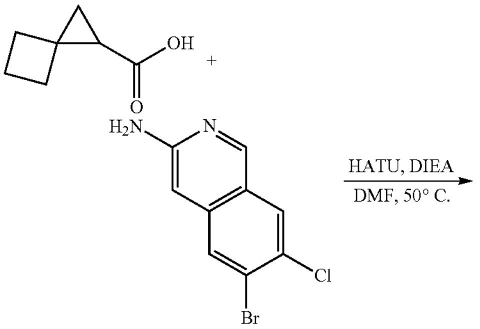

3

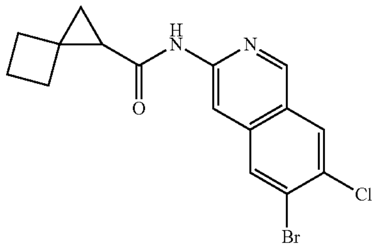

50

A vial was charged with spiro[2.3]hexane-1-carboxylic acid (0.539 g, 4.27 mmol), 6-bromo-7-chloroisoquinolin-3-amine 3 (1 g, 3.88 mmol) and HATU (2.215 g, 5.82 mmol). DMF (12.94 ml) was added followed by DIEA (1.017 ml, 5.82 mmol) and the reaction was heated to 50° C. overnight. The reaction was cooled to room temperature and then added to 50 mL of water to form a precipitate, affording title compound 50. No conditions were identified to sufficiently separate the stereoisomers. MS (ESI): m/z calc'd for $C_{16}H_{15}BrClN_2O$ $[M+H]^+$: 365, found 365.

Scheme 24. Synthesis of Rac-N-(6-bromo-7-chloroisoquinolin-3-yl)-3-oxabicyclo[3.1.0]hexane-6-carboxamide (51)

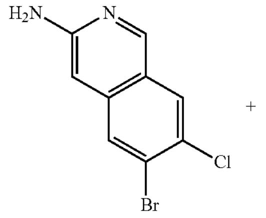

3

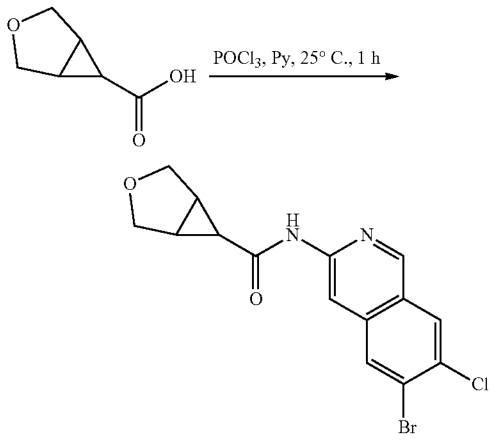

51

To a solution of 6-bromo-7-chloroisoquinolin-3-amine 3 (500 mg, 1.942 mmol) and 3-oxabicyclo[3.1.0]hexane-6-carboxylic acid (249 mg, 1.942 mmol) in pyridine (10 mL) was added $POCl_3$ (0.362 mL, 3.88 mmol) at 25° C., and the mixture was stirred at 25° C. for 1 hour. The mixture was added into ice water (20 mL) slowly. EtOAc (20 mL) was added into the mixture. The organic layer was separated. The aqueous was extracted with EtOAc (10 mL×3). The combined organic layer was dried by anhydrous $Na_2SO_4$, filtered and concentrated in vacuo to give the crude product, Pet. ether (50 mL) was added to the crude product, and the mixture was filtered and concentrated to afford the title compound 51. MS (ESI): m/z calc'd for $C_{15}H_{13}BrClN_2O_2$ $[M+H]^+$: 367, found 367.

Scheme 25. Synthesis of Rac-N-(6-bromo-7-chloroisoquinolin-3-yl)-5-oxaspiro[2.5]octane-1-carboxamide (52)

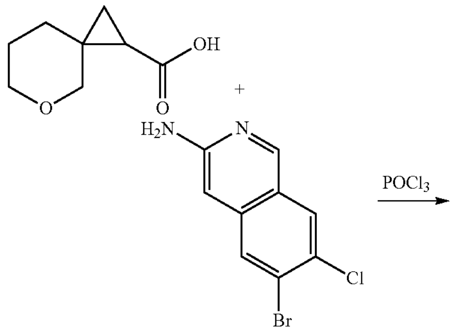

3

-continued

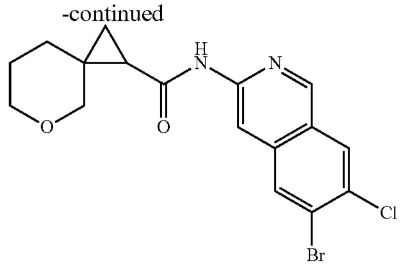

52

To a solution of 6-bromo-7-chloroisoquinolin-3-amine 3 (500 mg, 1.942 mmol) and 5-oxaspiro[2.5]octane-1-carboxylic acid (303 mg, 1.942 mmol) in pyridine (5 mL) was added $POCl_3$ (0.362 ml, 3.88 mmol) at 25° C. and the mixture was stirred at 25° C. for 0.5 hour. The mixture was added into ice water (50 mL) slowly. EtOAc (50 mL) was added into the mixture. The organic layer was separated. The aqueous was extracted with EtOAc (50 mL×3). The combined organic layers were dried by anhydrous $Na_2SO_4$, filtered and concentrated in vacuo to give the crude product which was purified by column chromatography (silica gel, Pet. ether:EtOAc=1:1) to afford the title compound 52. MS (ESI): m/z calc'd for $C_{17}H_{17}BrClN_2O_2$ $[M+H]^+$: 395, found 395.

Scheme 26. Synthesis of Rac-N-(6-bromo-7-chloroisoquinolin-3-yl)-6,6-difluorospiro[2.5]octane-1-carboxamide (53)

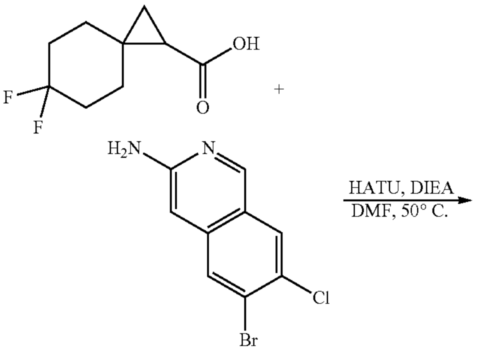

3

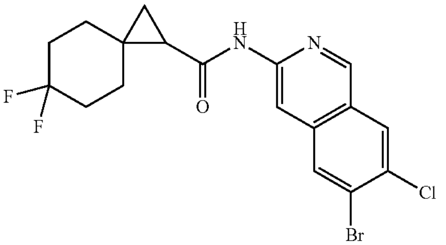

53

To a vial was added 6,6-difluorospiro[2.5]octane-1-carboxylic acid (91 mg, 0.480 mmol), 6-bromo-7-chloroisoquinolin-3-amine 3 (103 mg, 0.4 mmol) and HATU (304 mg, 0.800 mmol). The flask was evacuated and back filled with nitrogen 3 times. The solids were dissolved in DMF (2000 μl) and DIPEA (140 μl, 0.800 mmol) was added. The reaction was heated to 50° C. for 2 days. The reaction was then cooled to room temperature, poured into water to crash out the product and filtered. The residue was purified by column chromatography on silica gel, eluting with hexanes/3:1 ethyl acetate:ethanol to afford the title compound 53. MS (ESI): m/z calc'd for $C_{18}H_{16}BrClFN_2O$ $[M+H]^+$: 429, found 429.

Scheme 27. Synthesis of Rac-N-(6-bromo-7-chloroisoquinolin-3-yl)-5,5-dimethyltetrahydrofuran-3-carboxamide (54)

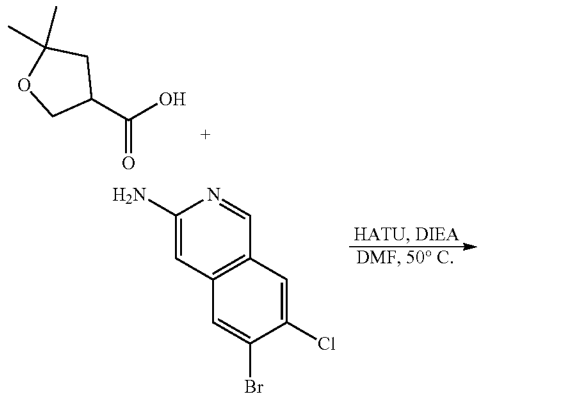

3

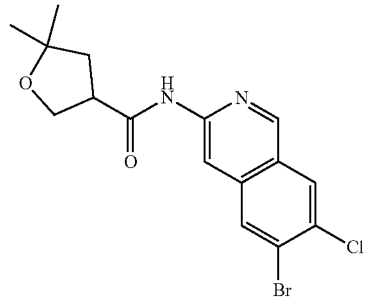

54

6-bromo-7-chloroisoquinolin-3-amine 3 (250 mg, 0.971 mmol), 5,5-dimethyltetrahydrofuran-3-carboxylic acid (280 mg, 1.942 mmol), HATU (738 mg, 1.942 mmol), DMF (3500 μl), and DIEA (848 μl, 4.85 mmol) were added to a vial. The vial was sealed and its contents were allowed to stir overnight at 50° C. The reaction was cooled to room temperature and added to water to form a precipitate. The solids were collected by vacuum filtration and dried to afford the title compound 54. The crude reaction mixture was used directly in a subsequent reaction without further purification. MS (ESI): m/z calc'd for $C_{16}H_{17}BrClN_2O_2$ $[M+H]^+$: 383, found 383.

Scheme 28. Synthesis of Rac-N-(6-bromo-7-chloroisoquinolin-3-yl)-2,2-dimethyltetrahydrofuran-3-carboxamide (55)

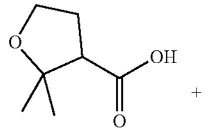

-continued

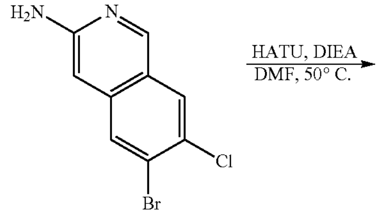

3

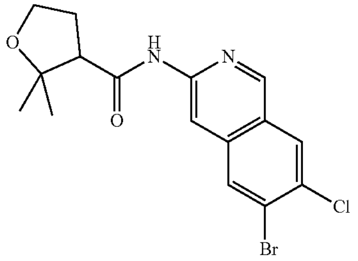

55

6-bromo-7-chloroisoquinolin-3-amine 3 (250 mg, 0.971 mmol), 2,2-dimethyltetrahydrofuran-3-carboxylic acid (280 mg, 1.942 mmol), HATU (738 mg, 1.942 mmol), DMF (3500 μl), and DIEA (848 μl, 4.85 mmol) were added to a vial. The vial was sealed and its contents were allowed to stir overnight at 80° C. The reaction was cooled to room temperature and water was added to form a precipitate. The solids were collected by vacuum filtration and dried to afford the title compound 55. The crude reaction mixture was used directly in a subsequent reaction without further purification. MS (ESI): m/z calc'd for $C_{16}H_{17}BrClN_2O_2$ $[M+H]^+$: 383, found 383.

Scheme 29. Synthesis of N-(6-bromo-7-chloroisoquinolin-3-yl)-1-methyl-2-oxabiyclo[2.1.1]hexane-4-carboxamide (56)

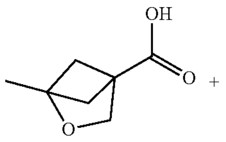

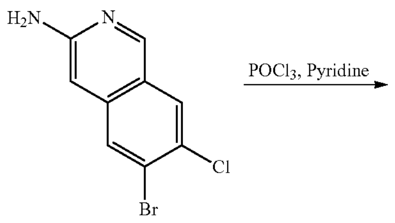

3

-continued

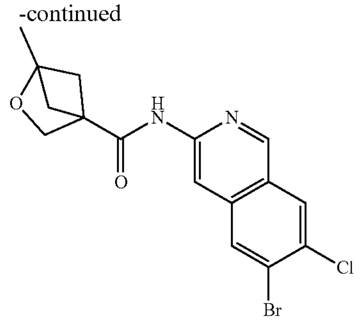

56

To a solution of 6-bromo-7-chloroisoquinolin-3-amine 3 (344 mg, 1.338 mmol) and bicyclo[1.1.1]pentane-1-carboxylic acid (150 mg, 1.338 mmol) in pyridine (5 mL) was added $POCl_3$ (0.249 ml, 2.68 mmol) at 25° C. The mixture was stirred at 25° C. for 0.5 hour then slowly added into ice water (50 ml). EtOAc (50 mL) was added into the mixture. The organic layer was separated. The aqueous was extracted with EtOAc (50 mL×3). The combined organic layers were dried by anhydrous $Na_2SO_4$, filtered and concentrated in vacuo to give the crude product which was purified by column chromatography (silica gel, Pet. Ether:EtOAc=1:1) to afford the title compound 56. MS (ESI): m/z calc'd for $C_{16}H_{15}BrClN_2O_2$ $[M+H]^+$: 381, found 381.

Scheme 30. Synthesis of N-(6-bromo-7-chloroisoquinolin-3-yl)bicyclo[1.1.1]pentane-1-carboxamide (57)

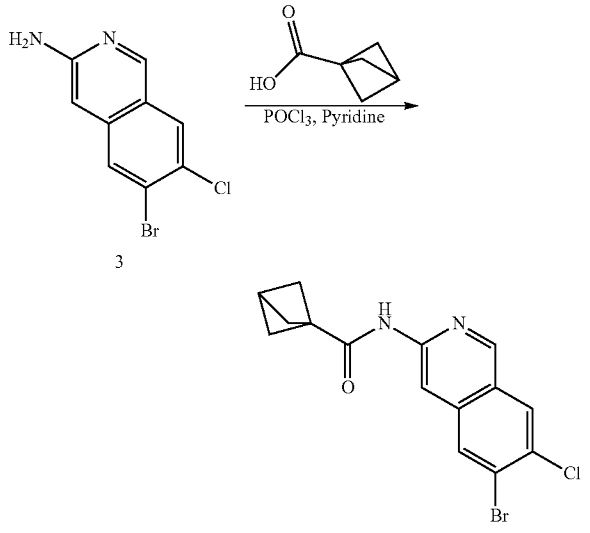

3

57

To a solution of 6-bromo-7-chloroisoquinolin-3-amine 3 (344 mg, 1.338 mmol) and bicyclo[1.1.1]pentane-1-carboxylic acid (150 mg, 1.338 mmol) in pyridine (5 mL) was added $POCl_3$ (0.249 ml, 2.68 mmol) at 25° C. And the mixture was stirred at 25° C. for 0.5 hour. The mixture was added into ice water slowly. EtOAc (50 mL) was added into the mixture. The organic layer was separated. The aqueous was extracted with EtOAc (50 mL×3). The combined organic layer was dried by anhydrous $Na_2SO_4$, filtered and concentrated in vacuo to give the crude product which was purified by column chromatography (silica gel, Pet. Ether: EtOAc=1:1) to afford the title compound 57. MS (ESI): m/z calc'd for $C_{15}H_{13}BrClN_2O$ $[M+H]^+$: 351, found 351.

Scheme 31. Synthesis of (R)-N-(6-bromo-7-chloroisoquinolin-3-yl)-6-oxaspiro[2.5]octane-1-carboxamide or (S)-N-(6-bromo-7-chloroisoquinolin-3-yl)-6-oxaspiro[2.5]octane-1-carboxamide (58.1) and (58.2)

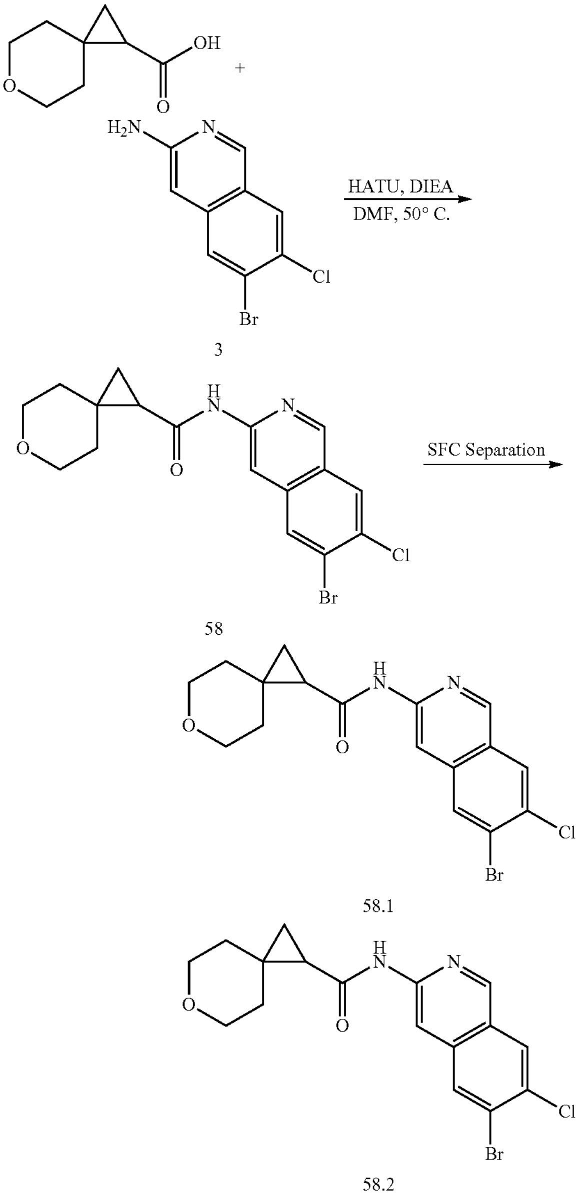

3

58

58.1

58.2

A round bottom flask was charged with 6-bromo-7-chloroisoquinolin-3-amine 3 (10 g, 38.8 mmol), 6-oxaspiro[2.5]octane-1-carboxylic acid (12.13 g, 78 mmol), and HATU (29.5 g, 78 mmol). DMF (97 ml), and DIEA (33.9 ml, 194 mmol) were added and the reaction was allowed to stir 72 h. at 50° C. The reaction was cooled to room temperature and added to 1.6 L of water to form a precipitate. The solids were collected by vacuum filtration and dried under reduced pressure. The residue was purified by column chromatography on silica (20-100% EtOAc:hexanes). The mixture of two stereoisomers was purified by chiral SFC (OJ-H, 21×250 (mm), Mobile phase A: 25% $CO_2$ Mobile phase B:

75% MeOH 0.1% $NH_4OH$) and concentrated to afford the title compounds 58.1 (tR=4.0 min) and 58.2 (tR=5.4 min). 58.1: MS (ESI): m/z calc'd for $C_{17}H_{17}BrClN_2O_2$ $[M+H]^+$: 395, found 395. 58.2: MS (ESI): m/z calc'd for $C_{17}H_{17}BrClN_2O_2$ $[M+H]^+$: 395, found 395.

Scheme 32. Synthesis of (1R,3R)-N-(6-bromo-7-chloroisoquinolin-3-yl)-5-oxaspiro[2.4]heptane-1-carboxamide, (1R,3S)-N-(6-bromo-7-chloroisoquinolin-3-yl)-5-oxaspiro[2.4]heptane-1-carboxamide, (1S,3R)-N-(6-bromo-7-chloroisoquinolin-3-yl)-5-oxaspiro[2.4]heptane-1-carboxamide, or (1S,3S)-N-(6-bromo-7-chloroisoquinolin-3-yl)-5-oxaspiro[2.4]heptane-1-carboxamide (59.1), (59.2), (59.3), and (59.4) Stereochemistry not assigned

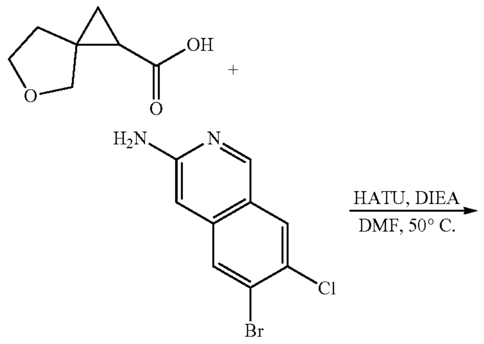

3

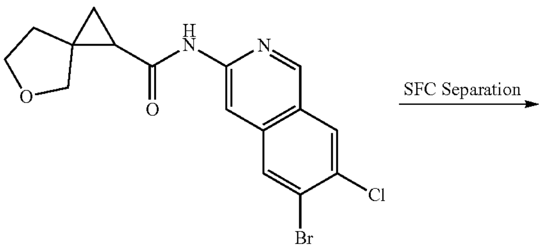

59

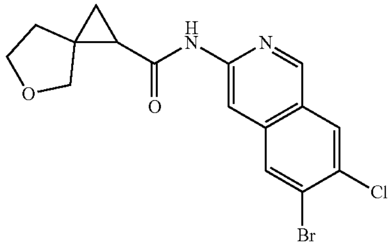

59.1

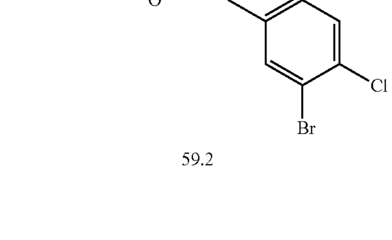

59.2

-continued

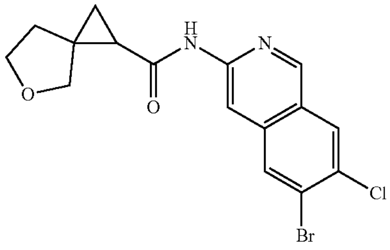

59.3

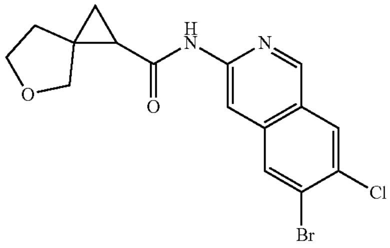

59.4

A vial was charged with 5-oxaspiro[2.4]heptane-1-carboxylic acid (331 mg, 2.330 mmol), 6-bromo-7-chloroisoquinolin-3-amine 3 (500 mg, 1.942 mmol) and HATU (1477 mg, 3.88 mmol). DMF (6472 μl) and DIPEA (678 μl, 3.88 mmol) were added and the reaction was heated to 50° C. overnight. The reaction was cooled to room temperature and then the product was added to 30 mL of water. The solid was filtered and collected. The solid was purified through a silica gel column 0-100% 3:1 EtOAc:EtOH/hexanes. The mixture of two stereoisomers was purified by chiral SFC (Lux-3, 21×250 (mm), Mobile phase A: 15% $CO_2$ Mobile phase B: 85% MeOH 0.1% $NH_4OH$) and concentrated to afford the title compounds 59.1 (tR=6.0 min), 59.2 (tR=6.9 min), 59.3 (tR=7.3 min) and 59.4 (tR=8.9 min). 59.1: MS (ESI): m/z calc'd for $C_{16}H_{15}BrClN_2O_2$ $[M+H]^+$: 381, found 381. 59.2: MS (ESI): m/z calc'd for $C_{16}H_{15}BrClN_2O_2$ $[M+H]^+$: 381, found 381. 59.3: MS (ESI): m/z calc'd for $C_{16}H_{15}BrClN_2O_2$ $[M+H]^+$: 381, found 381. 59.4: MS (ESI): m/z calc'd for $C_{16}H_{15}BrClN_2O_2$ $[M+H]^+$: 381, found 381.

Scheme 33. Synthesis of (R)-N-(6-bromo-7-chloroisoquinolin-3-yl)spiro[2.2]pentane-1-carboxamide or (S)-N-(6-bromo-7-chloroisoquinolin-3-yl)spiro[2.2]pentane-1-carboxamide (60.1) and (60.2)

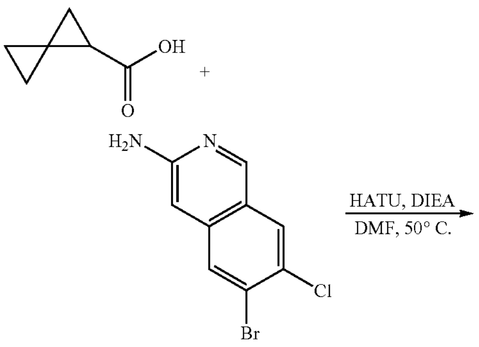

3

-continued

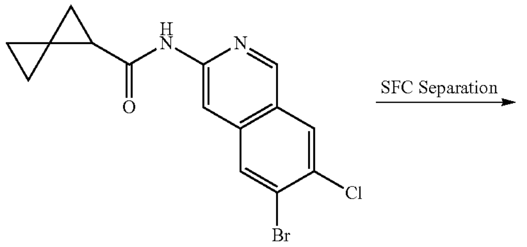

60

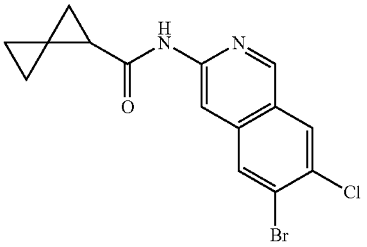

60.1

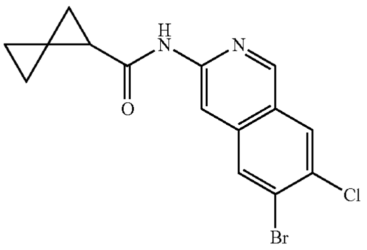

60.2

A vial was charged with 6-bromo-7-chloroisoquinolin-3-amine 3 (250 mg, 0.971 mmol), spiro[2.2]pentane-1-carboxylic acid (169 mg, 1.507 mmol), and HATU (517 mg, 1.359 mmol). DMF (5000 μl), and DIEA (1000 μl, 5.73 mmol) were added to the reaction and allowed to stir overnight at 50° C. The reaction was cooled to room temperature and water was added to form a precipitate. The solids were collected by vacuum filtration and dried. The residue was purified by column chromatography on silica (0-100% EtOAc/hexanes). The mixture of two stereoisomers was purified by chiral SFC (OJ-H, 21×250 (mm), Mobile phase A: $CO_2$: Mobile phase B: MeOH 0.1% $NH_4OH$) to afford the title compounds 60.1 (tR=4.0 min) and 60.2 (tR=5.4 min). 60.1: MS (ESI): m/z calc'd for $C_{15}H_{13}BrClN_2O$ $[M+H]^+$: 351, found 351. 60.2: MS (ESI): m/z calc'd for $C_{15}H_{13}BrClN_2O$ $[M+H]^+$: 351, found 351.

Scheme 34. Synthesis of (1R,3R)-N-(6-bromo-7-chloroisoquinolin-3-yl)-4,4-difluorospiro[2.2]pentane-1-carboxamide, (1R,3S)-N-(6-bromo-7-chloroisoquinolin-3-yl)-4,4-difluorospiro[2.2]pentane-1-carboxamide, (1S,3R)-N-(6-bromo-7-chloroisoquinolin-3-yl)-4,4-difluorospiro[2.2]pentane-1-carboxamide or (1S,3S)-N-(6-bromo-7-chloroisoquinolin-3-yl)-4,4-difluorospiro[2.2]pentane-1-carboxamide (61.1) and (61.2) Stereochemistry not assigned

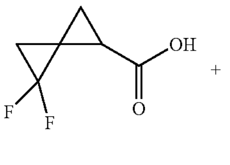

-continued

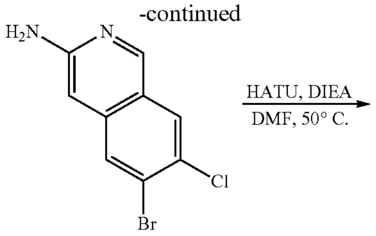

3

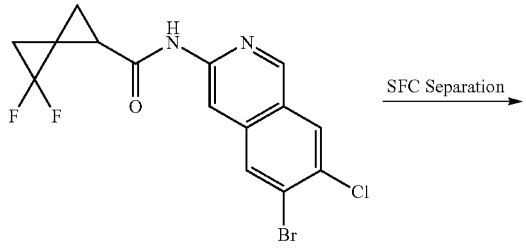

61

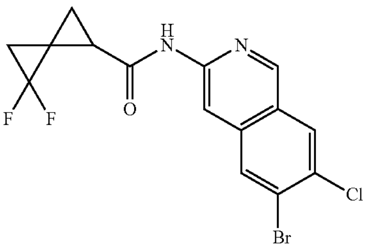

61.1

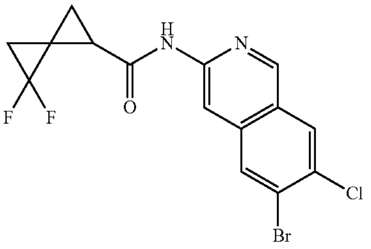

61.1

A vial was charged with 4,4-difluorospiro[2.2]pentane-1-carboxylic acid (444 mg, 3.00 mmol), 6-bromo-7-chloroisoquinolin-3-amine 3 (644 mg, 2.5 mmol) and HATU (1.9 g, 5.00 mmol). DMF (8.3 ml) and DIPEA (873 μl, 5.00 mmol) were added and the reaction was heated to 50° C. overnight. The reaction was diluted with ethyl acetate and washed with water. The organic layers were then combined and concentrated in vacuo. The residue was purified by column chromatography on silica gel, eluting with hexanes/3:1 EtOAc:EtOH to give N-(6-bromo-7-chloroisoquinolin-3-yl)-4,4-difluorospiro[2.2]pentane-1-carboxamide. 2 sets of 2 stereoisomers were isolated by chiral SFC (OJ-H, 21×250 (mm), Mobile phase A: $CO_2$: Mobile phase B: MeOH+0.1% $NH_4OH$) to afford the title compounds 61.1 (tR=3.3 min) and 61.2 (tR=5.0 min). 61.1: MS (ESI): m/z calc'd for $C_{15}H_{11}BrClF_2N_2O$ $[M+H]^+$: 387, found 387. 61.2: MS (ESI): m/z calc'd for $C_{15}H_{11}BrClF_2N_2O$ $[M+H]^+$: 387, found 387.

Scheme 35. Synthesis of Rac-N-(7-chloro-6-(4-(4-hydroxy-3-methyltetrahydrofuran-3-yl)piperazin-1-yl)isoquinolin-3-yl)-2-(methoxymethyl)cyclobutane-1-carboxamide (64)

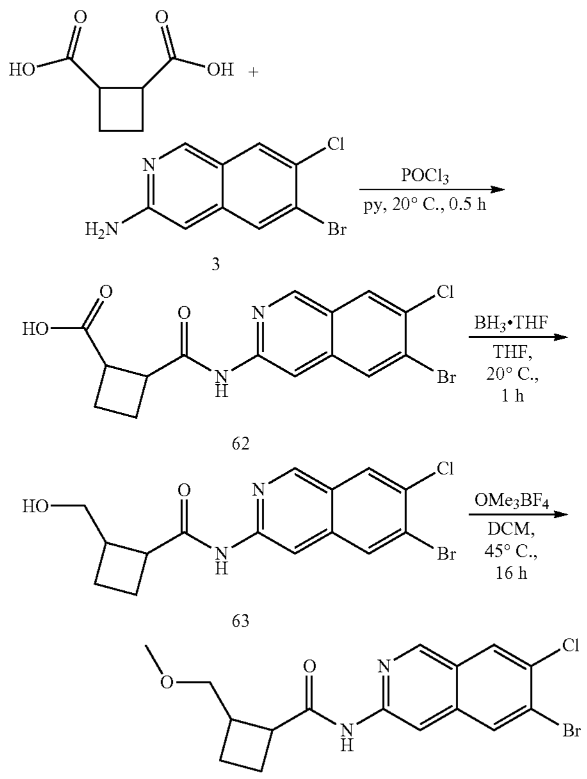

64

2-((6-bromo-7-chloroisoquinolin-3-yl)carbamoyl) cyclobutane-1-carboxylic acid (62)

To a solution of 6-bromo-7-chloroisoquinolin-3-amine (1 g, 3.88 mmol) and cyclobutane-1,2-dicarboxylic acid (1.12 g, 7.77 mmol) in pyridine (5 mL) was added $POCl_3$ (1.810 mL, 19.42 mmol) dropwise at 0° C. and the mixture was stirred at 20° C. for 0.5 hour. The mixture was added into ice water (8 mL) slowly and the pH was adjusted to 8 using saturated $NaHCO_3$. The mixture was extracted with EtOAc (50 mL×3). The combined organic layers were dried over anhydrous $Na_2SO_4$, filtered and concentrated in vacuo. The residue was purified by prep-HPLC (TFA) to afford title compound 62. MS (ESI): m/z calc'd for $C_{15}H_{13}BrClN_2O_3$ $[M+H]^+$: 383, found 383.

Rac-N-(6-bromo-7-chloroisoquinolin-3-yl)-2-(hydroxymethyl)cyclobutane-1-carboxamide (63)

To a solution of 2-((6-bromo-7-chloroisoquinolin-3-yl) carbamoyl)cyclobutane-1-carboxylic acid 62 (500 mg, 1.30 mmol) in THF (3 mL) was added $BH_3$·THF (336 mg, 3.91 mmol) at 0° C. The resulting mixture was stirred at 20° C. for 1 h. The reaction was poured into water (20 mL), extracted with EtOAc (30 mL×3) and the combined organic layers were washed with brine (50 mL) and dried over $Na_2SO_4$. The solution was filtered and concentrated in vacuo and the residue was purified by silica gel chromatography (ISCO®; 4 g SepaFlash® Silica Flash Column, Eluent of 0-100% EtOAc/Pet. ether gradient at 30 mL/min) to afford the title compound 63. MS (ESI): m/z calc'd for $C_{15}H_{15}BrClN_2O_2$ $[M+H]^+$: 369, found 369.

Rac-N-(6-bromo-7-chloroisoquinolin-3-yl)-2-(methoxymethyl)cyclobutane-1-carboxamide (64)

To a solution of N-(6-bromo-7-chloroisoquinolin-3-yl)-2-(hydroxymethyl) cyclobutane-1-carboxamide 63 (120 mg, 0.33 mmol) in anhydrous DCM (5 mL) was added trimethyloxonium tetrafluoroborate (134 mg, 0.91 mmol) and the resulting mixture was stirred at 45° C. for 16 hours. After filtration and evaporation, the residue was purified by prep-HPLC (TFA) to afford the title compound 64. MS (ESI): m/z calc'd for $C_{16}H_{17}BrClN_2O_2$ $[M+H]^+$: 383, found 383.

Scheme 36. Synthesis of Rac-N-(6-bromo-7-chloroisoquinolin-3-yl)-7-oxaspiro[3.5]nonane-1-carboxamide (65)

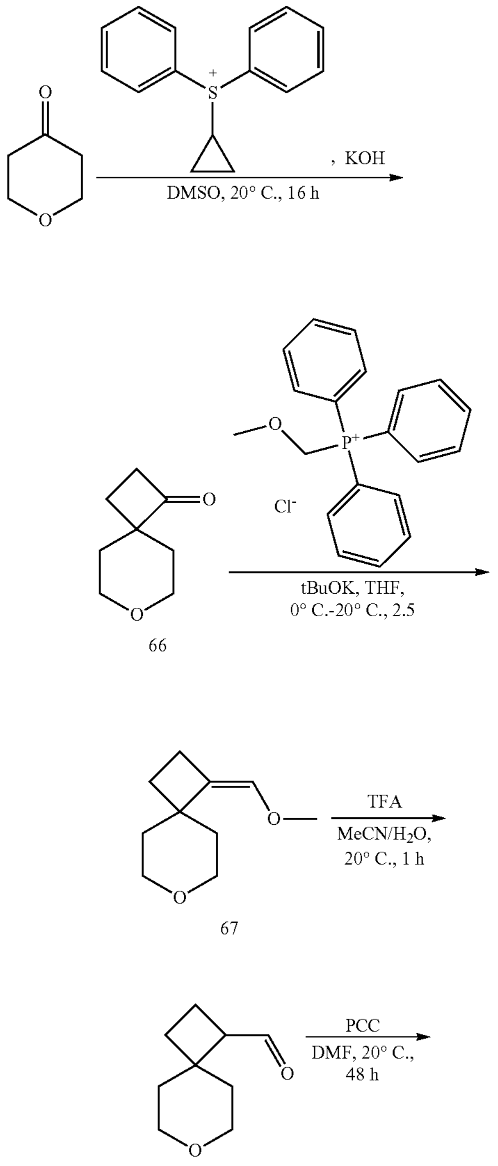

68

-continued

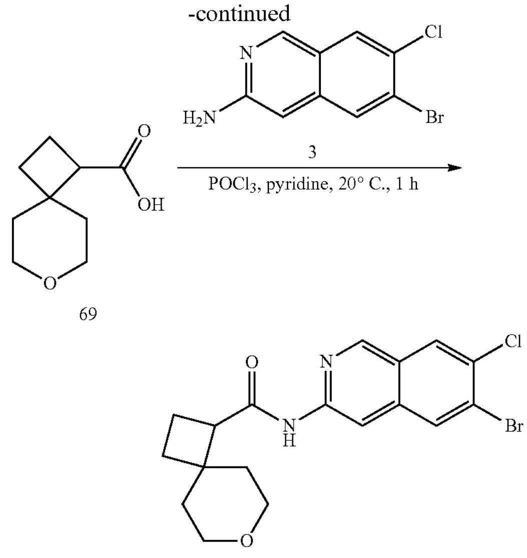

70

7-oxaspiro[3.5]nonan-1-one (66)

To a solution of tetrahydro-4H-pyran-4-one (1.5 g, 14.98 mmol) and cyclopropyldiphenylsulfonium (3.75 g, 16.5 mmol) in DMSO (40 mL) was added KOH (2.52 g, 44.9 mmol), and the resulting mixture was stirred at 20° C. for 16 h. The reaction was diluted with EtOAc (80 mL) and washed with brine (50 mL×3). The organic layer was dried over $Na_2SO_4$. After filtration and evaporation, the residue was purified by silica gel chromatography (ISCO®; 12 g Sepa-Flash® Silica Flash Column, Eluent of 0-15% EtOAc/Pet.ether gradient at 30 mL/min) to afford the title compound 66. $^1$H NMR (500 MHz, $CDCl_3$-d) δ 3.82 (m, 2H), 3.64 (m, 2H), 3.02 (t, J=8.5 Hz, 2H), 1.96-1.91 (m, 2H), 1.80 (m, 2H), 1.65 (m, 2H).

1-(methoxymethylene)-7-oxaspiro[3.5]nonane (67)

To a solution of (methoxymethyl)triphenylphosphonium chloride (4769 mg, 13.91 mmol) in THF (5 mL) was added KOtBu (1561 mg, 13.91 mmol), and then the resulting mixture was stirred at 20° C. for 0.5 h, then a solution of 7-oxaspiro[3.5]nonan-1-one 66 (650 mg, 4.64 mmol) in THF (3 mL) was added. The reaction mixture was stirred at 20° C. for 2 h. The reaction was poured into water (10 mL) and extracted with EtOAc (15 mL×3). The combined organic layer was dried over $Na_2SO_4$. After filtration and evaporation, the residue was purified by silica gel chromatography (ISCO®; 12 g SepaFlash© Silica Flash Column, Eluent of 0-3% EtOAc/Pet.ether gradient at 30 mL/min) to afford the title compound 67 as a mixture of E and Z isomers. $^1$H NMR (500 MHz, $CDCl_3$-d) δ 5.69 (t, J=2.0 Hz, 1H), 3.84 (m, 2H), 3.48 (s, 3H), 3.47-3.41 (m, 2H), 2.49 (m, 2H), 2.06 (m, 2H), 1.88-1.74 (m, 2H), 1.54 (m, 2H).

Rac-7-oxaspiro[3.5]nonane-1-carbaldehyde (68)

To a solution of 1-(methoxymethylene)-7-oxaspiro[3.5] nonane 57 (300 mg, 1.78 mmol) in MeCN (2 mL) and water (1 mL) was added TFA (0.2 mL). The resulting mixture was stirred at 20° C. for 1 h. Solvent was evaporated and the residue was used in the next step without further purification.

Rac-7-oxaspiro[3.5]nonane-1-carboxylic acid (69)

To a solution of 7-oxaspiro[3.5]nonane-1-carbaldehyde 68 (200 mg, 1.30 mmol) in DCM (8 mL) was added PCC (559 mg, 2.59 mmol) and silica gel (700 mg). The resulting mixture was stirred at 20° C. for 48 h. After filtration and evaporation, the residue was purified by prep-TLC ($SiO_2$, Pet.ether:EtOAc=1:1, v/v) to afford title compound 69.

Rac-N-(6-bromo-7-chloroisoquinolin-3-yl)-7-oxaspiro[3.5] nonane-1-carboxamide (70)

To a solution of 7-oxaspiro[3.5]nonane-1-carboxylic acid 69 (132 mg, 0.777 mmol) and 6-bromo-7-chloroisoquinolin-3-amine (200 mg, 0.777 mmol) in pyridine (5 mL) was added $POCl_3$ (0.145 mL, 1.553 mmol) dropwise at 0° C. The mixture was stirred at 20° C. for 1 hour. The mixture was added into water (8 mL) slowly and adjusted pH to 8 using saturated $NaHCO_3$. The mixture was extracted with EtOAc (30 mL). The organic layer was separated. The aqueous was extracted with EtOAc (40 mL×3). The combined organic layers were dried by anhydrous $Na_2SO_4$, filtered and concentrated in vacuo and the residue was purified by silica gel chromatography (ISCO®; 4 g SepaFlash® Silica Flash Column, Eluent of 0-45% EtOAc/Pet.ether gradient @ 30 mL/min) to afford title compound 70. MS (ESI): m/z calc'd for $C_{18}H_{19}BrClN_2O_2$ $[M+H]^+$: 409, found 409.

GENERAL SYNTHETIC SCHEMES AND PREPARATIVE EXAMPLES

The compounds of the invention may be prepared by methods known in the art of organic synthesis as set forth in part by the following general synthetic schemes and specific preparative examples. Starting materials are available commercially or may be prepared by known methods. In Tables 1 through 11, generally the racemic compounds, although isolated, were not tested unless otherwise indicated. Example numbers are assigned only to the isolated resolved compounds. The stereochemistry of some, but not all, peaks herein is assigned.

General Scheme 1

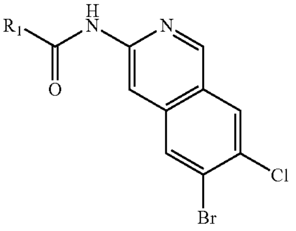

+

$R_1$ = alkyl
Gen-1

-continued

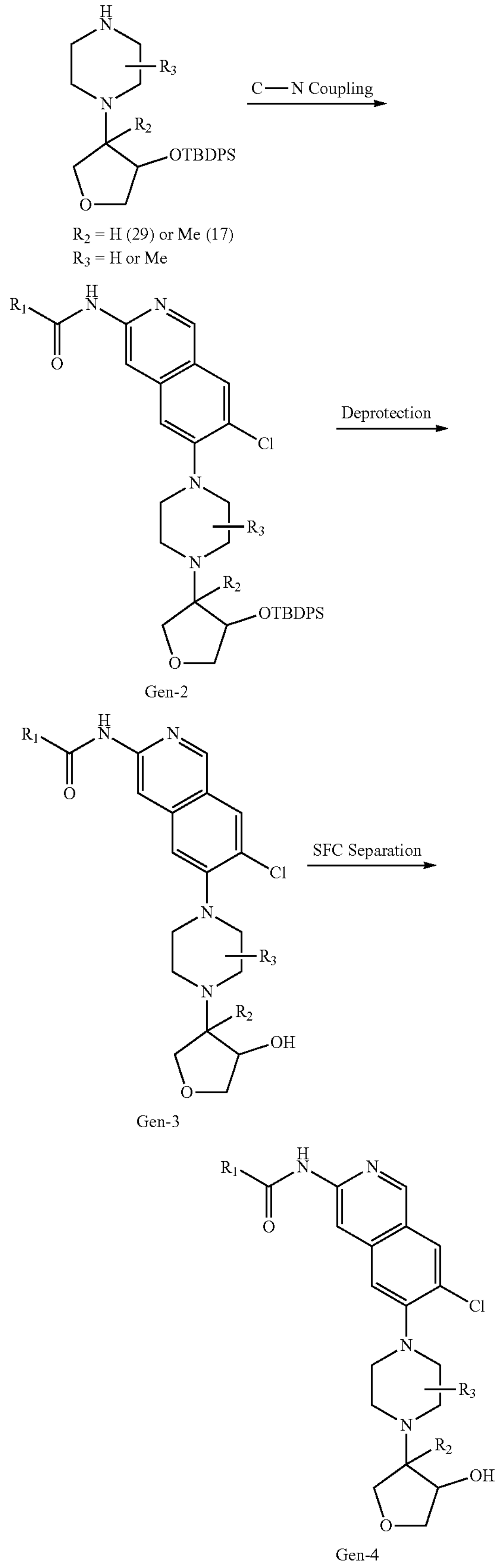

In General Scheme 1, Gen-2 was prepared through a Palladium-catalyzed C—N cross-coupling of 6-bromo-7-chloroisoquinolin-3-amides (Gen-1) with synthetically prepared intermediates 29 or 17. The corresponding protected alcohols were then deprotected to afford Gen-3 and the stereoisomers could then be separated by chiral SFC to provide fully elaborated products in the form of Gen-4. The representative compounds are described in more detail shown below.

Scheme 37. Synthesis of (3R,4R or 3S,4S)-N-(7-chloro-6-(4-(4-hydroxy-3-methyltetrahydrofuran-3-yl)piperazin-1-yl)isoquinolin-3-yl)cyclopropanecarboxamide(Ex-1.1) and (Ex-1.2)

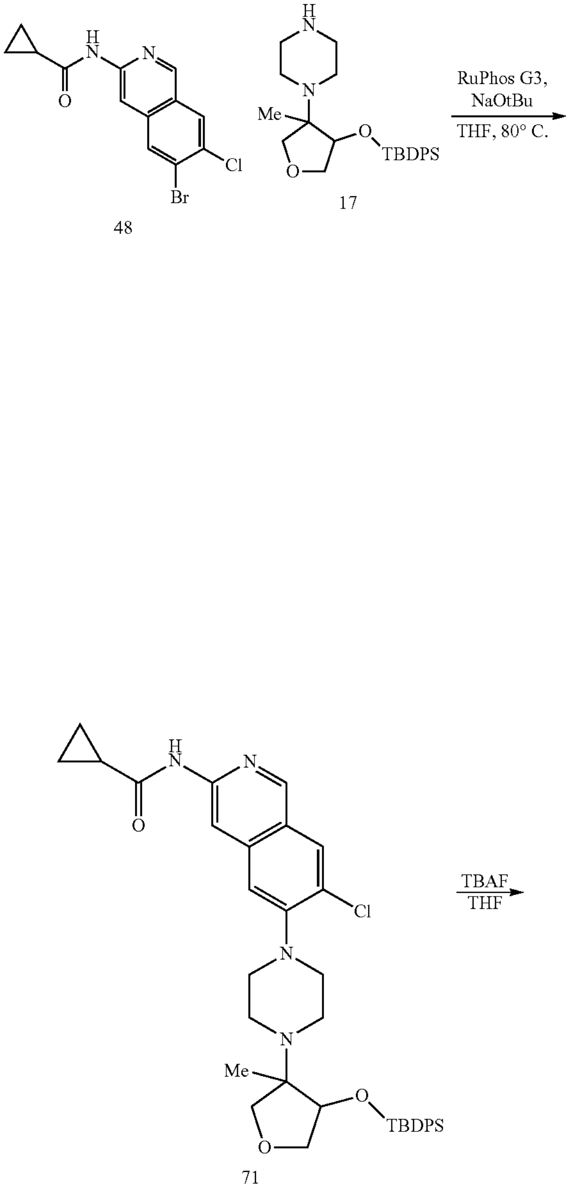

-continued

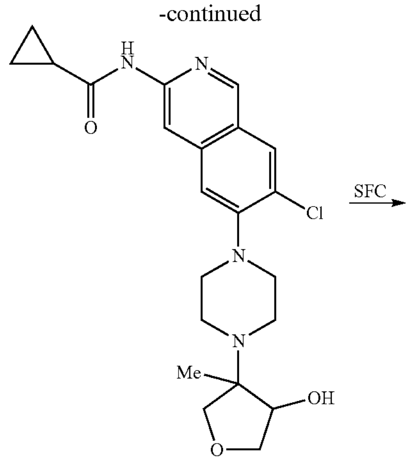

72

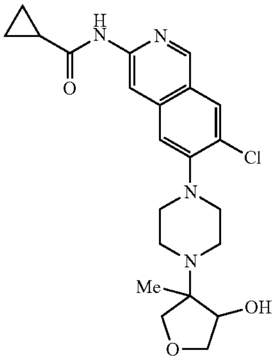

Ex-1.1

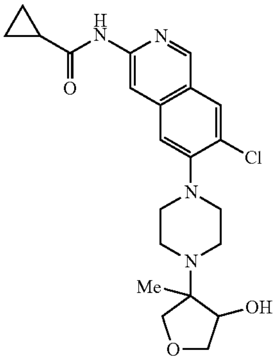

Ex-1.2

(3R,4R or 3S,4S)-N-(6-((4-(4-((tert-butyldiphenylsilyl)oxy)-3-methyltetrahydrofuran-3-yl)piperazin-1-yl)-7-chloroisoquinolin-3-yl)cyclopropanecarboxamide (71)

A vial was charged with N-(6-bromo-7-chloroisoquinolin-3-yl)cyclopropanecarboxamide 48 (100 mg, 0.307 mmol), (3R,4R) and (3S,4S)-1-(4-((tert-butyldiphenylsilyl)oxy)-3-methyltetrahydrofuran-3-yl)piperazine 17 (196 mg, 0.461 mmol), and RuPhos Pd G3 (64.2 mg, 0.077 mmol). The vial was sealed, and its contents were placed under an inert atmosphere by performing 3 vacuum/nitrogen cycles. THF (1536 μl) and 2M sodium tert-butoxide in THF (461 μl, 0.921 mmol) were added through the septum and the resulting mixture was allowed to stir for 1 hour at 80° C. The reaction mixture was cooled, diluted with EtOAc, and washed twice with saturated ammonium chloride and once with brine. The combined organic fractions were dried over anhydrous sodium sulfate, filtered and concentrated under reduced pressure. The residue was purified by column chromatography on silica (0-100% EtOAc/hexanes). The desired fractions were pooled and concentrated under reduced pressure to afford the title compound 71. MS (ESI): m/z calc'd for $C_{38}H_{46}ClN_4O_3Si$ $[M+H]^+$: 669, found 669.

(3R,4R or 3S,4S)-N-(7-chloro-6-(4-(4-hydroxy-3-methyltetrahydrofuran-3-yl)piperazin-1-yl)isoquinolin-3-yl)cyclopropanecarboxamide (Ex-1.1 and Ex-1.2)

A vial was charged with 71 (110 mg, 0.164 mmol) which was dissolved in THF (3287 μl) and chilled to 0° C. TBAF (1M in THF) (493 μl, 0.493 mmol) was added and the resulting mixture was allowed to stir overnight. The reaction mixture was diluted with EtOAc and washed twice with saturated ammonium chloride and once with brine. The combined organic fractions were dried over anhydrous sodium sulfate, filtered and concentrated under reduced pressure. The residue was purified by column chromatography on silica (0-100% EtOAc/hexanes). The desired fractions were pooled and concentrated under reduced pressure to afford the title compound as racemic mixture 72. The mixture of two stereoisomers was purified by chiral SFC (IB, 21×250 (mm), 40%/60% Methanol/$CO_2$+0.10% $NH_4OH$) and lyophilized to afford the chiral resolved stereoisomers of the title compound Ex-1.1 (tR=4.2 mm) and Ex-1.2 (tR=6.0 min). Ex-1.1: MS (ESI): m/z calc'd for $C_{22}H_{28}ClN_4O_3$ $[M+H]^+$: 431, found 431. $^1H$ NMR (499 MHz, DMSO-$d_6$) δ 10.87 (s, 1H), 8.97 (s, 1H), 8.37 (s, 1H), 8.15 (s, 1H), 7.41 (s, 1H), 4.35 (m, 1H), 3.98 (mm, 1H), 3.83-3.79 (m, 1H), 3.71 (m, 1H), 3.66 (m, 1H), 3.55 (m, 1H), 3.17 (s, 2H), 2.80-2.73 (m, 2H), 2.56-2.52 (m, 2H), 2.52-2.49 (m, 2H), 2.10-2.02 (m, 1H), 1.06 (s, 3H), 0.88-0.79 (m, 4H). Ex-1.2: MS (ESI): m/z calc'd for $C_{22}H_{28}ClN_4O_3$ $[M+H]^+$: 431, found 431. $^1H$ NMR (499 MHz, DMSO-$d_6$) δ $^1H$ NMR (499 MHz, DMSO-$d_6$) δ 10.87 (s, 1H), 8.97 (s, 1H), 8.37 (s, 1H), 8.15 (s, 1H), 7.41 (s, 1H), 4.35 (s, 1H), 3.98 (m, 1H), 3.81 (s, 1H), 3.71 (m, 1H), 3.66 (m, 1H), 3.55 (m, 1H), 3.18 (s, 3H), 2.76 (s, 2H), 2.51 (s, 4H), 2.14-2.00 (m, 1H), 1.06 (s, 3H), 0.84 (m, 4H).

Compounds in Table 1 below were prepared in accordance with the synthetic sequence illustrated in General Scheme 1 and Scheme 37 using the corresponding starting materials.

TABLE 1

| Example | Structure Name | Observed m/z [M + H]+ |
|---|---|---|
| 1.1 & 1.2 | 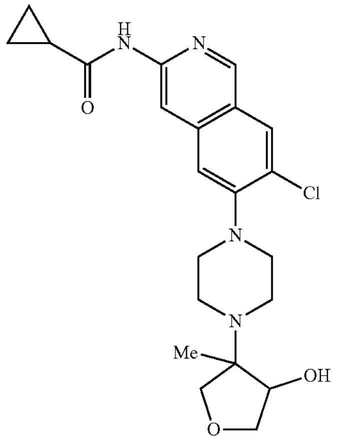 [SMILES: CC1(N2CCN(c3cc4cc(NC(=O)C5CC5)ncc4cc3Cl)CC2)COCC1O] Rac-N-(7-chloro-6-(4-(4-hydroxy-3-methyltetrahydrofuran-3-yl)piperazin-1-yl)isoquinolin-3-yl)cyclopropanecarboxamide, (3R,4R or 3S,4S)-N-(7-chloro-6-(4-(4-hydroxy-3-methyltetrahydrofuran-3-yl)piperazin-1-yl)isoquinolin-3-yl)cyclopropanecarboxamide, (3R,4R or 3S,4S)-N-(7-chloro-6-(4-(4-hydroxy-3-methyltetrahydrofuran-3-yl)piperazin-1-yl)isoquinolin-3-yl)cyclopropanecarboxamide | Cal'c: 431 Found: 431 |
| 1.3 & 1.4 | 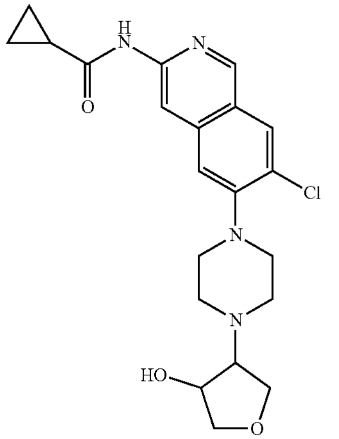 [SMILES: O=C(Nc1cc2cc(N3CCN(C4COCC4O)CC3)c(Cl)cc2cn1)C1CC1] Rac-N-(7-chloro-6-(4-(4-hydroxytetrahydrofuran-3-yl)piperazin-1-yl)isoquinolin-3-yl)cyclopropanecarboxamide, (3R,4R or 3S,4S)-N-(7-chloro-6-(4-(4-hydroxytetrahydrofuran-3-yl)piperazin-1-yl)isoquinolin-3-yl)cyclopropanecarboxamide, (3R,4R or 3S,4S)-N-(7-chloro-6-(4-(4-hydroxytetrahydrofuran-3-yl)piperazin-1-yl)isoquinolin-3-yl)cyclopropanecarboxamide | Cal'c: 417 Found: 417 |

TABLE 1-continued

| Example | Structure Name | Observed m/z [M + H]+ |
|---|---|---|
| 1.5 & 1.6 | 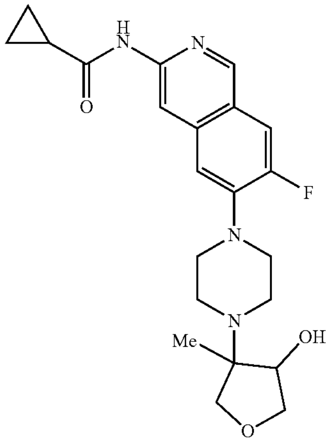 [SMILES: CC1(N2CCN(c3cc4cc(NC(=O)C5CC5)ncc4cc3F)CC2)COCC1O] Rac-N-(7-fluoro-6-(4-(4-hydroxy-3-methyltetrahydrofuran-3-yl)piperazin-1-yl)isoquinolin-3-yl)cyclopropanecarboxamide, (3R,4R or 3S,4S)-N-(7-fluoro-6-(4-(4-hydroxy-3-methyltetrahydrofuran-3-yl)piperazin-1-yl)isoquinolin-3-yl)cyclopropanecarboxamide, (3R,4R or 3S,4S)-N-(7-fluoro-6-(4-(4-hydroxy-3-methyltetrahydrofuran-3-yl)piperazin-1-yl)isoquinolin-3-yl)cyclopropanecarboxamide | Cal'c: 415 Found: 415 |
| 1.7 & 1.8 | 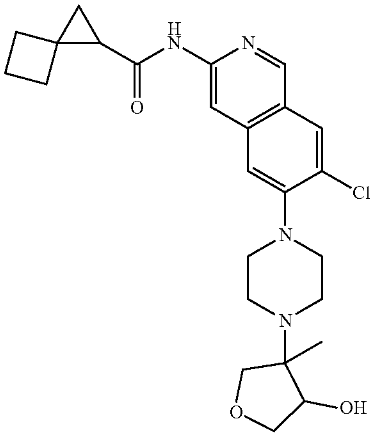 [SMILES: CC1(N2CCN(c3cc4cc(NC(=O)C5CC56CCC6)ncc4cc3Cl)CC2)COCC1O] Rac-N-(7-chloro-6-(4-(4-hydroxy-3-methyltetrahydrofuran-3-yl)piperazin-1-yl)isoquinolin-3-yl)spiro[2.3]hexane-1-carboxamide, (1R or 1S)-N-(7-chloro-6-(4-((3R,4R or 3S,4S)-4-hydroxy-3-methyltetrahydrofuran-3-yl)piperazin-1-yl)isoquinolin-3-yl)spiro[2.3]hexane-1-carboxamide, (1R or 1S)-N-(7-chloro-6-(4-((3R,4R or 3S,4S)-4-hydroxy-3-methyltetrahydrofuran-3-yl)piperazin-1-yl)isoquinolin-3-yl)spiro[2.3]hexane-1-carboxamide | Cal'c: 471 Found: 471 |

TABLE 1-continued

| Example | Structure<br>Name | Observed<br>m/z<br>[M + H]+ |
|---|---|---|
| 1.9, 1.10 | 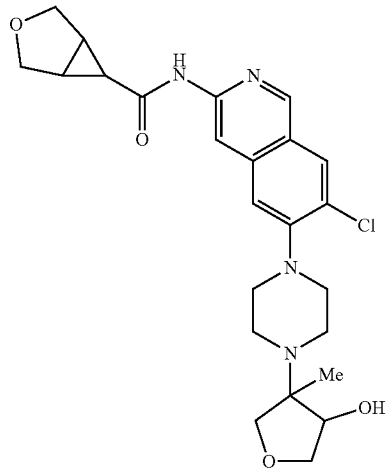 [SMILES: CC1(N2CCN(c3cc4cc(NC(=O)C5C6COCC65)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-3-oxabicyclo[3.1.0]hexane-6-carboxamide,<br>(1R or S)-N-(7-chloro-6-(4-((3R,4R or 3S,4S)-4-hydroxy-3-methyltetrahydrofuran-3-yl)piperazin-1-yl)isoquinolin-3-yl)-3-oxabicyclo[3.1.0]hexane-6-carboxamide,<br>(1R or S)-N-(7-chloro-6-(4-((3R,4R or 3S,4S)-4-hydroxy-3-methyltetrahydrofuran-3-yl)piperazin-1-yl)isoquinolin-3-yl)-3-oxabicyclo[3.1.0]hexane-6-carboxamide | Cal'c:<br>473<br>Found:<br>473 |

TABLE 1-continued

| Example | Structure Name | Observed m/z [M + H]+ |
|---|---|---|
| 1.11, 1.12, 1.13, 1.14, 1.15, 1.16, 1.17, & 1.18 | 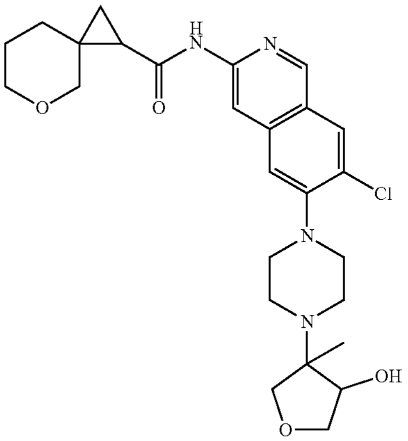 [SMILES: CC1(N2CCN(c3cc4cc(NC(=O)C5CC56CCCOC6)ncc4cc3Cl)CC2)COCC1O] Rac-N-(7-chloro-6-(4-((3S,4S or 3R,4R)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide, (1R,3S, or 1R,3R, or 1S,3S, or 1S,3R)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.5]octane-1-carboxamide | Cal'c: 501 Found: 501 |

TABLE 1-continued

| Example | Structure<br>Name | Observed<br>m/z<br>[M + H]+ |
|---|---|---|
| 1.19 & 1.20 | 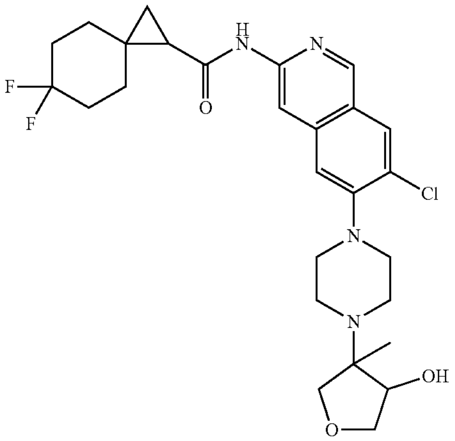 [SMILES: CC1(N2CCN(c3cc4cc(NC(=O)C5CC56CCC(F)(F)CC6)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-6,6-difluorospiro[2.5]octane-1-carboxamide,<br>(1R or 1S)-N-(7-chloro-6-(4-((3R,4R or 3S,4S)-4-hydroxy-3-methyltetrahydrofuran-3-yl)piperazin-1-yl)isoquinolin-3-yl)-6,6-difluorospiro[2.5]octane-1-carboxamide, (1R or 1S)-N-(7-chloro-6-(4-((3R,4R or 3S,4S)-4-hydroxy-3-methyltetrahydrofuran-3-yl)piperazin-1-yl)isoquinolin-3-yl)-6,6-difluorospiro[2.5]octane-1-carboxamide | Cal'c: 535<br>Found: 535 |
| 1.21 & 1.22 | 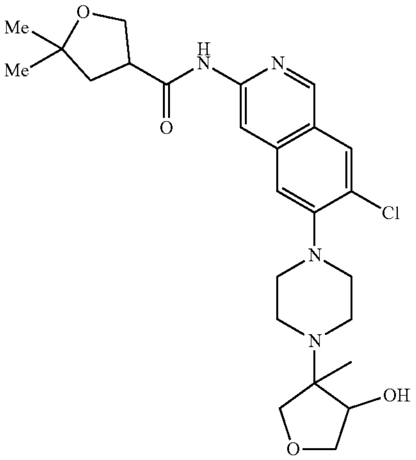 [SMILES: CC1(C)CC(C(=O)Nc2cc3cc(N4CCN(C5(C)COCC5O)CC4)c(Cl)cc3cn2)CO1]<br>Rac-N-(7-chloro-6-(4-(4-hydroxy-3-methyltetrahydrofuran-3-yl)piperazin-1-yl)isoquinolin-3-yl)-5,5-dimethyltetrahydrofuran-3-carboxamide,<br>(R or S)-N-(7-chloro-6-(4-((3R,4R or 3S,4S)-4-hydroxy-3-methyltetrahydrofuran-3-yl)piperazin-1-yl)isoquinolin-3-yl)-5,5-dimethyltetrahydrofuran-3-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-5,5-dimethyltetrahydrofuran-3-carboxamide | Cal'c: 489<br>Found: 489 |

TABLE 1-continued

| Example | Structure<br>Name | Observed<br>m/z<br>[M + H]+ |
|---|---|---|
| 1.23 & 1.24 | 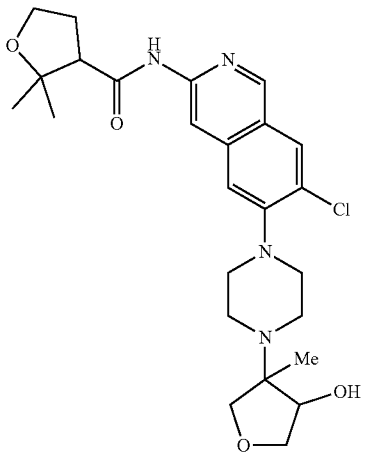 [SMILES: CC1(C)OCCC1C(=O)Nc1cc2cc(N3CCN(C4(C)COCC4O)CC3)c(Cl)cc2cn1]<br>Rac-N-(7-chloro-6-(1-(4-hydroxy-3-methyltetrahydrofuran-3-yl)piperazin-4-yl)isoquinolin-3-yl)-2,2-dimethyltetrahydrofuran-3-carboxamide,<br>(R or S)-N-(7-chloro-6-(1-((3R,4R or 3S,4S)-4-hydroxy-3-methyltetrahydrofuran-3-yl)piperazin-4-yl)isoquinolin-3-yl)-2,2-dimethyltetrahydrofuran-3-carboxamide, (R or S)-N-(7-chloro-6-(1-((3R,4R or 3S,4S)-4-hydroxy-3-methyltetrahydrofuran-3-yl)piperazin-4-yl)isoquinolin-3-yl)-2,2-dimethyltetrahydrofuran-3-carboxamide | Cal'c:<br>489<br>Found:<br>489 |
| 1.25 & 126 | 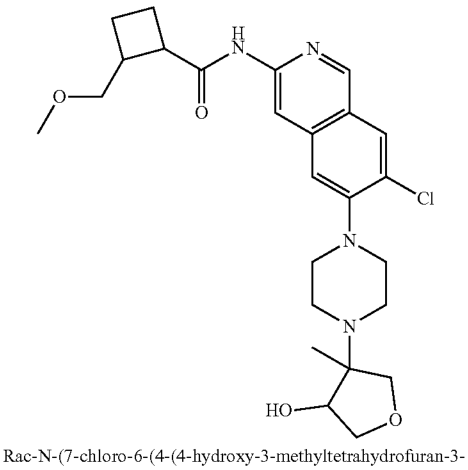<br>Rac-N-(7-chloro-6-(4-(4-hydroxy-3-methyltetrahydrofuran-3-yl)piperazin-1-yl)isoquinolin-3-yl)-2-(methoxymethyl)cyclobutane-1-carboxamide,<br>(1R,2S or 1R,2R, or 1S,2S, or 1S,2R)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide, (1R,2S or 1R,2R, or 1S,2S, or 1S,2R)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide | Cal'c:<br>489<br>Found:<br>489 |

TABLE 1-continued

| Example | Structure<br>Name | Observed<br>m/z<br>[M + H]+ |
|---|---|---|
| 1.27 & 1.28 | 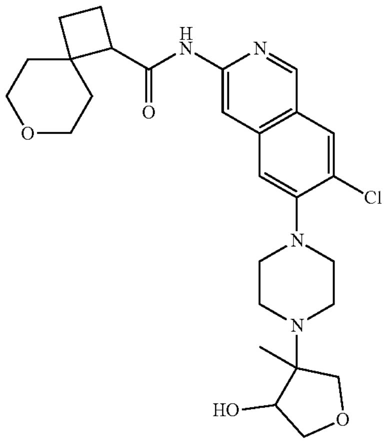 [SMILES: CC1(N2CCN(c3cc4cc(NC(=O)C5CCC56CCOCC6)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-7-oxaspiro[3.5]nonane-1-carboxamide,<br>(R or S)-N-(7-chloro-6-(4-((3R,4R or 3S,4S)-4-hydroxy-3-methyltetrahydrofuran-3-yl)piperazin-1-yl)isoquinolin-3-yl)-7-oxaspiro[3.5]nonane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-7-oxaspiro[3.5]nonane-1-carboxamide | Cal'c:<br>515<br>Found:<br>515 |

General Scheme 2.

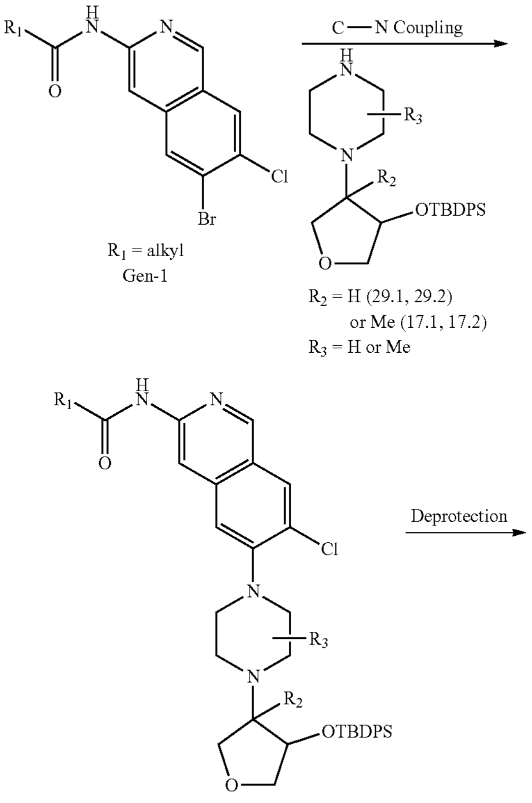

Gen-5

-continued

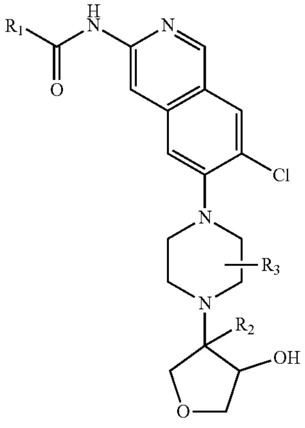

Gen-6

In General Scheme 2, Palladium-catalyzed C—N coupling of 6-bromo-7-chloroisoqulnolin-3-amides (Gen-1) with synthetically prepared chiral piperazines intermediates (29.1, 29.2, 17.1 or 17.2) was performed to afford Gen-5. The corresponding TBDPS protected alcohol was then deprotected to access fully elaborated products in the form of Gen-6. The representative compounds are shown below.

Scheme 38. Synthesis of N-(7-chloro-6-(4-(4-hydroxy-3-methyltetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-6-oxaspiro[2.5]octane-1-carboxamide (Ex-2.1)

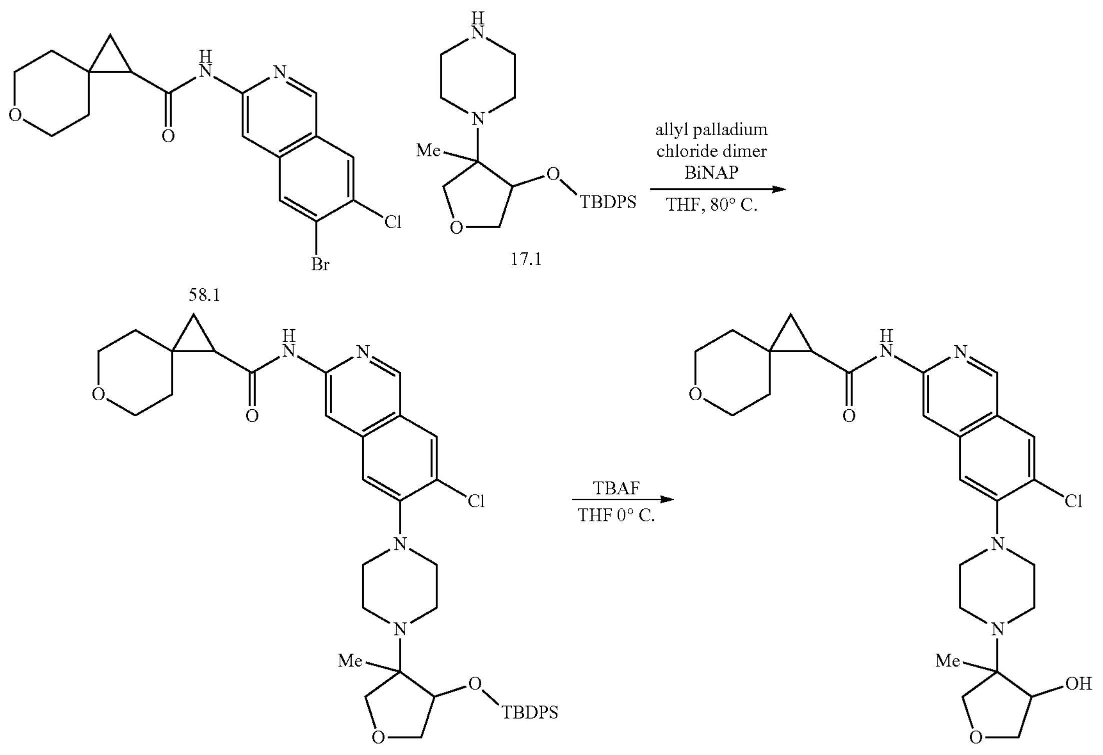

58.1

17.1

73

Ex-2.1

N-(6-(4-(4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide, (R or S)-N-(6-(4-((3R,4R or 3S,4S)-4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide (63)

A vial was charged with allylpalladium chloride dimer (0.042 g, 0.114 mmol) and BINAP (0.142 g, 0.227 mmol). The vial was evacuated and back filled with nitrogen 3 times, and 5 mL of THF was added to the vial and stirred for 10 minutes to make the palladium complex. In a 100 mL round bottom flask was added N-(6-bromo-7-chloroisoquinolin-3-yl)-6-oxaspiro[2.5]octane-1-carboxamide 58.1 (1.8 g, 4.55 mmol) and (3R,4R) 1-(4-(tert-butyldiphenylsilyl)oxy)-3-methyltetrahydrofuran-3-yl)piperazine or (3S,4S) 1-(4-(tert-butyldiphenylsilyl)oxy)-3-methyltetrahydrofuran-3-yl)piperazine 17.1 (3.86 g, 9.10 mmol). The flask was evacuated and back filled with nitrogen 3 times and the remainder of THF (22.75 ml) was added. The palladium complex was added to the round bottom followed by sodium tert-butoxide (11.37 ml, 22.75 mmol). The reaction was heated to 60° C. for 4 hours. The reaction was cooled, diluted with ethyl acetate, washed with ammonium chloride and concentrated in vacuo. The title compound 73 was used directly in a subsequent reaction without further purification. MS (ESI): m/z calc'd for $C_{42}H_{52}ClN^4O_4Si$ $[M+H]^+$: 739, found 739.

N-(7-chloro-6-(4-(4-hydroxy-3-methyltetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-6-oxaspiro[2.5]octane-1-carboxamide (Ex-2.1)

N-(6-(4-(4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide, (R)-N-(6-(4-((3R,4R)-4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide, (R)-N-(6-(4-((3S,4S)-4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide, (S)-N-(6-(4-((3R,4R)-4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide, or (S)-N-(6-(4-((3S,4S)-4-((tert-butyldiphenylsilyl)oxy)-3-methyltetrahydrofuran-3-yl)piperazin-1-yl)-7-chloroisoquinolin-3-yl)-6-oxaspiro[2.5]octane-1-carboxamide 73 (60 mg, 0.081 mmol), was dissolved in THF (811 μl) and chilled to 0° C. TBAF (243 μl, 0.243 mmol) was added and the resulting mixture was allowed to stir for 1 hour at room temperature. The reaction mixture was diluted with EtOAc and washed twice with saturated $NH_4Cl$ and once with brine. The combined organic fractions were dried over anhydrous sodium sulfate, filtered and concentrated under reduced pressure. The residue was purified twice by column chromatography on silica (0-100% EtOAc/hexanes) to afford the title compound Ex-2.1. MS (ESI): m/z calc'd for $C_{26}H_{34}ClN_4O_4$ $[M+H]^+$: 501, found 501. $^1H$ NMR (499 MHz, DMSO-$d_6$) δ 10.87 (s, 1H), 8.98 (s, 1H), 8.38 (s, 1H), 8.15 (s, 1H), 7.43 (s, 1H), 4.36 (s, 1H), 3.98 (dd, J=9.6, 3.3 Hz, 1H), 3.81 (s, 1H), 3.75-3.63 (m, 5H), 3.63-3.57 (m, 1H), 3.55 (d, J=7.3 Hz, 1H), 3.45-3.39 (m, 2H), 3.17 (s, 4H), 2.81-2.72 (m, 2H), 2.02 (t, 1H), 1.76-1.61 (m, 2H), 1.57-1.49 (m, 1H), 1.40-1.33 (m, 1H), 1.11 (t, 1H), 1.05 (s, 3H), 0.96-0.91 (m, 1H).

Compounds in Table 2 below were prepared in accordance with the synthetic sequence illustrated in General Scheme 2 and Scheme 38 using the corresponding starting materials.

TABLE 2

| Example | Structure Name | Observed m/z $[M + H]^+$ |
|---|---|---|
| 2.1 & 2.2 | 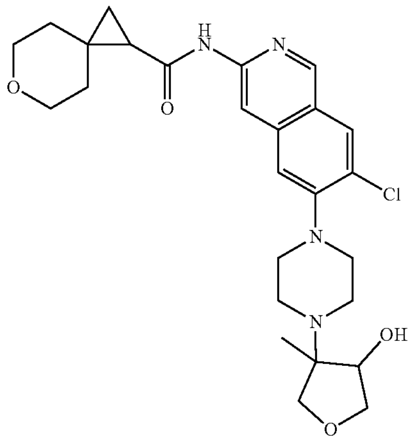 [SMILES: CC1(N2CCN(c3cc4cc(NC(=O)C5CC56CCOCC6)ncc4cc3Cl)CC2)COCC1O] Rac-N-(7-chloro-6-(4-(4-hydroxy-3-methyltetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)-6-oxaspiro[2.5]octane-1-carboxamide | Cal'c: 501 Found: 501 |
| 2.3 & 2.4 | 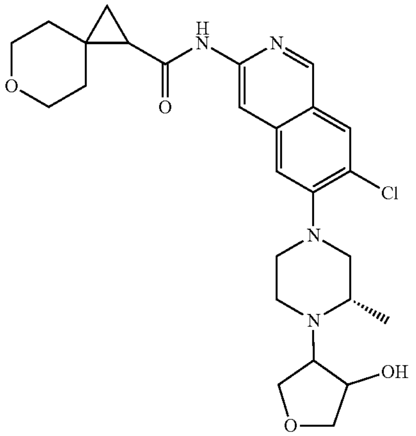 [SMILES: C[C@H]1CN(c2cc3cc(NC(=O)C4CC45CCOCC5)ncc3cc2Cl)CCN1C1COCC1O] Rac-N-{7-chloro-6-[(3S)-4-hydroxyoxolan-3-yl)-3-methylpiperazin-1-yl]isoquinolin-3-yl}-6-oxaspiro[2.5]octane-1-carboxamide, (R or S)-N-{7-chloro-6-[(3S or 3R)-4-(3R,4R or 3S,4S)-4-hydroxyoxolan-3-yl)-3-methylpiperazin-1-yl]isoquinolin-3-yl}-6-oxaspiro[2.5]octane-1-carboxamide, (R or S)-N-{7-chloro-6-[(3S or 3R)-4-(3R, 4R or 3S,4S)-4-hydroxyoxolan-3-yl)-3-methylpiperazin-1-yl]isoquinolin-3-yl}-6-oxaspiro[2.5]octane-1-carboxamide | Cal'c: 501 Found: 501 |

TABLE 2-continued

| Example | Structure<br>Name | Observed<br>m/z<br>[M + H]+ |
|---|---|---|
| 2.5, 2.6, 2.7, 2.8 | 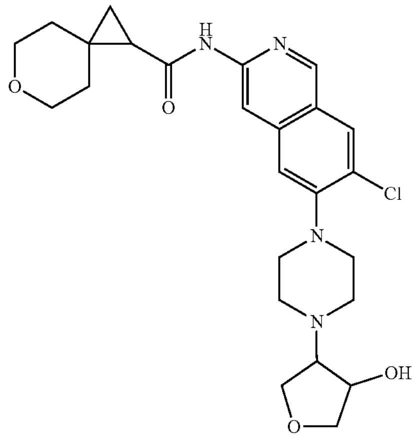 [SMILES: O=C(Nc1cc2cc(N3CCN(C4COCC4O)CC3)c(Cl)cc2cn1)C1CC12CCOCC2]<br>Rac-N-(7-chloro-6-(4-(4-hydroxytetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxytetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxytetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxytetrahydrofuran-3-yl)piperazin-1-yl)isoquinolin-3-yl)-6-oxaspiro[2.5]octane-1-carboxamide, (R or S)-N-(7-chloro-6-(4-((3R,4R or 3S,4S)-4-hydroxytetrahydrofuran-3-yl)piperazin-1-yl)isoquinolin-3-yl)-6-oxaspiro[2.5]octane-1-carboxamide | Cal'c: 487<br>Found: 487 |
| 2.9, 2.10, 2.11 | 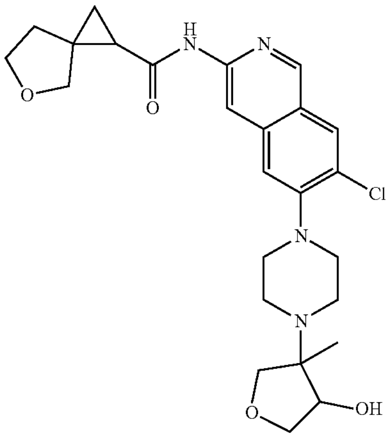 [SMILES: CC1(N2CCN(c3cc4cc(NC(=O)C5CC56CCOC6)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-5-oxaspiro[2.4]heptane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.4]heptane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.4]heptane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5-oxaspiro[2.4]heptane-1-carboxamide | Cal'c: 487<br>Found: 487 |

TABLE 2-continued

| Example | Structure<br>Name | Observed m/z [M + H]+ |
|---|---|---|
| 2.12, 2.13, 2.14, 2.15 | 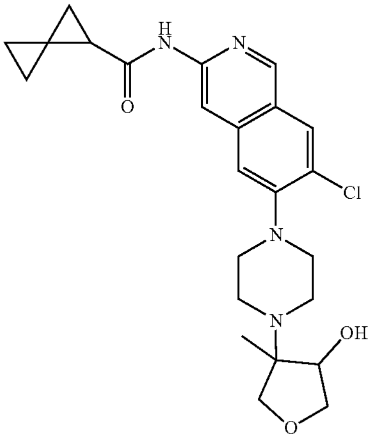 [SMILES: CC1(N2CCN(c3cc4cc(NC(=O)C5CC56CC6)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)spiro[2.2]pentane-1-carboxamide, (R or S)-N-(7-chloro-6-(4-((3R, 4R or 3S,4S)-4-hydroxy-3-methyltetrahydrofuran-3-yl)piperazin-1-yl)isoquinolin-3-yl)spiro[2.2]pentane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)spiro[2.2]pentane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)spiro[2.2]pentane-1-carboxamide, (R or S)-N-(7-chloro-6-(4-((3R,4R or 3S,4S)-4-hydroxy-3-methyltetrahydrofuran-3-yl)piperazin-1-yl)isoquinolin-3-yl)spiro[2.2]pentane-1-carboxamide | Cal'c: 457<br>Found: 457 |
| 2.16 | 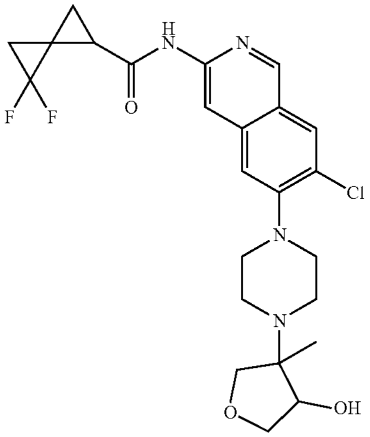 [SMILES: CC1(N2CCN(c3cc4cc(NC(=O)C5CC56CC6(F)F)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide,<br>(1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-4,4-difluorospiro[2.2]pentane-1-carboxamide | Cal'c: 493<br>Found: 493 |

TABLE 2-continued

| Example | Structure<br>Name | Observed<br>m/z<br>[M + H]+ |
|---|---|---|
| 2.17 | 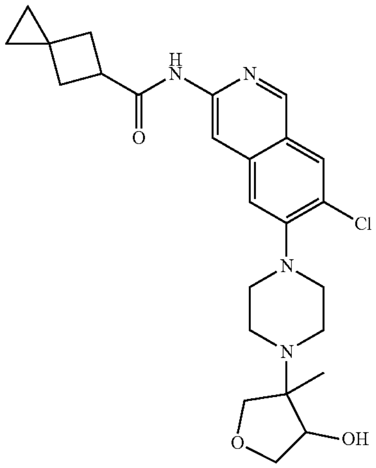 [SMILES: CC1(N2CCN(c3cc4cc(NC(=O)C5CC6(CC6)C5)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)spiro[2.3]hexane-5-carboxamide, N-(7-chloro-6-(4-((3R,4R or 3S,4S)-4-hydroxy-3-methyltetrahydrofuran-3-yl)piperazin-1-yl)isoquinolin-3-yl)spiro[2.3]hexane-5-carboxamide | Cal'c: 471 Found: 471 |
| 2.18 | 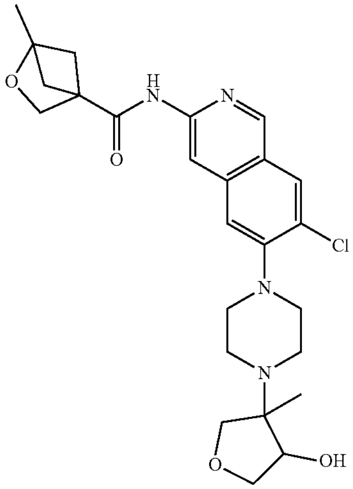 [SMILES: CC12CC(C(=O)Nc3cc4cc(N5CCN(C6(C)COCC6O)CC5)c(Cl)cc4cn3)(CO1)C2]<br>Rac-N-(7-chloro-6-(4-((35,4S or 3R,4R)-4-hydroxy-3-methyltetrahydrofuran-3-yl)piperazin-1-yl)isoquinolin-3-yl)-1-methyl-2-oxabicyclo[2.1.1]hexane-4-carboxamide, N-(7-chloro-6-(4-((3R,4R or 3S,4S)-4-hydroxy-3-methyltetrahydrofuran-3-yl)piperazin-1-yl)isoquinolin-3-yl)-1-methyl-2-oxabicyclo[2.1.1]hexane-4-carboxamide | Cal'c: 487 Found: 487 |

TABLE 2-continued

| Example | Structure<br>Name | Observed<br>m/z<br>$[M + H]^+$ |
|---|---|---|
| 2.19 | 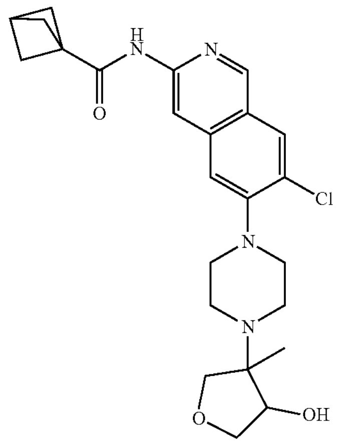 [SMILES: CC1(N2CCN(c3cc4cc(NC(=O)C56CC(C5)C6)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)bicyclo[1.1.1]pentane-1-carboxamide,<br>N-(7-chloro-6-(4-((3R,4R or 3S,4S)-4-hydroxy-3-methyltetrahydrofuran-3-yl)piperazin-1-yl)isoquinolin-3-yl)bicyclo[1.1.1]pentane-1-carboxamide | Cal'c:<br>457<br>Found:<br>457 |
| 2.20 & 2.21 | 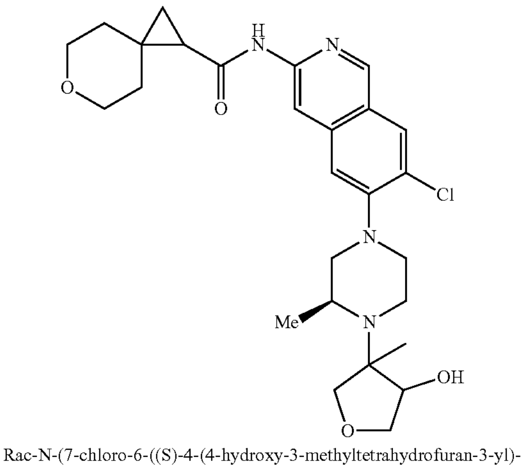<br>Rac-N-(7-chloro-6-((S)-4-(4-hydroxy-3-methyltetrahydrofuran-3-yl)-3-methylpiperazin-1-yl)isoquinolin-3-yl)-6-oxaspiro[2.5]octane-1-carboxamide,<br>(R or S)-N-(7-chloro-6-((S or R)-4-((3R,4R, or 3S,4S)-4-hydroxy-3-methyltetrahydrofuran-3-yl)-3-methylpiperazin-1-yl)isoquinolin-3-yl)-6-oxaspiro[2.5]octane-1-carboxamide, (R or S)-N-(7-chloro-6-((S or R)-4-((3R,4R, or 3S,4S)-4-hydroxy-3-methyltetrahydrofuran-3-yl)-3-methylpiperazin-1-yl)isoquinolin-3-yl)-6-oxaspiro[2.5]octane-1-carboxamide | Cal'c:<br>515<br>Found:<br>515 |

TABLE 2-continued

| Example | Structure Name | Observed m/z [M + H]+ |
|---|---|---|
| 2.22 | 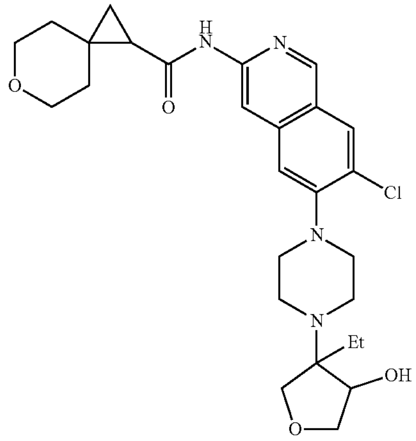 [SMILES: CCC1(N2CCN(c3cc4cc(NC(=O)C5CC56CCOCC6)ncc4cc3Cl)CC2)COCC1O] Rac-N-(7-chloro-6-(4-(3-ethyl-4-hydroxytetrahydrofuran-3-yl)piperazin-1-yl)isoquinolin-3-yl)-6-oxaspiro[2.5]octane-1-carboxamide , (R or S)-N-(7-chloro-6-(4-((3R,4R or 3S,4S)-3-ethyl-4-hydroxytetrahydrofuran-3-yl)piperazin-1-yl)isoquinolin-3-yl)-6-oxaspiro[2.5]octane-1-carboxamide | Cal'c: 515 Found: 515 |
| 2.23 | 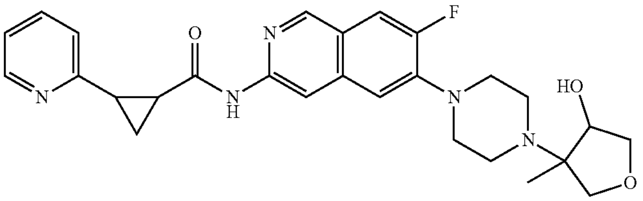 [SMILES: CC1(N2CCN(c3cc4cc(NC(=O)C5CC5c5ccccn5)ncc4cc3F)CC2)COCC1O] Rac-N-[7-fluoro-6-[4-[4-hydroxy-3-methyl-tetrahydrofuran-3-yl]piperazin-1-yl]-3-isoquinolyl]-2-(2-pyridyl)cyclopropanecarboxamide, (1R,2R or 1S,2S)-N-[7-fluoro-6-[4-[(3R,4R or 3S,4S)-4-hydroxy-3-methyl-tetrahydrofuran-3-yl]piperazin-1-yl]-3-isoquinolyl]-2-(2-pyridyl)cyclopropanecarboxamide, | Cal'c: 492 Found: 492 |

General Scheme 3.

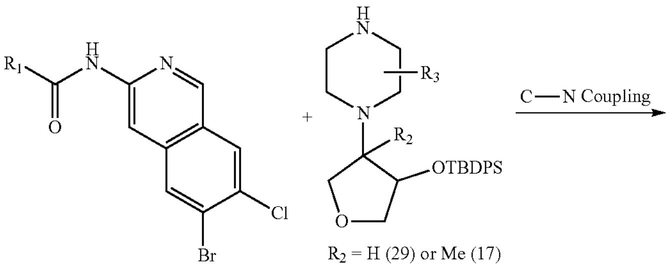

$R_1$ = alkyl
Gen-1

$R_2$ = H (29) or Me (17)
$R_3$ = H or Me

-continued

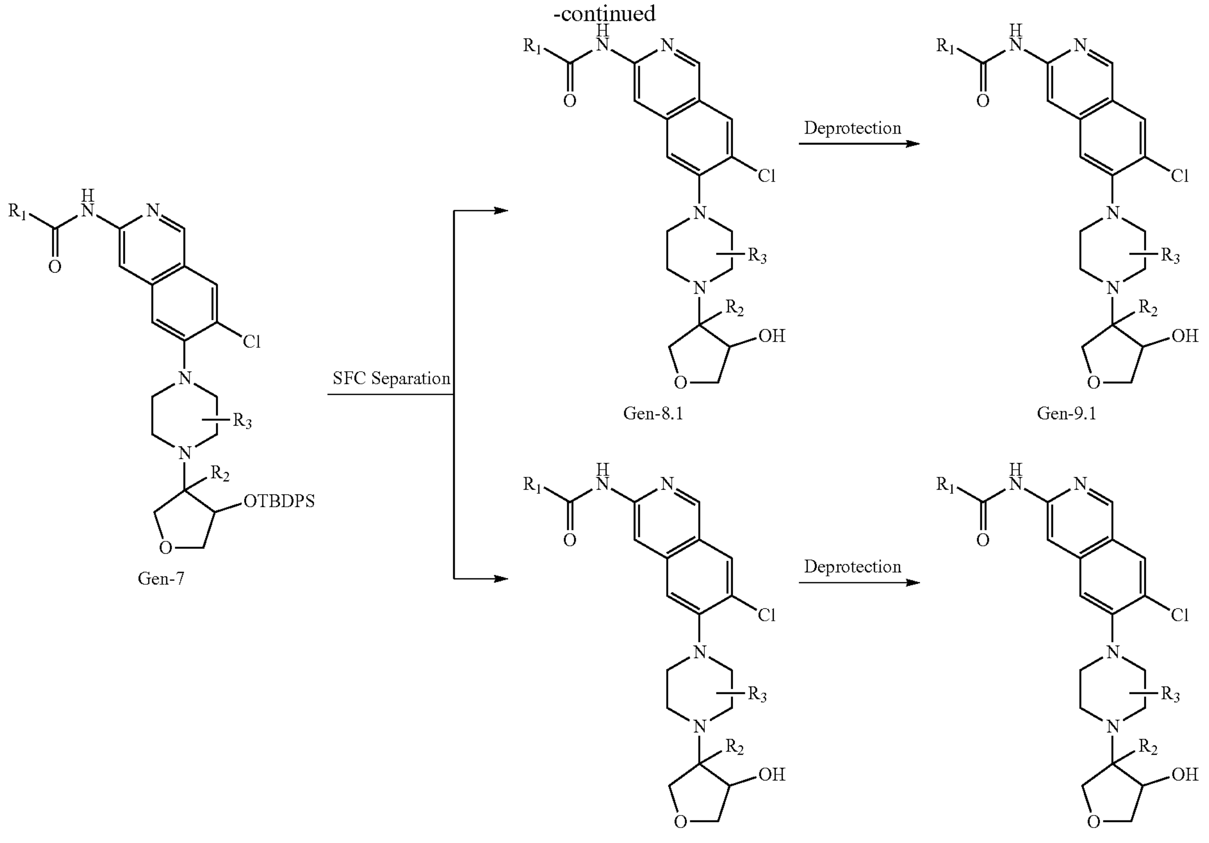

Gen-7

Gen-8.1

Gen-9.1

Gen-8.2

Gen-9.2

In General Scheme 3, Palladium-catalyzed C—N cross-coupling of 6-bromo-7-chloroisoquinolin-3-amides (Gen-1) with synthetically prepared intermediates 17 or 29 was performed to afford Gen-7 as a racemic mixture. The stereoisomers of the corresponding protected intermediates could be resolved by chiral SFC to provide Gen-8.1 and Gen-8.2. A subsequent deprotection accessed fully elaborated products in the form of Gen-9.1 and Gen-9.2. The representative compounds are shown in more detail below.

Scheme 39. Synthesis of N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-4,4-difluorospiro[2.2]pentane-1-carboxamide (Ex-3.1)

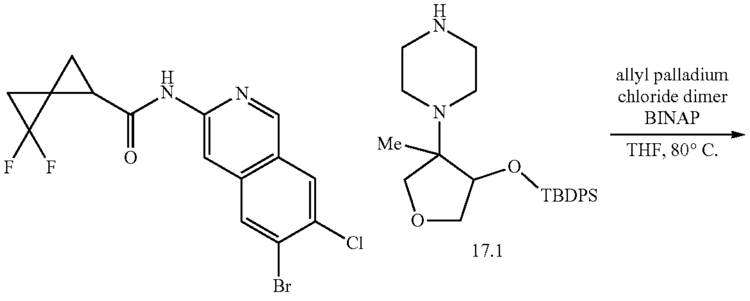

61.1 or 61.2

17.1

-continued
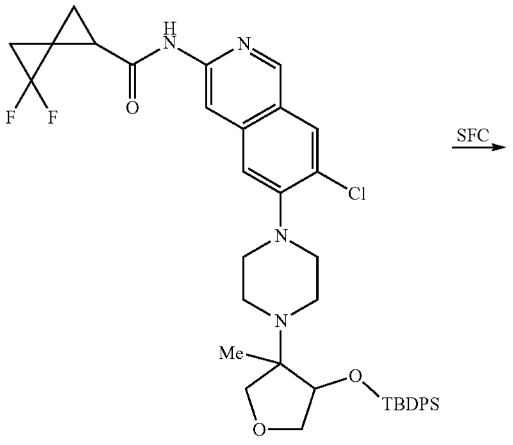
74
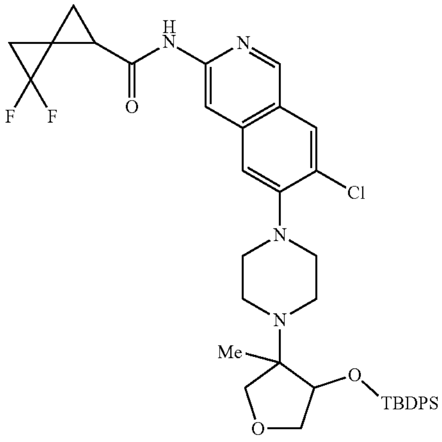
74.1
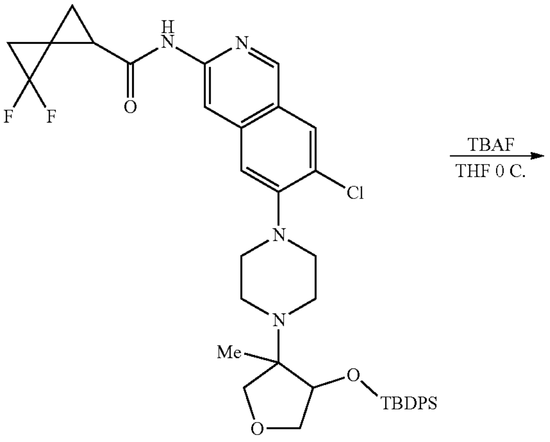
74.2
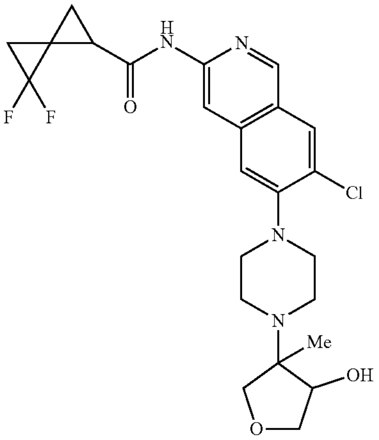
Ex-3.1
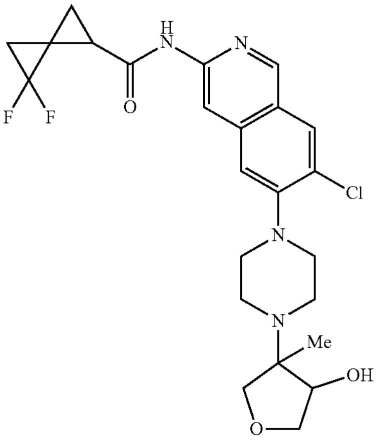
Ex-3.2

N-(6-(4-(4-((tert-butyldiphenylsilyl)oxy)-3-methyltetrahydrofuran-3-yl)piperazin-1-yl)-7-chloroisoquinolin-3-yl)-4,4-difluorospiro[2.2]pentane-1-carboxamide, (1R,3S or 1R,3R or 1S,3S, or 1S,3R)—N-(6-(4-((3R,4R or 3S,4S)-4-((tert-butyldiphenylsilyl)oxy)-3-methyltetrahydrofuran-3-yl)piperazin-1-yl)-7-chloroisoquinolin-3-yl)-4,4-difluorospiro[2.2]pentane-1-carboxamide (74.1) and (74.2)

A vial was charged with N-(6-bromo-7-chloroisoquinolin-3-yl)-4,4-difluorospiro[2.2]pentane-1-carboxamide 61.1 (160 mg, 0.413 mmol), and (3R,4R) 1-(4-(tert-butyldiphenylsilyl)oxy)-3-methyltetrahydrofuran-3-yl)piperazine or (3S,4S) 1-(4-(tert-butyldiphenylsilyl)oxy)-3-methyltetrahydrofuran-3-yl)piperazine 17.1 (351 mg, 0.826 mmol). The flask was evacuated and back filled with nitrogen 3 times. In a separate vial was charged with allyl palladium chloride dimer (3.78 mg, 10.32 μmol) and BINAP (12.85 mg, 0.021 mmol). The flask was evacuated and back filled with nitrogen 3 times. The solids were dissolved in THF (2064 μl) and stirred for 10 minutes to complex. The palladium complex solution was added to the main vial and sodium tert-butoxide (1032 μl, 2.064 mmol) was added. The reaction was heated to 80° C. for 2 hours. The residue was purified by column chromatography on silica gel, eluting with 0-100% 3:1 ethyl acetate:ethanol/hexanes to give a mixture of stereoisomers which were purified by chiral SFC (OJ-H, 21×250 (mm), Mobile phase A: 20% $CO_2$: Mobile phase B: 80% MeOH+0.1% $NH_4OH$) to afford the title compounds 74.1 (tR=4.1 min) MS (ESI): m/z calc'd for $C_{40}H_{46}ClF_2N_4O_3Si$ $[M+H]^+$: 731, found 731 and 74.2 (tR=5.2 min). MS (ESI): m/z calc'd for $C_{40}H_{46}ClF_2N_4O_3Si$ $[M+H]^+$: 731, found 731.

N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide, (1R,3R or 1R,3S, 1S,3R, 1S,3S)-N-(7-chloro-6-(4-((3R,4R or 3S,4S)-4-hydroxy-3-methyltetrahydrofuran-3-yl)piperazin-1-yl)isoquinolin-3-yl)-4,4-difluorospiro[2.2]pentane-1-carboxamide (Ex-3.1)

A vial was charged with 74.1 (20 mg, 0.027 mmol) and dissolved in THF (547 1). TBAF (82 1, 0.082 mmol) was added and the reaction was stirred for 5 hours. The reaction was concentrated and the residue was purified by column chromatography on silica gel, eluting with 0-100% 3:1 EtOAc:EtOH/hexanes to afford the title compound Ex-3.1. MS (ESI): m/z calc'd for $C_{24}H_{28}ClF_2N_4O_3$ $[M+H]^+$: 493, found 493. $^1H$ NMR (499 MHz, DMSO-$d_6$) δ $^1H$ NMR (499 MHz, DMSO) δ 11.01 (s, 1H), 8.98 (s, 1H), 8.41 (s, 1H), 8.16 (s, 1H), 7.43 (s, 1H), 4.36 (s, 1H), 3.98 (d, J=9.6, 1H), 3.81 (s, 1H), 3.68 (m, 2H), 3.55 (d, J=7.2 Hz, 1H), 3.18 (s, 3H), 2.89-2.70 (m, 3H), 2.56-2.51 (s, 1H), 1.98 (s, 1H), 1.70 (m, 3H), 1.24 (s, 1H), 1.06 (s, 3H).

Compounds in Table 3 below were prepared in accordance with the synthetic sequence illustrated in General Scheme 3 and Scheme 39 using the corresponding starting materials.

TABLE 3

| Example | Structure Name | Observed m/z $[M + H]^+$ |
| --- | --- | --- |
| 3.1, 3.2 | 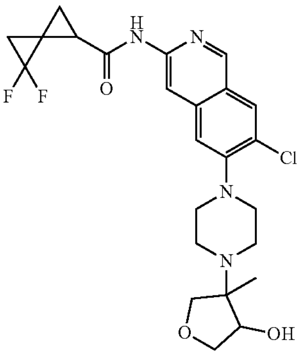 Rac-N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-4,4-difluorospiro[2.2]pentane-1-carboxamide, (1R, 3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-4,4-difluorospiro[2.2]pentane-1-carboxamide | Cal'c: 493 Found : 493 |

General Scheme 4.

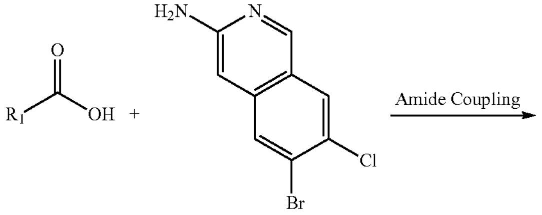

Int-3

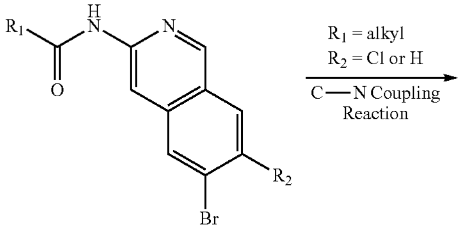

$R_1$ = alkyl
Gen-10

-continued

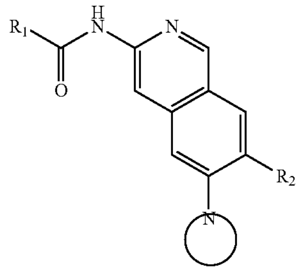

Gen-11

In General Scheme 4, commercially available carboxylic acids or acid chlorides were coupled with synthetically prepared intermediate 3 through amide coupling conditions to provide Gen-10. Palladium-catalyzed C—N cross-coupling with commercially available or synthetically prepared cyclic amines afforded elaborated compounds in the form of Gen-11. The representative compounds are described in more detail below.

Scheme 40. Synthesis of (R or S)-N-(6-(4-methyl-2-oxooxazolidin-3-yl)isoquinolin-3-yl)cyclopropanecarboxamide, TFA (Ex-4.1)

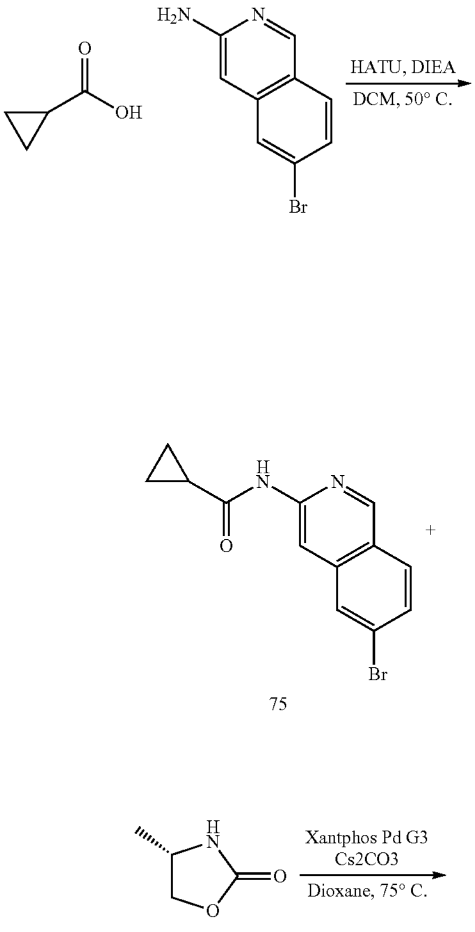

75

-continued

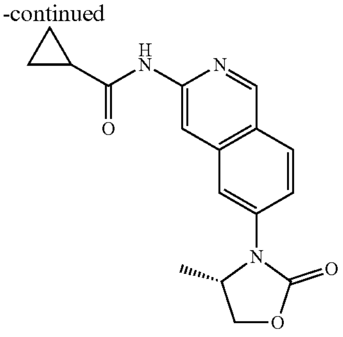

Ex-4.1

N-(6-bromoisoquinolin-3-yl)cyclopropanecarboxamide (75)

A vial was charged with 6-bromoisoquinolin-3-amine (870 mg, 3.90 mmol), cyclopropanecarboxylic acid (776 μl, 9.75 mmol), HATU (3707 mg, 9.75 mmol), DIEA (2725 μl, 15.60 mmol), and DMF (9750 μl). The resulting mixture was allowed to stir overnight at room temperature. Water was added to form a precipitate. The solids were collected by vacuum filtration and dried to afford the title compound 65. MS (ESI): m/z calc'd for $C_{13}H_{12}BrN_2O$ $[M+H]^+$: 291, found 291.

(R or S)-N-(6-(4-methyl-2-oxooxazolidin-3-yl)isoquinolin-3-yl)cyclopropanecarboxamide, TFA (Ex-4.1)

N-(6-bromoisoquinolin-3-yl)cyclopropanecarboxamide 75 (50 mg, 0.172 mmol), (S)-4-methyloxazolidin-2-one (19.10 mg, 0.189 mmol), Xantphos Pd G3 (16.29 mg, 0.017 mmol), and cesium carbonate (112 mg, 0.343 mmol) were added to a vial. Dioxane (859 μl) was added through the septum and the resulting mixture was allowed to stir for 72 hours at 75° C. The reaction mixture was filtered and concentrated under reduced pressure. The reaction mixture submitted directly for HPLC purification (purified by HPLC, eluting acetonitrile/water gradient with 0.100 TFA modifier, linear gradient) and lyophilized to afford the title compound Ex-4.1. MS (ESI): m/z calc'd for $C_{17}H_{18}N_3O_3$ $[M+H]^+$: 312, found 312. $^1H$ NMR (499 MHz, DMSO-$d_6$) δ 10.89 (s, 1H), 9.07 (s, 1H), 8.41 (s, 1H), 8.07 (m, 1H), 7.88-7.84 (m, 1H), 7.83 (s, 1H), 4.89-4.82 (m, 1H), 4.62 (m, 1H), 4.11 (m, 1H), 2.10-2.04 (m, 1H), 1.30 (m, 3H), 0.89-0.81 (m, 4H).

Compounds in Table 4 below were prepared in accordance with the synthetic sequence illustrated in General Scheme 4 and Scheme 40 using the corresponding starting materials.

TABLE 4
| Example | Structure<br>Name | Observed m/z [M + H]$^+$ |
|---|---|---|
| 4.1 | 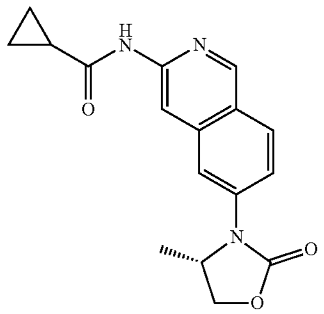<br>(R or S)-N-(6-(4-methyl-2-oxooxazolidin-3-yl)isoquinolin-3-yl)cyclopropanecarboxamide, TFA | Cal'c: 312 Found: 312 |
| 4.2 | 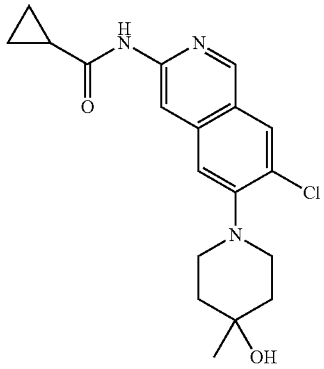<br>N-[7-chloro-6-(4-hydroxy-4-methylpiperidin-1-yl)isoquinolin-3-yl]cyclopropanecarboxamide | Cal'c: 360 Found: 360 |
| 4.3 | 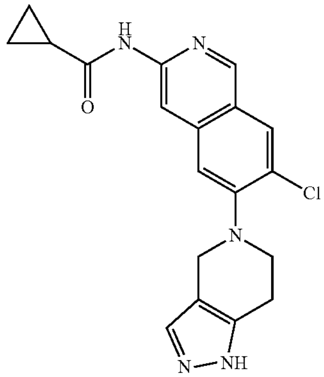<br>N-[7-chloro-6-(1,4,6,7-tetrahydro-5H-pyrazolo[4,3-c]pyridin-5-yl)isoquinolin-3-yl]cyclopropanecarboxamide | Cal'c: 368 Found: 368 |

TABLE 4-continued

| Example | Structure<br>Name | Observed m/z [M + H]$^+$ |
|---|---|---|
| 4.4 | 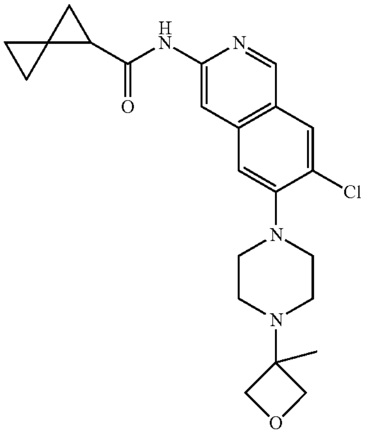<br>Rac-N-{7-chloro-6-[4-(3-methyloxetan-3-yl)piperazin-1-yl]isoquinolin-3-yl}spiro[2.2]pentane-1-carboxamide | Cal'c: 427 Found: 427 |
| 4.5 | 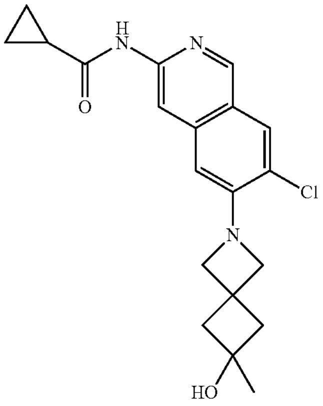<br>N-[7-chloro-6-(6-hydroxy-6-methyl-2-azaspiro[3.3]heptan-2-yl)isoquinolin-3-yl]cyclopropanecarboxamide | Cal'c: 372 Found: 372 |
| 4.6 | 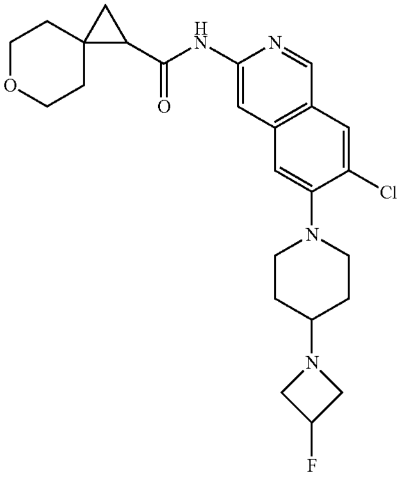<br>Rac-N-(7-chloro-6-(4-(3-fluoroazetidin-1-yl)piperidin-1-yl)isoquinolin-3-yl)-6-oxaspiro[2.5]octane-1-carboxamide, 1S N-(7-chloro-6-(4-(3-fluoroazetidin-1-yl)piperidin-1-yl)isoquinolin-3-yl)-6-oxaspiro[2.5]octane-1-carboxamide, 1R-N-(7-chloro-6-(4-(3-fluoroazetidin-1-yl)piperidin-1-yl)isoquinolin-3-yl)-6-oxaspiro[2.5]octane-1-carboxamide | Cal'c: 473 Found: 473 |

TABLE 4-continued

| Example | Structure<br>Name | Observed m/z [M + H]$^+$ |
| --- | --- | --- |
| 4.7 | 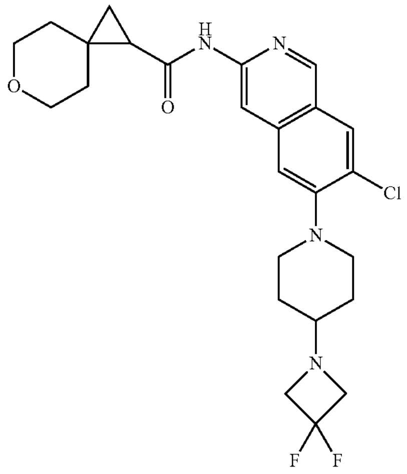<br>Rac-N-(7-chloro-6-(4-(3,3-difluoroazetidin-1-yl)piperidin-1-yl)isoquinolin-3-yl)-6-oxaspiro[2.5]octane-1-carboxamide, (1R or 1S)-N-(7-chloro-6-(4-(3,3-difluoroazetidin-1-yl)piperidin-1-yl)isoquinolin-3-yl)-6-oxaspiro[2.5]octane-1-carboxamide | Cal'c: 491 Found: 491 |
| 4.8 | 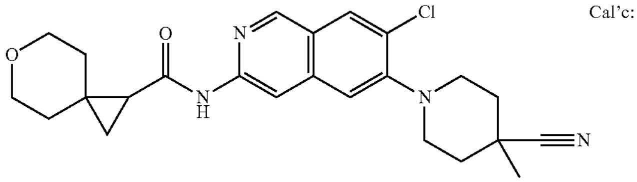<br>Rac-N-[7-chloro-6-(4-cyano-4-methyl-1-piperidyl)-3-isoquinolyl]-6-oxaspiro[2.5]octane-2-carboxamide, (R or S)-N-[7-chloro-6-(4-cyano-4-methyl-1-piperidyl)-3-isoquinolyl]-6-oxaspiro[2.5]octane-2-carboxamide, | Cal'c: 439 Found: 439 |
| 4.9 | 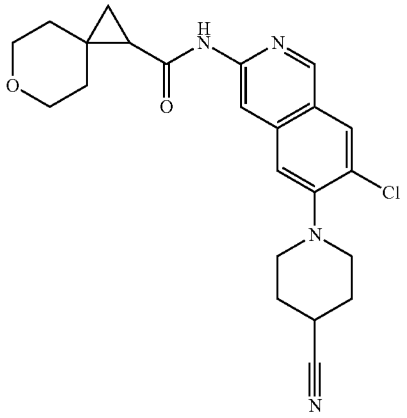<br>Rac-N-[7-chloro-6-(4-cyano-1-piperidyl)-3-isoquinolyl]-6-oxaspiro[2.5]octane-2-carboxamide, (R or S)-N-[7-chloro-6-(4-cyano-1-piperidyl)-3-isoquinolyl]-6-oxaspiro[2.5]octane-2-carboxamide | Cal'c: 430 Found: 430 |

TABLE 4-continued

| Example | Structure<br>Name | Observed m/z $[M + H]^+$ |
| --- | --- | --- |
| 4.10 | 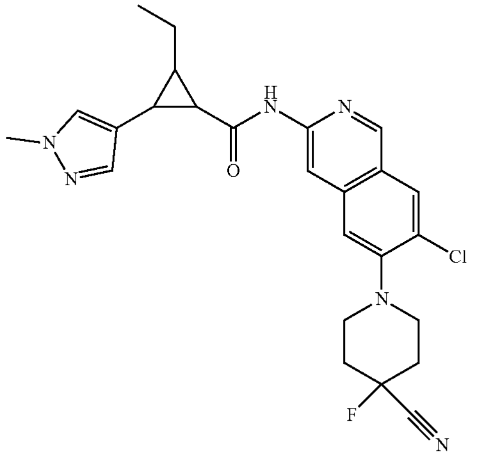<br>Rac-N-[7-chloro-6-(4-cyano-4-fluoro-1-piperidyl)-3-isoquinolyl]-2-ethyl-3-(1-methylpyrazol-4-yl)cyclopropanecarboxamide, (1R,2R or 1S,2S)-N-[7-chloro-6-(4-cyano-4-fluoro-1-piperidyl)-3-isoquinolyl]-2-ethyl-3-(1-methylpyrazol-4-yl)cyclopropanecarboxamide | Cal'c: 481 Found: 481 |
| 4.11 | 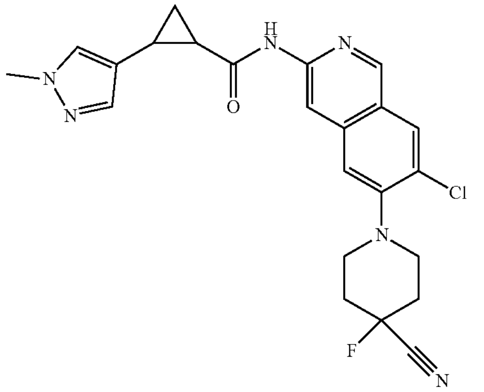<br>Rac-N-[7-chloro-6-(4-cyano-4-fluoro-1-piperidyl)-3-isoquinolyl]-2-(1-methylpyrazol-4-yl)cyclopropanecarboxamide, (1R,2R or 1S,2S)-N-[7-chloro-6-(4-cyano-4-fluoro-1-piperidyl)-3-isoquinolyl]-2-(1-methylpyrazol-4-yl)cyclopropanecarboxamide | Cal'c: 453 Found: 453 |

General Scheme 5.

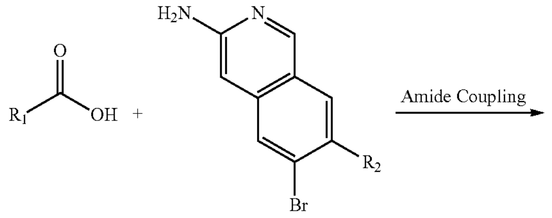

Int-3

$R_2$ = H or Cl

-continued

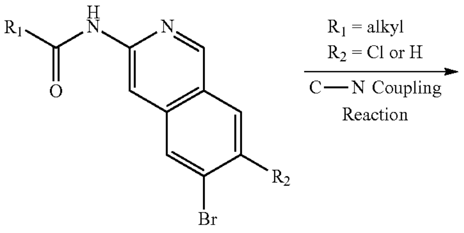

$R_1$ = alkyl

Gen-12

-continued

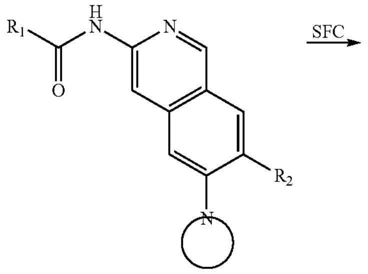

Gen-13

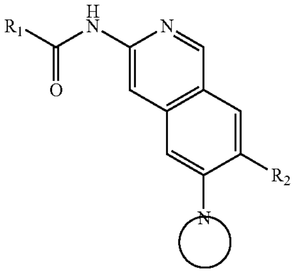

Gen-14

In General Scheme 5, commercially available carboxylic acids or acid chlorides were coupled with synthetically prepared intermediate 3 through amide coupling conditions to provide Gen-12. Palladium-catalyzed C—N cross-coupling with commercially available or synthetically prepared cyclic amines afforded elaborated compounds in the form of Gen-13 and the stereoisomers were separated by chiral SFC to provide fully elaborated products in the form of Gen-14. The representative compounds are described in more detail shown below.

Scheme 41. N-(6-(3-oxo-2-azabicyclo[2.2.1]heptane-2-yl)isoquinolin-3-yl)cyclopropanecarboxamide, N-(6-((1S,4R or 1R,4S)-3-oxo-2-azabicyclo[2.2.1]heptan-2-yl)isoquinolin-3-yl) cyclopropanecarboxamide (Ex-5.1) and (Ex-5.2)

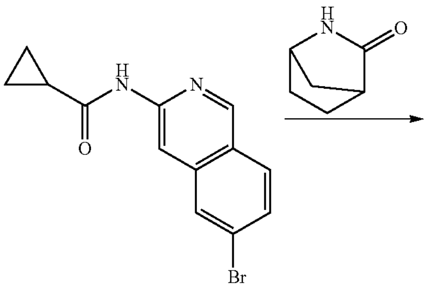

75

-continued

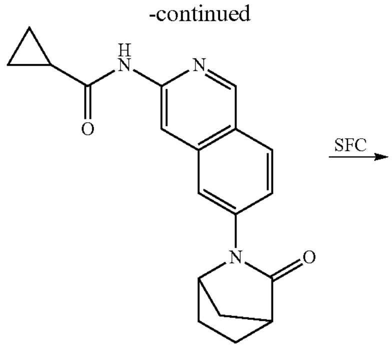

76

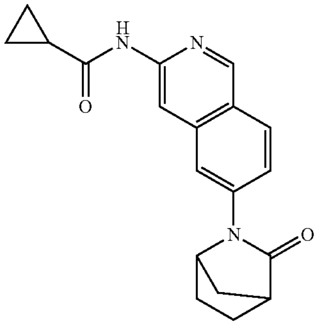

Ex-5.1

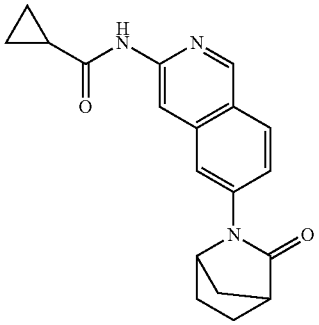

Ex-5.2

N-(6-bromoisoquinolin-3-yl)cyclopropanecarboxamide 75 (50 mg, 0.172 mmol), 2-azabicyclo[2.2.1]heptan-3-one (21.00 mg, 0.189 mmol), 3rd Gen Xantphos Pre-Catalyst (16.29 mg, 0.017 mmol), and cesium carbonate (112 mg, 0.343 mmol) were added to a vial. Dioxane (859 μl) was added through the septum and the resulting mixture was allowed to stir for 48 hours at 75° C. The reaction mixture was filtered and concentrated under reduced pressure. The residue was purified by column chromatography on silica (0-100% EtOAc/hexane) and concentrated under reduced pressure to afford a crude mixture or the title compounds 76. The mixture of two stereoisomers was purified by chiral SFC (Lux-2, 21×250 (mm), 45%/55% isopropanol/$CO_2$+0.1% $NH_4OH$) and lyophilized to afford the title compounds Ex-5.1 (tR=6.3 min) and Ex-5.2 (tR=8.2 min). Ex-5.1: MS (ESI): m/z calc'd for $C_{19}H_{20}N_3O_2$ $[M+H]^+$: 322, found 322. $^1$H NMR (499 MHz, DMSO-$d_6$) δ $^1$H NMR (499 MHz, DMSO-$d_6$) δ 10.83 (s, 1H), 9.01 (s, 1H), 8.39 (s, 1H), 8.00 (m, 1H), 7.95 (m, 1H), 7.80 (s, 1H), 4.81 (s, 1H), 2.88 (s, 1H), 2.15-2.04 (m, 1H), 2.03-1.92 (m, 3H), 1.78 (d, J=10.3 Hz, 1H), 1.59 (dd, J=13.1, 8.4 Hz, 2H), 0.96-0.76 (m, 4H). Ex-5.2. MS (ESI): m/z calc'd for $C_{19}H_{20}N_3O_2$ $[M+H]^+$: 322, found 322. $^1$H NMR (499 MHz, DMSO-$d_6$) δ 10.83 (s, 1H), 9.01 (s, 1H), 8.39 (s, 1H), 8.05-7.88 (m, 2H), 7.80 (s, 1H), 4.81 (s, 1H), 2.88 (s, 1H), 2.07 (m, 1H), 2.03-1.96 (m, 3H), 1.78 (m, 1H), 1.64-1.53 (m, 2H), 0.84 (m, 4H).

Compounds in Table 5 below were prepared in accordance with the synthetic sequence illustrated in General Scheme 5 and Scheme 41 using the corresponding starting materials.

TABLE 5

| Example | Structure<br>Name | Observed m/z [M + H]$^+$ |
|---|---|---|
| 5.1, 5.2 | 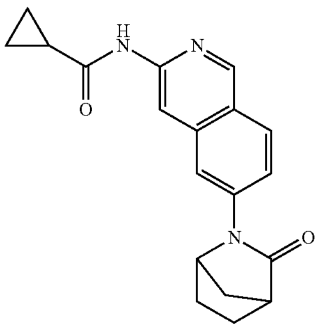<br>Rac-N-(6-(3-oxo-2-azabicyclo[2.2.1]heptan-2-yl)isoquinolin-3-yl)cyclopropanecarboxamide, N-(6-((1S,4R or 1R,4S)-3-oxo-2-azabicyclo[2.2.1]heptan-2-yl)isoquinolin-3-yl)cyclopropanecarboxamide, N-(6-((1S,4R or 1R,4S)-3-oxo-2-azabicyclo[2.2.1]heptan-2-yl)isoquinolin-3-yl)cyclopropanecarboxamide | Cal'c: 322 Found: 322 |
| 5.3, 5.4, 5.5, 5.6 | 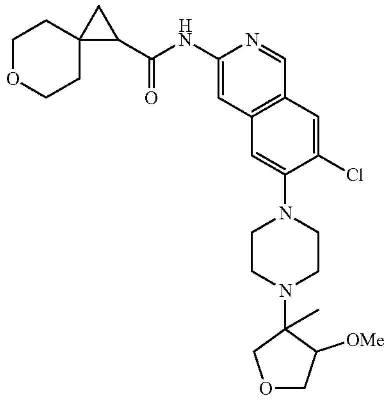<br>Rac-N-(7-chloro-6-(4-((3S, 4S or 3R,4R)-4-methoxy-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxy-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxy-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxy-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxy-3-methyltetrahydrofuran-3-yl)piperazin-1-yl)isoquinolin-3-yl)-6-oxaspiro[2.5]octane-1-carboxamide | Cal'c: 515 Found: 515 |

TABLE 5-continued

| Example | Structure<br>Name | Observed m/z [M + H]+ |
| --- | --- | --- |
| 5.7, 5.8, 5.9, 5.10 | 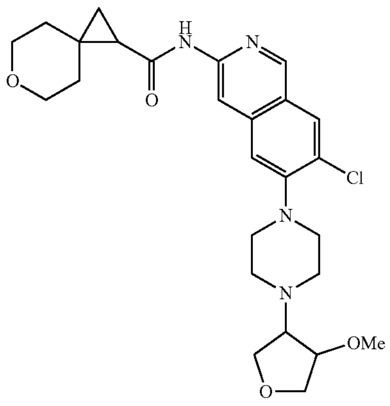<br>Rac-N-(7-chloro-6-(4-(4-methoxytetrahydrofuran-3-yl)piperazin-1-yl)isoquinolin-3-yl)-6-oxaspiro[2.5]octane-1-carboxamide, (1R or 1S)-N-(7-chloro-6-(4-((3R, 4R or 3S,4S)-4-methoxytetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxytetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxytetrahydrofuran-3-yl)piperazin-1-yl)isoquinolin-3-yl)-6-oxaspiro[2.5]octane-1-carboxamide, (1R or 1S)-N-(7-chloro-6-(4-((3R,4R or 3S,4S)-4-methoxytetrahydrofuran-3-yl)piperazin-1-yl)isoquinolin-3-yl)-6-oxaspiro[2.5]octane-1-carboxamide | Cal'c: 501 Found: 501 |
| 5.11, 5.12, 5.13, 5.14 | 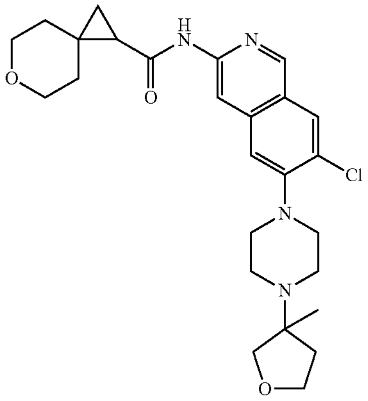<br>Rac-N-(7-chloro-6-(4-((R or S)-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((R or S)-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((R or S)-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((R or S)-3-methyltetrahydrofuran-3-yl)piperazin-1-yl)isoquinolin-3-yl)-6-oxaspiro[2.5]octane-1-carboxamide, (1R or 1S)-N-(7-chloro-6-(4-((R or S)-3-methyltetrahydrofuran-3-yl)piperazin-1-yl)isoquinolin-3-yl)-6-oxaspiro[2.5]octane-1-carboxamide | Cal'c: 485 Found: 485 |
| 5.15, 5.16 | 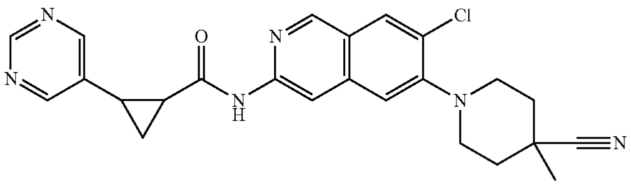<br>Rac-N-[7-chloro-6-(4-cyano-4-methyl-1-piperidyl)-3-isoquinolyl]-2-pyrimidin-5-yl-cyclopropanecarboxamide, (1R,2R or 1S,2S)-N-[7-chloro-6-(4-cyano-4-methyl-1-piperidyl)-3-isoquinolyl]-2-pyrimidin-5-yl-cyclopropanecarboxamide, (1R,2R or 1S,2S)-N-[7-chloro-6-(4-cyano-4-methyl-1-piperidyl)-3-isoquinolyl]-2-pyrimidin-5-yl-cyclopropanecarboxamide | Cal'c: 447 Found: 447 |

TABLE 5-continued

| Example | Structure<br>Name | Observed m/z [M + H]$^+$ |
|---|---|---|
| 5.17, 5.18 | 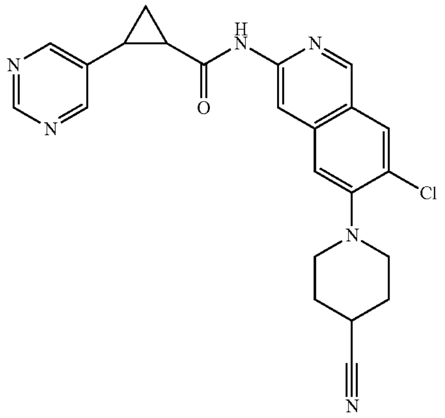<br>Rac-N-[7-chloro-6-(4-cyano-1-piperidyl)-3-isoquinolyl]-2-pyrimidin-5-yl-cyclopropanecarboxamide, (1R,2R or 1S,2S)-N-[7-chloro-6-(4-cyano-1-piperidyl)-3-isoquinolyl]-2-pyrimidin-5-yl-cyclopropanecarboxamide, (1R,2R or 1S,2S)-N-[7-chloro-6-(4-cyano-1-piperidyl)-3-isoquinolyl]-2-pyrimidin-5-yl-cyclopropanecarboxamide | Cal'c: 433 Found: 433 |
| 5.19, 5.20 | 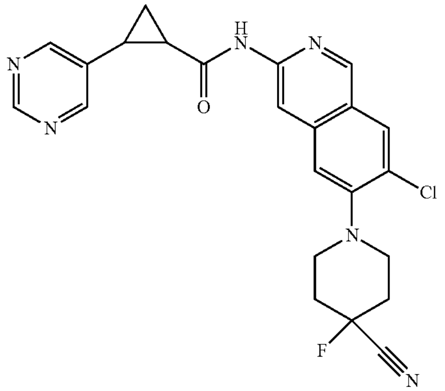<br>Rac-N-[7-chloro-6-(4-cyano-4-fluoro-1-piperidyl)-3-isoquinolyl]-2-pyrimidin-5-yl-cyclopropanecarboxamide, (1R,2R, 1S,2S)-N-[7-chloro-6-(4-cyano-4-fluoro-1-piperidyl)-3-isoquinolyl]-2-pyrimidin-5-yl-cyclopropanecarboxamide, (1R,2R, 1S,2S)-N-[7-chloro-6-(4-cyano-4-fluoro-1-piperidyl)-3-isoquinolyl]-2-pyrimidin-5-yl-cyclopropanecarboxamide | Cal'c: 451 Found: 451 |

General Scheme 6.

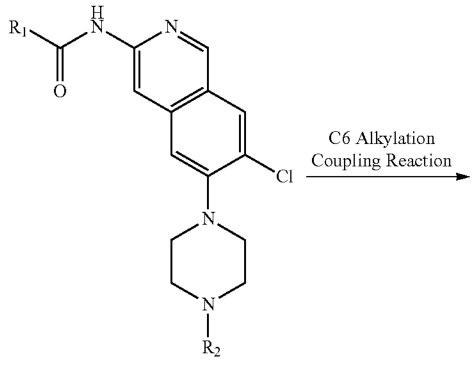

$R_2$ = alkyl
Gen-4
Gen-6
Gen-9.1
Gen-9.2
Gen-11
Gen-14

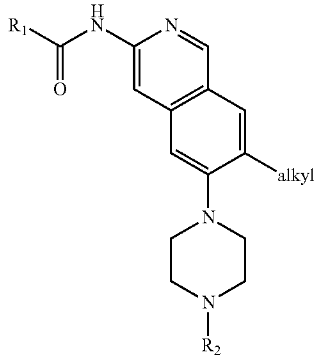

Gen-15

In General Scheme 6, the aforementioned intermediates in the form of Gen-4/Gen-6/Gen-9.1/Gen-9.2/Gen-11/Gen-14 were converted to Gen-15 via Palladium catalyzed cross-coupling with trimethylboroxine or appropriate alkyl boronic acid. The representative compounds are described in more detail below.

Scheme 42. Synthesis of N-(6-(4-(4-hydroxy-3-methyltetrahydrofuran-3-yl)piperazin-1-yl)-7-methylisoquinolin-3-yl)-6-oxaspiro[2.5]octane-1-carboxamide, (R or S)-N-(6-(4-((3R,4R or #S, 4S)-4-hydroxy-3-methyltetrahydrofuran-3-yl)piperazine-1-yl)-7-methylisoquinolin-3-yl)-6-oxaspiro[2.5]octane-1-carboxamide (Ex-6.1)

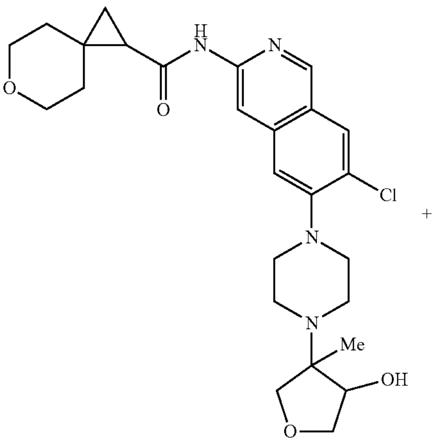

Ex-2.1

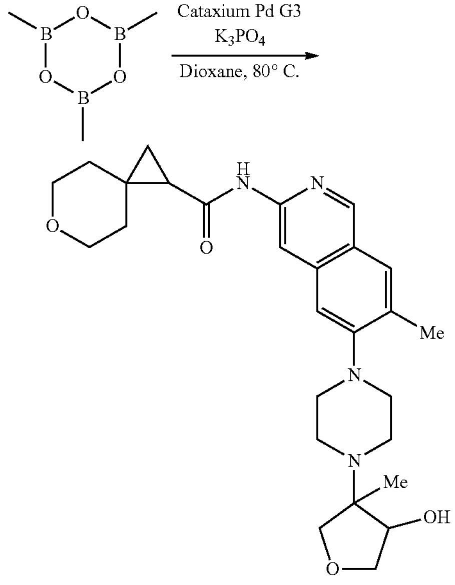

Ex-6.1

A vial was charged with Ex-2.1 (34 mg, 0.068 mmol), Cataxium Pd G3 (9.88 mg, 0.014 mmol) and potassium phosphate tribasic (16.88 μl, 0.204 mmol). The flask was evacuated and back filled with nitrogen 3 times. The solids were dissolved in dioxane (339 μl) and trimethyl boroxine (37.9 μl, 0.271 mmol) was added. The reaction was heated to 80° C. for 5 hours. The reaction was cooled to room temperature and concentrated in vacuo. The residue was purified by column chromatography on silica gel, eluting with EtOAc/hexanes (0-100%) to afford the title compound Ex-6.1. MS (ESI): m/z calc'd for $C_{27}H_{37}N_4O_4$ $[M+H]^+$: 481, found 481. $^1H$ NMR (400 MHz, DMSO-$d_6$, 25° C.) δ 10.73 (s, 1H), 8.89 (s, 1H), 8.32 (s, 1H), 7.78 (s, 1H), 7.25 (s, 1H), 4.36 (s, 1H), 3.98 (m, 1H), 3.81 (s, 1H), 3.72 (m, 2H), 3.66 (m, 2H), 3.57 (m, 2H), 3.47-3.39 (m, 2H), 3.05 (s, 3H), 2.75 (s, 2H), 2.53-2.50 (m, 2H), 2.05-1.96 (m, 1H), 1.76-1.69 (m, 1H), 1.68-1.61 (m, 1H), 1.52 (s, 1H), 1.38 (s, 1H), 1.14-1.08 (m, 2H), 1.06 (s, 3H), 0.92 (dd, J=7.7, 3.9 Hz, 1H).

Compounds in Table 6 below were prepared in accordance with the synthetic sequence illustrated in General Scheme 6 and Scheme 42 using the corresponding starting materials.

TABLE 6

| Example | Structure<br>Name | Observed m/z [M + H]$^+$ |
|---|---|---|
| 6.1 | 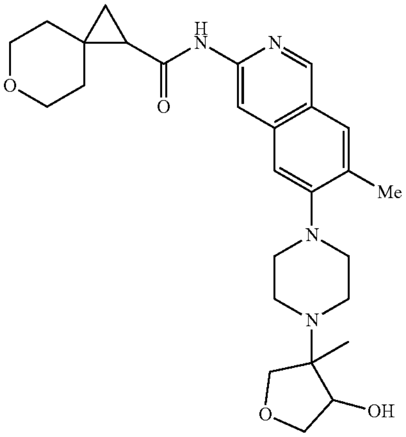<br>Rac-N-(6-(4-(4-hydroxy-3-methyltetrahydrofuran-3-yl)piperazin-1-yl)-7-methylisoquinolin-3-yl)-6-oxaspiro[2.5]octane-1-carboxamide, (R or S)-N-(6-(4-((3R,4R or 3S,4S)-4-hydroxy-3-methyltetrahydrofuran-3-yl)piperazin-1-yl)-7-methylisoquinolin-3-yl)-6-oxaspiro[2.5]octane-1-carboxamide | Cal'c: 467 Found : 467 |
| 6.2 6.3, 6.4, 6.5, 6.6, 6.7, 6.8, 6.9 | 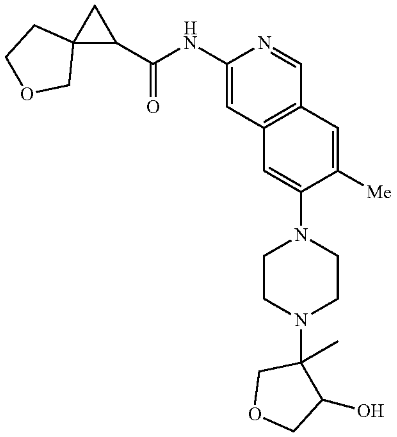 [SMILES: Cc1cc2cnc(NC(=O)C3CC34CCOC4)cc2cc1N1CCN(C2(C)COCC2O)CC1]<br>Rac-N-(6-(4-(4-hydroxy-3-methyltetrahydrofuran-3-yl)piperazin-1-yl)-7-methylisoquinolin-3-yl)-5-oxaspiro[2.4]heptane-1-carboxamide, (1R, 3S or 1S,3R, or IR,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R, 3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R, 3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R,3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R, 3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7- | Cal'c: 467 Found : 467 |

TABLE 6-continued

| Example | Structure<br>Name | Observed m/z [M + H]+ |
|---|---|---|
| | methylisoquinolin-3-yl)-5-oxaspiro[2.4]heptane-1-carboxamide, (1R,3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R,3S or 1S,3R, or 1R,3S, or 1S,3S)-N-(6-(4-((3R, 4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R, 3S or 1S,3R, or 1R,3S, or 1S,3S)-N-(6-(4-((3R,4R or 3S,4S)-4-hydroxy-3-methyltetrahydrofuran-3-yl)piperazin-1-yl)-7-methylisoquinolin-3-yl)-5-oxaspiro[2.4]heptane-1-carboxamide | |
| 6.10 | 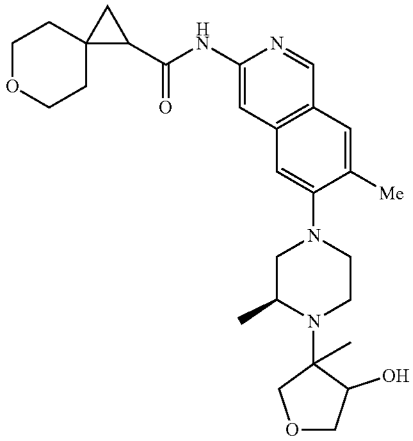<br>Rac-N-(6-(4-(4-hydroxy-3-methyltetrahydrofuran-3-yl)-3-methylpiperazin-1-yl)-7-methylisoquinolin-3-yl)-6-oxaspiro[2.5]octane-1-carboxamide, (1R or 1S)-N-(6-((R or S)-4-((3R,4R or 3S,4S)-4-hydroxy-3-methyltetrahydrofuran-3-yl)-3-methylpiperazin-1-yl)-7-methylisoquinolin-3-yl)-6-oxaspiro[2.5]octane-1-carboxamide | Cal'c: 495 Found : 495 |
| 6.11 | 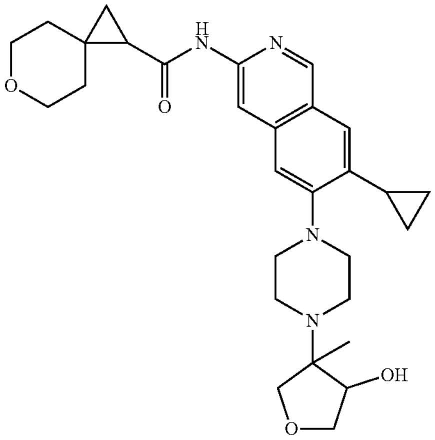<br>Rac-N-(7-cyclopropyl-6-(4-(4-hydroxy-3-methyltetrahydrofuran-3-yl)piperazin-1-yl)isoquinolin-3-yl)-6-oxaspiro[2.5]octane-1-carboxamide, (1R or 1S)-N-(7-cyclopropyl-6-(4-((3R,4R or 3S,4S)-4-hydroxy-3-methyltetrahydrofuran-3-yl)piperazin-1-yl)isoquinolin-3-yl)-6-oxaspiro[2.5]octane-1-carboxamide | Cal'c: 507 Found: 507 |

TABLE 6-continued

| Example | Structure<br>Name | Observed m/z $[M + H]^+$ |
|---|---|---|
| 6.12 | 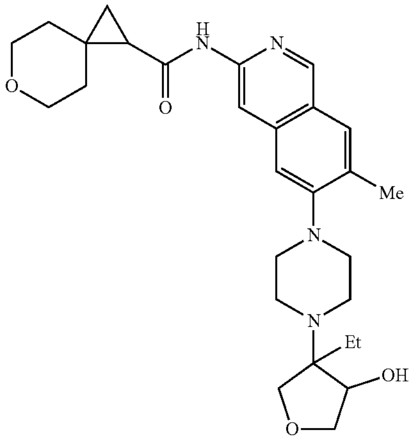<br>Rac-N-(6-(4-(3-ethyl-4-hydroxytetrahydrofuran-3-yl)piperazin-1-yl)-7-methylisoquinolin-3-yl)-6-oxaspiro[2.5]octane-1-carboxamide, (1R or 1S)-N-(6-(4-((3R,4R or 3S,4S)-3-ethyl-4-hydroxytetrahydrofuran-3-yl)piperazin-1-yl)-7-methylisoquinolin-3-yl)-6-oxaspiro[2.5]octane-1-carboxamide | Cal'c: 495 Found: 495 |
| 6.13, 6.14 | 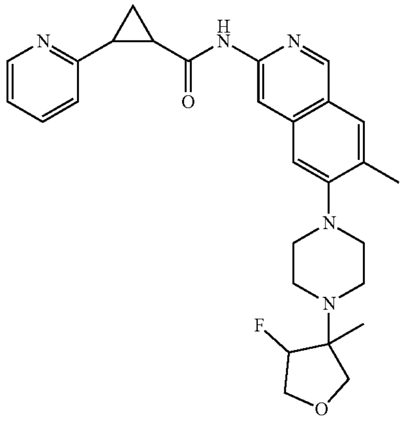<br>Rac-N-[6-[4-(4-fluoro-3-methyl-tetrahydrofuran-3-yl)piperazin-1-yl]-7-methyl-3-isoquinolyl]-2-(2-pyridyl)cyclopropanecarboxamide, (1R,2R or 1S,2S)-N-[6-[4-((3R,4R or 3S,4S)-4-fluoro-3-methyl-tetrahydrofuran-3-yl)piperazin-1-yl]-7-methyl-3-isoquinolyl]-2-(2-pyridyl)cyclopropanecarboxamide, (1R,2R or 1S,2S)-N-[6-[4-((3R,4R or 3S,4S)-4-fluoro-3-methyl-tetrahydrofuran-3-yl)piperazin-1-yl]-7-methyl-3-isoquinolyl]-2-(2-pyridyl)cyclopropanecarboxamide | Cal'c: 490 Found: 490 |

General Scheme 7.

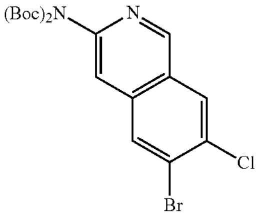

5

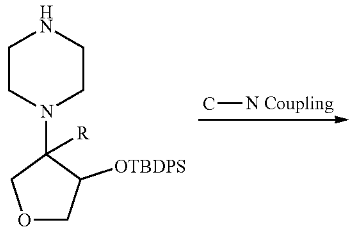

R = H (29.2),
Me (17.1)

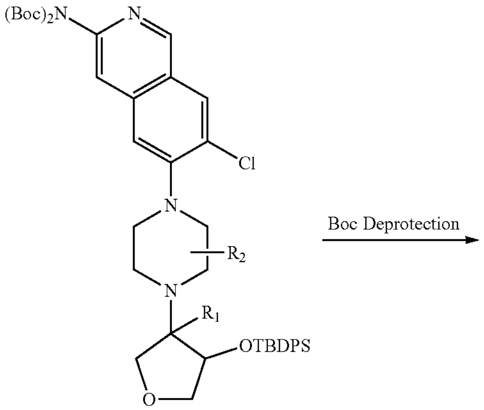

$R_1$ = alkyl
$R_2$ = alkyl
Gen-16

-continued

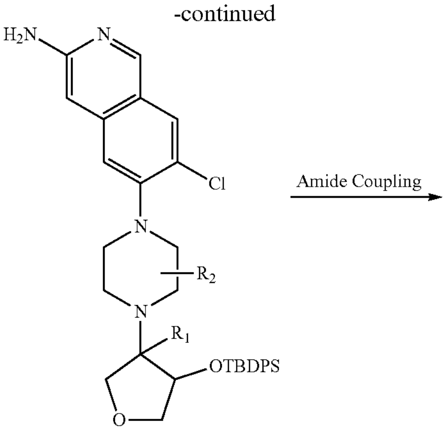

Gen-17

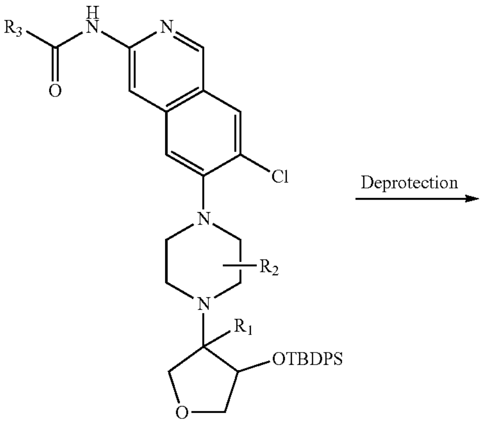

$R_3$ = alkyl
Gen-18

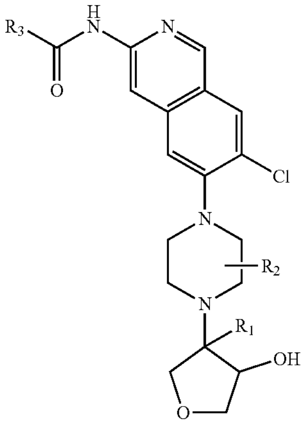

Gen-19

In General Scheme 7, synthetically prepared intermediate 5 was coupled with piperazine intermediate 29.1 or 17.2 through Palladium catalyzed cross-coupling to arrive at Gen-16 which was deprotected to afford Gen-17. Acylation by amide coupling resulted in Gen-18, which in-turn could be deprotected to afford Gen-19. The representative compounds are described in more detail below.

Scheme 43. Synthesis of N-(6-(4-4-((tert-butyldiphenylsilyl)-oxy)-3-methyltetrahydrofuran-3-yl)piperazin-1-yl)-7-chloroisoquinolin-3-yl)-3-methoxycryclobutane-1-carboxamide, cis or trans-(3R,4R or 3S,4S)-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide (Ex-7.1) and (Ex-7.2)
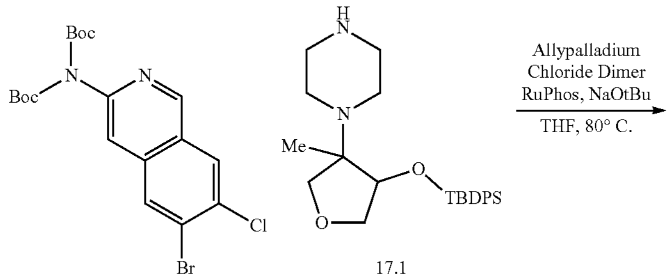
5 17.1
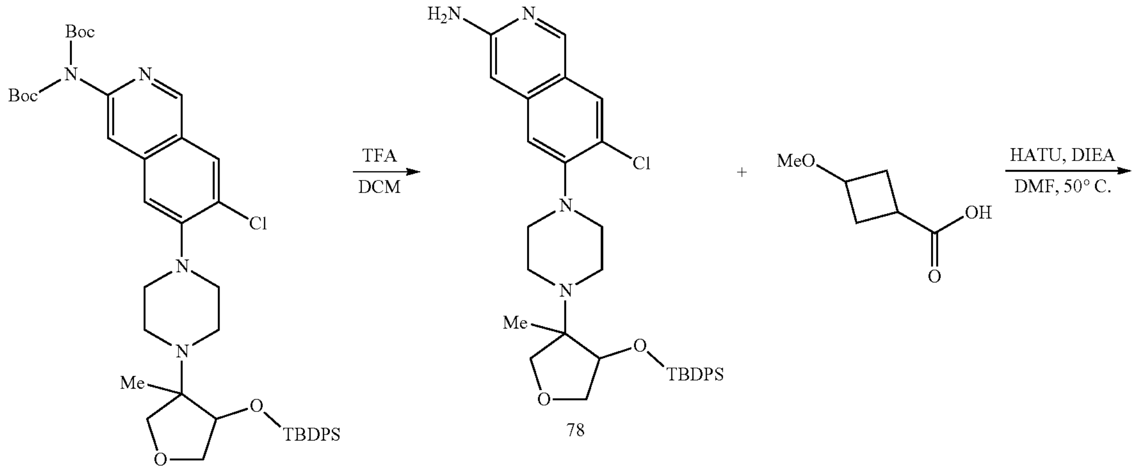
77 78
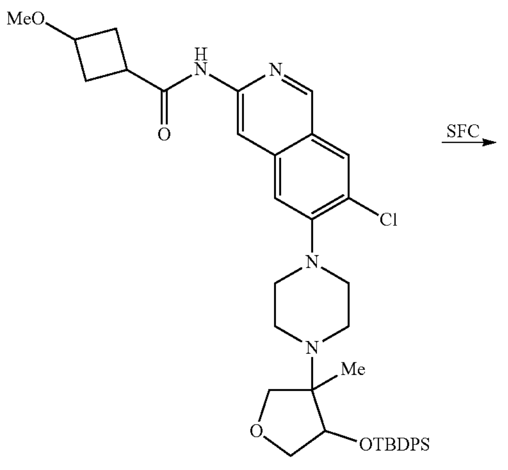
79

-continued

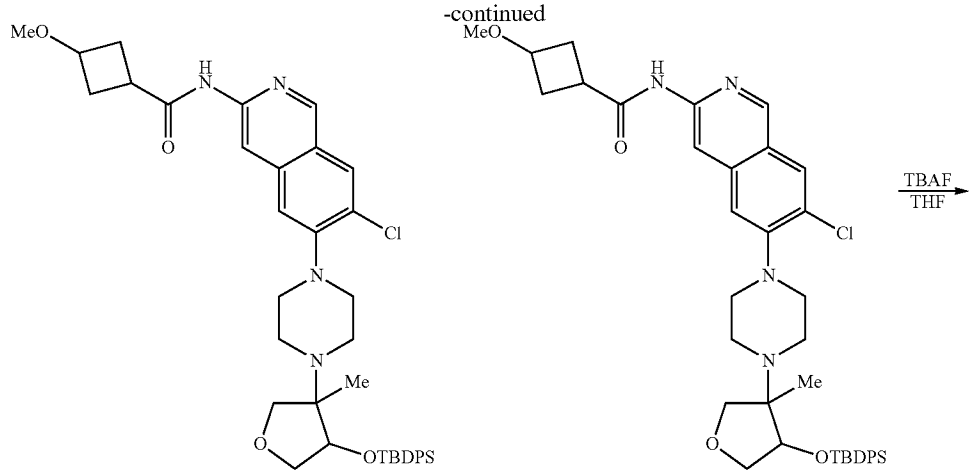

79.1 79.2

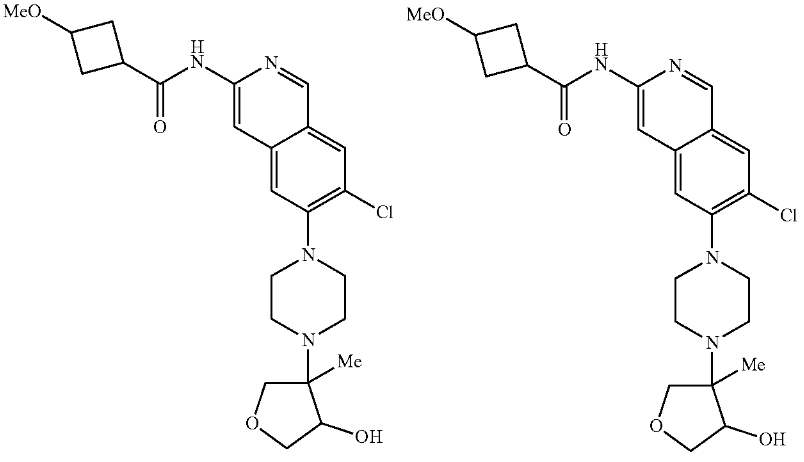

Ex-7.1 Ex-7.2 tert-butyl (tert-butoxycarbonyl)(6-(4-(4-((tert-butyldiphenylsilyl)oxy)-3-methyltetrahydrofuran-3-yl)piperazin-1-yl)-7-chloroisoquinolin-3-yl)carbamate, (3R,4R or 3S,4S)-tert-butyl (tert-butoxycarbonyl)(6-(4-(4-((tert-butyldiphenylsilyl)oxy)-3-methyltetrahydrofuran-3-yl)piperazin-1-yl)-7-chloroisoquinolin-3-yl)carbamate (77)

A vial was charged with allylpalladium chloride dimer (120 mg, 0.328 mmol) and RuPhos (306 mg, 0.655 mmol). The vial was sealed and its contents were placed under an inert atmosphere by performing 3 vacuum and nitrogen cycles. THF (30 mL) was added through the septum and the resulting mixture was allowed to stir for 5 minutes at room temperature to form a complex. Tert-butyl (6-bromo-7-chloroisoquinolin-3-yl)(tert-butoxycarbonyl)carbamate 5 (3000 mg, 6.55 mmol) and (3R,4R) 1-(4-(tert-butyldiphenylsilyl)oxy)-3-methyltetrahydrofuran-3-yl)piperazine or (3R,4R) 1-(4-(tert-butyldiphenylsilyl)oxy)-3-methyltetrahydrofuran-3-yl)piperazine 17.1 (3340 mg, 7.86 mmol) were added to a separate vial. The vial was sealed and its contents were placed under an inert atmosphere by performing 3 vacuum/nitrogen cycles. The aforementioned palladium complex was added, followed by sodium tert-butoxide (2M in THF) (9.83 mL, 19.66 mmol). The resulting mixture was allowed to stir overnight at 80° C. The reaction mixture was cooled to room temperature, diluted with EtOAc and washed twice with saturated sodium bicarbonate and once with brine. The combined organic fractions were dried over anhydrous sodium sulfate, filtered and concentrated under reduced pressure. The residue was purified by column chromatography on silica (0-100% EtOAc/hexanes). The desired fractions were pooled and concentrated under reduced pressure to afford the title compound 77. MS (ESI): m/z calc'd for $C_{34}H_{41}ClN_4O_2Si$ $[M+H-C_5H_8O_2]^+$: 701, found 701.

6-(4-(4-((tert-butyldiphenylsilyl)oxy)-3-methyltetrahydrofuran-3-yl)piperazin-1-yl)-7-chloroisoquinolin-3-amine, (3R,4R or 3S,4S)-6-(4-(4-((tert-butyldiphenylsilyl)oxy)-3-methyltetrahydrofuran-3-yl)piperazin-1-yl)-7-chloroisoquinolin-3-amine (78)

TFA (3.25 ml, 42.2 mmol) was added to a solution of 77 (1.69 g, 2.109 mmol) in DCM (5.27 ml). The resulting mixture was allowed to stir at room temperature for 2 hours. The reaction mixture was first quenched with a saturated sodium bicarbonate solution, then transferred to a separatory funnel and extracted twice with DCM. The organic fraction was washed once with brine. The combined organic fractions were dried over anhydrous sodium sulfate, filtered and concentrated under reduced pressure. 10 mL of isopropyl acetate was added to the vial and the contents were sonicated. The solid was collected by vacuum filtration and dried in vacuo to afford the title compound 78. MS (ESI): m/z calc'd for $C_{34}H_{41}ClN_4O_2Si$ $[M+H]^+$: 601, found 601.

N-(6-(4-(4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, Cis or trans (3R,4R or3S,4S)-N-(6-(4-(4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide (79.1) and (79.2)

A vial was charged with 3-methoxycyclobutane-1-carboxylic acid (26.0 mg, 0.200 mmol), 78 (100 mg, 0.166 mmol), HATU (126 mg, 0.333 mmol), DMF (554 μl) and DIPEA (58.1 μl, 0.333 mmol). The resulting mixture was heated to 50° C. overnight. The reaction was cooled to room temperature and then poured into water to form a precipitate. The solids were collected by vacuum filtration and dried. The crude residue was subjected to purification by flash chromatography over silica gel (3:1 EtOAc:ethanol/hexanes, 0-100%) to afford the title compound as a mixture of stereoisomers. The mixture of two stereoisomers was purified by chiral SFC ((R,R)-Whelk-O1, 21×250 (mm), 40%/60% Methanol/$CO_2$+0.1% $NH_4OH$) and lyophilized to afford the chiral resolved stereoisomers of the title compound 79.1 (tR=5.9 min) and 79.2 (tR=6.6 min). MS (ESI): m/z calc'd for $C_{40}H_{49}ClN_4O_4Si$ $[M+H]^+$: 713, found 713.

N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, (3R,4R or 3S,4S)-N-(6-(4-4-((ter-butyldiphenylsilyl)oxy)-3-methyltetrahydrofuran-3-yl)piperazin-1-yl)-7-chloroisoquinolin-3-yl)-3-methoxycyclobutane-1-carboxamide (Ex-7.1) and (Ex-7.2)

A vial was charged with a solution of 79.1 (36 mg, 0.050 mmol) in THF (1009 μl) and TBAF (151 μl, 0.151 mmol) was added dropwise. The resulting mixture was stirred for 3 hours. The reaction was then concentrated under reduced pressure and the crude residue was subjected to purification by flash chromatography over silica gel (3:1 EtOAc:EtOH/hexanes, 0-100%) to afford the title compounds Ex-7.1 MS (ESI): m/z calc'd for $C_{24}H_{32}ClN_4O_4$ $[M+H]^+$: 475, found 475. $^1H$ NMR (499 MHI-z, DMSO-$d_6$) δ 10.54 (s, 1H), 8.96 (s, 1H), 8.44 (s, 1H), 8.15 (s, 1H), 7.45 (s, 1H), 4.36 (s, 1H), 4.05 (m, 1H), 3.98 (m, 1H), 3.82 (s, 1H), 3.71 (m, 1H), 3.66 (m, 1H), 3.56 (m, 1H), 3.34-3.28 (m, 2H), 3.19 (s, 3H), 3.15 (s, 3H), 2.80-2.74 (m, 2H), 2.56-2.53 (m, 2H), 2.45-2.39 (m, 2H), 2.16-2.08 (m, 2H), 1.06 (s, 3H).

Compounds in Table 7 below were prepared in accordance with the synthetic sequence illustrated in General Scheme 7 and Scheme 43 using the corresponding starting materials.

TABLE 7

| Example | Structure<br>Name | Observed m/z<br>$[M + H]^+$ |
|---|---|---|
| 7.1,<br>7.2 | 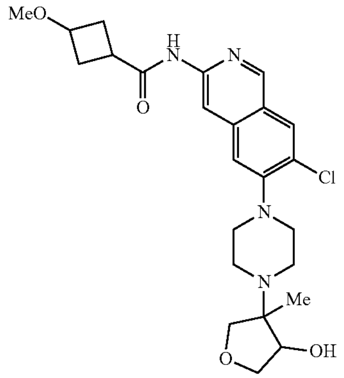<br>Rac-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, (3R,4R or 3S,4S)-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, (3R,4R or 3S,4S)-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide | Cal'c: 475<br>Found: 475 |
| 7.3,<br>7.4,<br>7.5 | 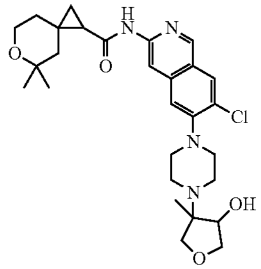<br>Rac-N-(7-chloro-6-(4-(4-hydroxy-3-methyltetrahydrofuran-3-yl)piperazin-1-yl)isoquinolin-3-yl)-5,5-dimethyl-6-oxaspiro[2.5]octane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide,, (1R,3R or 1S,3S)-N-(7-chloro-6-(4-((3R,4R or 3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide | Cal'c: 529<br>Found: 529 |

General Scheme 8.

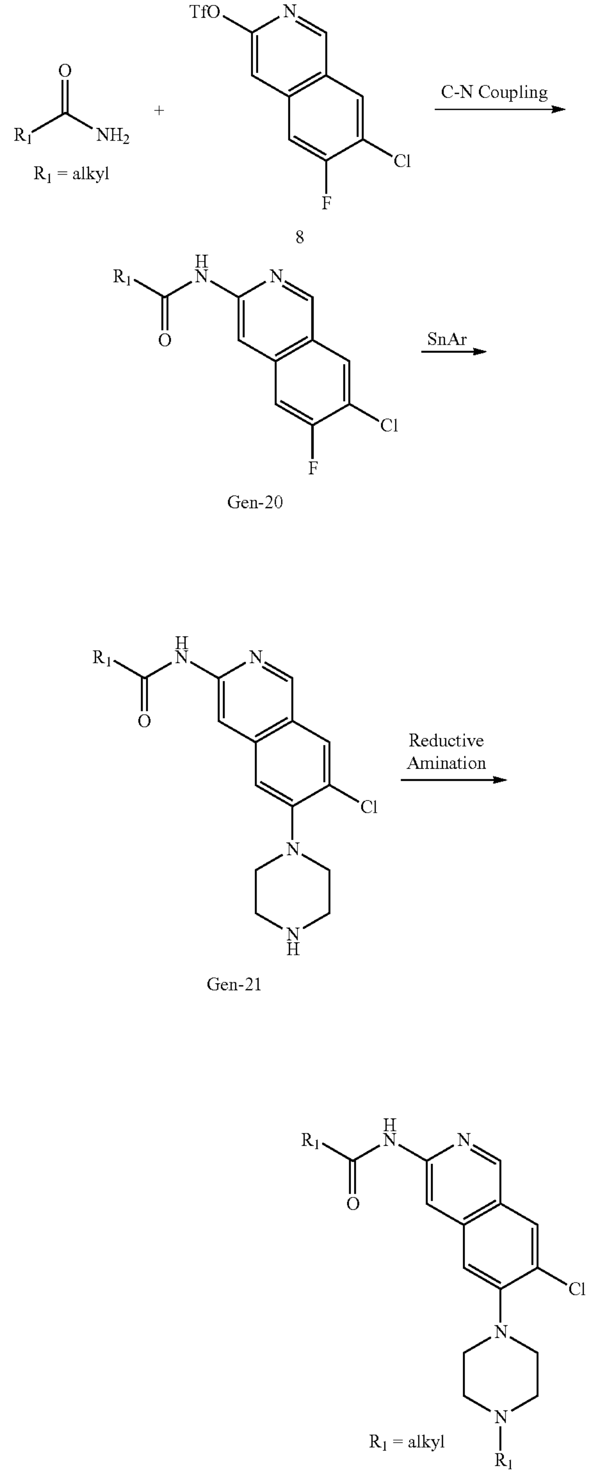

8

Gen-20

Gen-21

Gen-22

In General Scheme 8, Gen-20 was synthesized by the Palladium catalyzed cross-coupling of synthetically prepared intermediate 8 with aliphatic amides. Piperazine was then added via an SnAr reaction to produce Gen-21 which was subsequently functionalized by reductive amination, to afford fully elaborated compounds in the form of Gen-22.

Scheme 44. Synthesis of N-(7-chloro-6-(4-(oxetan-3-yl)piperazin-1-yl)isoquinolin-3-yl)cyclopropanecarboxamide (Ex-8.1)

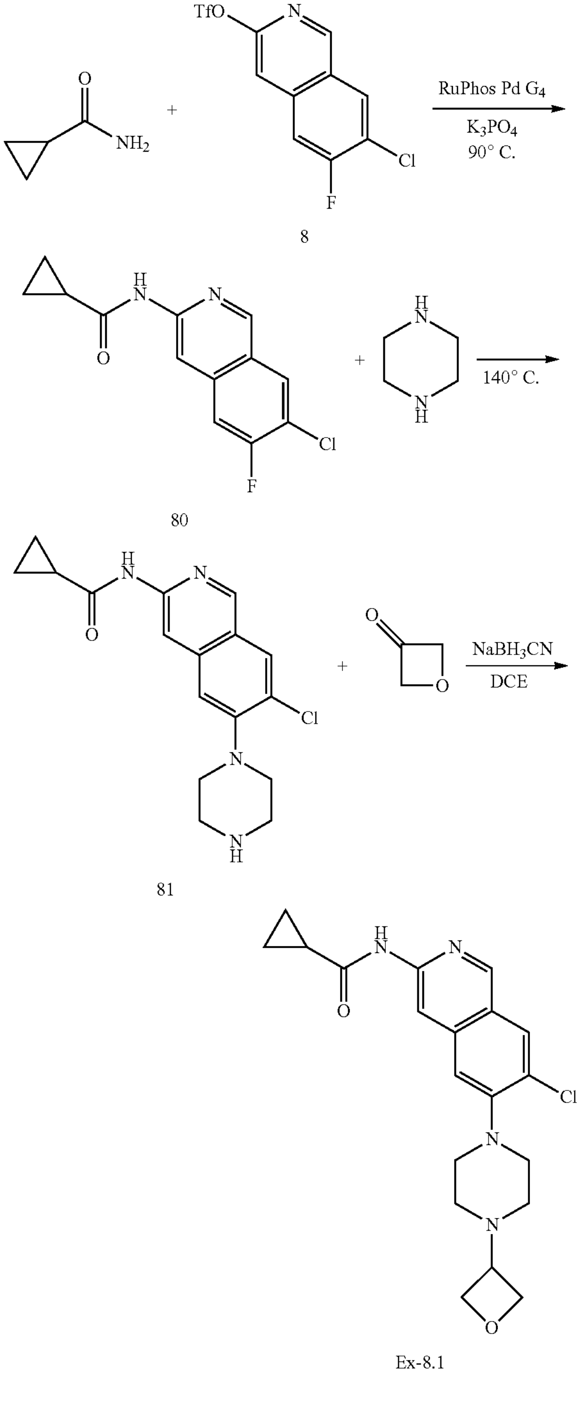

8

80

81

Ex-8.1

N-(7-chloro-6-fluoroisoquinolin-3-yl)cyclopropanecarboxamide (80)

A vial was charged with a mixture of 7-chloro-6-fluoroisoquinolin-3-yl trifluoromethanesulfonate 8 (540 mg, 1.638 mmol), cyclopropanecarboxamide (181 mg, 2.129 mmol), RuPhos Pd G4 (139 mg, 0.164 mmol) and $K_3PO_4$ (695 mg, 3.28 mmol) in Dioxane (10 ml) was stirred at 90° C. under $N_2$ for 8 h to give a brown mixture. The reaction mixture was quenched with sat. $NH_4Cl$ (30 mL) and extracted with EtOAc (15 mL 3×). The combined organic phases were washed with brine (60 mL), dried over anhydrous $Na_2SO_4$, filtered and concentrated under reduced pressure. The residue was purified by silica gel chromatography eluenting with 0-30% EtOAc/PE to afford the title compound 80. MS (ESI): m/z calc'd for $C_{13}H_{11}ClFN_2O$ $[M+H]^+$: 265, found 265. $^1H$ NMR (500 MHz, DMSO-$d_6$) δ=11.03 (s, 1H), 9.13 (s, 1H), 8.49 (s, 1H), 8.39 (m, 1H), 7.95 (m, 1H), 2.11-2.04 (m, 1H), 0.88-0.83 (m, 4H).

N-(7-chloro-6-(piperazin-1-yl)isoquinolin-3-yl)cyclopropanecarboxamide (81)

A mixture of N-(7-chloro-6-fluoroisoquinolin-3-yl)cyclopropanecarboxamide 80 (80 mg, 0.302 mmol) and piperazine (1.0 g, 11.61 mmol) was stirred at 140° C. under microwave irradiation for 1 h to give a yellow mixture. The reaction was diluted with EtOAc (20 mL) and MeOH (1 mL). The mixture was washed with washed with brine (20 mL), dried over anhydrous $Na_2SO_4$, filtered and concentrated under reduced pressure to afford the title compound 81 which was used in the next step without further purification. MS (ESI): m/z calc'd for $C_{17}H_{20}ClN_4O$ $[M+H]^+$: 331, found 331.

N-(7-chloro-6-(4-(oxetan-3-yl)piperazin-1-yl)isoquinolin-3-yl)cyclopropanecarboxamide (Ex-8.1)

$NaBH_3(CN)$ (76 mg, 1.209 mmol) was added to a solution of N-(7-chloro-6-(piperazin-1-yl)isoquinolin-3-yl)cyclopropanecarboxamide 81 (50 mg, 0.151 mmol) and oxetan-3-one (54.5 mg, 0.756 mmol) in DCE (2 mL) at 15° C. The resulting mixture was stirred at 15° C. for 24 h. The mixture was filtered and the filtrate was concentrated under reduced pressure.

The residue was purified by Pre-HPLC (Column Boston Green ODS 150*30 mm*5 um

Condition water (0.1% TFA)-ACN Begin 15% B to 65% B Gradient Time (10 min) 100% B Hold Time (2 m)

FlowRate (25 ml/min) followed by Chiral-SFC (Column DAICEL CHIRALCEL OJ-H (250 mm*30 mm, 5 um) Condition 0.1%/$NH_4OH$ EtOH Begin 30% B to 100% B FlowRate (60 ml/min) to afford the title compound Ex-8.1. MS (ESI): m/z calc'd for ($C_{20}H_{24}ClN_4O_2$) (ESI, m/z): 387 $[M+H]^+$, found 387. $^1H$ NMR (500 MHz chloroform-d) δ 8.98 (br s, 1H), 8.76 (s, 1H), 8.48 (s, 1H), 7.88 (s, 1H), 7.24 (s, 1H), 4.73 (m, 4H), 3.74-3.64 (m, 1H), 3.34-3.21 (m, 4H), 2.74-2.57 (m, 4H), 1.71-1.61 (m, 1H), 1.19-1.09 (m, 2H), 0.96-0.87 (m, 2H)

Compounds in Table 8 below were prepared in accordance with the synthetic sequence illustrated in General Scheme 8 and Scheme 44 using the corresponding starting materials.

TABLE 8

| Example | Structure<br>Name | Observed m/z [M + H]+ |
|---|---|---|
| 8.1 | 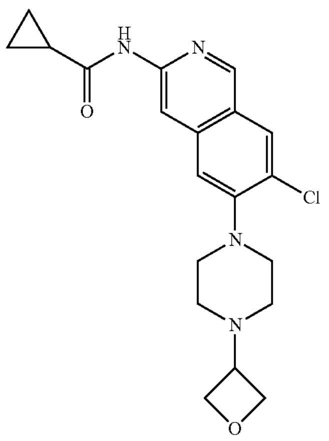<br>N-(7-chloro-6-(4-(oxetan-3-yl)piperazin-1-yl)isoquinolin-3-yl)cyclopropanecarboxamide | Cal'c: 387 Found: 387 |
| 8.2 | 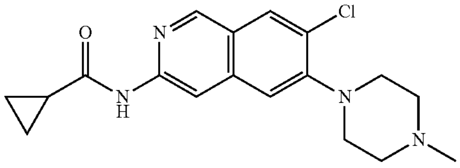<br>N-[7-chloro-6-(4-methylpiperazin-1-yl)isoquinolin-3-yl]cyclopropanecarboxamide | Cal'c: 345 Found: 345 |

General Scheme 9.

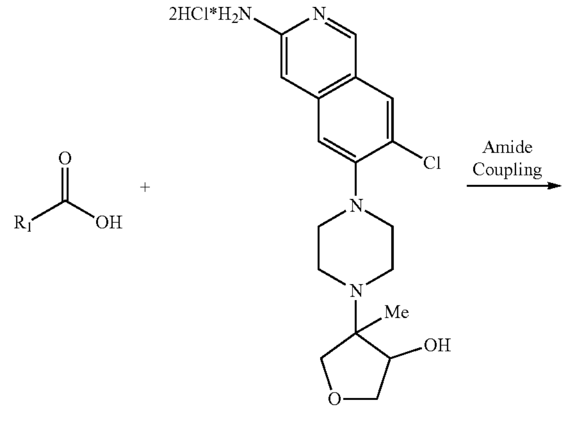

Int-37

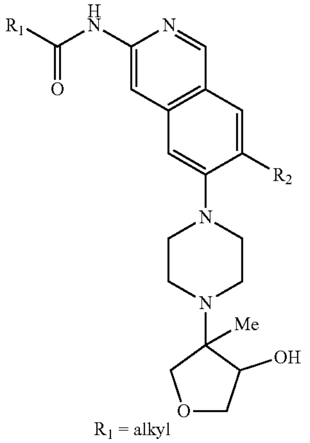

$R_1$ = alkyl

Gen-23

In General Scheme 9, commercially available carboxylic acids or acid chlorides were coupled with synthetically prepared intermediate 37 through amide coupling conditions to provide Gen-23. The representative compounds are described in more detail shown below.

Scheme 45. N-(7-chloro-6-(4-(4-hydroxy-3-methyltetrahydrofuran-3-yl)piperazin-1-yl)isoquinolin-3-yl)-3-methoxypropanamide, TFA, N-(7-chloro-6-(4-((3R,4R or 3S,4S)-4-hydroxy-3-methyltetrahydrofuran-3-yl)piperazin-1-yl)isoquinolin-3-yl)-3-methoxypropanamide, TFA(Ex-9.1)

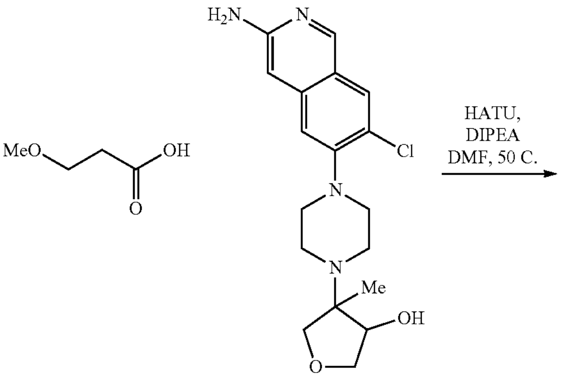

37

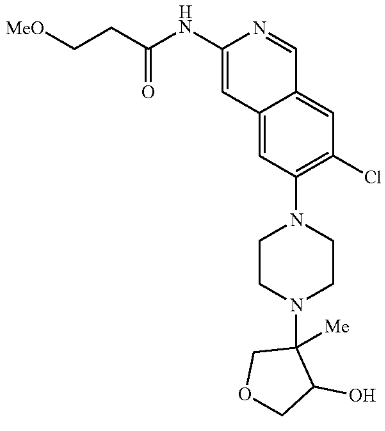

Ex-9.1

To a vial was added 3-methoxypropanoic acid (12.05 mg, 0.116 mmol), 37 (35 mg, 0.096 mmol) and HATU (73.4 mg, 0.193 mmol) The vial was evacuated and back filled with nitrogen 3 times. The solids were dissolved in DMF (482 μl) and DIPEA (33.7 μl, 0.193 mmol) was added. The reaction was heated to 50° C. overnight. The reaction mixture was filtered and purified by HPLC, eluting acetonitrile/water gradient with 0.1% TFA modifier, linear gradient and lyophilized to afford the title compound Ex-9.1. MS (ESI): m/z calc'd for $C_{22}H_{30}ClN_4O_4$ $[M+H]^+$: 449, found 449. $^1H$ NMR (500 MHz chloroform-d) δ $^1H$ NMR (499 MHz, DMSO-$d_6$) δ 10.62 (s, 1H), 9.53 (br s, 1H), 9.02 (s, 1H), 8.49 (s, 1H), 8.21 (s, 1H), 7.60 (s, 1H), 4.19 (m, 2H), 3.99 (m, 1H), 3.83 (m, 2H), 3.65 (m, 4H), 3.53 (m, 4H), 3.30 (m, 1H), 3.26 (s, 3H), 3.11 (s, 1H), 2.69 (m, 2H), 1.43 (s, 3H).

Compounds in Table 9 below were prepared in accordance with the synthetic sequence illustrated in General Scheme 9 and Scheme 45 using the corresponding starting materials.

TABLE 9

| Example | Structure<br>Name | Observed m/z [M + H]$^+$ |
|---|---|---|
| 9.1 | 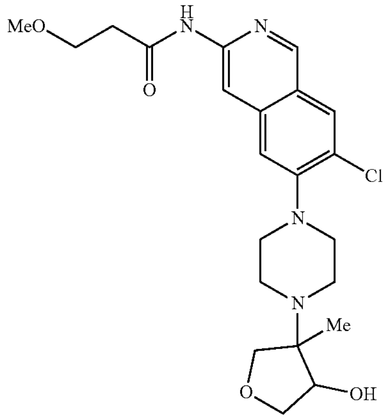<br>Rac-N-(7-chloro-6-(4-(4-hydroxy-3-methyltetrahydrofuran-3-yl)piperazin-1-yl)isoquinolin-3-yl)-3-methoxypropanamide, TFA, N-(7-chloro-6-(4-((3R,4R or 3S,4S)-4-hydroxy-3-methyltetrahydrofuran-3-yl)piperazin-1-yl)isoquinolin-3-yl)-3-methoxypropanamide, TFA | Cal'c: 449 Found: 449 |
| 9.2 | 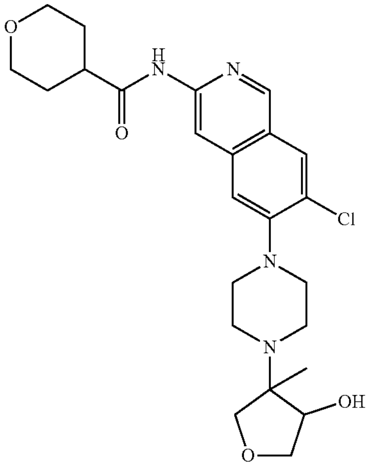<br>Rac-N-(7-chloro-6-(4-(4-hydroxy-3-methyltetrahydrofuran-3-yl)piperazin-1-yl)isoquinolin-3-yl)tetrahydro-2H-pyran-4-carboxamide, N-(7-chloro-6-(4-((3R,4R or 3S,4S)-4-hydroxy-3-methyltetrahydrofuran-3-yl)piperazin-1-yl)isoquinolin-3-yl)tetrahydro-2H-pyran-4-carboxamide | Cal'c: 475 Found: 475 |

TABLE 9-continued

| Example | Structure<br>Name | Observed m/z $[M + H]^+$ |
|---|---|---|
| 9.3 | 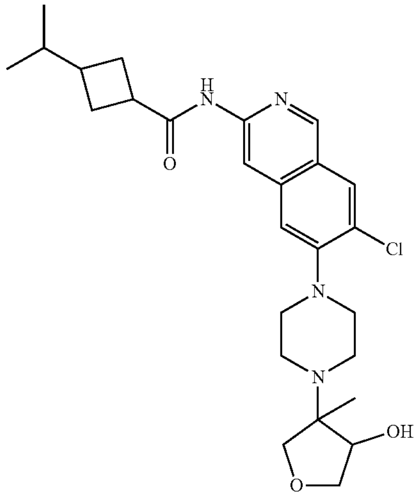<br>N-(7-chloro-6-(4-(4-hydroxy-3-methyltetrahydrofuran-3-yl)piperazin-1-yl)isoquinolin-3-yl)-3-isopropylcyclobutane-1-carboxamide | Cal'c: 487 Found: 487 |
| 9.4 | 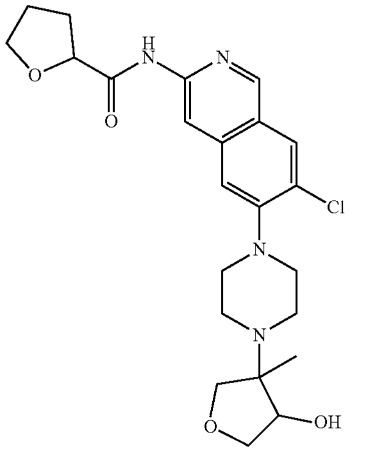<br>(S)-N-(7-chloro-6-(4-(4-hydroxy-3-methyltetrahydrofuran-3-yl)piperazin-1-yl)isoquinolin-3-yl)tetrahydrofuran-2-carboxamide, (S)-N-(7-chloro-6-(4-((3R,4R or 3S,4S)-4-hydroxy-3-methyltetrahydrofuran-3-yl)piperazin-1-yl)isoquinolin-3-yl)tetrahydrofuran-2-carboxamide | Cal'c: 461 Found: 461 |

TABLE 9-continued

| Example | Structure<br>Name | Observed m/z [M + H]+ |
|---|---|---|
| 9.5 | 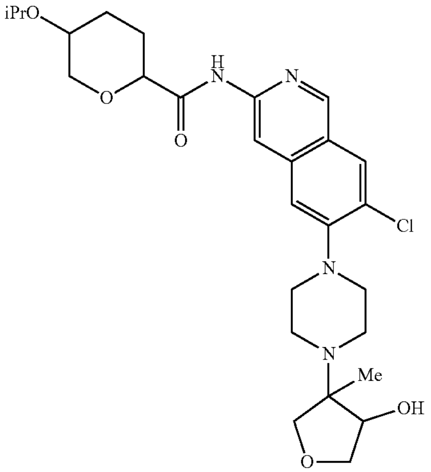<br>(2R,5S)-N-(7-chloro-6-(1-(4-hydroxy-3-methyltetrahydrofuran-3-yl)piperidin-4-yl)isoquinolin-3-yl)-5-isopropoxytetrahydro-2H-pyran-2-carboxamide, (2R,5S)-N-(7-chloro-6-(1-((3R,4R or 3S,4S)-4-hydroxy-3-methyltetrahydrofuran-3-yl)piperidin-4-yl)isoquinolin-3-yl)-5-isopropoxytetrahydro-2H-pyran-2-carboxamide | Cal'c: 533 Found: 533 |
| 9.6 | 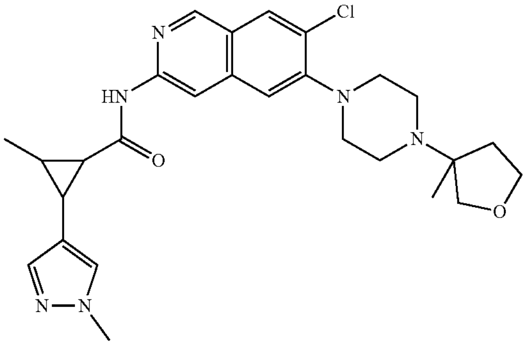<br>Rac-N-[7-chloro-6-[4-(3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R, or 1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-methyl-3-(1-methylpyrazol-4-yl)cyclopropanecarboxamide | Cal'c: 509 Found: 509 |

TABLE 9-continued

| Example | Structure<br>Name | Observed m/z [M + H]$^+$ |
|---|---|---|
| 9.7, 9.8, 9.9 | 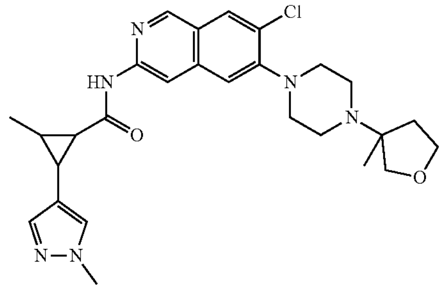<br>Rac-N-[7-chloro-6-[4-(3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R, or 1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R, or 1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-methyl-3-(1-methylpyrazol-4-yl)cyclopropanecarboxamide , (1R,2R,3R, or 1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-methyl-3-(1-methylpyrazol-4-yl)cyclopropanecarboxamide | Cal'c: 509 Found: 509 |
| 9.10, 9.11 | 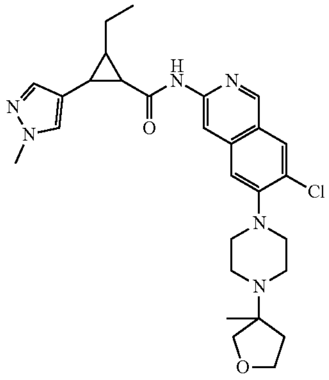<br>Rac-N-[7-chloro-6-[4-(3-methyltetrahydrofuran-3-yl)piperazin-4-ium-1-yl]-3-isoquinolyl]-2-ethyl-3-(1-methylpyrazol-4-yl)cyclopropanecarboxamide, (1R,2R,3R,1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-ethyl-3-(1-methylpyrazol-4-yl)cyclopropanecarboxamide, (1R,2R,3R,1R,2S,3R, or 1S,2R,3S, or 1S,2S,3S)-N-[7-chloro-6-[4-((R or S)-3-methyltetrahydrofuran-3-yl)piperazin-4-ium-1-yl]-3-isoquinolyl]-2-ethyl-3-(1-methylpyrazol-4-yl)cyclopropanecarboxamide | Cal'c: 523 Found: 523 |

TABLE 9-continued

| Example | Structure<br>Name | Observed m/z [M + H]$^+$ |
| --- | --- | --- |
| 9.12, 9.13, 9.14, 9.15 | 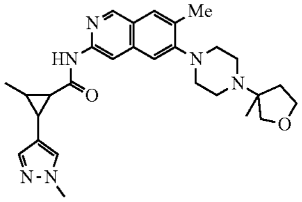<br>Rac-2-methyl-N-[7-methyl-6-[4-(3-methyltetrahydrofuran-3-yl)piperazin-4-ium-1-yl]-3-isoquinolyl]-3-(1-methylpyrazol-4-yl)cyclopropanecarboxamide, (1R,2R,3R, 1R,2S,3R, or 1S,2R,3S or 1S,2S,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2R,3R, 1R,2S,3R, or 1S,2R,3S or 1S,2S,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2R,3R,1R,2S,3R, or 1S,2R,3S or 1S,2S,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2R,3R,1R,2S,3R, or 1S,2R,3S or 1S,2S,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide | Cal'c: 489 Found: 489 |
| 9.16, 9.17, 9.18 | 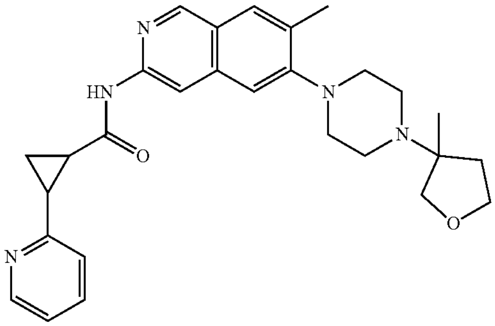<br>Rac-N-[7-methyl-6-[4-(3-methyltetrahydrofuran-3-yl)piperazin-4-ium-1-yl]-3-isoquinolyl]-2-(2-pyridyl)cyclopropanecarboxamide, (1R,2R or 1S,2S)-N-[7-methyl-6-[4-((3R or 3S)-3-methyltetrahydrofuran-3-yl)piperazin-4-ium-1-yl]-3-isoquinolyl]-2-(2-pyridyl)cyclopropanecarboxamide, (1R,2R or 1S,2S)-N-[7-methyl-6-[4-((3R or 3S)-3-methyltetrahydrofuran-3-yl)piperazin-4-ium-1-yl]-3-isoquinolyl]-2-(2-pyridyl)cyclopropanecarboxamide, (1R,2R or 1S,2S)-N-[7-methyl-6-[4-((3R or 3S)-3-methyltetrahydrofuran-3-yl)piperazin-4-ium-1-yl]-3-isoquinolyl]-2-(2-pyridyl)cyclopropanecarboxamide | Cal'c: 472 Found: 472 |

TABLE 9-continued

| Example | Structure<br>Name | Observed m/z [M + H]$^+$ |
| --- | --- | --- |
| 9.19 | 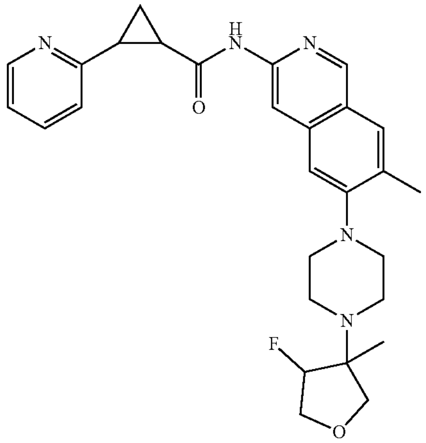<br>Rac-N-[6-[4-(4-fluoro-3-methyl-tetrahydrofuran-3-yl)piperazin-1-yl]-7-methyl-3-isoquinolyl]-2-(2-pyridyl)cyclopropanecarboxamide, (1R,2R or 1S,2S)-N-[6-[4-((3R,4R or 3S-4S)-4-fluoro-3-methyl-tetrahydrofuran-3-yl)piperazin-1-yl]-7-methyl-3-isoquinolyl]-2-(2-pyridyl)cyclopropanecarboxamide, | Cal'c: 490 Found: 490 |
| 9.20 | 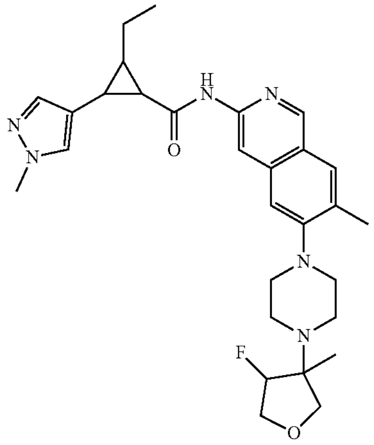<br>Rac-2-ethyl-N-[6-[4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1R,2R,3R, or 1R,2S,3R, or 1S,2R,3S, or 1S,2S,3S)-2-ethyl-N-[6-[(3R,4R or 3S,4S)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide | Cal'c: 521 Found: 521 |

TABLE 9-continued

| Example | Structure<br>Name | Observed m/z [M + H]$^+$ |
|---|---|---|
| 9.21 | 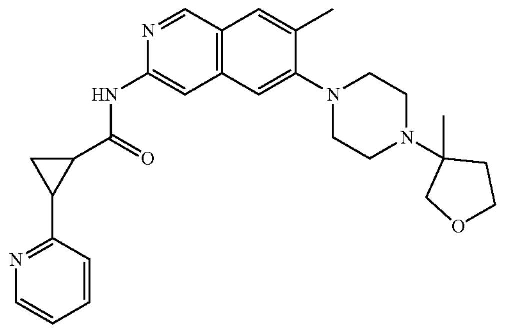<br>Rac-N-[7-methyl-6-[4-(3-methyltetrahydrofuran-3-yl)piperazin-4-ium-1-yl]-3-isoquinolyl]-2-(2-pyridyl)cyclopropanecarboxamide, (1R,2R or 1S,2S)-N-[7-methyl-6-[4-((R or S)-3-methyltetrahydrofuran-3-yl)piperazin-4-ium-1-yl]-3-isoquinolyl]-2-(2-pyridyl)cyclopropanecarboxamide | Cal'c: 472 Found: 472 |

General Scheme 10.

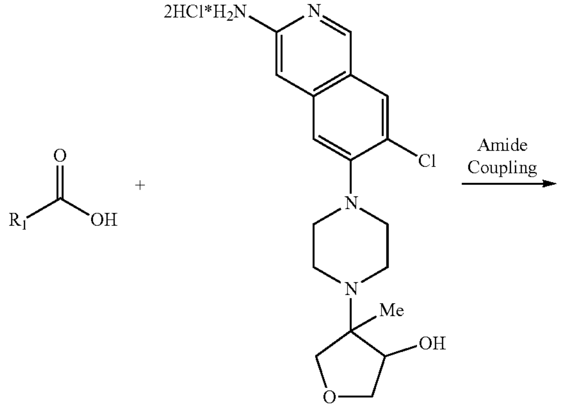

37

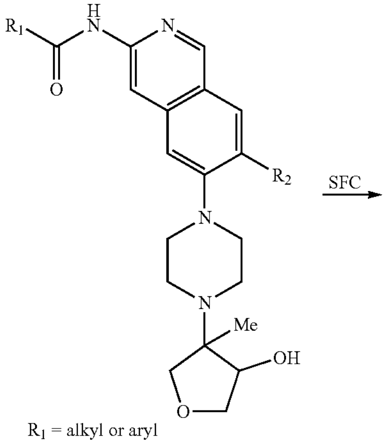

$R_1$ = alkyl or aryl

Gen-24

-continued

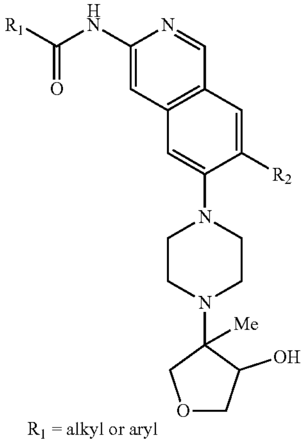

$R_1$ = alkyl or aryl

Gen-25

In General Scheme 10, commercially available carboxylic acids or acid chlorides were coupled with synthetically prepared intermediate 37 through amide coupling conditions to provide Gen-24 and the stereoisomers were separated by chiral SFC to provide fully elaborated products in the form of Gen-25. The representative compounds are described in more detail shown below.

Scheme 46. N-(7-chloro-6-(4-(4-hydroxy-3-methyltetrahydrofuran-3-yl)piperazin-1-yl)isoquinolin-3-yl)-5,5-difluorotetrahydro-2H-pyran-2-carboxamide, (2R or 2S)-N-(7-chloro-6-((3R,4R or 3S,4S)-4-(4-hydroxy-3-methyltetrahydrofuran-3-yl)piperazin-1-yl)isoquinolin-3-yl)-5,5-difluorotetrahydro-2H-pyran-2-carboxamide (Ex-10.1) and (Ex-10.2).

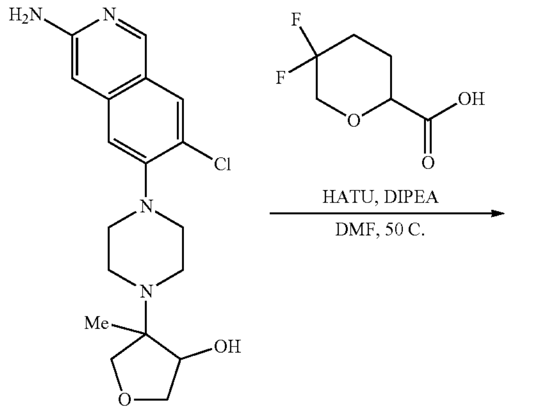

37

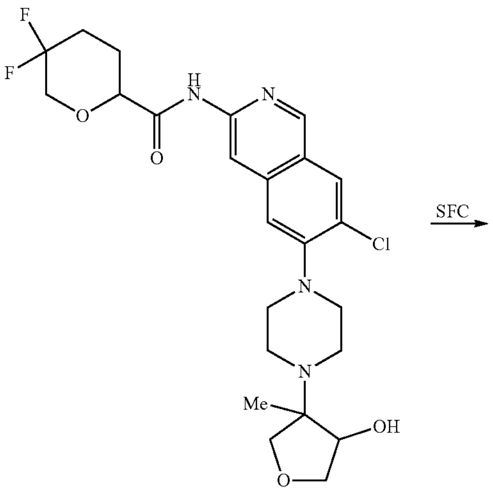

82

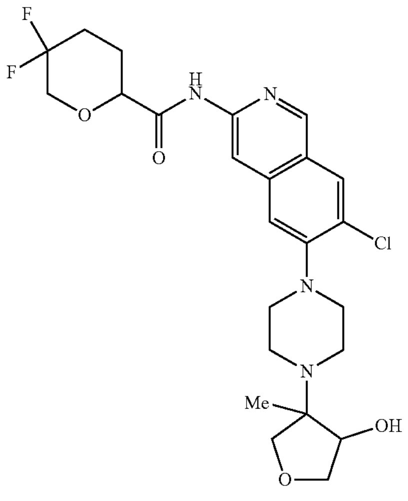

Ex-10.1

-continued

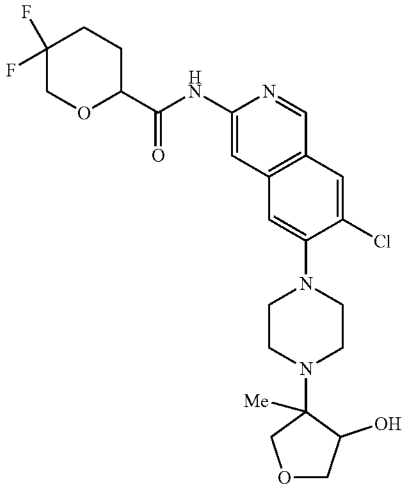

Ex-10.2

4-(4-(3-amino-7-chloroisoquinolin-6-yl)piperazin-1-yl)-4-methyltetrahydrofuran-3-ol37 (100 mg, 0.276 mmol), 5,5-difluorotetrahydro-2H-pyran-2-carboxylic acid (54.9 mg, 0.331 mmol), HATU (210 mg, 0.551 mmol), DMF (1378 μl), and DIEA (96 μl, 0.551 mmol) were added to a vial. The resulting mixture was allowed to stir overnight at room temperature. The reaction mixture was filtered, purified by HPLC, eluting acetonitrile/water gradient with 0.1% TFA modifier, linear gradient and lyophilized to afford the product as a TFA salt. The product was diluted with DCM and washed with saturated sodium bicarbonate, and concentrated in vacuo to afford compound 82. The mixture of two stereoisomers was purified by chiral SFC (OJ-H, 21×250 (mm), 30%/70% Methanol/$CO_2$+0.1% $NH_4OH$) and to afford title compounds Ex-10.1 (Tr=3.65 min) and Ex-10.2 (Tr=5.90 min). Ex-10.1: MS (ESI) m/z calc'd for $C_{24}H_{30}ClF_2N_4O_4$ $[M+H]^+$: 511, found 511. H NMR (500 MHz chloroform-d) δ 9.88 (s, 1H), 9.00 (s, 1H), 8.38 (s, 1H), 8.19 (s, 1H), 7.51 (s, 1H), 4.42-4.24 (m, 2H), 4.09 (m, 1H), 3.98 (m, 1H), 3.80 (m, 1H), 3.73 (m, 1H), 3.66 (m, 1H), 3.56 (m, 1H), 3.19 (s, 3H), 2.76 (s, 2H), 2.53 (s, 1H), 2.26 (s, 1H), 2.21-2.06 (m, 2H), 1.90-1.77 (m, 1H), 1.24 (s, 1H), 1.06 (s, 3H). Ex-10.2: MS (ESI): m/z calc'd for $C_{24}H_{30}ClF_2N_4O_4$ $[M+H]^+$: 511, found 511. $^1H$ NMR (499 MHz, DMSO-$d_6$) δ 9.89 (s, 1H), 9.00 (s, 1H), 8.38 (s, 1H), 8.19 (s, 1H), 7.51 (s, 1H), 4.36-4.26 (m, 2H), 4.09 (m, 1H), 3.98 (d, J=7.4 Hz, 1H), 3.80 (m, 2H), 3.71 (m, 1H), 3.66 (m, 2H), 3.55 (s, 1H), 3.19 (s, 3H), 2.76 (s, 2H), 2.53 (s, 1H), 2.26 (s, 1H), 2.16 (m, 1H) 1.83 (m, 1H), 1.06 (s, 3H).

Compounds in Table 10 below were prepared in accordance with the synthetic sequence illustrated in General Scheme 10 and Scheme 46 using the corresponding starting materials.

TABLE 10

| Example | Structure<br>Name | Observed<br>m/z<br>$[M + H]^+$ |
|---|---|---|
| 10.1,<br>10.2 | 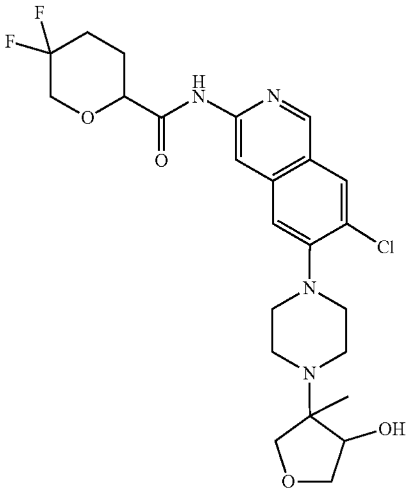 [SMILES: CC1(N2CCN(c3cc4cc(NC(=O)C5CCC(F)(F)CO5)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-5,5-difluorotetrahydro-2H-pyran-2-carboxamide,<br>(2R or 2S)-N-(7-chloro-6-((3R, 4R or 3S, 4S)-4-(4-hydroxy-3-methyltetrahydrofuran-3-yl)piperazin-1-yl)isoquinolin-3-yl)-5,5-difluorotetrahydro-2H-pyran-2-carboxamide, (2R or 2S)-N-(7-chloro-6-((3R, 4R or 3S, 4S)-4-(4-hydroxy-3-methyltetrahydrofuran-3-yl)piperazin-1-yl)isoquinolin-3-yl)-5,5-difluorotetrahydro-2H-pyran-2-carboxamide | Cal'c:<br>511<br>Found:<br>511 |
| 10.3,<br>10.4 | 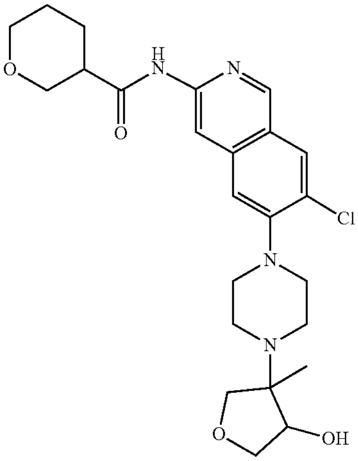 [SMILES: CC1(N2CCN(c3cc4cc(NC(=O)C5CCCOC5)ncc4cc3Cl)CC2)COCC1O]<br>N-(7-chloro-6-(4-((3S, 4S or 3R, 4R)-4-hydroxy-3-methyltetrahydrofuran-3-yl)piperazin-1-yl)isoquinolin-3-yl) tetrahydro-2H-pyran-3-carboxamide ,<br>(3R or 3S)-N-(7-chloro-6-(4-((3R, 4R or 3S, 4S)-4-hydroxy-3-methyltetrahydrofuran-3-yl)piperazin-1-yl)isoquinolin-3-yl)tetrahydro-2H-pyran-3-carboxamide, (3R or 3S)-N-(7-chloro-6-(4-((3R, 4R or 3S,4S)-4-hydroxy-3-methyltetrahydrofuran-3-yl)piperazin-1-yl)isoquinolin-3-yl)tetrahydro-2H-pyran-3-carboxamide | Cal'c:<br>475<br>Found:<br>475 |

TABLE 10-continued

| Example | Structure<br>Name | Observed<br>m/z<br>[M + H]+ |
|---|---|---|
| 10.5,<br>10.6 | 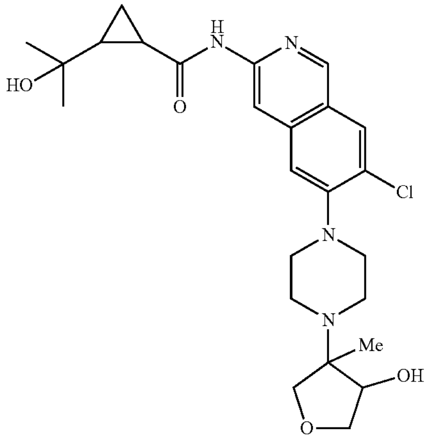 [SMILES: CC(C)(O)C1CC1C(=O)Nc1cc2cc(N3CCN(C4(C)COCC4O)CC3)c(Cl)cc2cn1]<br>Rac-N-(7-chloro-6-(1-(4-hydroxy-3-methyltetrahydrofuran-3-yl)piperidin-4-yl)isoquinolin-3-yl)-2-(2-hydroxypropan-2-yl)cyclopropane-1-carboxamide,<br>(IR, 2R or 1S,2S)-N-(7-chloro-6-(1-((3R, 4R or 3S, 4S)-4-hydroxy-3-methyltetrahydrofuran-3-yl)piperidin-4-yl)isoquinolin-3-yl)-2-(2-hydroxypropan-2-yl)cyclopropane-1-carboxamide, (1R, 2R or 1S,2S)-N-(7-chloro-6-(1-((3R, 4R or 3S,4S)-4-hydroxy-3-methyltetrahydrofuran-3-yl)piperidin-4-yl)isoquinolin-3-yl)-2-(2-hydroxypropan-2-yl)cyclopropane-1-carboxamide | Cal'c:<br>489<br>Found:<br>489 |
| 10.7,<br>10.8 | 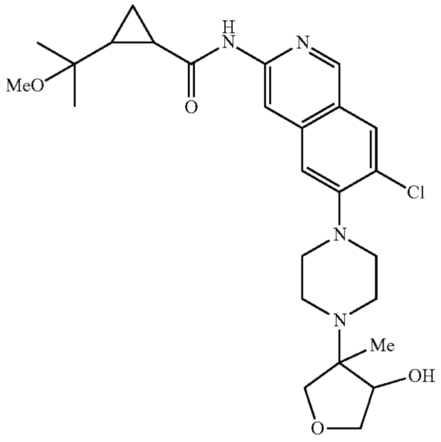 [SMILES: COC(C)(C)C1CC1C(=O)Nc1cc2cc(N3CCN(C4(C)COCC4O)CC3)c(Cl)cc2cn1]<br>Rac-N-(7-chloro-6-(1-(4-hydroxy-3-methyltetrahydrofuran-3-yl)piperidin-4-yl)isoquinolin-3-yl)-2-(2-methoxypropan-2-yl)cyclopropane-1-carboxamide,<br>(IR, 2R, 1S,2S)-N-(7-chloro-6-(1-((3R, 4R or 3S, 4S)-4-hydroxy-3-methyltetrahydrofuran-3-yl)piperidin-4-yl)isoquinolin-3-yl)-2-(2-methoxypropan-2-yl)cyclopropane-1-carboxamide, (IR, 2R, IS,2S)-N-(7-chloro-6-(1-((3R, 4R or 3S,4S)-4-hydroxy-3-methyltetrahydrofuran-3-yl)piperidin-4-yl)isoquinolin-3-yl)-2-(2-methoxypropan-2-yl)cyclopropane-1-carboxamide | Cal'c:<br>503<br>Found:<br>503 |

TABLE 10-continued

| Example | Structure<br>Name | Observed m/z [M + H]+ |
|---|---|---|
| 10.9, 10.10 | 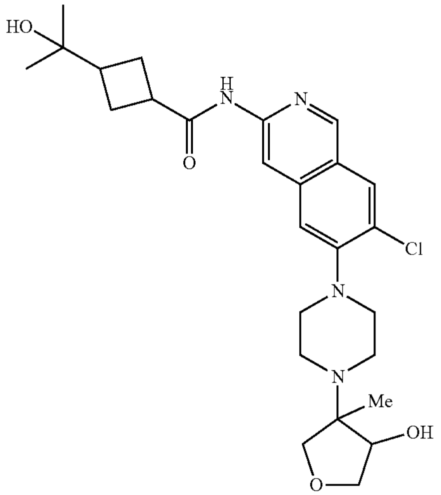 [SMILES: CC(C)(O)C1CC(C(=O)Nc2cc3cc(N4CCN(C5(C)COCC5O)CC4)c(Cl)cc3cn2)C1]<br>Rac-N-(7-chloro-6-(1-(4-hydroxy-3-methyltetrahydrofuran-3-yl)piperidin-4-yl)isoquinolin-3-yl)-3-(2-hydroxypropan-2-yl) cyclobutane-1-carboxamide), Cis or trans-N-(7-chloro-6-(1-((3R, 4R or 3S, 4S)-4-hydroxy-3-methyltetrahydrofuran-3-yl)piperidin-4-yl)isoquinolin-3-yl)-3-(2-hydroxypropan-2-yl)cyclobutane-1-carboxamide | Cal'c: 503 Found: 503 |
| 10.11, 10.12 | 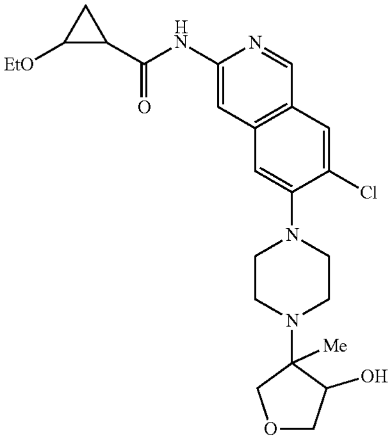 [SMILES: CCOC1CC1C(=O)Nc1cc2cc(N3CCN(C4(C)COCC4O)CC3)c(Cl)cc2cn1]<br>Rac-N-(7-chloro-6-(1-(4-hydroxy-3-methyltetrahydrofuran-3-yl)piperidin-4-yl)isoquinolin-3-yl)-2-ethoxycyclopropane-1-carboxamide, (1R,2S or 1S,2R)-N-(7-chloro-6-(1-((3R,4R or 3S,4S)-4-hydroxy-3-methyltetrahydrofuran-3-yl)piperidin-4-yl)isoquinolin-3-yl)-2-ethoxycyclopropane-1-carboxamide, (1R,2S or 1S,2R)-N-(7-chloro-6-(1-((3R,4R or 3S,4S)-4-hydroxy-3-methyltetrahydrofuran-3-yl)piperidin-4-yl)isoquinolin-3-yl)-2-ethoxycyclopropane-1-carboxamide | Cal'c: 475 Found: 475 |
| 10.13, 10.14 | 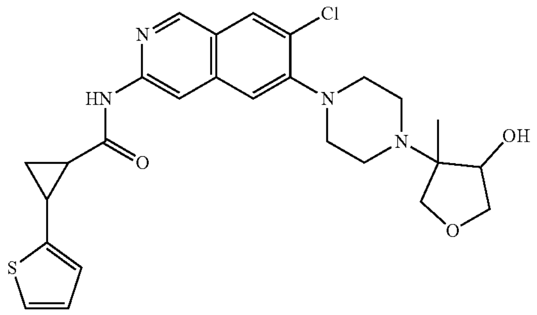 [SMILES: CC1(N2CCN(c3cc4cc(NC(=O)C5CC5c5cccs5)ncc4cc3Cl)CC2)COCC1O] | Cal'c: 513 Found: 513 |

TABLE 10-continued

| Example | Structure<br>Name | Observed m/z [M + H]+ |
|---|---|---|
| | Rac-N-[7-chloro-6-[4-(4-hydroxy-3-methyl-tetrahydrofuran-3-yl)piperazin-1-yl]-3-isoquinolyl]-2-(2-thienyl)cyclopropanecarboxamide, (1R,2R or 1R,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-thienyl)cyclopropanecarboxamide, (1R,2R or 1R,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-thienyl)cyclopropanecarboxamide | |
| 10.15, 10.16 | 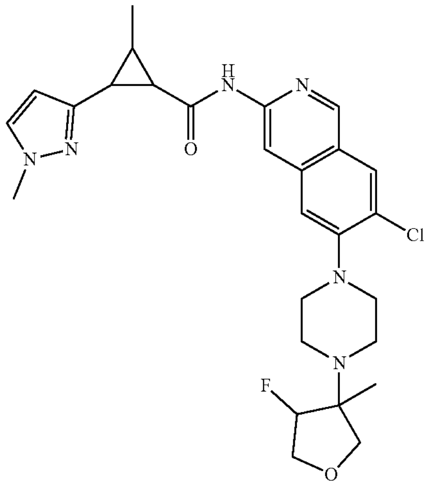 [SMILES: CC1C(C(=O)Nc2cc3cc(N4CCN(C5(C)COCC5F)CC4)c(Cl)cc3cn2)C1c1ccn(C)n1]<br>Rac-N-[7-chloro-6-[4-(4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide | Cal'c: 527 Found: 527 |
| 10.17, 10.18 | 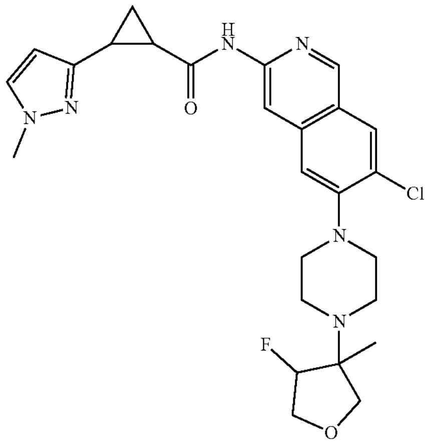 [SMILES: Cn1ccc(C2CC2C(=O)Nc2cc3cc(N4CCN(C5(C)COCC5F)CC4)c(Cl)cc3cn2)n1] | Cal'c: 513 Found: 513 |

TABLE 10-continued

| Example | Structure<br>Name | Observed<br>m/z<br>[M + H]+ |
|---|---|---|
| | Rac-N-[7-chloro-6-[4-(4-fluoro-3-methyl-tetrahydrofuran-3-yl)piperazin-1-yl]-3-isoquinolyl]-2-(1-methylpyrazol-3-yl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(1-methylpyrazol-3-yl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(1-methylpyrazol-3-yl)cyclopropanecarboxamide | |
| 10.19,<br>10.20 | 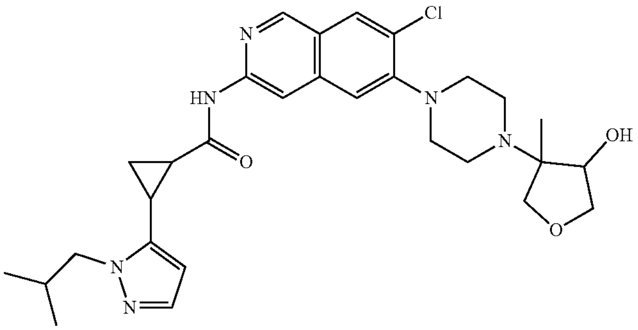 [SMILES: CC(C)Cn1nccc1C1CC1C(=O)Nc1cc2cc(N3CCN(C4(C)COCC4O)CC3)c(Cl)cc2cn1]<br>Rac-N-[7-chloro-6-[4-(4-hydroxy-3-methyl-tetrahydrofuran-3-yl)piperazin-1-yl]-3-isoquinolyl]-2-(2-isobutylpyrazol-3-yl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-isobutylpyrazol-3-yl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-isobutylpyrazol-3-yl)cyclopropanecarboxamide | Cal'c:<br>553<br>Found:<br>553 |
| 10.21,<br>10.22 | 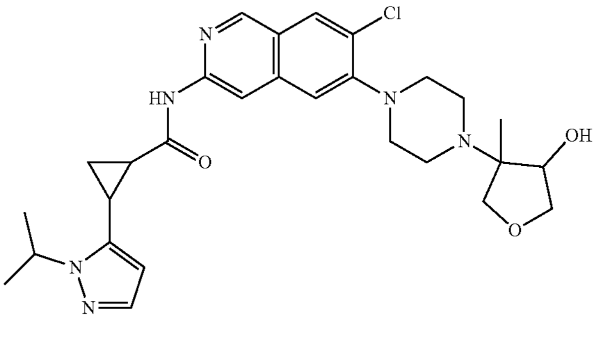 [SMILES: CC(C)n1nccc1C1CC1C(=O)Nc1cc2cc(N3CCN(C4(C)COCC4O)CC3)c(Cl)cc2cn1]<br>Rac-N-[7-chloro-6-[4-(4-hydroxy-3-methyl-tetrahydrofuran-3-yl)piperazin-1-yl]-3-isoquinolyl]-2-(2-isopropylpyrazol-3-yl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-isopropylpyrazol-3-yl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-isopropylpyrazol-3-yl)cyclopropanecarboxamide | Cal'c:<br>539<br>Found:<br>5359 |

TABLE 10-continued

| Example | Structure<br>Name | Observed m/z [M + H]+ |
|---|---|---|
| 10.23,<br>10.24 | 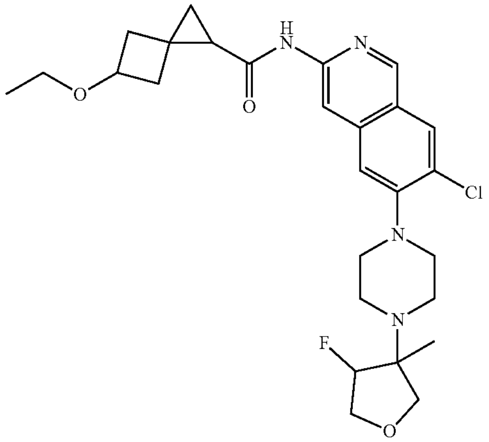 [SMILES: CCOC1CC2(C1)CC2C(=O)Nc1cc2cc(N3CCN(C4(C)COCC4F)CC3)c(Cl)cc2cn1]<br>Rac-N-[7-chloro-6-[4-(4-fluoro-3-methyl-tetrahydrofuran-3-yl)piperazin-1-yl]-3-isoquinolyl]-5-ethoxy-spiro[2.3]hexane-2-carboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-5-ethoxy-spiro[2.3]hexane-2-carboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-5-ethoxy-spiro[2.3]hexane-2-carboxamide | Cal'c: 517<br>Found: 517 |
| 10.25,<br>10.26,<br>10.27,<br>10.28 | 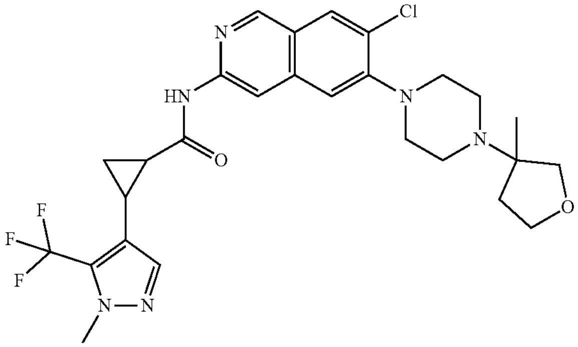 [SMILES: Cn1ncc(C2CC2C(=O)Nc2cc3cc(N4CCN(C5(C)CCOC5)CC4)c(Cl)cc3cn2)c1C(F)(F)F]<br>Rac-N-[7-chloro-6-[4-(3-methyltetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((R or S)-3-methyltetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((R or S)-3-methyltetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((R or S)-3-methyltetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((R or S)-3-methyltetrahydrofuran-3-yl)piperazin-4-ium-1-yl]-3-isoquinolyl]-2-[1-methyl-5-(trifluoromethyl)pyrazol-4-yl]cyclopropanecarboxamide | Cal'c: 563<br>Found: 563 |

TABLE 10-continued

| Example | Structure<br>Name | Observed m/z [M + H]+ |
| --- | --- | --- |
| 10.29, 10.30 | 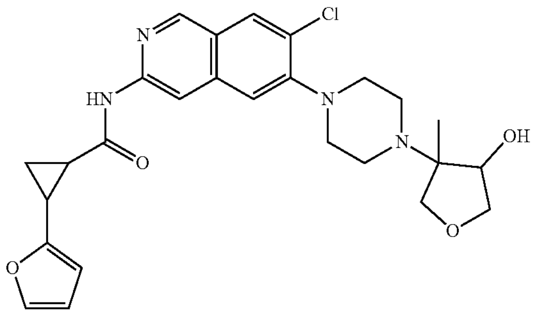 [SMILES: CC1(N2CCN(c3cc4cc(NC(=O)C5CC5c5ccco5)ncc4cc3Cl)CC2)COCC1O]<br>Rac-N-[7-chloro-6-[4-(4-hydroxy-3-methyl-tetrahydrofuran-3-yl)piperazin-1-yl]-3-isoquinolyl]-2-(2-furyl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-furyl)cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-(2-furyl)cyclopropanecarboxamide | Cal'c: 497 Found: 497 |
| 10.31, 10.32 | 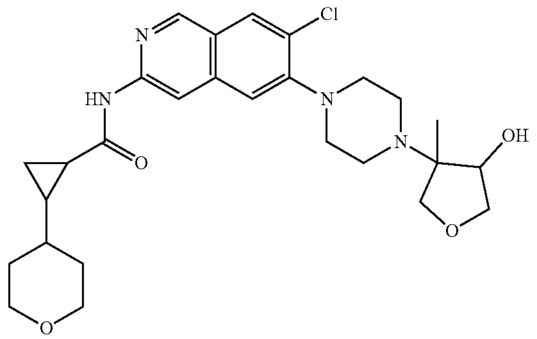 [SMILES: CC1(N2CCN(c3cc4cc(NC(=O)C5CC5C5CCOCC5)ncc4cc3Cl)CC2)COCC1O]<br>Rac-N-[7-chloro-6-[4-(4-hydroxy-3-methyl-tetrahydrofuran-3-yl)piperazin-1-yl]-3-isoquinolyl]-2-tetrahydropyran-4-yl-cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-tetrahydropyran-4-yl-cyclopropanecarboxamide, (1R,2R or 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-tetrahydropyran-4-yl-cyclopropanecarboxamide | Cal'c: 515 Found: 515 |
| 10.33, 10.34, 10.35, 10.36 | 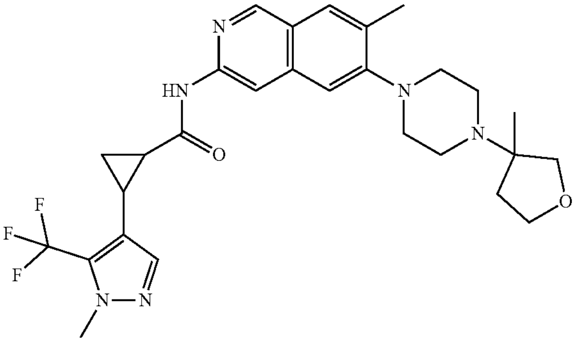 [SMILES: Cc1cc2cnc(NC(=O)C3CC3c3cnn(C)c3C(F)(F)F)cc2cc1N1CCN(C2(C)CCOC2)CC1]<br>Rac-N-[7-methyl-6-[4-(3-methyltetrahydrofuran-3-yl)piperazin-1-yl]-3-isoquinolyl]-2-[1-methyl-5-(trifluoromethyl)pyrazol-4-yl]cyclopropanecarboxamide, (1R,2R or 1S,2S)-N-[7-methyl-6-[4-((R or S)-3-methyltetrahydrofuran-3-yl)piperazin-1-yl]-3-isoquinolyl]-2-[1-methyl-5-(trifluoromethyl)pyrazol-4-yl]cyclopropanecarboxamide, (1R,2R or 1S,2S)-N-[7-methyl-6-[4-((R | Cal'c: 543 Found: 543 |

TABLE 10-continued

| Example | Structure<br>Name | Observed m/z [M + H]+ |
|---|---|---|
| | or S)-3-methyltetrahydrofuran-3-yl)piperazin-1-yl]-3-isoquinolyl]-2-[1-methyl-5-(trifluoromethyl)pyrazol-4-yl]cyclopropanecarboxamide, (1R,2R or 1S,2S)-N-[7-methyl-6-[4-((R or S)-3-methyltetrahydrofuran-3-yl)piperazin-1-yl]-3-isoquinolyl]-2-[1-methyl-5-(trifluoromethyl)pyrazol-4-yl]cyclopropanecarboxamide, (1R,2R or 1S,2S)-N-[7-methyl-6-[4-((R or S)-3-methyltetrahydrofuran-3-yl)piperazin-1-yl]-3-isoquinolyl]-2-[1-methyl-5-(trifluoromethyl)pyrazol-4-yl]cyclopropanecarboxamide | |
| 10.37, 10.38 | 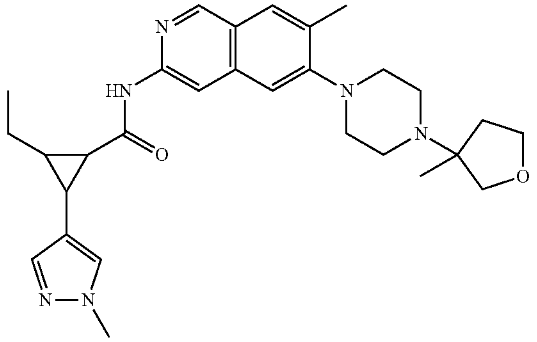 [SMILES: CCC1C(C(=O)Nc2cc3cc(N4CCN(C5(C)CCOC5)CC4)c(C)cc3cn2)C1c1cnn(C)c1]<br>Rac-2-ethyl-N-[7-methyl-6-[4-(3-methyltetrahydrofuran-3-yl)piperazin-4-ium-1-yl]-3-isoquinolyl]-3-(1-methylpyrazol-4-yl)cyclopropanecarboxamide, (1R,2R,3R, IR,2S,3R, 1S,2R,3S, or 1S,2S,3S)-2-ethyl-N-[7-methyl-6-[4-((R or S)-3-methyltetrahydrofuran-3-yl)piperazin-4-ium-1-yl]-3-isoquinolyl]-3-(1-methylpyrazol-4-yl)cyclopropanecarboxamide, (1R,2R,3R, 1R,2S,3R, 1S,2R,3S, or 1S,2S,3S)-2-ethyl-N-[7-methyl-6-[4-((R or S)-3-methyltetrahydrofuran-3-yl)piperazin-4-ium-1-yl]-3-isoquinolyl]-3-(1-methylpyrazol-4-yl)cyclopropanecarboxamide | Cal'c: 503 Found: 503 |
| 10.39, 10.40 | 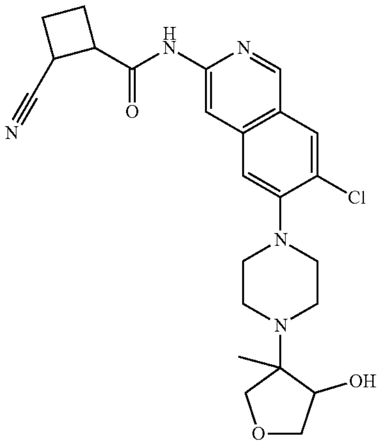 [SMILES: CC1(N2CCN(c3cc4cc(NC(=O)C5CCC5C#N)ncc4cc3Cl)CC2)COCC1O]<br>Rac-N-[7-chloro-6-[4-(4-hydroxy-3-methyl-tetrahydrofuran-3-yl)piperazin-1-yl]-3-isoquinolyl]-2-cyano-cyclobutanecarboxamide, (1R,2R of 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-cyano-cyclobutanecarboxamide, (1R,2R of 1S,2S)-N-[7-chloro-6-[4-((3R,4R or 3S,4S)-4-hydroxy-3-methyl-tetrahydrofuran-3-yl)piperazin-1-yl]-3-isoquinolyl]-2-cyano-cyclobutanecarboxamide | Cal'c: 470 Found: 470 |

TABLE 10-continued

| Example | Structure<br>Name | Observed m/z [M + H]$^+$ |
|---|---|---|
| 10.41,<br>10.42,<br>10.43,<br>10.44 | 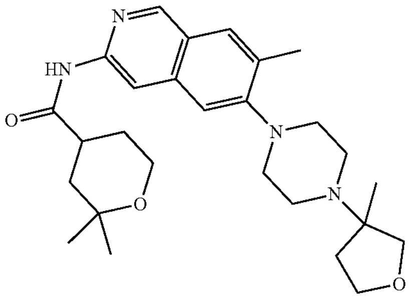 [SMILES: Cc1cc2cnc(NC(=O)C3CCOC(C)(C)C3)cc2cc1N1CCN(C2(C)CCOC2)CC1]<br>Rac-2,2-dimethyl-N-[7-methyl-6-[4-(3-methyltetrahydrofuran-3-yl)piperazin-1-yl]-3-isoquinolyl]tetrahydropyran-4-carboxamide, (4R or 4S)-2,2-dimethyl-N-[7-methyl-6-[4-((R or S)-3-methyltetrahydrofuran-3-yl)piperazin-1-yl]-3-isoquinolyl]tetrahydropyran-4-carboxamide, (4R or 4S)-2,2-dimethyl-N-[7-methyl-6-[4-((R or S)-3-methyltetrahydrofuran-3-yl)piperazin-1-yl]-3-isoquinolyl]tetrahydropyran-4-carboxamide, (4R or 4S)-2,2-dimethyl-N-[7-methyl-6-[4-((R or S)-3-methyltetrahydrofuran-3-yl)piperazin-1-yl]-3-isoquinolyl]tetrahydropyran-4-carboxamide, (4R or 4S)-2,2-dimethyl-N-[7-methyl-6-[4-((R or S)-3-methyltetrahydrofuran-3-yl)piperazin-1-yl]-3-isoquinolyl]tetrahydropyran-4-carboxamide | Cal'c:<br>467<br>Found:<br>467 |
| 10.45,<br>10.46,<br>10.47,<br>10.48 | 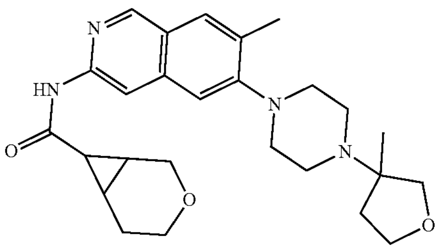 [SMILES: Cc1cc2cnc(NC(=O)C3C4CCOCC43)cc2cc1N1CCN(C2(C)CCOC2)CC1]<br>Rac-N-[7-methyl-6-[4-(3-methyltetrahydrofuran-3-yl)piperazin-1-yl]-3-isoquinolyl]-3-oxabicyclo[4.1.0]heptane-7-carboxamide. (1S,6R,7R, 1R,6S,7R, or 1R, 6S,7S, or 1S,6S,7S)-N-(7-methyl-6-(4-((R or S)-3-methyltetrahydrofuran-3-yl)piperazin-1-yl)isoquinolin-3-yl)-3-oxabicyclo[4.1.0]heptane-7-carboxamide, (1S,6R,7R, 1R,6S,7R, or 1R, 6S,7S, or 1S,6S,7S)-N-(7-methyl-6-(4-((R or S)-3-methyltetrahydrofuran-3-yl)piperazin-1-yl)isoquinolin-3-yl)-3-oxabicyclo[4.1.0]heptane-7-carboxamide, (1S,6R,7R, 1R,6S,7R, or 1R, 6S,7S, or 1S,6S,7S)-N-(7-methyl-6-(4-((R or S)-3-methyltetrahydrofuran-3-yl)piperazin-1-yl)isoquinolin-3-yl)-3-oxabicyclo[4.1.0]heptane-7-carboxamide, (1S,6R,7R, 1R,6S,7R, or 1R, 6S,7S, or 1S,6S,7S)-N-(7-methyl-6-(4-((R or S)-3-methyltetrahydrofuran-3-yl)piperazin-1-yl)isoquinolin-3-yl)-3-oxabicyclo[4.1.0]heptane-7-carboxamide | Cal'c:<br>451<br>Found:<br>451 |

TABLE 10-continued

| Example | Structure<br>Name | Observed m/z [M + H]$^+$ |
|---|---|---|
| 10.49, 10.50, 10.51, 10.52 | 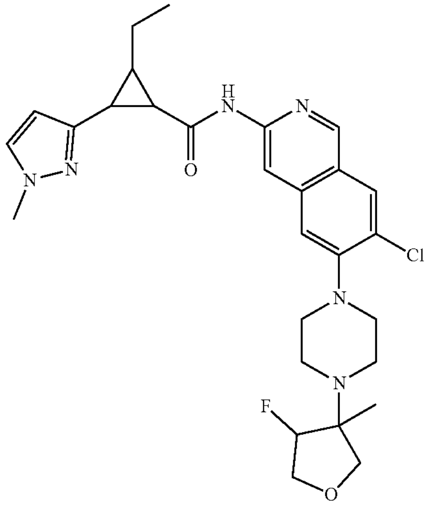 [SMILES: CCC1C(C(=O)Nc2cc3cc(N4CCN(C5(C)COCC5F)CC4)c(Cl)cc3cn2)C1c1ccn(C)n1]<br>Rac-N-[7-chloro-6-[4-(4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide | Cal'c: 541 Found: 541 |
| 10.53, 10.54, 10.55, 10.56 | 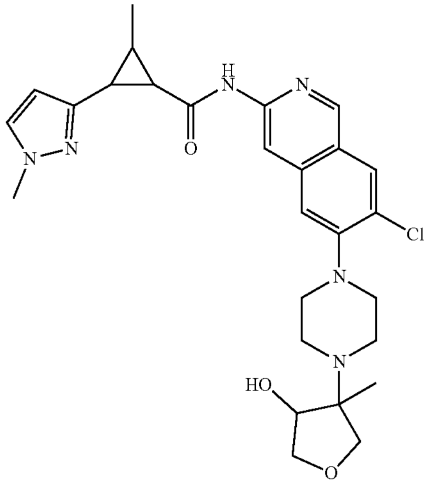 [SMILES: CC1C(C(=O)Nc2cc3cc(N4CCN(C5(C)COCC5O)CC4)c(Cl)cc3cn2)C1c1ccn(C)n1]<br>Rac-N-[7-chloro-6-[4-(4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3- | Cal'c: 525 Found: 525 |

TABLE 10-continued

| Example | Structure Name | Observed m/z [M + H]+ |
|---|---|---|
| | yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide | |
| 10.57, 10.58 | 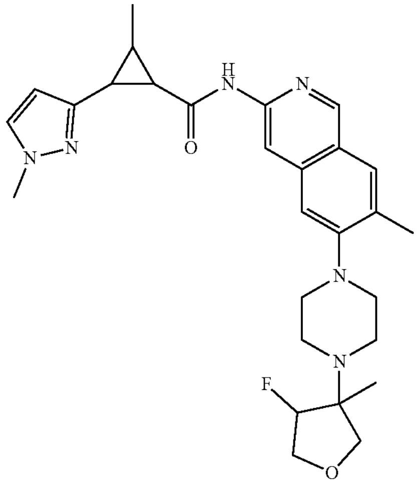 [SMILES: Cc1cc2cnc(NC(=O)C3C(C)C3c3ccn(C)n3)cc2cc1N1CCN(C2(C)COCC2F)CC1] Rac-N-[6-[4-(4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2R,3R, or 1R,2S,3R, or 1S,2R,3S, or 1S,2S,3S)-N-[6-[4-((3R,4R or 3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2R,3R, or 1R,2S,3R, or 1S,2R,3S, or 1S,2S,3S)-N-[6-[4-((3R,4R or 3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide | Cal'c: 507 Found: 507 |
| 10.59, 10.60 | 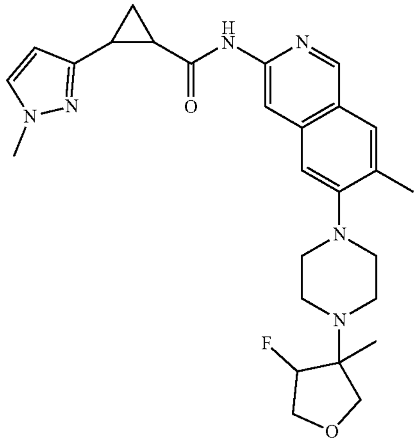 [SMILES: Cc1cc2cnc(NC(=O)C3CC3c3ccn(C)n3)cc2cc1N1CCN(C2(C)COCC2F)CC1] Rac-N-[6-[4-(4-fluoro-3-methyl-tetrahydrofuran-3-yl)piperazin-1-yl]-7-methyl-3-isoquinolyl]-2-(1-methylpyrazol-3-yl)cyclopropanecarboxamide, (1R,2R or 1S,2S)-N-[6-[4-((3R,4R or 3S,4S)-4-fluoro-3-methyl-tetrahydrofuran-3-yl)piperazin-1-yl]-7-methyl-3-isoquinolyl]-2-(1-methylpyrazol-3-yl)cyclopropanecarboxamide, (1R,2R or 1S,2S)-N-[6-[4-((3R,4R or 3S,4S)-4-fluoro-3-methyl-tetrahydrofuran-3-yl)piperazin-1-yl]-7-methyl-3-isoquinolyl]-2-(1-methylpyrazol-3-yl)cyclopropanecarboxamide | Cal'c: 507 Found: 507 |

TABLE 10-continued

| Example | Structure<br>Name | Observed m/z [M + H]+ |
|---|---|---|
| 10.61, 10.62 | 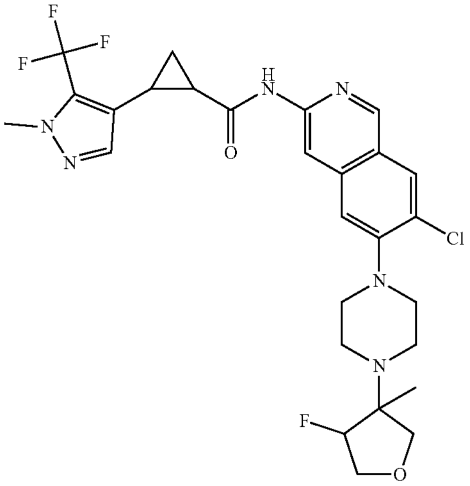 [SMILES: Cn1ncc(C2CC2C(=O)Nc2cc3cc(N4CCN(C5(C)COCC5F)CC4)c(Cl)cc3cn2)c1C(F)(F)F]<br>Rac-N-[7-chloro-6-[4-(4-fluoro-3-methyl-tetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-4-ium-1-yl]-3-isoquinolyl]-2-[1-methyl-5-(trifluoromethyl)pyrazol-4-yl]cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-4-ium-1-yl]-3-isoquinolyl]-2-[1-methyl-5-(trifluoromethyl)pyrazol-4-yl]cyclopropanecarboxamide | Cal'c: 581 Found: 581 |
| 10.63, 10.64 | 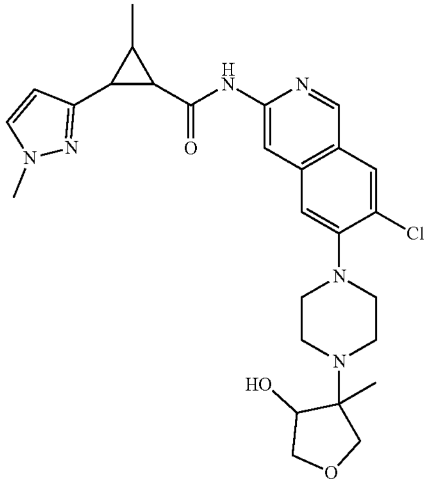 [SMILES: CC1C(C(=O)Nc2cc3cc(N4CCN(C5(C)COCC5O)CC4)c(Cl)cc3cn2)C1c1ccn(C)n1]<br>Rac-N-[7-chloro-6-[4-(4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide | Cal'c: 525 Found: 525 |

TABLE 10-continued

| Example | Structure<br>Name | Observed m/z [M + H]$^+$ |
|---|---|---|
| 10.65, 10.66 | 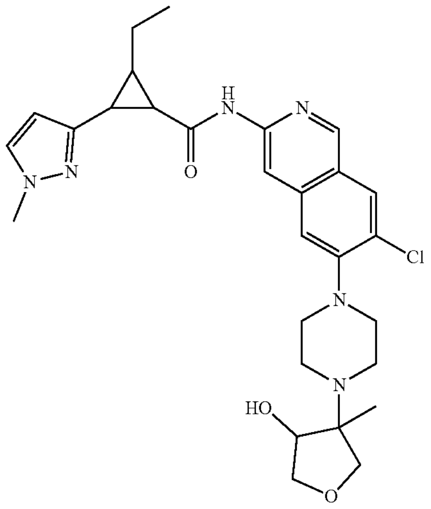 [SMILES: CCC1C(C(=O)Nc2cc3cc(N4CCN(C5(C)COCC5O)CC4)c(Cl)cc3cn2)C1c1ccn(C)n1]<br>Rac-N-[7-chloro-6-[4-(4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, or 1R,2S,3R, or 1S,2R,3S, or 1S,2S,3S)-N-[7-chloro-6-[4-( (3R,4R or 3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R, or 1R,2S,3R, or 1S,2R,3S, or 1S,2S,3S)-N-[7-chloro-6-[4-( (3R,4R or 3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide | Cal'c: 539 Found: 539 |
| 10.67, 10.68 | 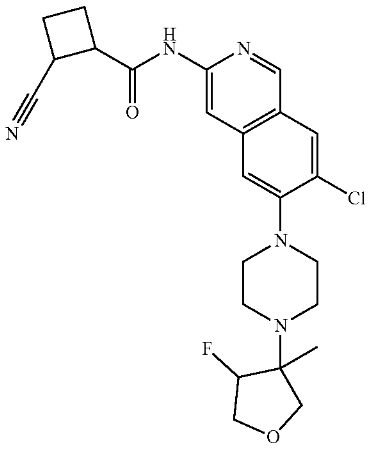 [SMILES: CC1(N2CCN(c3cc4cc(NC(=O)C5CCC5C#N)ncc4cc3Cl)CC2)COCC1F]<br>Rac-N-[7-chloro-6-[4-(4-fluoro-3-methyl-tetrahydrofuran-3-yl)piperazin-1-yl]-3-isoquinolyl]-2-cyano-cyclobutanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-cyano-cyclobutanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-cyano-cyclobutanecarboxamide | Cal'c: 472 Found: |

TABLE 10-continued

| Example | Structure<br>Name | Observed<br>m/z<br>[M + H]$^+$ |
|---|---|---|
| 10.69,<br>10.70 | 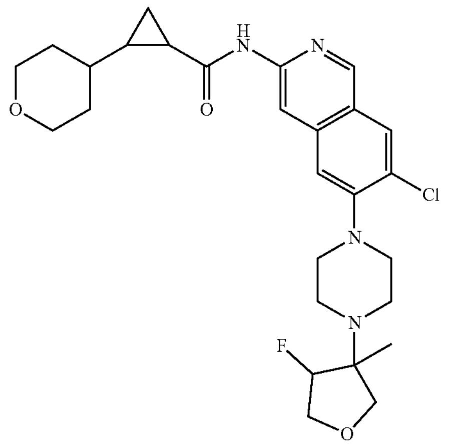 [SMILES: CC1(N2CCN(c3cc4cc(NC(=O)C5CC5C5CCOCC5)ncc4cc3Cl)CC2)COCC1F]<br>Rac-N-[7-chloro-6-[4-(4-fluoro-3-methyl-tetrahydrofuran-3-yl)piperazin-1-yl]-3-isoquinolyl]-2-tetrahydropyran-4-yl-cyclopropanecarboxamide, (1R,2R or 1S,2S)-N-[7-chloro-6-[4-((3R,4R or 3S,3S)-4-fluoro-3-methyl-tetrahydrofuran-3-yl)piperazin-1-yl]-3-isoquinolyl]-2-tetrahydropyran-4-yl-cyclopropanecarboxamide, (1R,2R or 1S,2S)-N-[7-chloro-6-[4-((3R,4R or 3S,3S)-4-fluoro-3-methyl-tetrahydrofuran-3-yl)piperazin-1-yl]-3-isoquinolyl]-2-tetrahydropyran-4-yl-cyclopropanecarboxamide | Cal'c:<br>517<br>Found:<br>517 |
| 10.71,<br>10.72 | 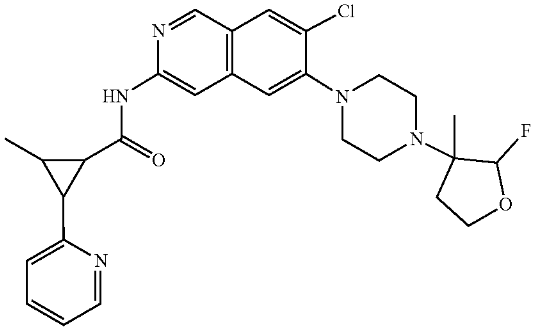 [SMILES: CC1C(C(=O)Nc2cc3cc(N4CCN(C5(C)CCOC5F)CC4)c(Cl)cc3cn2)C1c1ccccn1]<br>Rac-N-[7-chloro-6-[4-(4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2R,3R, or 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2R,3R, or 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide | Cal'c:<br>524<br>Found:<br>524 |

TABLE 10-continued

| Example | Structure<br>Name | Observed m/z [M + H]$^+$ |
|---|---|---|
| 10.73, 10.74 | 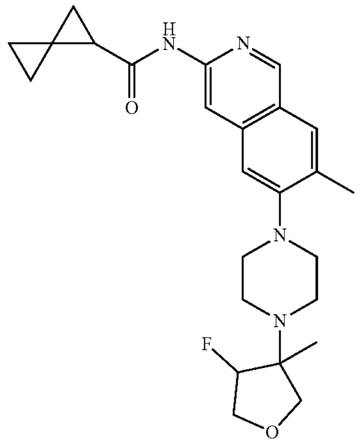 [SMILES: Cc1cc2cnc(NC(=O)C3CC34CC4)cc2cc1N1CCN(C2(C)COCC2F)CC1]<br>Rac-N-[7-chloro-6-[4-(4-fluoro-3-methyl-tetrahydrofuran-3-yl)piperazin-1-yl]-3-isoquinolyl]-2-tetrahydropyran-4-yl-cyclopropanecarboxamide, (R or S)-N-[7-chloro-6-[4-((3R,4R or 3S,4S)-4-fluoro-3-methyl-tetrahydrofuran-3-yl)piperazin-1-yl]-3-isoquinolyl]-2-tetrahydropyran-4-yl-cyclopropanecarboxamide, (R or S)-N-[7-chloro-6-[4-((3R,4R or 3S,4S)-4-fluoro-3-methyl-tetrahydrofuran-3-yl)piperazin-1-yl]-3-isoquinolyl]-2-tetrahydropyran-4-yl-cyclopropanecarboxamide | Cal'c: 439 Found: 439 |
| 10.75, 10.76, 10.77, 10.78 | 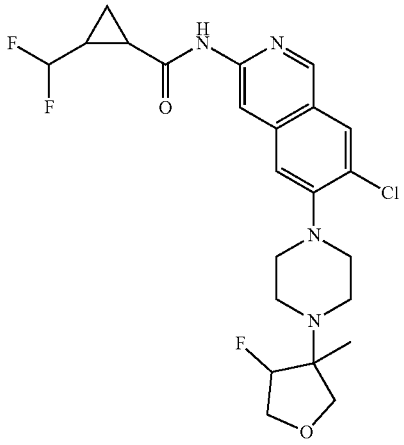 [SMILES: CC1(N2CCN(c3cc4cc(NC(=O)C5CC5C(F)F)ncc4cc3Cl)CC2)COCC1F]<br>Rac-N-[7-chloro-6-[4-(4-fluoro-3-methyl-tetrahydrofuran-3-yl)piperazin-1-yl]-3-isoquinolyl]-2-(difluoromethyl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(difluoromethyl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(difluoromethyl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(difluoromethyl)cyclopropanecarboxamide, (1R,2R or 1S,2S)-N-[7-chloro-6-[4-((3R,4R or 3S,4S)-4-fluoro-3-methyl-tetrahydrofuran-3-yl)piperazin-1-yl]-3-isoquinolyl]-2-(difluoromethyl)cyclopropanecarboxamide | Cal'c: 483 Found: 483 |

TABLE 10-continued

| Example | Structure<br>Name | Observed m/z [M + H]+ |
|---|---|---|
| 10.79,<br>10.80 | 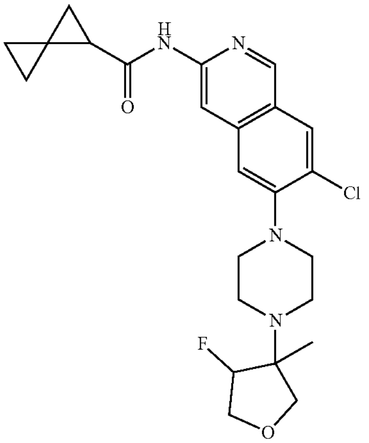 [SMILES: CC1(N2CCN(c3cc4cc(NC(=O)C5CC56CC6)ncc4cc3Cl)CC2)COCC1F]<br>Rac-N-[7-chloro-6-[4-(4-fluoro-3-methyl-tetrahydrofuran-3-yl)piperazin-1-yl]-3-isoquinolyl]spiro[2.2]pentane-2-carboxamide, (R or S)-N-[7-chloro-6-[4-((3R,4R or 3S,4S)-4-fluoro-3-methyl-tetrahydrofuran-3-yl)piperazin-1-yl]-3-isoquinolyl]spiro[2.2]pentane-2-carboxamide, (R or S)-N-[7-chloro-6-[4-((3R,4R or 3S,4S)-4-fluoro-3-methyl-tetrahydrofuran-3-yl)piperazin-1-yl]-3-isoquinolyl]spiro[2.2]pentane-2-carboxamide | Cal'c: 459<br>Found: 459 |
| 10.81,<br>10.82,<br>10.83,<br>10.84,<br>10.85,<br>10.86,<br>10.87,<br>10.88 | 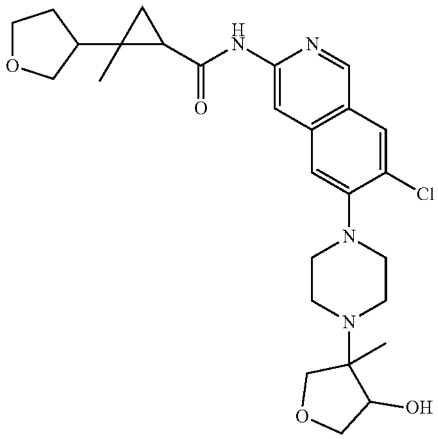 [SMILES: CC1(C2CCOC2)CC1C(=O)Nc1cc2cc(N3CCN(C4(C)COCC4O)CC3)c(Cl)cc2cn1]<br>Rac-N-[7-chloro-6-[4-(4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R or | Cal'c 515<br>Found: 515 |

TABLE 10-continued

| Example | Structure<br>Name | Observed<br>m/z<br>[M + H]+ |
|---|---|---|
| | 1S,2S, or 1R,2S, or 1S,2R)-N-[7-chloro-6-[4-((3R,4R or 3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide | |
| 10.89,<br>10.90 | 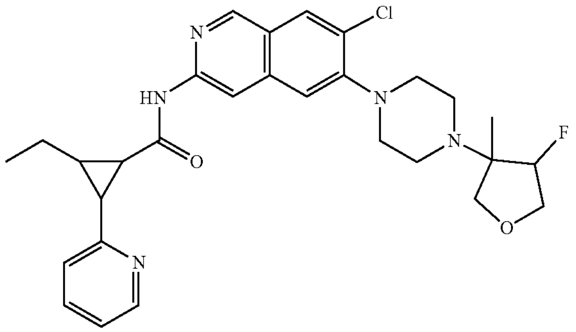 [SMILES: CCC1C(C(=O)Nc2cc3cc(N4CCN(C5(C)COCC5F)CC4)c(Cl)cc3cn2)C1c1ccccn1]<br>Rac-N-[7-chloro-6-[4-(4-fluoro-3-methyl-tetrahydrofuran-3-yl)piperazin-1-yl]-3-isoquinolyl]-2-ethyl-3-(2-pyridyl)cyclopropanecarboxamide, (1R,2R,3R, or 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(2-pyridyl)cyclopropanecarboxamide, (1R,2R,3R, or 1R,2S,3R, or 1S,2R,3S, or 1S,2S,3S)-N-[7-chloro-6-[4-((3R,4R or 3S,4S)-4-fluoro-3-methyl-tetrahydrofuran-3-yl)piperazin-1-yl]-3-isoquinolyl]-2-ethyl-3-(2-pyridyl)cyclopropanecarboxamide | Cal'c:<br>538<br>Found:<br>538 |
| 10.91,<br>10.92 | 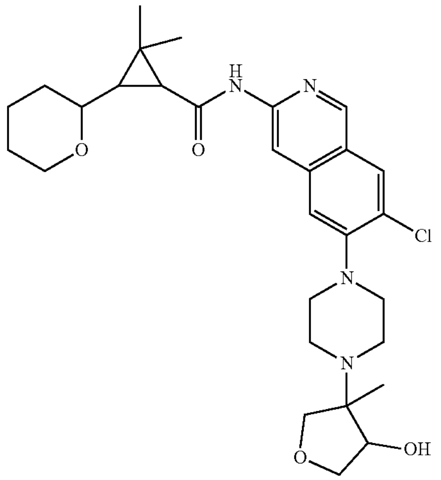 [SMILES: CC1(C)C(C(=O)Nc2cc3cc(N4CCN(C5(C)COCC5O)CC4)c(Cl)cc3cn2)C1C1CCCCO1]<br>Rac-N-[7-chloro-6-[4-(4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2R,3R, 1R,2S,3R, or 1S,2R,3S, or 1S,2S,3S)-N-[7-chloro-6-[4-((3R,4R or 3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide | Cal'c:<br>543<br>Found:<br>543 |

TABLE 10-continued

| Example | Structure<br>Name | Observed<br>m/z<br>[M + H]$^+$ |
|---|---|---|
| 10.93,<br>10.94,<br>10.95,<br>10.96 | 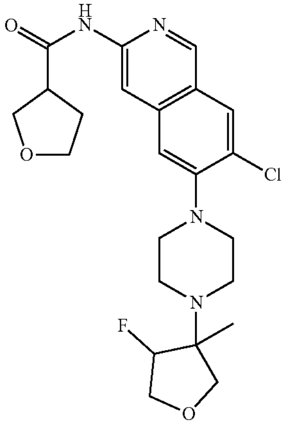 [SMILES: CC1(N2CCN(c3cc4cc(NC(=O)C5CCOC5)ncc4cc3Cl)CC2)COCC1F]<br>Rac-N-[6-[4-(4-fluoro-3-methyl-tetrahydrofuran-3-yl)piperazin-1-yl]-7-methyl-3-isoquinolyl]-5,5-dimethyl-tetrahydrofuran-3-carboxamide, (3R or 3S)-N-[6-[4-((3R,4R or 3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide, (3R or 3S)-N-[6-[4-((3R,4R or 3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide, (3R or 3S)-N-[6-[4-((3R,4R or 3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide, (3R or 3S)-N-[6-[4-((3R,4R or 3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide | Cal'c:<br>490<br>Found:<br>490 |

General Scheme 11.

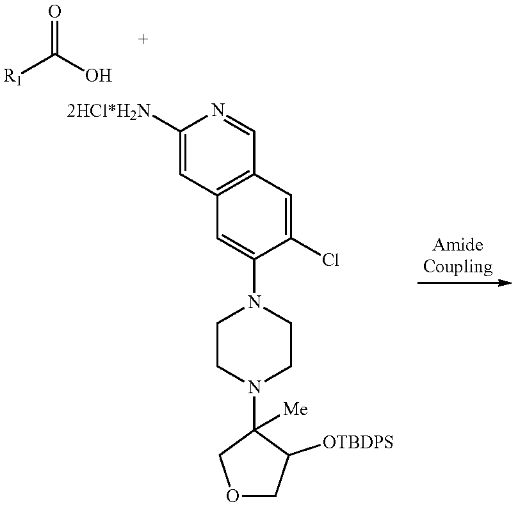

37

-continued

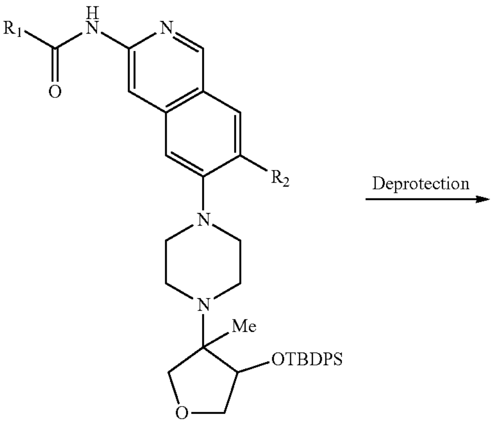

$R_1$ = alkyl or aryl

Gen-26

-continued

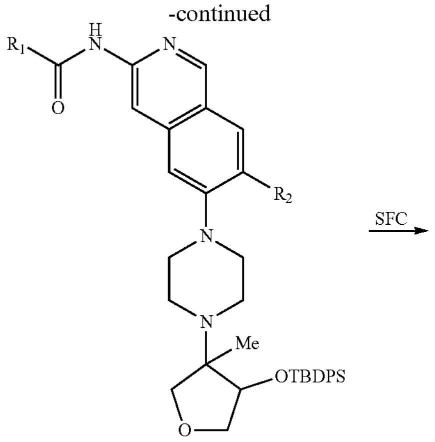

$R_1$ = alkyl or aryl

Gen-27

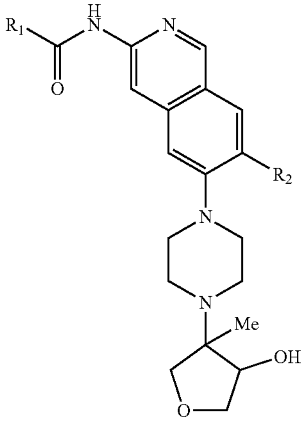

$R_1$ = alkyl or aryl

Gen-28

In General Scheme 10, commercially available carboxylic acids or acid chlorides were coupled with synthetically prepared intermediate 37 through amide coupling conditions to provide Gen-26 and were subsequently deprotected to afford Gen-27. The stereoisomers were separated by chiral SFC to provide fully elaborated products in the form of Gen-28. The representative compounds are described in more detail shown below.

Scheme 47. Synthesis of (1R,2R)(3R,4R)- or (1R,2S)(3R,4R)- or (1S,2R)(3R,4R)- or (1S,2S)(3R,4R)- or (1R,2R)(3S,4S)- or (1R,2S)(3S,4S)- or (1S,2R)(3S,4S)- or (1S,2S)(3S,4S)-N-(7-chloro-6-(4-(4-hydroxy-3-methyltetrahydrofuran-3-yl)piperazin-1-yl)isoquinolin-3-yl)-2-methyl-2-(pyridin-2-yl)cyclopropane-1-carboxamide (Ex-11.1 and Ex-11.2)

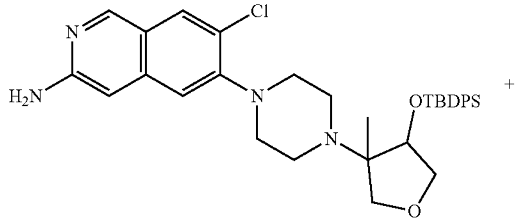

37

-continued

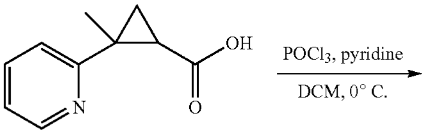

83

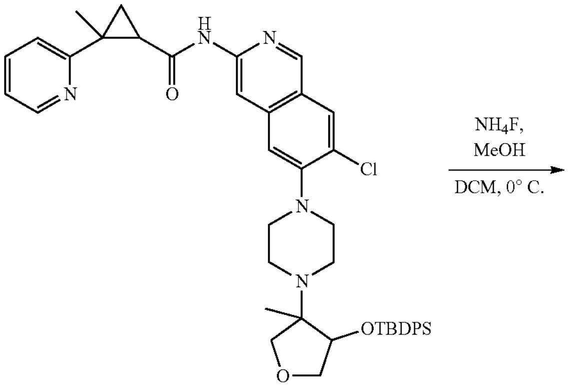

84

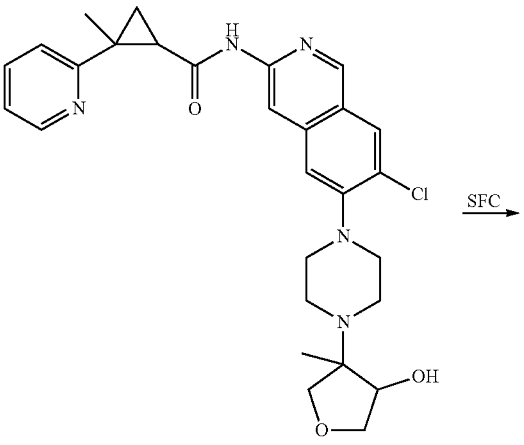

85

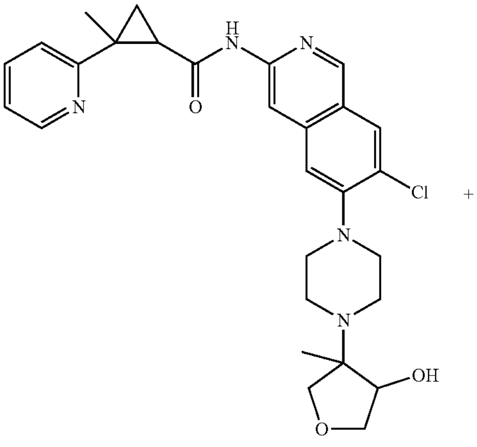

Ex.-11.1

-continued

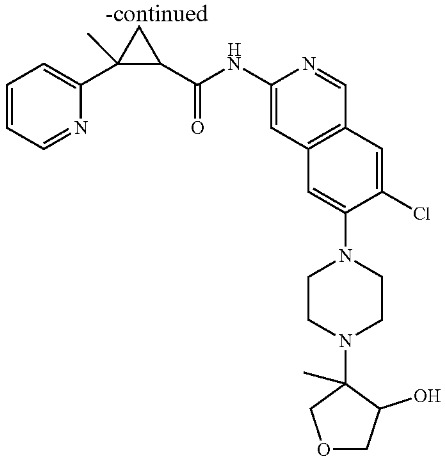

Ex.-11.2

(1R,2R)(3R,4R)- or (1R,2S)(3R,4R)- or (1S,2R)(3R,4R)- or (1S,2S)(3R,4R)- or (1R,2R)(3S,4S)- or (1R,2S)(3S,4S)- or (1S,2R)(3S,4S)- or (1S,2S)(3S,4S)-N-(6-(4-(4-((tert-butyldiphenylsilyl)oxy)-3-methyltetrahydrofuran-3-yl)piperazin-1-yl)-7-chloroisoquinolin-3-yl)-2-methyl-2-(pyridin-2-yl)cyclopropane-1-carboxamide (84)

To a solution of 6-(4-(4-((tert-butyldiphenylsilyl)oxy)-3-methyltetrahydrofuran-3-yl) piperazin-1-yl)-7-chloroisoquinolin-3-amine 37 (100 mg, 0.166 mmol) and 2-methyl-2-(pyridin-2-yl)cyclopropane-1-carboxylic acid 83 (44 mg, 0.249 mmol) in DCM (2 mL) was added pyridine (108 μL, 1.331 mmol) and the mixture was cooled to 0° C. Phosphoryl trichloride (31 μL, 0.333 mmol) was added slowly, and the mixture was stirred at 0° C. for 30 minutes. The reaction was quenched by slowly pouring into ice water (10 mL). The mixture was transferred to a separatory funnel where it was extracted with EtOAc (3×15 mL). The combined organic layers were washed with brine, dried over anhydrous $Na_2SO_4$, filtered, and solvent was removed from the collected filtrate under reduced pressure. The resultant crude title compound 84 was carried forward to the next step without further purification.

(1R,2R)(3R,4R)— or (1R,2S)(3R,4R)— or (1S,2R)(3R,4R)— or (1S,2S)(3R,4R)— or (1R,2R)(3S,4S)— or (1R,2S)(3S,4S)— or (1S,2R)(3S,4S)— or (1S,2S)(3S,4S)-N-(7-chloro-6-(4-(4-hydroxy-3-methyltetrahydrofuran-3-yl)piperazin-1-yl)isoquinolin-3-yl)-2-methyl-2-(pyridin-2-yl)cyclopropane-1-carboxamide (Ex-11.1 and Ex-11.2)

To a solution of intermediate 84 (120 mg, 0.158 mmol) in MeOH (2 ml) was added ammonium fluoride (47 mg, 1.262 mmol). The resultant mixture was stirred at room temperature for 1 h. Volatiles were then removed under reduced pressure to give a crude residue, which was subjected to purification by preparative HPLC ($H_2O$/MeCN/TFA) to afford the desired product 85 as a mixture of diastereomers. This mixture of stereoisomers was then subjected to chiral separation by prepative SFC (Column: Chiralcel OD-3 50×4.6 mm I.D., 3 um.; Mobile phase: A: $CO_2$ B: EtOH with 0.05% DEA; Isocratic 40% B; Flow rate: 4 mL/min. Column temp.: 35° C.) to afford the chiral resolved stereoisomers of the title compound Ex-11.1 (tR=0.85 min) and Ex-11.2 (tR=1.25 min). Ex-11.1: MS (ESI): m/z calc'd for $C_{28}H_{33}ClN_5O_3$ $[M+H]^+$: 522.3, found 522.3. $^1$H NMR (400 MHz, $CDCl_3$): δ 9.11 (s, 1H), 8.60 (s, 1H), 8.49 (s, 1H), 8.43 (m, 1H), 7.71 (s, 1H), 7.64 (m, 1H), 7.41 (d, J=8.0 Hz, 1H), 7.25 (s, 1H), 7.10 (dd, J=4.9, 7.0 Hz, 1H), 4.14-4.07 (m, 1H), 4.03-3.97 (m, 1H), 3.88-3.80 (m, 2H), 3.64 (d, J=7.3 Hz, 1H), 3.24 (br s, 4H), 2.86 (m, 2H), 2.66 (br s, 2H), 2.54 (dd, J=6.4, 7.9 Hz, 1H), 1.79 (dd, J=4.0, 8.3 Hz, 1H), 1.70 (s, 3H), 1.68 (br s, 1H), 1.20 (s, 3H). Ex-11.2: MS (ESI): m/z calc'd for $C_{28}H_{33}ClN_5O_3$ $[M+H]^+$: 522.3, found 522.3. $^1$H NMR (400 MHz, $CDCl_3$): δ 9.19 (br s, 1H), 8.66 (s, 1H), 8.53-8.47 (m, 2H), 7.77 (s, 1H), 7.68 (m, 1H), 7.45 (d, J=8.0 Hz, 1H), 7.28 (s, 1H), 7.15 (dd, J=4.9, 6.8 Hz, 1H), 4.21 (m, 1H), 4.02-3.97 (m, 3H), 3.67 (d, J=8.0 Hz, 1H), 3.41 (br s, 4H), 3.18 (br s, 2H), 2.89 (br s, 2H), 2.56 (m, 1H), 1.77 (dd, J=4.1, 8.3 Hz, 1H), 1.73-1.70 (m, 1H), 1.70 (s, 3H), 1.31 (s, 3H).

Compounds in Table 11 below were prepared in accordance with the synthetic sequence illustrated in General Scheme 11 and Scheme 47 using the corresponding starting materials.

TABLE 11

| Example | Structure<br>Name | Observed m/z $[M + H]^+$ |
|---|---|---|
| 11.3, 11.4 | 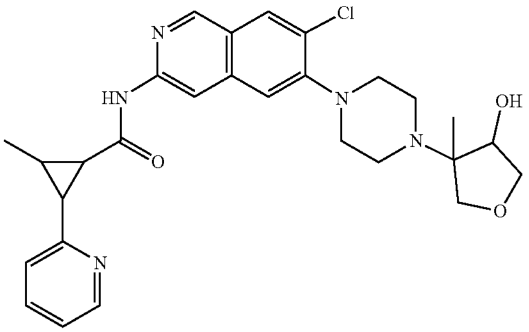 [SMILES: CC1C(C(=O)Nc2cc3cc(N4CCN(C5(C)COCC5O)CC4)c(Cl)cc3cn2)C1c1ccccn1]<br>Rac-N-(7-chloro-6-(4-(4-hydroxy-3-methyltetrahydrofuran-3-yl)piperazin-1-yl)isoquinolin-3-yl)-2-methyl-3-(pyridin-2-yl)cyclopropane-1-carboxamide, (1R,2R,3R, or 1R,2S,3R, or 1S,2R,3S, or 1S,2S,3S)-N-(7-chloro-6-(4-((3R,4R or 3S,4S)-4- | Cal'c: 522 Found: 522 |

TABLE 11-continued

| Example | Structure<br>Name | Observed<br>m/z<br>$[M + H]^+$ |
|---|---|---|
| | hydroxy-3-methyltetrahydrofuran-3-yl)piperazin-1-yl)isoquinolin-3-yl)-2-methyl-3-(pyridin-2-yl)cyclopropane-1-carboxamide, (1R,2R,3R, or 1R,2S,3R, or 1S,2R,3S, or 1S,2S,3S)-N-(7-chloro-6-(4-((3R,4R or 3S,4S)-4-hydroxy-3-methyltetrahydrofuran-3-yl)piperazin-1-yl)isoquinolin-3-yl)-2-methyl-3-(pyridin-2-yl)cyclopropane-1-carboxamide | |
| 11.5, 11.6 | 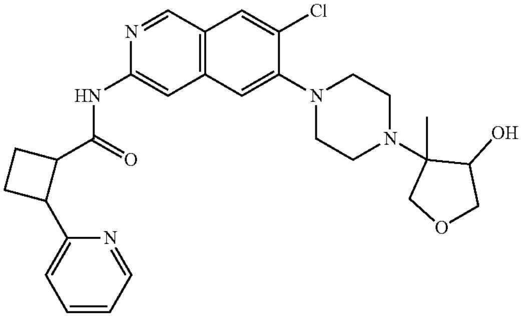 [SMILES: CC1(N2CCN(c3cc4cc(NC(=O)C5CCC5c5ccccn5)ncc4cc3Cl)CC2)COCC1O]<br>Rac-N-(7-chloro-6-(4-(4-hydroxy-3-methyltetrahydrofuran-3-yl)piperazin-1-yl)isoquinolin-3-yl)-2-(pyridin-2-yl)cyclobutane-1-carboxamide, (1R,2R or 1S,2S)-N-(7-chloro-6-(4-((3R,4R or 3S,4S)-4-hydroxy-3-methyltetrahydrofuran-3-yl)piperazin-1-yl)isoquinolin-3-yl)-2-(pyridin-2-yl)cyclobutane-1-carboxamide, (1R,2R or 1S,2S)-N-(7-chloro-6-(4-((3R,4R or 3S,4S)-4-hydroxy-3-methyltetrahydrofuran-3-yl)piperazin-1-yl)isoquinolin-3-yl)-2-(pyridin-2-yl)cyclobutane-1-carboxamide | Cal'c:<br>522<br>Found:<br>522 |

Scheme 48. N-(7-ethyl-6-(4-(4-hydroxy-3-methyltetrahydrofuran-3-yl)piperazin-1-yl)isoquinolin-3-yl)-6-oxaspiro[2.5]octane-1-carboxamide, TFA; (R or S)-N-(7-ethyl-6-(4-(4-(3R,4R or 3S,4S)-hydroxy-3-methyltetrahydrofuran-3-yl)piperazin-1-yl)isoquinolin-3-yl)-6-oxaspiro[2.5]octane-1-carboxamide, TFA (Ex-12)

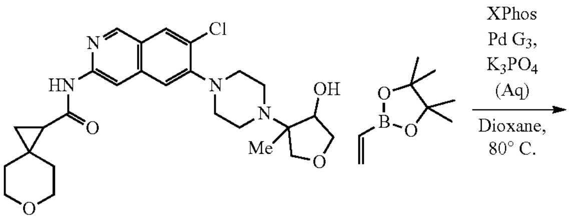

Ex-2.1

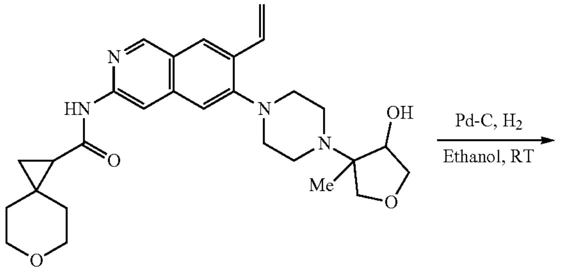

86

-continued

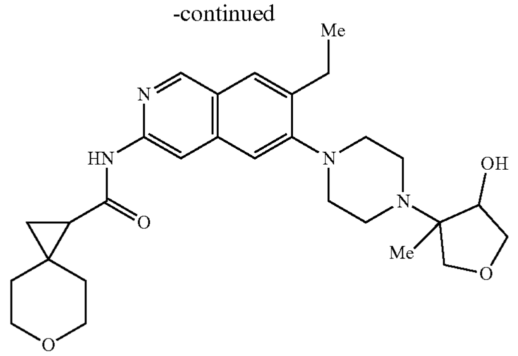

Ex-12

N-(6-(4-(4-hydroxy-3-methyltetrahydrofuran-3-yl)piperazin-1-yl)-7-vinylisoquinolin-3-yl)-6-oxaspiro[2.5]octane-1-carboxamide, (R or S)-N-(6-(4-(4-(3R,4R or 3S,4S)-hydroxy-3-methyltetrahydrofuran-3-yl)piperazin-1-yl)-7-vinylisoquinolin-3-yl)-6-oxaspiro[2.5]octane-1-carboxamide (86)

Ex-2.1 (100 mg, 0.20 mmol) and XPhos Pd G3 (33.8 mg, 0.040 mmol) were added to a vial. The vial was sealed, and its contents were placed under an inert atmosphere. A solution of 4,4,5,5-tetramethyl-2-vinyl-1,3,2-dioxaborolane (51.2 µl, 0.299 mmol) in dioxane (998 µl) was added through the septum followed by aqueous potassium phosphate, tribasic (299 µl, 0.599 mmol). The resulting mixture was allowed to stir for 2 hours at 80° C. The reaction mixture was diluted with ethyl acetate and washed twice with saturated ammonium chloride and once with brine. The combined organic fractions were dried over anhydrous sodium sulfate, filtered and concentrated under reduced pressure. The residue was purified by column chromatography on silica (0-100% DCM/Methanol (1% $NH_3$)) to afford the title compound 86. MS (ESI): m/z calc'd for $C_{28}H_{36}N_4O_4$ $[M+H]^+$: 493, found 493.

N-(7-ethyl-6-(4-(4-hydroxy-3-methyltetrahydrofuran-3-yl)piperazin-1-yl)isoquinolin-3-yl)-6-oxaspiro[2.5]octane-1-carboxamide, TFA (R or S)-N-(7-ethyl-6-(4-(4-(3R,4R or 3S,4S)-hydroxy-3-methyltetrahydrofuran-3-yl)piperazin-1-yl) isoquinolin-3-yl)-6-oxaspiro[2.5]octane-1-carboxamide, TFA, (Ex-12)

Pd—C(36.0 mg, 0.034 mmol) was added to a solution of N-(6-(4-(4-hydroxy-3-methyltetrahydrofuran-3-yl)piperazin-1-yl)-7-vinylisoquinolin-3-yl)-6-oxaspiro[2.5]octane-1-carboxamide, (R)-N-(6-(4-(4-(3R,4R)-hydroxy-3-methyltetrahydrofuran-3-yl)piperazin-1-yl)-7-vinylisoquinolin-3-yl)-6-oxaspiro[2.5]octane-1-carboxamide, (R)-N-(6-(4-(4-(3S,4S)-hydroxy-3-methyltetrahydrofuran-3-yl)piperazin-1-yl)-7-vinylisoquinolin-3-yl)-6-oxaspiro[2.5]octane-1-carboxamide, (S)-N-(6-(4-(4-(3R,4R)-hydroxy-3-methyltetrahydrofuran-3-yl)piperazin-1-yl)-7-vinylisoquinolin-3-yl)-6-oxaspiro[2.5]octane-1-carboxamide or (S)-N-(6-(4-(4-(3S,4S)-hydroxy-3-methyltetrahydrofuran-3-yl)piperazin-1-yl)-7-vinylisoquinolin-3-yl)-6-oxaspiro[2.5]octane-1-carboxamide 86 (111 mg, 0.225 mmol) in ethanol (2 ml). The flask was fitted with a stopcocked balloon and its contents were placed under an atmosphere of hydrogen by performing 3 vacuum/hydrogen cycles. The resulting mixture was allowed to stir for 2 hours at room temperature. The reaction mixture was de-gased and backfilled with nitrogen, filtered, and the residue was washed with methanol. The filtrate was concentrated under reduced pressure. The reaction mixture was filtered, purified by HPLC, eluting acetonitrile/water gradient with 0.1% TFA modifier, linear gradient) and lyophilized to afford the title compound Ex-12. MS (ESI): m/z calc'd for $C_{28}H_{39}N_4O_4$ $[M+H]^+$: 495, found 495. $^1$H NMR (499 MHz, DMSO-d6) δ 10.73 (s, 1H), 8.94 (s, 1H), 8.32 (s, 1H), 7.83 (s, 1H), 7.31 (s, 1H), 4.36 (s, 1H), 3.98 (dd, J=9.6, 3.4 Hz, 1H), 3.82-3.79 (m, 1H), 3.71 (d, J=9.7 Hz, 2H), 3.65 (d, J=7.2 Hz, 2H), 3.62-3.57 (m, 1H), 3.55 (d, J=7.3 Hz, 1H), 3.46-3.40 (m, 1H), 3.02 (s, 4H), 2.81-2.71 (m, 4H), 2.55-2.51 (m, 2H), 2.03-1.99 (m, 1H), 1.75-1.62 (m, 2H), 1.56-1.48 (m, 1H), 1.41-1.34 (m, 1H), 1.31 (t, J=7.5 Hz, 3H), 1.11 (t, J=4.6 Hz, 1H), 1.06 (s, 3H), 0.92 (dd, J=7.7, 3.9 Hz, 1H).

Scheme 49. N-(6-(4-hydroxy-3-methyltetrahydrofuran-3-yl)piperazin-1-yl)-7-methoxyisoquinolin-3-yl)-6-oxaspiro[2.5]octane-1-carboxamide TFA, (R or S)-N-(6-(4-(3R,4R or 3S,4S)-hydroxy-3-methyltetrahydrofuran-3-yl)piperazin-1-yl)-7-methoxyisoquinolin-3-yl)-6-oxaspiro[2.5]octane-1-carboxamide TFA (Ex-13)

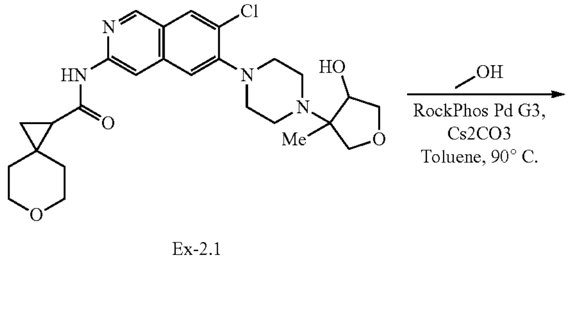

Ex-2.1

-continued

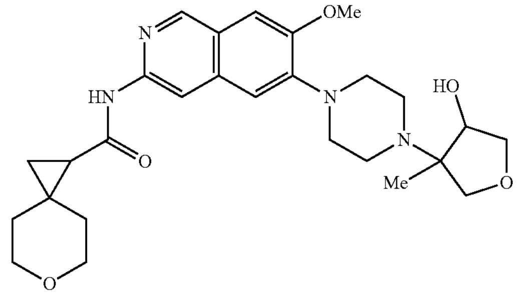

Ex-13

Ex-2.1 (30 mg, 0.060 mmol), RockPhos Pd G3 (10.04 mg, 0.012 mmol), and cesium carbonate (58.5 mg, 0.180 mmol) were added to a vial. The vial was sealed, and its contents were placed under an inert atmosphere by performing 3 vacuum/nitrogen cycles. A solution of methanol (38.4 mg, 1.198 mmol) in Toluene (299 μl) was added through the septum and the resulting mixture was allowed to stir overnight at 90° C. The crude reaction mixture was scavenged for 1 hour with Si-DMT. The reaction mixture was filtered and submitted directly for HPLC purification to the HTP group (purified by HPLC, eluting acetonitrile/water gradient with 0.1% TFA modifier, linear gradient) and lyophilized to afford the title compound Ex-13. MS (ESI): m/z calc'd for $C_{27}H_{37}N_4O_5$ $[M+H]^+$: 497, found 497. TH NMR (499 MHz, DMSO-d6) δ 10.77 (s, 1H), 9.47 (s, 1H), 8.90 (s, 1H), 8.31 (s, 1H), 7.48 (s, 1H), 7.29 (s, 1H), 4.19 (s, 2H), 4.18-4.16 (m, 1H), 3.98 (d, J=8.2 Hz, 2H), 3.94 (s, 3H), 3.82 (d, J=8.3 Hz, 3H), 3.75-3.65 (m, 3H), 3.62-3.57 (m, 1H), 3.55-3.49 (m, 2H), 3.47-3.41 (m, 2H), 3.23-3.15 (m, 1H), 3.11-3.04 (m, 1H), 2.02-1.97 (m, 1H), 1.76-1.64 (m, 2H), 1.57-1.49 (m, 1H), 1.41 (s, 3H), 1.11 (t, 1H), 0.96-0.91 (m, 1H).

Scheme 50. Synthesis of N-(7-chloro-6-((2S)-4-(4-(3R,4R)-hydroxy-3-methyltetrahydrofuran-3-yl)-2-methylpiperazin-1-yl)isoquinolin-3-yl)-6-oxaspiro[2.5]octane-1-carboxamide, (R or S)-N-(7-chloro-6-((2S or 2R)-4-(4-(3R,4R or 3S,4S)-hydroxy-3-methyltetrahydrofuran-3-yl)-2-methylpiperazin-1-yl)isoquinolin-3-yl)-6-oxaspiro[2.5]octane-1-carboxamide (Ex-14.1) and (Ex-14.2)

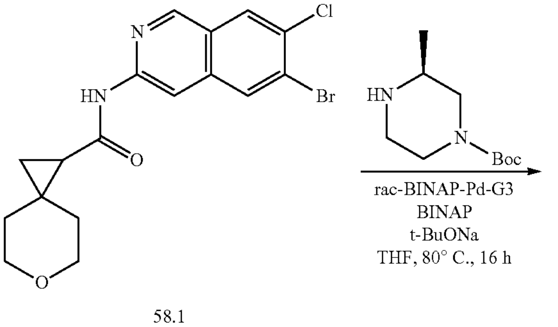

58.1

-continued

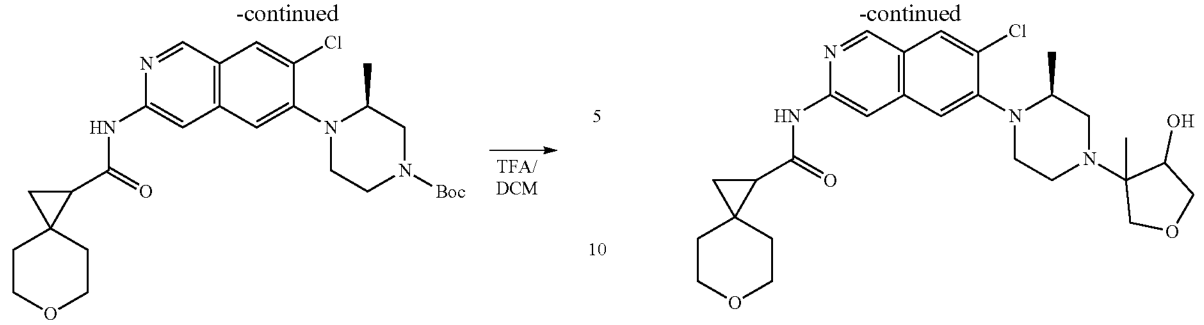

87

Ex-14.2

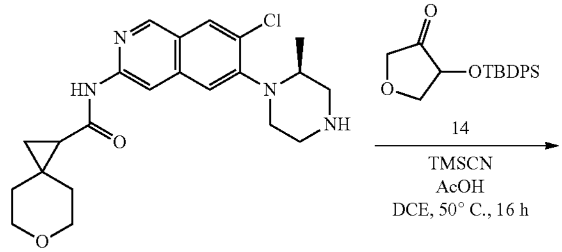

88

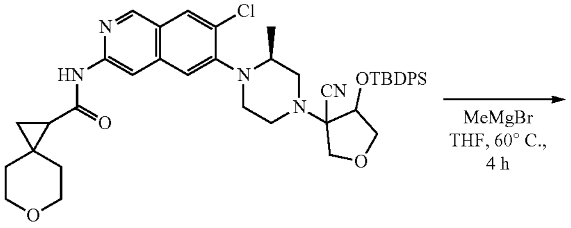

89

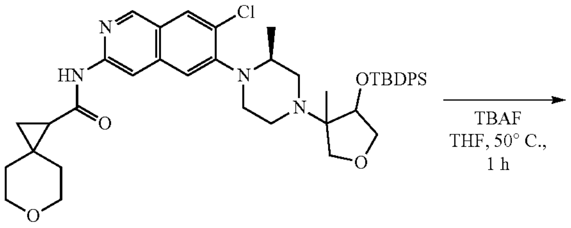

90

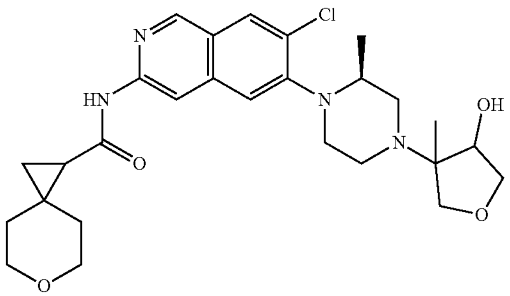

Ex-14.1

Tert-butyl 4-(7-chloro-3-(6-oxaspiro[2.5]octane-1-carboxamido)isoquinolin-6-yl)-3-methylpiperazine-1-carboxylate (87)

To a solution of N-(6-bromo-7-chloroisoquinolin-3-yl)-6-oxaspiro[2.5]octane-1-carboxamide 48.1 (500 mg, 1.264 mmol) and tert-butyl 3-methylpiperazine-1-carboxylate (506 mg, 2.53 mmol) in THF (8 mL) were added sodium tert-butoxide (364 mg, 3.79 mmol), Rac-BINAP Pd G3 (314 mg, 0.316 mmol) and BINAP (236 mg, 0.379 mmol). The mixture was stirred for 16 hours at 80° C. The mixture was added into water (80 mL), extracted with EtOAc (80 mL×3). The combined organic layers were dried by anhydrous $Na_2SO_4$, filtered and concentrated in vacuo. The resulting residue was purified by flash silica gel chromatography (silica gel, Pet. ether:EtOAc=3:1) to afford title compound 87. MS (ESI): m/z calc'd for $C_{27}H_{36}ClN_4O_4$ $[M+H]^+$: 515, found 515.

N-(7-chloro-6-((R or S)-2-methylpiperazin-1-yl)isoquinolin-3-yl)-6-oxaspiro[2.5]octane-1-carboxamide (88)

To a solution of tert-butyl (3S)-4-(7-chloro-3-(6-oxaspiro[2.5]octane-1-carboxamido) isoquinolin-6-yl)-3-methylpiperazine-1-carboxylate 87 (250 mg, 0.485 mmol) in DCM (2 mL) was added TFA (0.2 mL) at 25° C. The mixture was stirred at 25° C. for 2 hours. Saturated $K_2CO_3$ solution was added to the mixture and stirred for 30 minutes. Water (5 mL) was added to the suspension. The mixture was extracted with DCM (5 mL×3). The combined organic layers were washed with brine (10 mL), dried over anhydrous $Na_2SO_4$ and filtered. The filtrate was concentrated in vauco to afford title compound 88. MS (ESI): m/z calc'd for $C_{22}H_{27}ClN_4O_2$ $[M+H]^+$: 415, found 415.

N-(6-((2R or 2S)-4-(4-((tert-butyldiphenylsilyl)oxy)-3-cyanotetrahydrofuran-3-yl)-2-methylpiperazin-1-yl)-7-chloroisoquinolin-3-yl)-6-oxaspiro[2.5]octane-1-carboxamide (89)

A mixture of 4-((tert-butyldiphenylsilyl)oxy)dihydrofuran-3(2H)-one 14 (295 mg, 0.868 mmol), N-(7-chloro-6-((S)-2-methylpiperazin-1-yl)isoquinolin-3-yl)-6-oxaspiro[2.5]octane-1-carboxamide 88 (180 mg, 0.434 mmol) and AcOH (0.124 mL, 2.169 mmol) in anhydrous DCE (8 mL) was stirred at 60° C. for 30 mins. Trimethylsilyl cyanide (0.272 mL, 2.169 mmol) was added into the mixture. The final mixture was stirred at 50° C. for 16 hours and then concentrated in vacuo The resulting residue was purified by pre-TLC (silica gel, Pet. ether:EtOAc=2:1) to afford title compound 89. MS (ESI): m/z calc'd for $C_{43}H_{50}ClN_5O_4Si$ $[M+H]^+$: 764, found 765.

N-(6-((2R or 2S)-4-(4-((tert-butyldiphenylsilyl)oxy)-3-methyltetrahydrofuran-3-yl)-2-methylpiperazin-1-yl)-7-chloroisoquinolin-3-yl)-6-oxaspiro[2.5]octane-1-carboxamide (90)

To a solution of N-(6-((2S)-4-(4-((tert-butyldiphenylsilyl)oxy)-3-cyanotetrahydrofuran-3-yl)-2-methylpiperazin-1-yl)-7-chloroisoquinolin-3-yl)-6-oxaspiro[2.5]octane-1-carboxamide 89 (257 mg, 0.336 mmol) in THF (8 mL) was added methyl magnesium bromide (1.121 mL, 3.36 mmol) at 0° C. The resulting solution was stirred at 60° C. for 4 hours. The reaction quenched with saturated $NH_4Cl$, and extracted with EtOAc (50 mL×3). The organic layer was washed with water (50 mL), dried over $Na_2SO_4$. After filtration and concentration, the crude product was purified by pre-TLC (silica gel, Pet. ether:EtOAc=1:1) to afford title compound 90. MS (ESI): m/z calc'd for $C_{43}H_{53}ClN_4O_4Si$ $[M+H]^+$: 753, found 753.

N-(7-chloro-6-((2R or 2S)-4-(4-(3R,4R or 3S,4S)-hydroxy-3-methyltetrahydrofuran-3-yl)-2-methylpiperazin-1-yl)isoquinolin-3-yl)-6-oxaspiro[2.5]octane-1-carboxamide (Ex-14.1) and (Ex-14.2)

To a solution of N-(6-((2S)-4-(4-((tert-butyldiphenylsilyl)oxy)-3-methyltetrahydrofuran-3-yl)-2-methylpiperazin-1-yl)-7-chloroisoquinolin-3-yl)-6-oxaspiro[2.5]octane-1-carboxamide 90 (140 mg, 0.186 mmol) in THF (3 mL) was add TBAF (0.372 mL, 0.372 mmol), the mixture was stirred at 50° C. for 1 h. The mixture which was filtered and concentrated in vacuo to give the crude product which was purified by pre-HPLC (TFA). Crude product was purified by Prep-SFC using: Column, CHIRALPAK AD-3, 50*4.6 mm I.D., 3 um; mobile phase, $CO_2$ (40%) and IPA (0.5% DEA) (60%); Detector, UV, to afford title compound Ex-14.1 (Rt=1.330 min) and Ex-14.2 (Rt=2.050 min). Ex-14.1: MS (ESI): m/z calc'd for $C_{27}H_{36}ClN_4O_4$ $[M+H]^+$: 515, found 515. $^1$H NMR (400 MHz, $CDCl_3$-d) δ 8.79 (s, 1H), 8.53 (s, 1H), 8.43 (s, 1H), 7.89 (s, 1H), 7.29 (s, 1H), 4.13-4.07 (m, 1H), 4.03-3.97 (m, 1H), 3.87 (m, 1H), 3.79-3.72 (m, 3H), 3.70 (m, 2H), 3.60 (m, 1H), 3.47 (m, 1H), 2.96-2.79 (m, 3H), 2.54 (s, 1H), 2.33 (m, 1H), 1.88-1.82 (m, 3H), 1.64-1.56 (m, 2H), 1.52-1.43 (m, 1H), 1.38 (m, 1H), 1.28-1.24 (m, 1H), 1.17 (s, 3H), 1.03 (m, 3H). Ex-14.2: MS (ESI): m/z calc'd for $C_{27}H_{36}ClN_4O_4$ $[M+H]^+$: 515, found 515. $^1$H NMR (400 MHz, $CDCl_3$-d) δ 8.79 (s, 1H), 8.68 (s, 1H), 8.45 (s, 1H), 7.90 (s, 1H), 7.29 (s, 1H), 4.10 (m, 1H), 3.99 (m, 1H), 3.87 (m, 1H), 3.83 (m, 1H), 3.80-3.74 (m, 2H), 3.72-3.64 (m, 3H), 3.49 (s, 1H), 2.81 (s, 1H), 2.67-2.56 (m, 2H), 1.85 (m, 2H), 1.59 (m, 2H), 1.55-1.46 (m, 1H), 1.41-1.32 (m, 2H), 1.26 (s, 3H), 1.18 (s, 3H), 1.07-1.02 (m, 3H).

Scheme 51. Synthesis of N-(6-((2S)-4-(4-hydroxy-3-methyltetrahydrofuran-3-yl)-2-methylpiperazin-1-yl)-7-methylisoquinolin-3-yl)-6-oxaspiro[2.5]octane-1-carboxamide, (R or S)-N-(6-((2S)-4-(4-(3R,4R or 3S,4S)-hydroxy-3-methyltetrahydrofuran-3-yl)-2-methylpiperazin-1-yl)-7-methylisoquinolin-3-yl)-6-oxaspiro[2.5]octane-1-carboxamide (Ex-15.1) and (Ex-15.2)

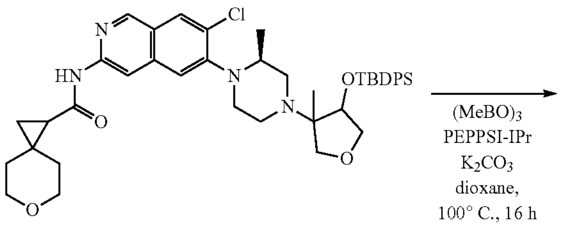

Ex-14

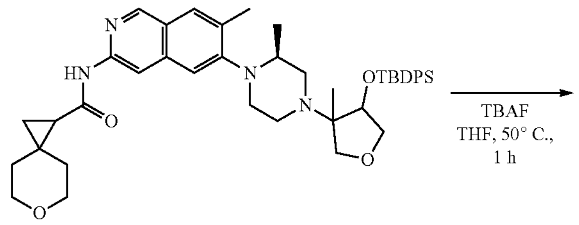

91

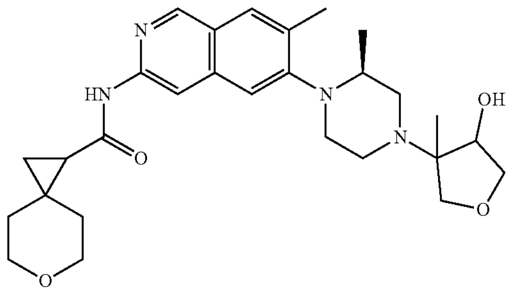

Ex-15.1

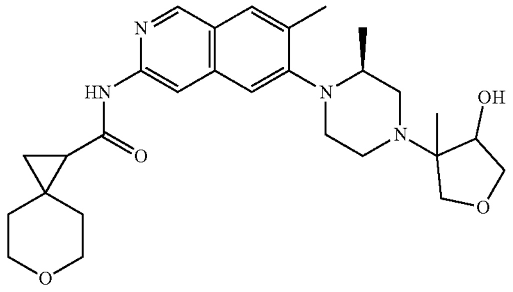

Ex-15.2

N-(6-((2R or 2S)-4-(4-((tert-butyldiphenylsilyl)oxy)-3-methyltetrahydrofuran-3-yl)-2-methylpiperazin-1-yl)-7-methylisoquinolin-3-yl)-6-oxaspiro[2.5]octane-1-carboxamide (91)

To a solution of Ex-14 (126 mg, 0.167 mmol), trimethylboroxine (0.070 ml, 0.502 mmol) and $K_2CO_3$ (69.3 mg, 0.502 mmol) in dioxane (4 mL) was added [1,3-bis(2,6-diisopropylphenyl)imidazol-2-ylidene](3-Chloropyridyl) palladium(II) dichloride (11.35 mg, 0.017 mmol) at 25° C. The mixture was stirred at 100° C. for 16 hours. The mixture was filtered, and concentrated in vacuo which was then purified by pre-TLC (silica gel, Pet. ether/EtOAc=1:1) to afford title compound 91. MS (ESI): m/z calc'd for $C_{44}H_{57}N_4O_4Si$ $[M+H]^+$: 733, found 733.

(R or S)-N-(6-((2R or 2S)-4-(4-(3R,4R or 3S,4S)-hydroxy-3-methyltetrahydrofuran-3-yl)-2-methylpiperazin-1-yl)-7-methylisoquinolin-3-yl)-6-oxaspiro[2.5]octane-1-carboxamide (Ex-15.1) and (Ex-15.2) To a solution of N-(6-((2S)-4-(4-((tert-butyldiphenylsilyl)oxy)-3-methyltetrahydrofuran-3-yl)-2-methylpiperazin-1-yl)-7-methylisoquinolin-3-yl)-6-oxaspiro[2.5]octane-1-carboxamide. (R)-N-(6-((2S)-4-(4-((tert-butyldiphenylsilyl)oxy)-3-methyltetrahydrofuran-3-yl)-2-methylpiperazin-1-yl)-7-methylisoquinolin-3-yl)-6-oxaspiro[2.5]octane-1-carboxamide or (S)-N-(6-((2S)-4-(4-((tert-butyldiphenylsilyl)oxy)-3-methyltetrahydrofuran-3-yl)-2-methylpiperazin-1-yl)-7-methylisoquinolin-3-yl)-6-oxaspiro[2.5]octane-1-carboxamide 91 (120 mg, 0.164 mmol) in THF (2 mL) was added TBAF (0.327 mL, 0.327 mmol), the mixture was stirred at 50° C. for 1 h. The mixture was filtered and concentrated in vacuo and was then purified by pre-HPLC (TFA). The mixture was separated by SFC Crude product was purified by Prep-SFC using: Column, CHIRALPAK AD-3, 50*4.6 mm I.D., 3 um; mobile phase, $CO_2$ (40%) and IPA (0.5% DEA) (60%); Detector, UV, to afford title compounds Ex-15.1 (Rt=0.934 min) and Ex-15.2 (Rt=1.684 min). Ex-15.1: MS (ESI): m/z calc'd for $C_{28}H_{39}N_4O_4$ $[M+H]^+$: 495, found 495. $^1H$ NMR (400 MHz, $CDCl_3$-d) δ 8.81 (s, 1H), 8.54 (s, 1H), 8.41 (s, 1H), 7.68 (s, 1H), 7.34 (s, 1H), 4.13-4.05 (m, 1H), 4.03-3.97 (m, 1H), 3.87 (m, 1H), 3.81-3.74 (m, 3H), 3.70 (m, 2H), 3.60 (m, 1H), 3.40 (s, 1H), 3.16 (s, 1H), 2.92-2.72 (m, 3H), 2.43 (s, 3H), 2.37-2.29 (m, 1H), 1.90-1.82 (m, 3H), 1.61-1.52 (m, 2H), 1.51-1.42 (m, 1H), 1.38 (m, 1H), 1.25 (s, 1H), 1.17 (s, 3H), 0.94 (m, 3H). Ex-15.2: MS (ESI): m/z calc'd for $C_{28}H_{39}N_4O_4$ $[M+H]^+$: 495, found 495. $^1H$ NMR (400 MHz, $CDCl_3$-d) δ 8.81 (s, 1H), 8.41 (s, 2H), 7.68 (s, 1H), 7.34 (s, 1H), 4.12-4.07 (m, 1H), 4.02-3.97 (m, 1H), 3.86 (m, 1H), 3.82 (m, 1H), 3.77 (m, 2H), 3.70 (m, 2H), 3.65 (m, 1H), 3.44 (s, 1H), 2.73 (s, 2H), 2.63 (s, 1H), 2.53 (m, 1H), 2.44 (s, 3H), 1.89-1.82 (m, 2H), 1.73 (s, 2H), 1.60-1.53 (m, 2H), 1.52-1.44 (m, 1H), 1.38 (m, 1H), 1.26 (s, 1H), 1.17 (s, 3H), 0.96 (m, 3H).

Scheme 52. Synthesis of N-(7-chloro-6-(4-(4-hydroxy-3-methyltetrahydrofuran-3-yl)piperazin-1-yl)isoquinolin-3-yl)-2-(2-methyl-2H-1,2,3-triazol-4-yl)cyclopropane-1-carboxamide (16.1) and (16.2)

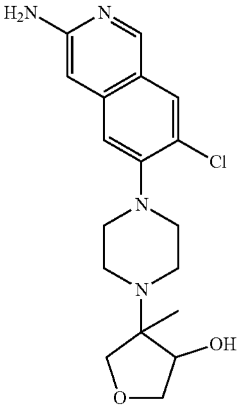

37

+

-continued

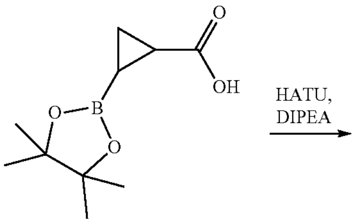

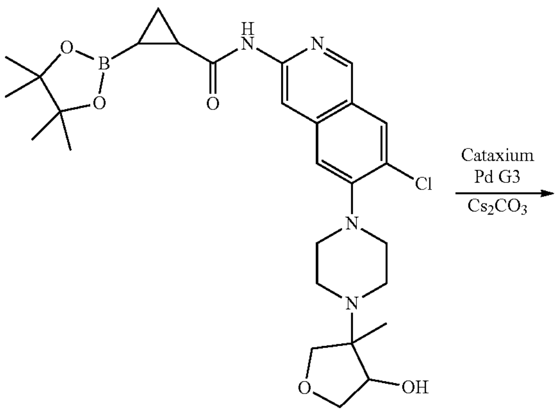

92

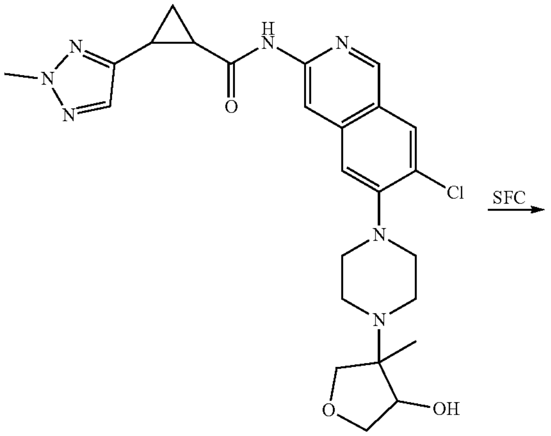

93

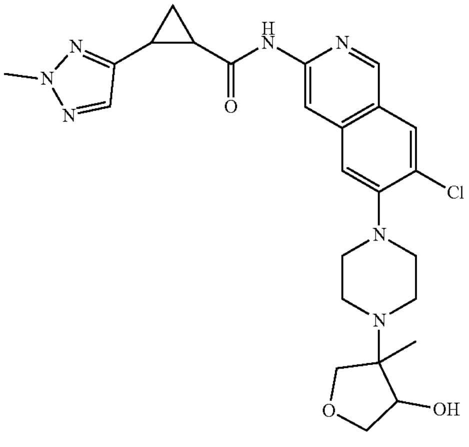

16.1 and 16.2

N-(7-chloro-6-(4-(4-hydroxy-3-methyltetrahydrofuran-3-yl)piperazin-1-yl)isoquinolin-3-yl)-2-(4,4,5,5-tetramethyl-1,3,2-dioxaborolan-2-yl)cyclopropane-1-carboxamide (92)

4-(4-(3-amino-7-chloroisoquinolin-6-yl)piperazin-1-yl)-4-methyltetrahydrofuran-3-ol, 2HCl, 37, (131 mg, 0.3 mmol), 2-(4,4,5,5-tetramethyl-1,3,2-dioxaborolan-2-yl)cyclopropane-1-carboxylic acid (105 mg, 0.495 mmol), HATU (0.171 g, 0.450 mmol), DMF (1 ml), and DIEA (0.262 ml, 1.500 mmol) were added to a vial. The resulting mixture was allowed to stir overnight at room temperature. The reaction mixture was added to water to form a precipitate. The solids were collected by vacuum filtration and dried to afford the title product. MS (ESI): m/z calc'd for $C_{28}H_{38}BClN_4O_5$ $[M+H]^+$: 557, found 557.

(1S,2R or 1S,2S)-N-(N-(7-chloro-6-(4-(4-hydroxy-3-methyltetrahydrofuran-3-yl)piperazin-1-yl)isoquinolin-3-yl)-2-(2-methyl-2H-1,2,3-triazol-4-yl)cyclopropane-1-carboxamide (Ex-16.1) and (Ex-16.2)

N-(7-chloro-6-(4-(4-hydroxy-3-methyltetrahydrofuran-3-yl)piperazin-1-yl)isoquinolin-3-yl)-2-(4,4,5,5-tetramethyl-1,3,2-dioxaborolan-2-yl)cyclopropane-1-carboxamide (80 mg, 0.144 mmol), 4-bromo-2-methyl-2H-1,2,3-triazole, 92, (46.5 mg, 0.287 mmol), Cataxium A Pd G3 (20.92 mg, 0.029 mmol), and cesium carbonate (140 mg, 0.431 mmol) were added to a vial. The vial was sealed and its contents were placed under an inert atmosphere by performing 3 vacuum/nitrogen cycles. 2-Methyltetrahydrofuran (1000 μl) and Water (100 μl) was added through the septum and the resulting mixture was stirred overnight at 80° C. The crude reaction mixture was scavenged for 1 hour at 50° C. with Si-DMT. The reaction mixture was filtered, and the residue was washed with 3:1 Chloroform:iPrOH. The reaction mixture was diluted with 3:1 Chloroform:iPrOH and washed with saturated ammonium chloride, the biphasic mixture was passed through a phase separator cartridge and concentrated under reduced pressure. The reaction mixture was filtered and submitted directly for HPLC purification, eluting acetonitrile/water gradient with 0.1% TFA modifier, linear gradient) and lyophilized to afford the product as a TFA salt. The purified fractions were dissolved in 3:1 Chloroform:iPrOH, washed with saturated sodium bicarbonate and passed through a phase separator. The organic fraction was concentrated under reduced pressure and lyophilized to afford 93 as a racemic mixture. The mixture of two stereoisomers was purified by chiral SFC (OJ-H, 21×250 (mm), 40%/60% Methanol/CO2+0.1% $NH_4OH$) and lyophilized to afford the resolved stereoisomers of the title compounds Ex-16.1 and Ex-16.2. MS (ESI): m/z calc'd for $C_{25}H_{30}ClN_7O_3$ $[M+H]^+$: 512, found 512. 1H NMR (499 MHz, DMSO-d6) δ 10.92 (s, 1H), 8.97 (s, 1H), 8.40 (s, 1H), 8.15 (s, 1H), 7.64 (s, 1H), 7.44 (s, 1H), 4.35 (s, 1H), 4.08 (s, 3H), 4.01-3.96 (m, 1H), 3.82 (s, 1H), 3.71 (d, J=9.7 Hz, 1H), 3.66 (d, J=7.2 Hz, 1H), 3.56 (d, J=7.2 Hz, 1H), 3.18 (s, 3H), 2.80-2.73 (m, 2H), 2.57-2.53 (m, 1H), 2.47-2.41 (m, 2H), 1.52-1.46 (m, 1H), 1.43-1.36 (m, 2H), 1.32-1.22 (m, 1H), 1.06 (s, 3H).

Scheme 53: Synthesis of (R) or (S)-N-(7-chloro-6-((3R,4R) or (3S,4S)-4-(4-hydroxy-3,4-dimethyltetrahydrofuran-3-yl)piperazin-1-yl)isoquinolin-3-yl)-6-oxaspiro[2.5]octane-1-carboxamide (Ex-17.1) and (Ex-17.2)

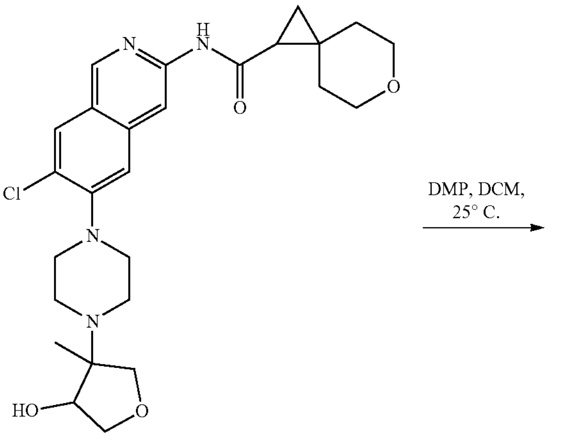

2.1

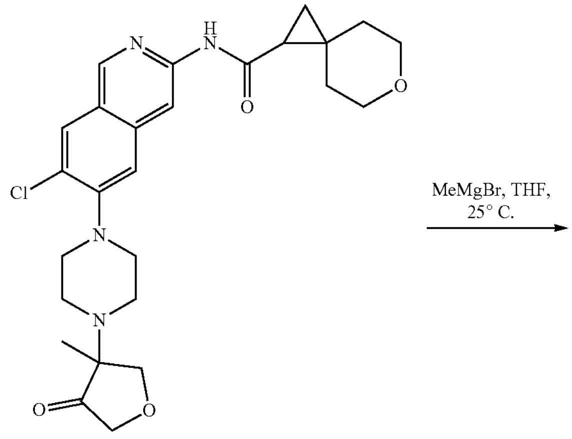

94

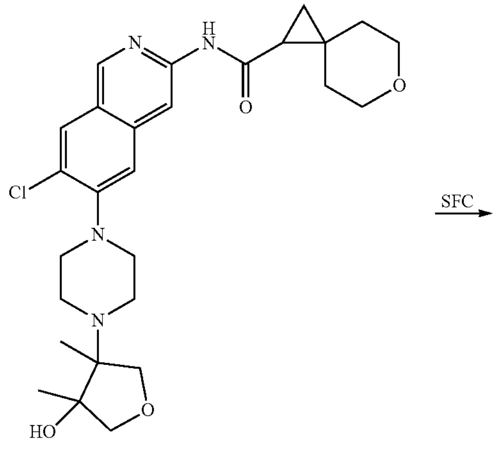

95

-continued

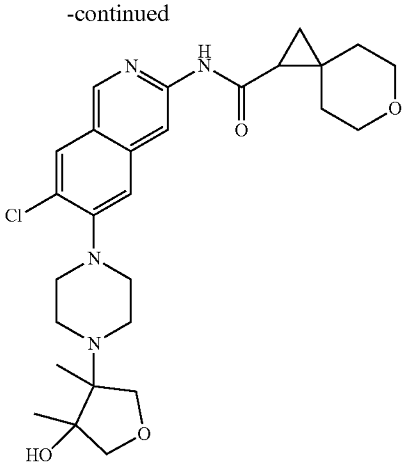

Ex-17.1

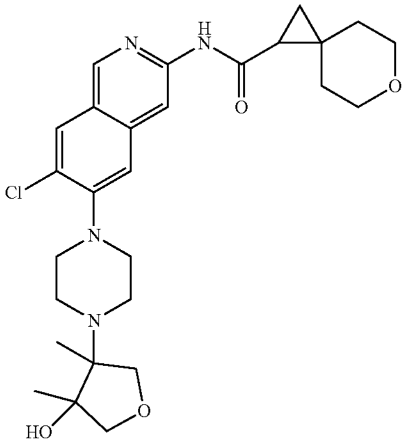

Ex-17.2

N-(7-chloro-6-(4-(3-methyl-4-oxotetrahydrofuran-3-yl)piperazin-1-yl)isoquinolin-3-yl)-6-oxaspiro[2.5]octane-1-carboxamide (94)

A vial was charged with N-(7-chloro-6-(4-(4-hydroxy-3-methyltetrahydrofuran-3-yl)piperazin-1-yl)isoquinolin-3-yl)-6-oxaspiro[2.5]octane-1-carboxamide (275 mg, 0.549 mmol), DCM (2744 μl) and DMP (698 mg, 1.647 mmol). The vial was sealed, and its contents were placed under an inert atmosphere by performing 3 vacuum/nitrogen cycles. The resulting mixture was allowed to stir overnight at room temperature. At 16 hours, the reaction was diluted with DCM (10 mL) and quenched by dropwise addition of saturated ammonium chloride (10 mL). The phases were separated, and the aqueous phase extracted with DCM (3×10 mL). The combined organic phases were washed with $H_2O$ (50 mL), dried over $Na_2SO_4$, and the solvent removed under reduced pressure. The resultant crude residue was subjected to purification by silica gel chromatography (Hexanes in 3:1 EtOAc/EtOH, 0-100%) to afford the title compound. MS (ESI) m/z calc'd for $C_{26}H_{31}ClN_4O_4$ $[M+H]^+$: 499, found 499.

(R) or (S)-N-(7-chloro-6-((3R,4R) or (3S,4S)-4-(4-hydroxy-3,4-dimethyltetrahydrofuran-3-yl)piperazin-1-yl)isoquinolin-3-yl)-6-oxaspiro[2.5]octane-1-carboxamide (Ex-17.1 and Ex-17.2)

A vial was charged with N-(7-chloro-6-(4-(3-methyl-4-oxotetrahydrofuran-3-yl)piperazin-1-yl)isoquinolin-3-yl)-6-oxaspiro[2.5]octane-1-carboxamide (55 mg, 0.110 mmol) and THF (1.1 mL). The vial was sealed, and its contents were placed under an inert atmosphere by performing 3 vacuum/nitrogen cycles. Under positive flow of nitrogen Methylmagnesium bromide (110 μl, 0.331 mmol) was added and the reaction mixture was stirred at 25° C. overnight. At 16 hours, the reaction was diluted with DCM (10 mL) and quenched by dropwise addition of saturated ammonium chloride (10 mL). The phases were separated, and the aqueous phase extracted with DCM (3×10 mL). The combined organic phases were washed with $H_2O$ (50 mL), dried over $Na_2SO_4$, and the solvent removed under reduced pressure. The crude residue was subject to purification by reversed phase HPLC, eluting with water (0.1% NH4OH)—ACN to afford the racemate. The racemic material could be resolved to its component enantiomers by chiral preparative SFC (Column & dimensions: AS-H, 21×250 mm, 5 um; Mobile phase A: $CO_2$; Mobile phase B: MeOH with 0.1% $NH_4OH$) to afford the title compounds (tR=3.2 and 4.75 min). MS (ESI) m/z calc'd for $C_{27}H_{35}ClN_4O_4$ $[M+H]^+$: 515, found 515. $^1H$ NMR (400 MHz, d-DMSO, 25° C.) δ 10.84 (s, 1H), 8.97 (s, 1H), 8.38 (s, 1H), 8.14 (s, 1H), 7.42 (s, 1H), 4.79 (s, 1H), 3.85 (d, J=7.7 Hz, 1H), 3.78-3.64 (m, 4H), 3.60 (dd, J=12.3, 6.6 Hz, 2H), 3.44 (d, J=7.5 Hz, 1H), 3.17 (s, 4H), 2.82 (d, J=4.7 Hz, 2H), 2.60-2.54 (m, 2H), 2.06-1.98 (m, 1H), 1.76-1.60 (m, 2H), 1.51 (s, 1H), 1.38 (s, 1H), 1.25 (s, 3H), 1.15 (s, 3H), 1.12 (t, J=4.6 Hz, 1H), 0.93 (dd, J=7.6, 3.9 Hz, 1H). MS (ESI) m/z calc'd for $C_{27}H_{35}ClN_4O_4$ $[M+H]^+$: 515, found 515. $^1H$ NMR (400 MHz, d-DMSO, 25° C.) δ: 10.83 (s, 1H), 8.96 (s, 1H), 8.37 (s, 1H), 8.13 (s, 1H), 7.42 (s, 1H), 4.81 (s, 1H), 3.75-3.63 (m, 5H), 3.63-3.56 (m, 1H), 3.54 (d, J=8.0 Hz, 1H), 3.43 (t, J=7.6 Hz, 1H), 3.09 (s, 4H), 2.90 (s, 1H), 2.41 (s, 2H), 2.05-1.98 (m, 1H), 1.77-1.61 (m, 2H), 1.51 (s, 1H), 1.34 (s, 4H), 1.25 (s, 1H), 1.16 (s, 3H), 1.11 (t, J=4.6 Hz, 1H), 0.93 (dd, J=7.5, 3.8 Hz, 1H).

Scheme 54. rac-N-(7-chloro-6-(4-(4-cyano-3-methyltetrahydrofuran-3-yl)piperazin-1-yl)isoquinolin-3-yl)-6-oxaspiro[2.5]octane-1-carboxamide (Ex-18)

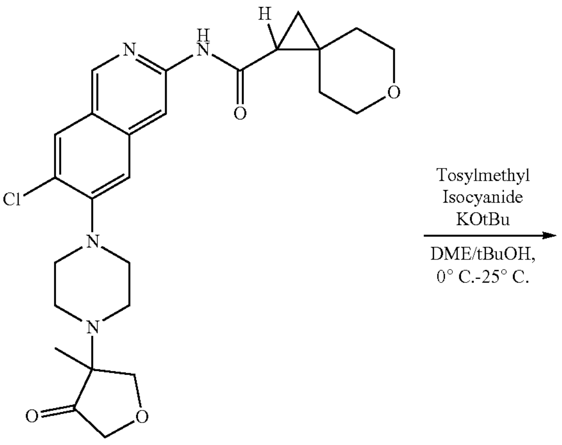

94

-continued

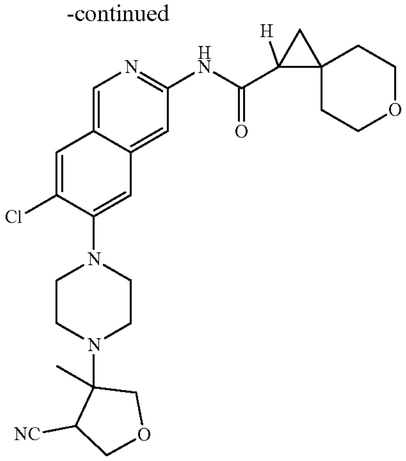

Ex-18

A solution of N-(7-chloro-6-(4-(3-methyl-4-oxotetrahydrofuran-3-yl)piperazin-1-yl)isoquinolin-3-yl)-6-oxaspiro[2.5]octane-1-carboxamide (80 mg, 0.160 mmol) and tosylmethyl isocyanide (46.9 mg, 0.240 mmol) in DME (802 µl) was chilled to 0° C. KOtBu (5.78 g, 50.0 mmol) in tBuOH (50 ml) and DME (802 µl) was added and the resulting reaction mixture was stirred overnight; eventually warming to room temperature. The reaction mixture was quenched by addition of saturated ammonium chloride. The desired product was extracted with DCM. Organic layers were combined, dried, and concentrated under reduced pressure. The reaction mixture was filtered and submitted directly for HPLC purification to the HTP group (purified by HPLC, eluting acetonitrile/water gradient with 0.1% Ammonium hydroxide modifier, linear gradient) and lyophilized to afford the title compound. MS (ESI): m/z calc'd for $C_{27}H_{32}ClN_5O_3$ $[M+H]^+$: 510, found 510.

Biological Assay: LRRK2 Km ATP LanthaScreen™ Assay

The LRRK2 kinase activity reported herein as IC50 values was determined with LanthaScreen™ technology from Life Technologies Corporation (Carlsbad, CA) using GST-tagged truncated human mutant G2019S LRRK2 in the presence of the fluorescein-labeled peptide substrate LRRKtide, also from Life Technologies. The data presented for the Km ATP LanthaScreen™ Assay represents mean $IC_{50}$ values based on several test results and may have reasonable deviations depending on the specific conditions and reagents used. Assays were performed in the presence of 134 µM ATP (Km ATP). Upon completion, the assay was stopped and phosphorylated substrate detected with a terbium (Tb)-labeled anti-pERM antibody (cat. no. PV4898). The compound dose response was prepared by diluting a 10 mM stock of compound to a maximum concentration of 9.99 µM in 100% dimethylsulfoxide followed by custom fold serial dilution in dimethylsulfoxide nine times. Twenty nanoliters of each dilution was spotted via a Labcyte Echo onto a 384-well black-sided plate (Corning 3575) followed by 15 µl of a 1.25 nM enzyme solution in 1× assay buffer (50 mM Tris pH 8.5, 10 mM MgCl2, 0.01% Brij-35, 1 mM EGTA, 2 mM dithiothreitol, 0.05 mM sodium orthovanadate). Following a 15-minute incubation at room temperature, the kinase reaction was started with the addition of 5 µl of 400 nM fluorescein-labeled LRRKtide peptide substrate and 134 µM ATP solution in 1× assay buffer. The reaction was allowed to progress at ambient temperature for 90 minutes. The reaction was then stopped by the addition of 20 µl of TR-FRET Dilution Buffer (Life Technologies, Carlsbad, CA) containing 2 nM Tb-labeled anti-phospho LRRKtide antibody and 10 mM EDTA (Life Technologies, Carlsbad, CA). After an incubation of 1 hour at room temperature, the plate was read on an EnVision multimode plate reader (Perkin Elmer, Waltham, MA) with an excitation wavelength of 337 nm (Laser) and a reading emission at both 520 and 495 nm. Compound IC50s were interpolated from nonlinear regression best fits of the log of the final compound concentration, plotted as a function of the 520/495-nm emission ratio using Activity base. Abase uses a 4 parameter (4P) logistic fit based on the Levenberg-Marquardt algorithm.

TABLE 12

| Ex | LRRK2 $pIC_{50}$ |
|---|---|
| Ex-1.1 | 9.2 |
| Ex-1.2 | 7.6 |
| Ex-1.3 | 8.71 |
| Ex-1.4 | 7.24 |
| Ex-1.5 | 8.15 |
| Ex-1.6 | 6.04 |
| Ex-1.7 | 8.18 |
| Ex-1.8 | 8.63 |
| Ex-1.9 | 9.10 |
| Ex-1.10 | 6.97 |
| Ex-1.11 | 8.77 |
| Ex-1.12 | 8.43 |
| Ex-1.13 | 6.56 |
| Ex-1.14 | 9.22 |
| Ex-1.15 | 7.33 |
| Ex-1.16 | 6.95 |
| Ex-1.17 | 6.11 |
| Ex-1.18 | 9.14 |
| Ex-1.19 | 8.96 |
| Ex-1.20 | 7.20 |
| Ex-1.21 | 8.76 |
| Ex-1.22 | 8.93 |
| Ex-1.23 | 8.13 |
| Ex-1.24 | 7.16 |
| Ex-1.25 | 9.80 |
| Ex-1.26 | 8.84 |
| Ex-1.27 | 8.89 |
| Ex-1.28 | 7.92 |
| Ex-2.1 | 9.41 |
| Ex-2.2 | 8.44 |
| Ex-2.3 | 7.76 |
| Ex-2.4 | 9.42 |
| Ex-2.5 | 7.38 |
| Ex-2.6 | 8.51 |
| Ex-2.7 | 6.42 |
| Ex-2.8 | 7.62 |
| Ex-2.9 | 9.71 |
| Ex-2.10 | 9.23 |
| Ex-2.11 | 8.84 |
| Ex-2.12 | 9.29 |
| Ex-2.13 | 7.47 |
| Ex-2.14 | 9.33 |
| Ex-2.15 | 7.52 |
| Ex-2.16 | 9.09 |
| Ex-2.17 | 9.02 |
| Ex-2.18 | 7.81 |
| Ex-2.19 | 8.54 |
| Ex-2.20 | 9.75 |
| Ex-2.21 | 9.23 |
| Ex-2.22 | 9.43 |
| Ex-2.23 | 9.50 |
| Ex-3.1 | 9.01 |
| Ex-3.2 | 8.97 |
| Ex-4.1 | 8.46 |
| Ex-4.2 | 7.98 |
| Ex-4.3 | 7.85 |
| Ex-4.4 | 7.85 |
| Ex-4.5 | 7.72 |
| Ex-4.6 | 8.61 |
| Ex-4.7 | 7.93 |

TABLE 12-continued

| Ex | LRRK2 $pIC_{50}$ |
|---|---|
| Ex-4.8 | 6.68 |
| Ex-4.9 | 8.26 |
| Ex-4.10 | 7.29 |
| Ex-4.11 | 7.39 |
| Ex-5.1 | 8.02 |
| Ex-5.2 | 7.59 |
| Ex-5.3 | 9.43 |
| Ex-5.4 | 7.54 |
| Ex-5.5 | 8.58 |
| Ex-5.6 | 6.50 |
| Ex-5.7 | 8.58 |
| Ex-5.8 | 6.72 |
| Ex-5.9 | 5.82 |
| Ex-5.10 | 7.42 |
| Ex-5.11 | 8.61 |
| Ex-5.12 | 6.90 |
| Ex-5.13 | 7.08 |
| Ex-5.14 | 6.52 |
| Ex-5.15 | 8.21 |
| Ex-5.16 | 6.37 |
| Ex-5.17 | 10.09 |
| Ex-5.18 | 7.17 |
| Ex-5.19 | 6.93 |
| Ex-5.20 | 8.04 |
| Ex-6.1 | 9.45 |
| Ex-6.2 | 8.86 |
| Ex-6.3 | 9.08 |
| Ex-6.4 | 8.97 |
| Ex-6.5 | 8.98 |
| Ex-6.6 | 7.34 |
| Ex-6.7 | 6.90 |
| Ex-6.8 | 6.20 |
| Ex-6.9 | 6.49 |
| Ex-6.10 | 9.26 |
| Ex-6.11 | 9.57 |
| Ex-6.12 | 9.67 |
| Ex-6.13 | 10.09 |
| Ex-6.14 | 9.83 |
| Ex-7.1 | 9.08 |
| Ex-7.2 | 9.01 |
| Ex-7.3 | 8.43 |
| Ex-7.4 | 9.11 |
| Ex-7.5 | 9.81 |
| Ex-8.1 | 7.99 |
| Ex-8.2 | 7.53 |
| Ex-9.1 | 8.12 |
| Ex-9.2 | 8.74 |
| Ex-9.3 | 8.58 |
| Ex-9.4 | 8.40 |
| Ex-9.5 | 8.28 |
| Ex-9.6 | 9.0 |
| Ex-9.7 | 10.09 |
| Ex-9.8 | 8.31 |
| Ex-9.9 | 9.38 |
| Ex-9.10 | 10.09 |
| Ex-9.11 | 8.94 |
| Ex-9.12 | 10.09 |
| Ex-9.13 | 7.94 |
| Ex-9.14 | 10.09 |
| Ex-9.15 | 9.50 |
| Ex-9.16 | 8.95 |
| Ex-9.17 | 8.89 |
| Ex-9.18 | 7.0 |
| Ex-9.19 | 10.09 |
| Ex-9.20 | 10.09 |
| Ex-9.21 | 10.09 |
| Ex-10.1 | 9.03 |
| Ex-10.2 | 9.17 |
| Ex-10.3 | 8.80 |
| Ex-10.4 | 8.86 |
| Ex-10.5 | 8.32 |
| Ex-10.6 | 9.85 |
| Ex-10.7 | 8.73 |
| Ex-10.8 | 9.93 |
| Ex-10.9 | 9.21 |
| Ex-10.10 | 8.79 |
| Ex-10.11 | 9.07 |
| Ex-10.12 | 10.08 |

TABLE 12-continued

| Ex | LRRK2 $pIC_{50}$ |
|---|---|
| Ex-10.13 | 10.09 |
| Ex-10.14 | 8.37 |
| Ex-10.15 | 8.93 |
| Ex-10.16 | 8.10 |
| Ex-10.17 | 8.56 |
| Ex-10.18 | 8.06 |
| Ex-10.19 | 7.37 |
| Ex-10.20 | 8.65 |
| Ex-10.21 | 7.35 |
| Ex-10.22 | 8.57 |
| Ex-10.23 | 9.14 |
| Ex-10.24 | 10.09 |
| Ex-10.25 | 8.43 |
| Ex-10.26 | 6.28 |
| Ex-10.27 | 7.42 |
| Ex-10.28 | 7.25 |
| Ex-10.29 | 9.56 |
| Ex-10.30 | 10.09 |
| Ex-10.31 | 10.09 |
| Ex-10.32 | 10.09 |
| Ex-10.33 | 8.32 |
| Ex-10.34 | 7.16 |
| Ex-10.35 | 8.77 |
| Ex-10.36 | 6.97 |
| Ex-10.37 | 10.09 |
| Ex-10.38 | 9.12 |
| Ex-10.39 | 10.09 |
| Ex-10.40 | 10.09 |
| Ex-10.41 | 9.51 |
| Ex-10.42 | 9.28 |
| Ex-10.43 | 7.71 |
| Ex-10.44 | 6.68 |
| Ex-10.45 | 9.84 |
| Ex-10.46 | 9.34 |
| Ex-10.47 | 7.99 |
| Ex-10.48 | 7.76 |
| Ex-10.49 | 10.09 |
| Ex-10.50 | 10.09 |
| Ex-10.51 | 10.09 |
| Ex-10.52 | 9.22 |
| Ex-10.53 | 10.09 |
| Ex-10.54 | 10.09 |
| Ex-10.55 | 10.09 |
| Ex-10.56 | 10.09 |
| Ex-10.57 | 10.09 |
| Ex-10.58 | 10.09 |
| Ex-10.59 | 10.09 |
| Ex-10.60 | 10.09 |
| Ex-10.61 | 8.52 |
| Ex-10.62 | 10.09 |
| Ex-10.63 | 10.09 |
| Ex-10.64 | 10.09 |
| Ex-10.65 | 10.09 |
| Ex-10.66 | 10.09 |
| Ex-10.67 | 9.99 |
| Ex-10.68 | 10.09 |
| Ex-10.69 | 10.09 |
| Ex-10.70 | 10.09 |
| Ex-10.71 | 7.72 |
| Ex-10.72 | 10.09 |
| Ex-10.73 | 10.09 |
| Ex-10.74 | 10.09 |
| Ex-10.75 | 9.66 |
| Ex-10.76 | 10.09 |
| Ex-10.77 | 10.09 |
| Ex-10.78 | 10.09 |
| Ex-10.79 | 10.09 |
| Ex-10.80 | 9.91 |
| Ex-10.81 | 10.09 |
| Ex-10.82 | 10.00 |
| Ex-10.83 | 9.28 |
| Ex-10.84 | 9.67 |
| Ex-10.85 | 10.09 |
| Ex-10.86 | 10.09 |
| Ex-10.87 | 10.09 |
| Ex-10.88 | 9.74 |
| Ex-10.89 | 10.09 |
| Ex-10.90 | 8.69 |

TABLE 12-continued

| Ex | LRRK2 $pIC_{50}$ |
|---|---|
| Ex-10.91 | 10.09 |
| Ex-10.92 | 8.71 |
| Ex-10.93 | 9.90 |
| Ex-10.94 | 9.40 |
| Ex-10.95 | 9.64 |
| Ex-10.96 | 8.99 |
| Ex-11.1 | 10.09 |
| Ex-11.2 | 7.34 |
| Ex-11.3 | 10.09 |
| Ex-11.4 | 9.01 |
| Ex-11.5 | 10.09 |
| Ex-11.6 | 9.88 |
| Ex-12 | 9.28 |
| Ex-13 | 8.47 |
| Ex-14.1 | 7.06 |
| Ex-14.2 | 10.09 |
| Ex-15.1 | 8.33 |
| Ex-15.2 | 10.09 |
| Ex-16.1 | 9.84 |
| Ex-16.2 | 10.09 |
| Ex-17.1 | 10.09 |
| Ex-17.2 | 9.90 |
| Ex-18.1 | 9.04 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound of structural Formula (I):

I

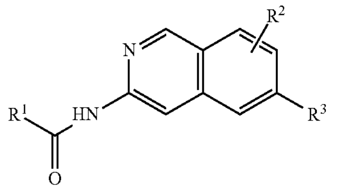

or a pharmaceutically acceptable salt thereof, wherein:

$R^1$ is selected from monocyclic or bicyclic $C_{3-8}$ carbocycle, said carbocycle optionally interrupted by an oxygen atom and optionally substituted with 1 to 3 groups selected from $C_{1-6}$ alkyl, $(CH_2)_nOC_{1-6}$alkyl, CN, $C_{1-3}$haloalkyl, $C_{3-10}$ heteroaryl, $C_{3-10}$ heterocyclyl, and halogen, said heteroaryl and heterocyclyl optionally substituted with 1 to 3 groups selected from $C_{1-6}$ alkyl, $CF_3$, and CN;

$R^2$ is selected from hydrogen, $C_{1-6}$ alkyl, $OC_{1-6}$alky, $C_{3-6}$ cycloalkyl, and halogen;

$R^3$ is selected from N-linked oxo-oxazolidinyl, oxoazabicycloheptanyl, azabicycloheptanyl, piperidinyl, tetrahydropyrazolopyridinyl, azaspiroheptanyl, and piperazinyl said N-linked oxazolidinyl, oxazolidinonyl, oxoazabicycloheptanyl, piperidinyl, tetrahydropyrazolopyridinyl, azaspiroheptanyl, and piperazinyl unsubstituted or substituted with 1 to 3 groups independently selected from $C_{1-6}$ alkyl, $OC_{1-6}$ alkyl, OH, halogen, CN, azetidinyl, wherein said piperazinyl is further substituted at available nitrogen atom with a group independently selected from $C_{1-6}$ alkyl, oxetanyl, azetidinyl, and tetrahydrofuranyl, said oxetanyl, azetidinyl, and tetrahydrofuranyl unsubstituted or substituted with 1 to 2 groups independently selected from $C_{1-6}$ alkyl, $OC_{1-6}$ alkyl, halogen, CN, and OH and n is selected from 0 to 3, provided that when $R^1$ is cyclopropyl and $R^2$ is halogen, then $R^3$ is not oxo-oxazolidinyl.

2. The compound according to claim 1 wherein $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, spirooctanyl, bicyclopentanyl, oxabicyclohexanyl, oxaspiroheptanyl, oxaspirooctanyl, and oxaspirononanyl, or a pharmaceutically acceptable salt thereof.

3. The compound according to claim 1 wherein $R^1$ is selected from substituted or unsubstituted oxabicyclohexanyl, oxaspiroheptanyl, oxaspirooctanyl, and oxaspirononanyl or a pharmaceutically acceptable salt thereof.

4. The compound according to claim 1 wherein $R^2$ is hydrogen, or a pharmaceutically acceptable salt thereof.

5. The compound according to claim 1 wherein $R^2$ is halogen, or a pharmaceutically acceptable salt thereof.

6. The compound according to claim 1 wherein $R^2$ is chlorine, or a pharmaceutically acceptable salt thereof.

7. The compound according to claim 1 wherein $R^3$ is selected from substituted or unsubstituted N-linked oxo-oxazolidinyl, or a pharmaceutically acceptable salt thereof.

8. The compound according to claim 1 wherein $R^3$ is substituted or unsubstituted N-linked oxoazabicycloheptanyl, azaspiroheptany or azabicycloheptanyl, or a pharmaceutically acceptable salt thereof.

9. The compound according to claim 1 wherein $R^3$ is substituted or unsubstituted N-linked piperazinyl, piperidinyl, or a pharmaceutically acceptable salt thereof.

10. The compound according to claim 1 wherein $R^3$ is substituted N-linked piperazinyl wherein the substitution is on the available nitrogen atom.

11. The compound according to claim 1 wherein $R^3$ is substituted or unsubstituted N-linked tetrahydropyrazolopyridinyl.

12. The compound according to claim 1 represented by structural Formula II:

II

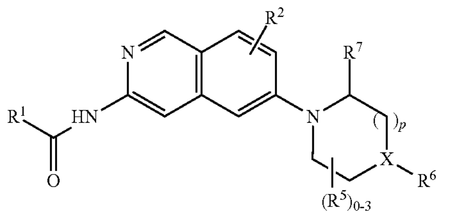

or a pharmaceutically acceptable salt thereof, wherein $R^1$ and $R^2$ are as described herein, p is 0 or 1, X is N, O, or CH, $R^5$ is selected from $C_{1-6}$ alkyl, $OC_{1-6}$ alkyl, OH, CN, and halogen, $R^7$ is selected from hydrogen, $C_{1-6}$ alkyl and =O, and $R^6$ is selected from 1) $R^4$, when X is N, p is 1 and $R^7$ is hydrogen or $C_{1-6}$ alkyl, 2) Absent, when X is O, p is 0, and $R^7$ is =O, and 3) Hydrogen, $C_{1-6}$ alkyl, or OH, when X is CH, p is 1, and $R^7$ is hydrogen or $C_{1-6}$ alkyl, wherein when p is 0 (or absent) a five membered ring is present and when p is 1 a six membered ring is present, and $R^4$ is selected from $C_{1-6}$ alkyl, oxetanyl and tetrahydrofuranyl said oxetanyl and tetrahydrofuranyl unsubstituted or substituted with 1 to 2 groups independently selected from $C_{1-6}$ alkyl, $OC_{1-6}$ alkyl, and OH.

13. The compound according to claim 12 wherein p is 1 and X is N or CH.

14. The compound according to claim 12 wherein p is 0 and X is O.

15. The compound according to claim 12 represented by structural Formula III:

III

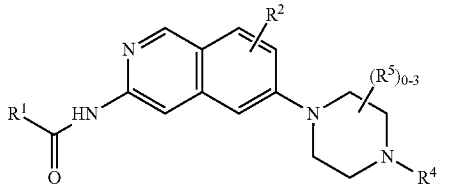

or a pharmaceutically acceptable salt thereof, wherein $R^5$ is selected from $C_{1-6}$ alkyl, $OC_{1-6}$ alkyl, OH, CN, and halogen, $R^1$ is selected from substituted or unsubstituted cyclopropyl, cyclobutyl, cyclopentyl, cyclohexyl, heptanyl, octanyl, tetrahydrofuranyl, tetrahydropyranyl, spirohexanyl, spiropentanyl, bicyclopentanyl, oxabicyclohexanyl, oxabicycloheptanyl, oxaspiroheptanyl, oxaspirooctanyl, and oxaspirononanyl, $R^2$ is hydrogen, methyl, chlorine, or fluorine, and $R^4$ is selected from methyl, ethyl, propyl, oxetanyl, tetrahydrofuranyl, said oxetanyl and tetrahydrofuranyl unsubstituted or substituted with 1 to 2 groups independently selected from $C_{1-6}$ alkyl, $OC_{1-6}$ alkyl and OH.

16. The compound according to claim 1 represented by structural Formula IV:

IV

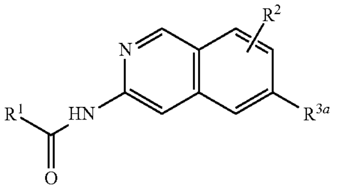

or a pharmaceutically acceptable salt thereof, wherein $R^1$ and $R^2$ are as described and $R^{3a}$ is selected from the group consisting of:

Ia

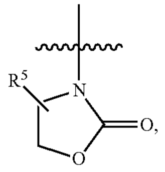

Ib

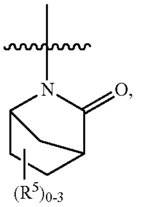

Ib'

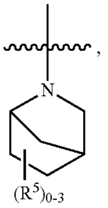

Ic

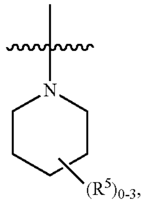

Id

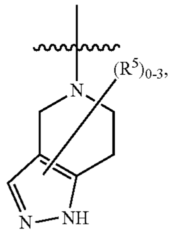

and

Ie

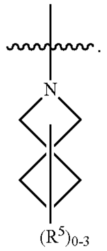

wherein $R^5$ is selected from hydrogen, $C_{1-6}$ alkyl, $OC_{1-6}$ alkyl, OH, CN, and halogen.

17. The compound of claim 1, or a pharmaceutically acceptable salt thereof, selected from:

N-(7-chloro-6-(4-(4-hydroxy-3-methyltetrahydrofuran-3-yl)piperazin-1-yl)isoquinolin-3-yl)cyclopropanecarboxamide, (3R,4R)-N-(7-chloro-6-(4-(4-hydroxy-3-methyltetrahydrofuran-3-yl)piperazin-1-yl)isoquinolin-3-yl)cyclopropanecarboxamide, (3S,4S)-N-(7-chloro-6-(4-(4-hydroxy-3-methyltetrahydrofuran-3-yl)piperazin-1-yl)isoquinolin-3-yl)cyclopropanecarboxamide, N-(7-chloro-6-(4-(4-hydroxytetrahydrofuran-3-yl)piperazin-1-yl)isoquinolin-3-yl)cyclopropanecarboxamide, (3R,4R)-N-(7-chloro-6-(4-(4-hydroxytetrahydrofuran-3-yl)piperazin-1-yl)isoquinolin-3-yl)cyclopropanecarboxamide, (3S,4S)-N-(7-chloro-6-(4-(4-hydroxytetrahydrofuran-3-yl)piperazin-1-yl)isoquinolin-3-yl)cyclopropanecarboxamide, N-(7-fluoro-6-(4-(4-hydroxy-3-methyltetrahydrofuran-3-yl)piperazin-1-yl)isoquinolin-3-yl)cyclopropanecarboxamide, (3R,4R)-N-(7-fluoro-6-(4-(4-hydroxy-3-methyltetrahydrofuran-3-yl)piperazin-1-yl)isoquinolin-3-yl)cyclopropanecarboxamide, (3S,4S)-N-(7-fluoro-6-(4-(4-hydroxy-3-methyltetrahydrofuran-3-yl)piperazin-1-yl)isoquinolin-3-yl)cyclopropanecarboxamide, N-(7-chloro-6-(4-(4-hydroxy-3-methyltetrahydrofuran-3-yl)piperazin-1-yl)isoquinolin-3-yl)spiro[2.3]hexane-1-carboxamide, (1R)-N-(7-chloro-6-(4-((3R,4R)-4-hydroxy-3-methyltetrahydrofuran-3-yl)piperazin-1-yl)isoquinolin-3-yl)spiro[2.3]hexane-1-carboxamide, (1R)-N-(7-chloro-6-(4-((3S,4S)-4-hydroxy-3-methyltetrahydrofuran-3-yl)piperazin-1-yl)isoquinolin-3-yl)spiro[2.3]hexane-1-carboxamide, (1S)-N-(7-chloro-6-(4-((3R,4R)-4-hydroxy-3-methyltetrahydrofuran-3-yl)piperazin-1-yl)isoquinolin-3-yl)spiro[2.3]hexane-1-carboxamide, (1S)-N-(7-chloro-6-(4-((3S,4S)-4-hydroxy-3-methyltetrahydrofuran-3-yl)piperazin-1-yl)isoquinolin-3-yl)spiro[2.3]hexane-1-carboxamide, N-(7-chloro-6-(4-(4-hydroxy-3-methyltetrahydrofuran-3-yl)piperazin-1-yl)isoquinolin-3-yl)-3-oxabicyclo[3.1.0]hexane-6-carboxamide, (1R)-N-(7-chloro-6-(4-((3R,4R)-4-hydroxy-3-methyltetrahydrofuran-3-yl)piperazin-1-yl)isoquinolin-3-yl)-3-oxabicyclo[3.1.0]hexane-6-carboxamide, (1R)-N-(7-chloro-6-(4-((3S,4S)-4-hydroxy-3-methyltetrahydrofuran-3-yl)piperazin-1-yl)isoquinolin-3-yl)-3-oxabicyclo[3.1.0]hexane-6-carboxamide, (1S)-N-(7-chloro-6-(4-((3R,4R)-4-hydroxy-3-methyltetrahydrofuran-3-yl)piperazin-1-yl)isoquinolin-3-yl)-3-oxabicyclo[3.1.0]hexane-6-carboxamide, (1S)-N-(7-chloro-6-(4-((3S,4S)-4-hydroxy-3-methyltetrahydrofuran-3-yl)piperazin-1-yl)isoquinolin-3-yl)-3-oxabicyclo[3.1.0]hexane-6-carboxamide, N-(7-chloro-6-(4-((3S,4S or 3R, 4R)-4-hydroxy-3-methyltetrahydrofuran-3-yl)piperazin-1-yl)isoquinolin-3-yl)-5-oxaspiro[2.5]octane-1-carboxamide, (1R,3S)-N-(7-chloro-6-(4-((3R,4R)-4-hydroxy-3-methyltetrahydrofuran-3-yl)piperazin-1-yl)isoquinolin-3-yl)-5-oxaspiro[2.5]octane-1-carboxamide, (1R,3S)-N-(7-chloro-6-(4-((3S,4S)-4-hydroxy-3-methyltetrahydrofuran-3-yl)piperazin-1-yl)isoquinolin-3-yl)-5-oxaspiro[2.5]octane-1-carboxamide, (1R,3R)-N-(7-chloro-6-(4-((3R,4R)-4-hydroxy-3-methyltetrahydrofuran-3-yl)piperazin-1-yl)isoquinolin-3-yl)-5-oxaspiro[2.5]octane-1-carboxamide, (1R,3R)-N-(7-chloro-6-(4-((3S,4S)-4-hydroxy-3-methyltetrahydrofuran-3-yl)piperazin-1-yl)isoquinolin-3-yl)-5-oxaspiro[2.5]octane-1-carboxamide, (1S,3S)-N-(7-chloro-6-(4-((3R,4R)-4-hydroxy-3-methyltetrahydrofuran-3-yl)piperazin-1-yl)isoquinolin-3-yl)-5-oxaspiro[2.5]octane-1-carboxamide, (1S,3S)-N-(7-chloro-6-(4-((3S,4S)-4-hydroxy-3-methyltetrahydrofuran-3-yl)piperazin-1-yl)isoquinolin-3-yl)-5-oxaspiro[2.5]octane-1-carboxamide, (1S,3R)-N-(7-chloro-6-(4-((3R,4R)-4-hydroxy-3-methyltetrahydrofuran-3-yl)piperazin-1-yl)isoquinolin-3-yl)-5-oxaspiro[2.5]octane-1-carboxamide o (1S,3R)-N-(7-chloro-6-(4-((3S,4S)-4-hydroxy-3-methyltetrahydrofuran-3-yl)piperazin-1-yl)isoquinolin-3-yl)-5-oxaspiro[2.5]octane-1-carboxamide, N-(7-chloro-6-(4-(4-hydroxy-3-methyltetrahydrofuran-3-yl)piperazin-1-yl)isoquinolin-3-yl)-6,6-difluorospiro[2.5]octane-1-carboxamide, (1R)-N-(7-chloro-6-(4-((3R,4R)-4-hydroxy-3-methyltetrahydrofuran-3-yl)piperazin-1-yl)isoquinolin-3-yl)-6,6-difluorospiro[2.5]octane-1-carboxamide, (1R)-N-(7-chloro-6-(4-((3S,4S)-4-hydroxy-3-methyltetrahydrofuran-3-yl)piperazin-1-yl)isoquinolin-3-yl)-6,6-difluorospiro[2.5]octane-1-carboxamide, (1S)-N-(7-chloro-6-(4-((3R,4R)-4-hydroxy-3-methyltetrahydrofuran-3-yl)piperazin-1-yl)isoquinolin-3-yl)-6,6-difluorospiro[2.5]octane-1-carboxamide, (1S)-N-(7-chloro-6-(4-((3S,4S)-4-hydroxy-3-methyltetrahydrofuran-3-yl)piperazin-1-yl)isoquinolin-3-yl)-6,6-difluorospiro[2.5]octane-1-carboxamide, N-(7-chloro-6-(4-(4-hydroxy-3-methyltetrahydrofuran-3-yl)piperazin-1-yl)isoquinolin-3-yl)-5,5-dimethyltetrahydrofuran-3-carboxamide, (R)-N-(7-chloro-6-(4-((3R,4R)-4-hydroxy-3-methyltetrahydrofuran-3-yl)piperazin-1-yl)isoquinolin-3-yl)-5,5-dimethyltetrahydrofuran-3-carboxamide, (R)-N-(7-chloro-6-(4-((3S,4S)-4-hydroxy-3-methyltetrahydrofuran-3-yl)piperazin-1-yl)isoquinolin-3-yl)-5,5-dimethyltetrahydrofuran-3-carboxamide, (S)-N-(7-chloro-6-(4-((3R,4R)-4-hydroxy-3-methyltetrahydrofuran-3-yl)piperazin-1-yl)isoquinolin-3-yl)-5,5-dimethyltetrahydrofuran-3-carboxamide, (S)-N-(7-chloro-6-(4-((3S,4S)-4-hydroxy-3-methyltetrahydrofuran-3-yl)piperazin-1-yl)isoquinolin-3-yl)-5,5-dimethyltetrahydrofuran-3-carboxamide, N-(7-chloro-6-(1-(4-hydroxy-3-methyltetrahydrofuran-3-yl)piperazin-4-yl)isoquinolin-3-yl)-2,2-dimethyltetrahydrofuran-3-carboxamide, (R)-N-(7-chloro-6-(1-((3R,4R)-4-hydroxy-3-methyltetrahydrofuran-3-yl)piperazin-4-yl)isoquinolin-3-yl)-2,2-dimethyltetrahydrofuran-3-carboxamide, (R)-N-(7-chloro-6-(1-((3S,4S)-4-hydroxy-3-methyltetrahydrofuran-3-yl)piperazin-4-yl)isoquinolin-3-yl)-2,2-dimethyltetrahydrofuran-3-carboxamide, (S)-N-(7-chloro-6-(1-((3R,4R)-4-hydroxy-3-methyltetrahydrofuran-3-yl)piperazin-4-yl)isoquinolin-3-yl)-2,2-dimethyltetrahydrofuran-3-carboxamide, (S)-N-(7-chloro-6-(1-((3S,4S)-4-hydroxy-3-methyltetrahydrofuran-3-yl)piperazin-4-yl)isoquinolin-3-yl)-2,2-dimethyltetrahydrofuran-3-carboxamide, N-(7-chloro-6-(4-(4-hydroxy-3-methyltetrahydrofuran-3-yl)piperazin-1-yl)isoquinolin-3-yl)-2-(methoxymethyl)cyclobutane-1-carboxamide, (1R,2S)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide, (1R,2S)-N-(7-chloro-6-(4-((3S,4S)-4-hydroxy-3-methyltetrahydrofuran-3-yl)piperazin-1-yl)isoquinolin-3-yl)-2-(methoxymethyl)cyclobutane-1-carboxamide, (1R,2R)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide, (1R,2R)-N-(7-chloro-6-(4-((3S,4S)-4-hydroxy-3-methyltetrahydrofuran-3-yl)piperazin-1-yl)isoquinolin-3-yl)-2-(methoxymethyl)cyclobutane-1-carboxamide, (1S,2S)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide, (1S,2S)-N-(7-chloro-6-(4-((3S,4S)-4-hydroxy-3-methyltetrahydrofuran-3-yl)piperazin-1-yl)isoquinolin-3-yl)-2-(methoxymethyl)cyclobutane-1-carboxamide, (1S,2R)-N-(7-chloro-6-(4-((3R,4R)-4-hydroxy-3-methyltetrahydrofuran-3-yl)piperazin-1-yl)isoquinolin-3-yl)-2-(methoxymethyl)cyclobutane-1-carboxamide, (1S,2R)-N-(7-chloro-6-(4-((3S,4S)-4-hydroxy-3-methyltetrahydrofuran-3-yl)piperazin-1-yl)isoquinolin-3-yl)-2-(methoxymethyl)cyclobutane-1-carboxamide, N-(7-chloro-6-(4-(4-hydroxy-3-methyltetrahydrofuran-3-yl)piperazin-1-yl)isoquinolin-3-yl)-7-oxaspiro[3.5]nonane-1-carboxamide, (R)-N-(7-chloro-6-(4-((3R,4R)-4-hydroxy-3-methyltetrahydrofuran-3-yl)piperazin-1-yl)isoquinolin-3-yl)-7-oxaspiro[3.5]nonane-1-carboxamide, (R)-N-(7-chloro-6-(4-((3S,4S)-4-hydroxy-3-methyltetrahydrofuran-3-yl)piperazin-1-yl)isoquinolin-3-yl)-7-oxaspiro[3.5]nonane-1-carboxamide, (S)-N-(7-chloro-6-(4-((3R,4R)-4-hydroxy-3-methyltetrahydrofuran-3-yl)piperazin-1-yl)isoquinolin-3-yl)-7-oxaspiro[3.5]nonane-1-carboxamide, (S)-N-(7-chloro-6-(4-((3S,4S)-4-hydroxy-3-methyltetrahydrofuran-3-yl)piperazin-1-yl)isoquinolin-3-yl)-7-oxaspiro[3.5]nonane-1-carboxamide, N-(7-chloro-6-(4-(4-hydroxy-3-methyltetrahydrofuran-3-yl)piperazin-1-yl)isoquinolin-3-yl)-6-oxaspiro[2.5]octane-1-carboxamide, (R)-N-(7-chloro-6-(4-((3R,4R)-4-hydroxy-3-methyltetrahydrofuran-3-yl)piperazin-1-yl)isoquinolin-3-yl)-6-oxaspiro[2.5]octane-1-carboxamide, (R)-N-(7-chloro-6-(4-((3S,4S)-4-hydroxy-3-methyltetrahydrofuran-3-yl)piperazin-1-yl)isoquinolin-3-yl)-6-oxaspiro[2.5]octane-1-carboxamide, (S)-N-(7-chloro-6-(4-((3R,4R)-4-hydroxy-3-methyltetrahydrofuran-3-yl)piperazin-1-yl)isoquinolin-3-yl)-6-oxaspiro[2.5]octane-1-carboxamide or (S)-N-(7-chloro-6-(4-((3S,4S)-4-hydroxy-3-methyltetrahydrofuran-3-yl)piperazin-1-yl)isoquinolin-3-yl)-6-oxaspiro[2.5]octane-1-carboxamide, N-{7-chloro-6-[(3S)-4-hydroxyoxolan-3-yl)-3-methylpiperazin-1-yl]isoquinolin-3-yl}-6-oxaspiro[2.5]octane-1-carboxamide, (R)-N-{7-chloro-6-[(3S)-4-(3R,4R)-4-hydroxyoxolan-3-yl)-3-methylpiperazin-1-yl]isoquinolin-3-yl}-6-oxaspiro[2.5]octane-1-carboxamide, (R)-N-{7-chloro-6-[(3S)-4-(3S,4S)-4-hydroxyoxolan-3-yl)-3-methylpiperazin-1-yl]isoquinolin-3-yl}-6-oxaspiro[2.5]octane-1-carboxamide, (S)-N-{7-chloro-6-[(3S)-4-(3R,4R)-4-hydroxyoxolan-3-yl)-3-methylpiperazin-1-yl]isoquinolin-3-yl}-6-oxaspiro[2.5]octane-1-carboxamide or (S)-N-{7-chloro-6-[(3S)-4-(3S,4S)-4-hydroxyoxolan-3-yl)-3-methylpiperazin-1-yl]isoquinolin-3-yl}-6-oxaspiro[2.5]octane-1-carboxamide, N-(7-chloro-6-(4-(4-hydroxytetrahydrofuran-3-yl)piperazin-1-yl)isoquinolin-3-yl)-6-oxaspiro[2.5]octane-1-carboxamide, (R)-N-(7-chloro-6-(4-((3R,4R)-4-hydroxytetrahydrofuran-3-yl)piperazin-1-yl)isoquinolin-3-yl)-6-oxaspiro[2.5]octane-1-carboxamide, (R)-N-(7-chloro-6-(4-((3S,4S)-4-hydroxytetrahydrofuran-3-yl)piperazin-1-yl)isoquinolin-3-yl)-6-oxaspiro[2.5]octane-1-carboxamide, (S)-N-(7-chloro-6-(4-((3R,4R)-4-hydroxytetrahydrofuran-3-yl)piperazin-1-yl)isoquinolin-3-yl)-6-oxaspiro[2.5]octane-1-carboxamide or (S)-N-(7-chloro-6-(4-((3S,4S)-4-hydroxytetrahydrofuran-3-yl)piperazin-1-yl)isoquinolin-3-yl)-6-oxaspiro[2.5]octane-1-carboxamide, N-(7-chloro-6-(4-(4-hydroxy-3-methyltetrahydrofuran-3-yl)piperazin-1-yl)isoquinolin-3-yl)-5-oxaspiro[2.4]heptane-1-carboxamide, (1R,3R)-N-(7-chloro-6-(4-((3R,4R)-4-hydroxy-3-methyltetrahydrofuran-3-yl)piperazin-1-yl)isoquinolin-3-yl)-5-oxaspiro[2.4]heptane-1-carboxamide, (1R,3R)-N-(7-chloro-6-(4-((3S,4S)-4-hydroxy-3-methyltetrahydrofuran-3-yl)piperazin-1-yl)isoquinolin-3-yl)-5-oxaspiro[2.4]heptane-1-carboxamide, (1R,3S)-N-(7-chloro-6-(4-((3R,4R)-4-hydroxy-3-methyltetrahydrofuran-3-yl)piperazin-1-yl)isoquinolin-3-yl)-5-oxaspiro[2.4]heptane-1-carboxamide, (1R,3S)-N-(7-chloro-6-(4-((3S,4S)-4-hydroxy-3-methyltetrahydrofuran-3-yl)piperazin-1-yl)isoquinolin-3-yl)-5-oxaspiro[2.4]heptane-1-carboxamide, (1S,3R)-N-(7-chloro-6-(4-((3R,4R)-4-hydroxy-3-methyltetrahydrofuran-3-yl)piperazin-1-yl)isoquinolin-3-yl)-5-oxaspiro[2.4]heptane-1-carboxamide, (1S,3R)-N-(7-chloro-6-(4-((3S,4S)-4-hydroxy-3-methyltetrahydrofuran-3-yl)piperazin-1-yl)isoquinolin-3-yl)-5-oxaspiro[2.4]heptane-1-carboxamide, (1S,3S)-N-(7-chloro-6-(4-((3R,4R)-4-hydroxy-3-methyltetrahydrofuran-3-yl)piperazin-1-yl)isoquinolin-3-yl)-5-oxaspiro[2.4]heptane-1-carboxamide, (1S,3S)-N-(7-chloro-6-(4-((3S,4S)-4-hydroxy-3-methyltetrahydrofuran-3-yl)piperazin-1-yl)isoquinolin-3-yl)-5-oxaspiro[2.4]heptane-1-carboxamide, N-(7-chloro-6-(4-(4-hydroxy-3-methyltetrahydrofuran-3-yl)piperazin-1-yl)isoquinolin-3-yl)spiro[2.2]pentane-1-carboxamide, (R)-N-(7-chloro-6-(4-((3R,4R)-4-hydroxy-3-methyltetrahydrofuran-3-yl)piperazin-1-yl)isoquinolin-3-yl)spiro[2.2]pentane-1-carboxamide, (R)-N-(7-chloro-6-(4-((3S,4S)-4-hydroxy-3-methyltetrahydrofuran-3-yl)piperazin-1-yl)isoquinolin-3-yl)spiro[2.2]pentane-1-carboxamide, (S)-N-(7-chloro-6-(4-((3R,4R)-4-hydroxy-3-methyltetrahydrofuran-3-yl)piperazin-1-yl)isoquinolin-3-yl)spiro[2.2]pentane-1-carboxamide or (S)-N-(7-chloro-6-(4-((3S,4S)-4-hydroxy-3-methyltetrahydrofuran-3-yl)piperazin-1-yl)isoquinolin-3-yl)spiro[2.2]pentane-1-carboxamide, N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide, (1R,3R)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1R,3R)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1R,3S)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1R,3S)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1S,3R)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1S,3R)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1S,3S)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide or (1S,3S)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, N-(7-chloro-6-(4-(4-hydroxy-3-methyltetrahydrofuran-3-yl)piperazin-1-yl)isoquinolin-3-yl)spiro[2.3]hexane-5-carboxamide, N-(7-chloro-6-(4-((3R,4R)-4-hydroxy-3-methyltetrahydrofuran-3-yl)piperazin-1-yl)isoquinolin-3-yl)spiro[2.3]hexane-5-carboxamide or N-(7-chloro-6-(4-((3S,4S)-4-hydroxy-3-methyltetrahydrofuran-3-yl)piperazin-1-yl)isoquinolin-3-yl)spiro[2.3]hexane-5-carboxamide, N-(7-chloro-6-(4-((3S,4S or 3R, 4R)-4-hydroxy-3-methyltetrahydrofuran-3-yl)piperazin-1-yl)isoquinolin-3-yl)-1-methyl-2-oxabicyclo[2.1.1]hexane-4-carboxamide, N-(7-chloro-6-(4-((3R,4R)-4-hydroxy-3-methyltetrahydrofuran-3-yl)piperazin-1-yl)isoquinolin-3-yl)-1-methyl-2-oxabicyclo[2.1.1]hexane-4-carboxamide or N-(7-chloro-6-(4-((3S,4S)-4-hydroxy-3-methyltetrahydrofuran-3-yl)piperazin-1-yl)isoquinolin-3-yl)-1-methyl-2-oxabicyclo[2.1.1]hexane-4-carboxamide, N-(7-chloro-6-(4-(4-hydroxy-3-methyltetrahydrofuran-3-yl)piperazin-1-yl)isoquinolin-3-yl) bicyclo[1.1.1]pentane-1-carboxamide, N-(7-chloro-6-(4-((3R,4R)-4-hydroxy-3-methyltetrahydrofuran-3-yl)piperazin-1-yl)isoquinolin-3-yl) bicyclo[1.1.1]pentane-1-carboxamide or N-(7-chloro-6-(4-((3S,4S)-4-hydroxy-3-methyltetrahydrofuran-3-yl)piperazin-1-yl)isoquinolin-3-yl) bicyclo[1.1.1]pentane-1-carboxamide, N-(7-chloro-6-((S)-4-(4-hydroxy-3-methyltetrahydrofuran-3-yl)-3-methylpiperazin-1-yl)isoquinolin-3-yl)-6-oxaspiro[2.5]octane-1-carboxamide, (R)-N-(7-chloro-6-((S)-4-((3R,4R)-4-hydroxy-3-methyltetrahydrofuran-3-yl)-3-methylpiperazin-1-yl)isoquinolin-3-yl)-6-oxaspiro[2.5]octane-1-carboxamide, (R)-N-(7-chloro-6-((S)-4-((3S,4S)-4-hydroxy-3-methyltetrahydrofuran-3-yl)-3-methylpiperazin-1-yl)isoquinolin-3-yl)-6-oxaspiro[2.5]octane-1-carboxamide, (S)-N-(7-chloro-6-((S)-4-((3R,4R)-4-hydroxy-3-methyltetrahydrofuran-3-yl)-3-methylpiperazin-1-yl)isoquinolin-3-yl)-6-oxaspiro[2.5]octane-1-carboxamide or (S)-N-(7-chloro-6-((S)-4-((3S,4S)-4-hydroxy-3-methyltetrahydrofuran-3-yl)-3-methylpiperazin-1-yl)isoquinolin-3-yl)-6-oxaspiro[2.5]octane-1-carboxamide, N-(7-chloro-6-(4-(3-ethyl-4-hydroxytetrahydrofuran-3-yl)piperazin-1-yl)isoquinolin-3-yl)-6-oxaspiro[2.5]octane-1-carboxamide, (R)-N-(7-chloro-6-(4-((3R,4R)-3-ethyl-4-hydroxytetrahydrofuran-3-yl)piperazin-1-yl)isoquinolin-3-yl)-6-oxaspiro[2.5]octane-1-carboxamide, (R)-N-(7-chloro-6-(4-((3S,4S)-3-ethyl-4-hydroxytetrahydrofuran-3-yl)piperazin-1-yl)isoquinolin-3-yl)-6-oxaspiro[2.5]octane-1-carboxamide, (S)-N-(7-chloro-6-(4-((3R,4R)-3-ethyl-4-hydroxytetrahydrofuran-3-yl)piperazin-1-yl)isoquinolin-3-yl)-6-oxaspiro[2.5]octane-1-carboxamide or (S)-N-(7-chloro-6-(4-((3S,4S)-3-ethyl-4-hydroxytetrahydrofuran-3-yl)piperazin-1-yl)isoquinolin-3-yl)-6-oxaspiro[2.5]octane-1-carboxamide, N-[7-fluoro-6-[4-[4-hydroxy-3-methyl-tetrahydrofuran-3-yl]piperazin-1-yl]-3-isoquinolyl]-2-(2-pyridyl)cyclopropanecarboxamide, (1R,2R)-N-[7-fluoro-6-[4-[(3R,4R)-4-hydroxy-3-methyltetrahydrofuran-3-yl]piperazin-1-yl]-3-isoquinolyl]-2-(2-pyridyl)cyclopropanecarboxamide, (1R,2R)-N-[7-fluoro-6-[4-[(3S,4S)-4-hydroxy-3-methyltetrahydrofuran-3-yl]piperazin-1-yl]-3-isoquinolyl]-2-(2-pyridyl)cyclopropanecarboxamide, (1S,2S)-N-[7-fluoro-6-[4-[(3R,4R)-4-hydroxy-3-methyltetrahydrofuran-3-yl]piperazin-1-yl]-3-isoquinolyl]-2-(2-pyridyl)cyclopropanecarboxamide, (1S,2S)-N-[7-fluoro-6-[4-[(3S,4S)-4-hydroxy-3-methyltetrahydrofuran-3-yl]piperazin-1-yl]-3-isoquinolyl]-2-(2-pyridyl)cyclopropanecarboxamide, N-(7-chloro-6-(4-(4-hydroxy-3-methyltetrahydrofuran-3-yl)piperazin-1-yl)isoquinolin-3-yl)-4,4-difluorospiro[2.2]pentane-1-carboxamide, (1R,3R)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1R,3R)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1R,3S)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1R,3S)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1S,3R)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide, (1S,3R)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (1S,3S)-N-(7-chloro-6-(4-((3R,4R)-4-hydroxy-3-methyltetrahydrofuran-3-yl)piperazin-1-yl)isoquinolin-3-yl)-4,4-difluorospiro[2.2]pentane-1-carboxamide or (1S,3S)-N-(7-chloro-6-(4-((3S,4S)-4-hydroxy-3-methyltetrahydrofuran-3-yl)piperazin-1-yl)isoquinolin-3-yl)-4,4-difluorospiro[2.2]pentane-1-carboxamide, (S)-N-(6-(4-methyl-2-oxooxazolidin-3-yl)isoquinolin-3-yl)cyclopropanecarboxamide, N-[7-chloro-6-(4-hydroxy-4-methylpiperidin-1-yl)isoquinolin-3-yl]cyclopropanecarboxamide, N-[7-chloro-6-(1,4,6,7-tetrahydro-5H-pyrazolo[4,3-c]pyridin-5-yl)isoquinolin-3-yl]cyclopropanecarboxamide, Rac-N-{7-chloro-6-[4-(3-methyloxetan-3-yl)piperazin-1-yl]isoquinolin-3-yl}spiro[2.2]pentane-1-carboxamide, N-[7-chloro-6-(6-hydroxy-6-methyl-2-azaspiro[3.3]heptan-2-yl)isoquinolin-3-yl]cyclopropanecarboxamide, N-(7-chloro-6-(4-(3-fluoroazetidin-1-yl) piperidin-1-yl) isoquinolin-3-yl)-6-oxaspiro[2.5]octane-1-carboxamide, 1S N-(7-chloro-6-(4-(3-fluoroazetidin-1-yl) piperidin-1-yl)isoquinolin-3-yl)-6-oxaspiro[2.5]octane-1-carboxamide, 1R-N-(7-chloro-6-(4-(3-fluoroazetidin-1-yl) piperidin-1-yl)isoquinolin-3-yl)-6-oxaspiro[2.5]octane-1-carboxamide, N-(7-chloro-6-(4-(3,3-difluoroazetidin-1-yl) piperidin-1-yl)isoquinolin-3-yl)-6-oxaspiro[2.5]octane-1-carboxamide, (1R)-N-(7-chloro-6-(4-(3,3-difluoroazetidin-1-yl) piperidin-1-yl)isoquinolin-3-yl)-6-oxaspiro[2.5]octane-1-carboxamide, or (1S)-N-(7-chloro-6-(4-(3,3-difluoroazetidin-1-yl) piperidin-1-yl)isoquinolin-3-yl)-6-oxaspiro[2.5]octane-1-carboxamide, N-[7-chloro-6-(4-cyano-4-methyl-1-piperidyl)-3-isoquinolyl]-6-oxaspiro[2.5]octane-2-carboxamide, (R)-N-[7-chloro-6-(4-cyano-4-methyl-1-piperidyl)-3-isoquinolyl]-6-oxaspiro[2.5]octane-2-carboxamide, (S)-N-[7-chloro-6-(4-cyano-4-methyl-1-piperidyl)-3-isoquinolyl]-6-oxaspiro[2.5]octane-2-carboxamide, N-[7-chloro-6-(4-cyano-1-piperidyl)-3-isoquinolyl]-6-oxaspiro[2.5]octane-2-carboxamide, (R)-N-[7-chloro-6-(4-cyano-1-piperidyl)-3-isoquinolyl]-6-oxaspiro[2.5]octane-2-carboxamide, (S)-N-[7-chloro-6-(4-cyano-1-piperidyl)-3-isoquinolyl]-6-oxaspiro[2.5]octane-2-carboxamide, N-[7-chloro-6-(4-cyano-4-fluoro-1-piperidyl)-3-isoquinolyl]-2-ethyl-3-(1-methylpyrazol-4-yl)cyclopropanecarboxamide, (1R,2R)-N-[7-chloro-6-(4-cyano-4-fluoro-1-piperidyl)-3-isoquinolyl]-2-ethyl-3-(1-methylpyrazol-4-yl)cyclopropanecarboxamide, (1S,2S)-N-[7-chloro-6-(4-cyano-4-fluoro-1-piperidyl)-3-isoquinolyl]-2-ethyl-3-(1-methylpyrazol-4-yl)cyclopropanecarboxamide, N-[7-chloro-6-(4-cyano-4-fluoro-1-piperidyl)-3-isoquinolyl]-2-(1-methylpyrazol-4-yl)cyclopropanecarboxamide, (1R,2R)-N-[7-chloro-6-(4-cyano-4-fluoro-1-piperidyl)-3-isoquinolyl]-2-(1-methylpyrazol-4-yl)cyclopropanecarboxamide, (1S,2S)-N-[7-chloro-6-(4-cyano-4-fluoro-1-piperidyl)-3-isoquinolyl]-2-(1-methylpyrazol-4-yl)cyclopropanecarboxamide, N-(6-(3-oxo-2-azabicyclo[2.2.1]heptan-2-yl)isoquinolin-3-yl)cyclopropanecarboxamide, N-(6-((1S,4R)-3-oxo-2-azabicyclo[2.2.1]heptan-2-yl)isoquinolin-3-yl)cyclopropanecarboxamide N-(6-((1R,4S)-3-oxo-2-azabicyclo[2.2.1]heptan-2-yl)isoquinolin-3-yl)cyclopropanecarboxamide, N-(7-chloro-6-(4-((3S,4S or 3R, 4R)-4-methoxy-3-methyltetrahydrofuran-3-yl)piperazin-1-yl)isoquinolin-3-yl)-6-oxaspiro[2.5]octane-1-carboxamide, (1R)-N-(7-chloro-6-(4-((3R,4R)-4-methoxy-3-methyltetrahydrofuran-3-yl)piperazin-1-yl)isoquinolin-3-yl)-6-oxaspiro[2.5]octane-1-carboxamide, (1R)-N-(7-chloro-6-(4-((3S,4S)-4-methoxy-3-methyltetrahydrofuran-3-yl)piperazin-1-yl)isoquinolin-3-yl)-6-oxaspiro[2.5]octane-1-carboxamide, (1S)-N-(7-chloro-6-(4-((3R,4R)-4-methoxy-3-methyltetrahydrofuran-3-yl)piperazin-1-yl)isoquinolin-3-yl)-6-oxaspiro[2.5]octane-1-carboxamide, (1S)-N-(7-chloro-6-(4-((3S,4S)-4-methoxy-3-methyltetrahydrofuran-3-yl)piperazin-1-yl)isoquinolin-3-yl)-6-oxaspiro[2.5]octane-1-carboxamide, N-(7-chloro-6-(4-(4-methoxytetrahydrofuran-3-yl)piperazin-1-yl)isoquinolin-3-yl)-6-oxaspiro[2.5]octane-1-carboxamide, (1R)-N-(7-chloro-6-(4-((3R,4R)-4-methoxytetrahydrofuran-3-yl)piperazin-1-yl)isoquinolin-3-yl)-6-oxaspiro[2.5]octane-1-carboxamide, (1R)-N-(7-chloro-6-(4-((3S,4S)-4-methoxytetrahydrofuran-3-yl)piperazin-1-yl)isoquinolin-3-yl)-6-oxaspiro[2.5]octane-1-carboxamide, (1S)-N-(7-chloro-6-(4-((3R,4R)-4-methoxytetrahydrofuran-3-yl)piperazin-1-yl)isoquinolin-3-yl)-6-oxaspiro[2.5]octane-1-carboxamide, (1S)-N-(7-chloro-6-(4-((3S,4S)-4-methoxytetrahydrofuran-3-yl)piperazin-1-yl)isoquinolin-3-yl)-6-oxaspiro[2.5]octane-1-carboxamide, N-(7-chloro-6-(4-((R or S)-3-methyltetrahydrofuran-3-yl)piperazin-1-yl)isoquinolin-3-yl)-6-oxaspiro[2.5]octane-1-carboxamide, (1R)-N-(7-chloro-6-(4-((R)-3-methyltetrahydrofuran-3-yl)piperazin-1-yl)isoquinolin-3-yl)-6-oxaspiro[2.5]octane-1-carboxamide, (1R)-N-(7-chloro-6-(4-((S)-3-methyltetrahydrofuran-3-yl)piperazin-1-yl)isoquinolin-3-yl)-6-oxaspiro[2.5]octane-1-carboxamide, (1S)-N-(7-chloro-6-(4-((R)-3-methyltetrahydrofuran-3-yl)piperazin-1-yl)isoquinolin-3-yl)-6-oxaspiro[2.5]octane-1-carboxamide, (1S)-N-(7-chloro-6-(4-((S)-3-methyltetrahydrofuran-3-yl)piperazin-1-yl)isoquinolin-3-yl)-6-oxaspiro[2.5]octane-1-carboxamide, N-[7-chloro-6-(4-cyano-4-methyl-1-piperidyl)-3-isoquinolyl]-2-pyrimidin-5-yl-cyclopropanecarboxamide, (1R,2R)-N-[7-chloro-6-(4-cyano-4-methyl-1-piperidyl)-3-isoquinolyl]-2-pyrimidin-5-yl-cyclopropanecarboxamide, (1S,2S)-N-[7-chloro-6-(4-cyano-4-methyl-1-piperidyl)-3-isoquinolyl]-2-pyrimidin-5-yl-cyclopropanecarboxamide, N-[7-chloro-6-(4-cyano-1-piperidyl)-3-isoquinolyl]-2-pyrimidin-5-yl-cyclopropanecarboxamide, (1R,2R)-N-[7-chloro-6-(4-cyano-1-piperidyl)-3-isoquinolyl]-2-pyrimidin-5-yl-cyclopropanecarboxamide, (1S,2S)-N-[7-chloro-6-(4-cyano-1-piperidyl)-3-isoquinolyl]-2-pyrimidin-5-yl-cyclopropanecarboxamide, N-[7-chloro-6-(4-cyano-4-fluoro-1-piperidyl)-3-isoquinolyl]-2-pyrimidin-5-yl-cyclopropanecarboxamide, (1R,2R)-N-[7-chloro-6-(4-cyano-4-fluoro-1-piperidyl)-3-isoquinolyl]-2-pyrimidin-5-yl-cyclopropanecarboxamide, (1S,2S)-N-[7-chloro-6-(4-cyano-4-fluoro-1-piperidyl)-3-isoquinolyl]-2-pyrimidin-5-yl-cyclopropanecarboxamide, N-(6-(4-(4-hydroxy-3-methyltetrahydrofuran-3-yl)piperazin-1-yl)-7-methylisoquinolin-3-yl)-6-oxaspiro[2.5]octane-1-carboxamide, (R)-N-(6-(4-((3R,4R)-4-hydroxy-3-methyltetrahydrofuran-3-yl)piperazin-1-yl)-7-methylisoquinolin-3-yl)-6-oxaspiro[2.5]octane-1-carboxamide, (R)-N-(6-(4-((3S,4S)-4-hydroxy-3-methyltetrahydrofuran-3-yl)piperazin-1-yl)-7-methylisoquinolin-3-yl)-6-oxaspiro[2.5]octane-1-carboxamide, (S)-N-(6-(4-((3R,4R)-4-hydroxy-3-methyltetrahydrofuran-3-yl)piperazin-1-yl)-7-methylisoquinolin-3-yl)-6-oxaspiro[2.5]octane-1-carboxamide (S)-N-(6-(4-((3S,4S)-4-hydroxy-3-methyltetrahydrofuran-3-yl)piperazin-1-yl)-7-methylisoquinolin-3-yl)-6-oxaspiro[2.5]octane-1-carboxamide, N-(6-(4-(4-hydroxy-3-methyltetrahydrofuran-3-yl)piperazin-1-yl)-7-methylisoquinolin-3-yl)-5-oxaspiro[2.4]heptane-1-carboxamide, (1R,3S)-N-(6-(4-((3R,4R)-4-hydroxy-3-methyltetrahydrofuran-3-yl)piperazin-1-yl)-7-methylisoquinolin-3-yl)-5-oxaspiro[2.4]heptane-1-carboxamide, (1R,3S)-N-(6-(4-((3S,4S)-4-hydroxy-3-methyltetrahydrofuran-3-yl)piperazin-1-yl)-7-methylisoquinolin-3-yl)-5-oxaspiro[2.4]heptane-1-carboxamide, (1R,3R)-N-(6-(4-((3R,4R)-4-hydroxy-3-methyltetrahydrofuran-3-yl)piperazin-1-yl)-7-methylisoquinolin-3-yl)-5-oxaspiro[2.4]heptane-1-carboxamide, (1R,3R)-N-(6-(4-((3S,4S)-4-hydroxy-3-methyltetrahydrofuran-3-yl)piperazin-1-yl)-7-methylisoquinolin-3-yl)-5-oxaspiro[2.4]heptane-1-carboxamide, (1S,3S)-N-(6-(4-((3R,4R)-4-hydroxy-3-methyltetrahydrofuran-3-yl)piperazin-1-yl)-7-methylisoquinolin-3-yl)-5-oxaspiro[2.4]heptane-1-carboxamide, (1S,3S)-N-(6-(4-((3S,4S)-4-hydroxy-3-methyltetrahydrofuran-3-yl)piperazin-1-yl)-7-methylisoquinolin-3-yl)-5-oxaspiro[2.4]heptane-1-carboxamide, (1S,3R)-N-(6-(4-((3R,4R)-4-hydroxy-3-methyltetrahydrofuran-3-yl)piperazin-1-yl)-7-methylisoquinolin-3-yl)-5-oxaspiro[2.4]heptane-1-carboxamide, (1S,3R)-N-(6-(4-((3S,4S)-4-hydroxy-3-methyltetrahydrofuran-3-yl)piperazin-1-yl)-7-methylisoquinolin-3-yl)-5-oxaspiro[2.4]heptane-1-carboxamide, N-(6-((S)-4-(4-hydroxy-3-methyltetrahydrofuran-3-yl)-3-methylpiperazin-1-yl)-7-methylisoquinolin-3-yl)-6-oxaspiro[2.5]octane-1-carboxamide, (1R)-N-(6-((S)-4-((3R,4R)-4-hydroxy-3-methyltetrahydrofuran-3-yl)-3-methylpiperazin-1-yl)-7-methylisoquinolin-3-yl)-6-oxaspiro[2.5]octane-1-carboxamide, (1R)-N-(6-((S)-4-((3S,4S)-4-hydroxy-3-methyltetrahydrofuran-3-yl)-3-methylpiperazin-1-yl)-7-methylisoquinolin-3-yl)-6-oxaspiro[2.5]octane-1-carboxamide, (1S)-N-(6-((S)-4-((3R,4R)-4-hydroxy-3-methyltetrahydrofuran-3-yl)-3-methylpiperazin-1-yl)-7-methylisoquinolin-3-yl)-6-oxaspiro[2.5]octane-1-carboxamide, (1S)-N-(6-((S)-4-((3S,4S)-4-hydroxy-3-methyltetrahydrofuran-3-yl)-3-methylpiperazin-1-yl)-7-methylisoquinolin-3-yl)-6-oxaspiro[2.5]octane-1-carboxamide, N-(7-cyclopropyl-6-(4-(4-hydroxy-3-methyltetrahydrofuran-3-yl)piperazin-1-yl)isoquinolin-3-yl)-6-oxaspiro[2.5]octane-1-carboxamide, (1R)-N-(7-cyclopropyl-6-(4-((3R,4R)-4-hydroxy-3-methyltetrahydrofuran-3-yl)piperazin-1-yl)isoquinolin-3-yl)-6-oxaspiro[2.5]octane-1-carboxamide, (1R)-N-(7-cyclopropyl-6-(4-((3S,4S)-4-hydroxy-3-methyltetrahydrofuran-3-yl)piperazin-1-yl)isoquinolin-3-yl)-6-oxaspiro[2.5]octane-1-carboxamide, (1S)-N-(7-cyclopropyl-6-(4-((3R,4R)-4-hydroxy-3-methyltetrahydrofuran-3-yl)piperazin-1-yl)isoquinolin-3-yl)-6-oxaspiro[2.5]octane-1-carboxamide, (1S)-N-(7-cyclopropyl-6-(4-((3S,4S)-4-hydroxy-3-methyltetrahydrofuran-3-yl)piperazin-1-yl)isoquinolin-3-yl)-6-oxaspiro[2.5]octane-1-carboxamide, N-(6-(4-(3-ethyl-4-hydroxytetrahydrofuran-3-yl)piperazin-1-yl)-7-methylisoquinolin-3-yl)-6-oxaspiro[2.5]octane-1-carboxamide, (1R)-N-(6-(4-((3R,4R)-3-ethyl-4-hydroxytetrahydrofuran-3-yl)piperazin-1-yl)-7-methylisoquinolin-3-yl)-6-oxaspiro[2.5]octane-1-carboxamide, (1R)-N-(6-(4-((3S,4S)-3-ethyl-4-hydroxytetrahydrofuran-3-yl)piperazin-1-yl)-7-methylisoquinolin-3-yl)-6-oxaspiro[2.5]octane-1-carboxamide, (1S)-N-(6-(4-((3R,4R)-3-ethyl-4-hydroxytetrahydrofuran-3-yl)piperazin-1-yl)-7-methylisoquinolin-3-yl)-6-oxaspiro[2.5]octane-1-carboxamide, (1S)-N-(6-(4-((3S,4S)-3-ethyl-4-hydroxytetrahydrofuran-3-yl)piperazin-1-yl)-7-methylisoquinolin-3-yl)-6-oxaspiro[2.5]octane-1-carboxamide, N-[6-[4-(4-fluoro-3-methyl-tetrahydrofuran-3-yl)piperazin-1-yl]-7-methyl-3-isoquinolyl]-2-(2-pyridyl)cyclopropanecarboxamide, (1R,2R)-N-[6-[4-((3R,4R)-4-fluoro-3-methyl-tetrahydrofuran-3-yl)piperazin-1-yl]-7-methyl-3-isoquinolyl]-2-(2-pyridyl)cyclopropanecarboxamide, (1R,2R)-N-[6-[4-((3S,4S)-4-fluoro-3-methyl-tetrahydrofuran-3-yl)piperazin-1-yl]-7-methyl-3-isoquinolyl]-2-(2-pyridyl)cyclopropanecarboxamide, (1S,2S)-N-[6-[4-((3R,4R)-4-fluoro-3-methyl-tetrahydrofuran-3-yl)piperazin-1-yl]-7-methyl-3-isoquinolyl]-2-(2-pyridyl)cyclopropanecarboxamide, (1S,2S)-N-[6-[4-((3S,4S)-4-fluoro-3-methyl-tetrahydrofuran-3-yl)piperazin-1-yl]-7-methyl-3-isoquinolyl]-2-(2-pyridyl)cyclopropanecarboxamide, N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, (3R,4R)-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, (3S,4S)-N-(6-(4-4-((tert-butyldiphenylsilyl)oxy)-3-methyltetrahydrofuran-3-yl)piperazin-1-yl)-7-chloroisoquinolin-3-yl)-3-methoxycyclobutane-1-carboxamide, N-(7-chloro-6-(4-((3R,4R or 3S, 4S)-4-hydroxy-3-methyltetrahydrofuran-3-yl)piperazin-1-yl)isoquinolin-3-yl)-5,5-dimethyl-6-oxaspiro[2.5]octane-1-carboxamide, (1R,3R)-N-(7-chloro-6-(4-((3R,4R)-4-hydroxy-3-methyltetrahydrofuran-3-yl)piperazin-1-yl)isoquinolin-3-yl)-5,5-dimethyl-6-oxaspiro[2.5]octane-1-carboxamide, (1R,3R)-N-(7-chloro-6-(4-((3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide, (1R,3S)-N-(7-chloro-6-(4-((3R,4R)-4-hydroxy-3-methyltetrahydrofuran-3-yl)piperazin-1-yl)isoquinolin-3-yl)-5,5-dimethyl-6-oxaspiro[2.5]octane-1-carboxamide, (1R,3S)-N-(7-chloro-6-(4-((3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide, (1S,3R)-N-(7-chloro-6-(4-((3R,4R)-4-hydroxy-3-methyltetrahydrofuran-3-yl)piperazin-1-yl)isoquinolin-3-yl)-5,5-dimethyl-6-oxaspiro[2.5]octane-1-carboxamide, (1S,3R)-N-(7-chloro-6-(4-((3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide, (1S,3S)-N-(7-chloro-6-(4-((3R,4R)-4-hydroxy-3-methyltetrahydrofuran-3-yl)piperazin-1-yl)isoquinolin-3-yl)-5,5-dimethyl-6-oxaspiro[2.5]octane-1-carboxamide, (1S,3S)-N-(7-chloro-6-(4-((3S,4S)-4-hydroxy-3-methyltetrahydrofuran-3-yl)piperazin-1-yl)isoquinolin-3-yl)-5,5-dimethyl-6-oxaspiro[2.5]octane-1-carboxamide, N-(7-chloro-6-(4-(oxetan-3-yl)piperazin-1-yl)isoquinolin-3-yl)cyclopropanecarboxamide, N-[7-chloro-6-(4-methylpiperazin-1-yl)isoquinolin-3-yl]cyclopropanecarboxamide, N-(7-chloro-6-(4-(4-hydroxy-3-methyltetrahydrofuran-3-yl)piperazin-1-yl)isoquinolin-3-yl)-3-methoxypropanamide, N-(7-chloro-6-(4-((3R,4R)-4-hydroxy-3-methyltetrahydrofuran-3-yl)piperazin-1-yl)isoquinolin-3-yl)-3-methoxypropanamide, N-(7-chloro-6-(4-((3S,4S)-4-hydroxy-3-methyltetrahydrofuran-3-yl)piperazin-1-yl)isoquinolin-3-yl)-3-methoxypropanamide, N-(7-chloro-6-(4-(4-hydroxy-3-methyltetrahydrofuran-3-yl)piperazin-1-yl)isoquinolin-3-yl)tetrahydro-2H-pyran-4-carboxamide, N-(7-chloro-6-(4-((3R,4R)-4-hydroxy-3-methyltetrahydrofuran-3-yl)piperazin-1-yl)isoquinolin-3-yl)tetrahydro-2H-pyran-4-carboxamide, N-(7-chloro-6-(4-((3S,4S)-4-hydroxy-3-methyltetrahydrofuran-3-yl)piperazin-1-yl)isoquinolin-3-yl)tetrahydro-2H-pyran-4-carboxamide, N-(7-chloro-6-(4-(4-hydroxy-3-methyltetrahydrofuran-3-yl)piperazin-1-yl)isoquinolin-3-yl)-3-isopropylcyclobutane-1-carboxamide, (S)-N-(7-chloro-6-(4-(4-hydroxy-3-methyltetrahydrofuran-3-yl)piperazin-1-yl)isoquinolin-3-yl)tetrahydrofuran-2-carboxamide, (S)-N-(7-chloro-6-(4-(4-hydroxy-3-methyltetrahydrofuran-3-yl)piperazin-1-yl)isoquinolin-3-yl)tetrahydrofuran-2-carboxamide, (S)-N-(7-chloro-6-(4-((3R,4R)-4-hydroxy-3-methyltetrahydrofuran-3-yl)piperazin-1-yl)isoquinolin-3-yl)tetrahydrofuran-2-carboxamide, (S)-N-(7-chloro-6-(4-((3S,4S)-4-hydroxy-3-methyltetrahydrofuran-3-yl)piperazin-1-yl)isoquinolin-3-yl)tetrahydrofuran-2-carboxamide, (2R,5S)-N-(7-chloro-6-(1-(4-hydroxy-3-methyltetrahydrofuran-3-yl) piperidin-4-yl)isoquinolin-3-yl)-5-isopropoxytetrahydro-2H-pyran-2-carboxamide, (2R,5S)-N-(7-chloro-6-(1-((3R,4R)-4-hydroxy-3-methyltetrahydrofuran-3-yl) piperidin-4-yl)isoquinolin-3-yl)-5-isopropoxytetrahydro-2H-pyran-2-carboxamide, (2R,5S)-N-(7-chloro-6-(1-((3S,4S)-4-hydroxy-3-methyltetrahydrofuran-3-yl) piperidin-4-yl)isoquinolin-3-yl)-5-isopropoxytetrahydro-2H-pyran-2-carboxamide, N-[7-chloro-6-[4-(3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2S,3R)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2S,3R)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2R,3S)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2R,3S)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2S,3S)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2S,3S)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, N-[7-chloro-6-[4-(3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2R,3R)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2S,3R)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1R,2S,3R)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2R,3S)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2R,3S)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2S,3S)-N-[7-chloro-6-[4-((R)-3-methyltetrahydrofuran-3-yl)piperazin-4-ium-1-yl]-3-isoquinolyl]-2-methyl-3-(1-methylpyrazol-4-yl)cyclopropanecarboxamide, (1S,2S,3S)-N-[7-chloro-6-[4-((S)-3-methyltetrahydrofuran-3-yl)piperazin-4-ium-1-yl]-3-isoquinolyl]-2-methyl-3-(1-methylpyrazol-4-yl)cyclopropanecarboxamide N-[7-chloro-6-[4-(3-methyltetrahydrofuran-3-yl)piperazin-4-ium-1-yl]-3-isoquinolyl]-2-ethyl-3-(1-methylpyrazol-4-yl)cyclopropanecarboxamide, (1R,2R,3R)-N-[7-chloro-6-[4-((R)-3-methyltetrahydrofuran-3-yl)piperazin-4-ium-1-yl]-3-isoquinolyl]-2-ethyl-3-(1-methylpyrazol-4-yl)cyclopropanecarboxamide, (1R,2R,3R)-N-[7-chloro-6-[4-((S)-3-methyltetrahydrofuran-3-yl)piperazin-4-ium-1-yl]-3-isoquinolyl]-2-ethyl-3-(1-methylpyrazol-4-yl)cyclopropanecarboxamide, (1R,2S,3R)-N-[7-chloro-6-[4-((R)-3-methyltetrahydrofuran-3-yl)piperazin-4-ium-1-yl]-3-isoquinolyl]-2-ethyl-3-(1-methylpyrazol-4-yl)cyclopropanecarboxamide, (1R,2S,3R)-N-[7-chloro-6-[4-((S)-3-methyltetrahydrofuran-3-yl)piperazin-4-ium-1-yl]-3-isoquinolyl]-2-ethyl-3-(1-methylpyrazol-4-yl)cyclopropanecarboxamide, (1S,2R,3S)-N-[7-chloro-6-[4-((R)-3-methyltetrahydrofuran-3-yl)piperazin-4-ium-1-yl]-3-isoquinolyl]-2-ethyl-3-(1-methylpyrazol-4-yl)cyclopropanecarboxamide, (1S,2R,3S)-N-[7-chloro-6-[4-((S)-3-methyltetrahydrofuran-3-yl)piperazin-4-ium-1-yl]-3-isoquinolyl]-2-ethyl-3-(1-methylpyrazol-4-yl)cyclopropanecarboxamide, (1S,2S,3S)-N-[7-chloro-6-[4-((R)-3-methyltetrahydrofuran-3-yl)piperazin-4-ium-1-yl]-3-isoquinolyl]-2-ethyl-3-(1-methylpyrazol-4-yl)cyclopropanecarboxamide, (1S,2S,3S)-N-[7-chloro-6-[4-((S)-3-methyltetrahydrofuran-3-yl)piperazin-4-ium-1-yl]-3-isoquinolyl]-2-ethyl-3-(1-methylpyrazol-4-yl)cyclopropanecarboxamide, 2-methyl-N-[7-methyl-6-[4-(3-methyltetrahydrofuran-3-yl)piperazin-4-ium-1-yl]-3-isoquinolyl]-3-(1-methylpyrazol-4-yl)cyclopropanecarboxamide, (1R,2R,3R)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2R,3R)-2-methyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1R,2S,3R)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2S,3R)-2-methyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1S,2R,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1S,2R,3S)-2-methyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1S,2S,3S)-2-methyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1S,2S,3S)-2-methyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, N-[7-methyl-6-[4-(3-methyltetrahydrofuran-3-yl)piperazin-4-ium-1-yl]-3-isoquinolyl]-2-(2-pyridyl)cyclopropanecarboxamide, (1R,2R)-N-[7-methyl-6-[4-((3R)-3-methyltetrahydrofuran-3-yl)piperazin-4-ium-1-yl]-3-isoquinolyl]-2-(2-pyridyl)cyclopropanecarboxamide, (1R,2R)-N-[7-methyl-6-[4-((3S)-3-methyltetrahydrofuran-3-yl)piperazin-4-ium-1-yl]-3-isoquinolyl]-2-(2-pyridyl)cyclopropanecarboxamide, (1S,2S)-N-[7-methyl-6-[4-((3R)-3-methyltetrahydrofuran-3-yl)piperazin-4-ium-1-yl]-3-isoquinolyl]-2-(2-pyridyl)cyclopropanecarboxamide, (1S,2S)-N-[7-methyl-6-[4-((3S)-3-methyltetrahydrofuran-3-yl)piperazin-4-ium-1-yl]-3-isoquinolyl]-2-(2-pyridyl)cyclopropanecarboxamide, N-[6-[4-(4-fluoro-3-methyl-tetrahydrofuran-3-yl)piperazin-1-yl]-7-methyl-3-isoquinolyl]-2-(2-pyridyl)cyclopropanecarboxamide, (1R,2R)-N-[6-[4-((3R,4R)-4-fluoro-3-methyl-tetrahydrofuran-3-yl)piperazin-1-yl]-7-methyl-3-isoquinolyl]-2-(2-pyridyl)cyclopropanecarboxamide, (1R,2R)-N-[6-[4-((3S,4S)-4-fluoro-3-methyl-tetrahydrofuran-3-yl)piperazin-1-yl]-7-methyl-3-isoquinolyl]-2-(2-pyridyl)cyclopropanecarboxamide, (1S,2S)-N-[6-[4-((3R,4R)-4-fluoro-3-methyl-tetrahydrofuran-3-yl)piperazin-1-yl]-7-methyl-3-isoquinolyl]-2-(2-pyridyl)cyclopropanecarboxamide, (1S,2S)-N-[6-[4-((3S,4S)-4-fluoro-3-methyl-tetrahydrofuran-3-yl)piperazin-1-yl]-7-methyl-3-isoquinolyl]-2-(2-pyridyl)cyclopropanecarboxamide, 2-ethyl-N-[6-[4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1R,2R,3R)-2-ethyl-N-[6-[(3R,4R)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1R,2R,3R)-2-ethyl-N-[6-[(3S,4S)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1R,2S,3R)-2-ethyl-N-[6-[(3R,4R)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1R,2S,3R)-2-ethyl-N-[6-[(3S,4S)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1S,2R,3S)-2-ethyl-N-[6-[(3R,4R)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1S,2R,3S)-2-ethyl-N-[6-[(3S,4S)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1S,2S,3S)-2-ethyl-N-[6-[(3R,4R)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, (1S,2S,3S)-2-ethyl-N-[6-[(3S,4S)-4-(4-fluoro-3-methyl-tetrahydrofuran-3-yl)piperazin-1-yl]-7-methyl-3-isoquinolyl]-3-(1-methylpyrazol-4-yl)cyclopropanecarboxamide, N-[7-methyl-6-[4-(3-methyltetrahydrofuran-3-yl)piperazin-4-ium-1-yl]-3-isoquinolyl]-2-(2-pyridyl)cyclopropanecarboxamide, (1R,2R)-N-[7-methyl-6-[4-((R)-3-methyltetrahydrofuran-3-yl)piperazin-4-ium-1-yl]-3-isoquinolyl]-2-(2-pyridyl)cyclopropanecarboxamide, (1R,2R)-N-[7-methyl-6-[4-((S)-3-methyltetrahydrofuran-3-yl)piperazin-4-ium-1-yl]-3-isoquinolyl]-2-(2-pyridyl)cyclopropanecarboxamide, (1S,2S)-N-[7-methyl-6-[4-((R)-3-methyltetrahydrofuran-3-yl)piperazin-4-ium-1-yl]-3-isoquinolyl]-2-(2-pyridyl)cyclopropanecarboxamide, (1S,2S)-N-[7-methyl-6-[4-((S)-3-methyltetrahydrofuran-3-yl)piperazin-4-ium-1-yl]-3-isoquinolyl]-2-(2-pyridyl)cyclopropanecarboxamide, N-(7-chloro-6-(4-(4-hydroxy-3-methyltetrahydrofuran-3-yl)piperazin-1-yl)isoquinolin-3-yl)-5,5-difluorotetrahydro-2H-pyran-2-carboxamide, (2R)-N-(7-chloro-6-((3R,4R)-4-(4-hydroxy-3-methyltetrahydrofuran-3-yl)piperazin-1-yl)isoquinolin-3-yl)-5,5-difluorotetrahydro-2H-pyran-2-carboxamide, (2R)-N-(7-chloro-6-((3S,4S)-4-(4-hydroxy-3-methyltetrahydrofuran-3-yl)piperazin-1-yl)isoquinolin-3-yl)-5,5-difluorotetrahydro-2H-pyran-2-carboxamide, (2S)-N-(7-chloro-6-((3R,4R)-4-(4-hydroxy-3-methyltetrahydrofuran-3-yl)piperazin-1-yl)isoquinolin-3-yl)-5,5-difluorotetrahydro-2H-pyran-2-carboxamide or (2S)-N-(7-chloro-6-((3S,4S)-4-(4-hydroxy-3-methyltetrahydrofuran-3-yl)piperazin-1-yl)isoquinolin-3-yl)-5,5-difluorotetrahydro-2H-pyran-2-carboxamide, N-(7-chloro-6-(4-((3S,4S or 3R, 4R)-4-hydroxy-3-methyltetrahydrofuran-3-yl)piperazin-1-yl)isoquinolin-3-yl)tetrahydro-2H-pyran-3-carboxamide, (3R)-N-(7-chloro-6-(4-((3R,4R)-4-hydroxy-3-methyltetrahydrofuran-3-yl)piperazin-1-yl)isoquinolin-3-yl)tetrahydro-2H-pyran-3-carboxamide, (3R)-N-(7-chloro-6-(4-((3S,4S)-4-hydroxy-3-methyltetrahydrofuran-3-yl)piperazin-1-yl)isoquinolin-3-yl)tetrahydro-2H-pyran-3-carboxamide, (3S)-N-(7-chloro-6-(4-((3R,4R)-4-hydroxy-3-methyltetrahydrofuran-3-yl)piperazin-1-yl)isoquinolin-3-yl)tetrahydro-2H-pyran-3-carboxamide, (3S)-N-(7-chloro-6-(4-((3S,4S)-4-hydroxy-3-methyltetrahydrofuran-3-yl)piperazin-1-yl)isoquinolin-3-yl)tetrahydro-2H-pyran-3-carboxamide, N-(7-chloro-6-(1-(4-hydroxy-3-methyltetrahydrofuran-3-yl) piperidin-4-yl)isoquinolin-3-yl)-2-(2-hydroxypropan-2-yl) cyclopropane-1-carboxamide, (1R,2R)-N-(7-chloro-6-(1-((3R,4R)-4-hydroxy-3-methyltetrahydrofuran-3-yl) piperidin-4-yl)isoquinolin-3-yl)-2-(2-hydroxypropan-2-yl) cyclopropane-1-carboxamide, (1R,2R)-N-(7-chloro-6-(1-((3S,4S)-4-hydroxy-3-methyltetrahydrofuran-3-yl) piperidin-4-yl)isoquinolin-3-yl)-2-(2-hydroxypropan-2-yl) cyclopropane-1-carboxamide, (1S,2S)-N-(7-chloro-6-(1-((3R,4R)-4-hydroxy-3-methyltetrahydrofuran-3-yl) piperidin-4-yl)isoquinolin-3-yl)-2-(2-hydroxypropan-2-yl) cyclopropane-1-carboxamide, (1S,2S)-N-(7-chloro-6-(1-((3S,4S)-4-hydroxy-3-methyltetrahydrofuran-3-yl) piperidin-4-yl)isoquinolin-3-yl)-2-(2-hydroxypropan-2-yl) cyclopropane-1-carboxamide, N-(7-chloro-6-(1-(4-hydroxy-3-methyltetrahydrofuran-3-yl) piperidin-4-yl)isoquinolin-3-yl)-2-(2-methoxypropan-2-yl) cyclopropane-1-carboxamide, (1R,2R)-N-(7-chloro-6-(1-((3R,4R)-4-hydroxy-3-methyltetrahydrofuran-3-yl) piperidin-4-yl)isoquinolin-3-yl)-2-(2-methoxypropan-2-yl) cyclopropane-1-carboxamide, (1R,2R)-N-(7-chloro-6-(1-((3S,4S)-4-hydroxy-3-methyltetrahydrofuran-3-yl) piperidin-4-yl)isoquinolin-3-yl)-2-(2-methoxypropan-2-yl) cyclopropane-1-carboxamide, (1S,2S)-N-(7-chloro-6-(1-((3R,4R)-4-hydroxy-3-methyltetrahydrofuran-3-yl) piperidin-4-yl)isoquinolin-3-yl)-2-(2-methoxypropan-2-yl) cyclopropane-1-carboxamide, (1S,2S)-N-(7-chloro-6-(1-((3S,4S)-4-hydroxy-3-methyltetrahydrofuran-3-yl) piperidin-4-yl)isoquinolin-3-yl)-2-(2-methoxypropan-2-yl) cyclopropane-1-carboxamide, N-(7-chloro-6-(1-(4-hydroxy-3-methyltetrahydrofuran-3-yl) piperidin-4-yl)isoquinolin-3-yl)-3-(2-hydroxypropan-2-yl)cyclobutane-1-carboxamide), Cis or trans-N-(7-chloro-6-(1-((3R,4R)-4-hydroxy-3-methyltetrahydrofuran-3-yl) piperidin-4-yl)isoquinolin-3-yl)-3-(2-hydroxypropan-2-yl)cyclobutane-1-carboxamide, Cis or trans-N-(7-chloro-6-(1-((3S,4S)-4-hydroxy-3-methyltetrahydrofuran-3-yl) piperidin-4-yl)isoquinolin-3-yl)-3-(2-hydroxypropan-2-yl)cyclobutane-1-carboxamide, N-(7-chloro-6-(1-(4-hydroxy-3-methyltetrahydrofuran-3-yl) piperidin-4-yl)isoquinolin-3-yl)-2-ethoxycyclopropane-1-carboxamide, (1R,2S)-N-(7-chloro-6-(1-((3R,4R)-4-hydroxy-3-methyltetrahydrofuran-3-yl) piperidin-4-yl)isoquinolin-3-yl)-2-ethoxycyclopropane-1-carboxamide, (1R,2S)-N-(7-chloro-6-(1-((3S,4S)-4-hydroxy-3-methyltetrahydrofuran-3-yl) piperidin-4-yl)isoquinolin-3-yl)-2-ethoxycyclopropane-1-carboxamide, (1S,2R)-N-(7-chloro-6-(1-((3R,4R)-4-hydroxy-3-methyltetrahydrofuran-3-yl) piperidin-4-yl)isoquinolin-3-yl)-2-ethoxycyclopropane-1-carboxamide, (1S,2R)-N-(7-chloro-6-(1-((3S,4S)-4-hydroxy-3-methyltetrahydrofuran-3-yl) piperidin-4-yl)isoquinolin-3-yl)-2-ethoxycyclopropane-1-carboxamide, N-[7-chloro-6-[4-(4-hydroxy-3-methyl-tetrahydrofuran-3-yl)piperazin-1-yl]-3-isoquinolyl]-2-(2-thienyl)cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-(2-thienyl)cyclopropanecarboxamide, (1R,2R)-N-[7-chloro-6-[4-((3S,4S)-4-hydroxy-3-methyl-tetrahydrofuran-3-yl)piperazin-1-yl]-3-isoquinolyl]-2-(2-thienyl)cyclopropanecarboxamide, (1,2S)-N-[7-chloro-6-[4-((3R,4R)-4-hydroxy-3-methyl-tetrahydrofuran-3-yl)piperazin-1-yl]-3-isoquinolyl]-2-(2-thienyl)cyclopropanecarboxamide, 1S,2S)-N-[7-chloro-6-[4-((3S,4S)-4-hydroxy-3-methyl-tetrahydrofuran-3-yl)piperazin-1-yl]-3-isoquinolyl]-2-(2-thienyl)cyclopropanecarboxamide, N-[7-chloro-6-[4-(4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2R,3R)-N-[7-chloro-6-[4-((3R,4R)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2R,3R)-N-[7-chloro-6-[4-((3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2S,3R)-N-[7-chloro-6-[4-((3R,4R)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1R,2S,3R)-N-[7-chloro-6-[4-((3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1S,2R,3S)-N-[7-chloro-6-[4-((3R,4R)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1S,2R,3S)-N-[7-chloro-6-[4-((3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1S,2S,3S)-N-[7-chloro-6-[4-((3R,4R)-4-fluoro-3-methyl-tetrahydrofuran-3-yl)piperazin-1-yl]-3-isoquinolyl]-2-methyl-3-(1-methylpyrazol-4-yl)cyclopropanecarboxamide, (1S,2S,3S)-N-[7-chloro-6-[4-((3S,4S)-4-fluoro-3-methyl-tetrahydrofuran-3-yl)piperazin-1-yl]-3-isoquinolyl]-2-methyl-3-(1-methylpyrazol-4-yl)cyclopropanecarboxamide, N-[7-chloro-6-[4-(4-fluoro-3-methyl-tetrahydrofuran-3-yl)piperazin-1-yl]-3-isoquinolyl]-2-(1-methylpyrazol-3-yl)cyclopropanecarboxamide, (1R,2R)-N-[7-chloro-6-[4-((3R,4R)-4-fluoro-3-methyl-tetrahydrofuran-3-yl)piperazin-1-yl]-3-isoquinolyl]-2-(1-methylpyrazol-3-yl)cyclopropanecarboxamide, (1R,2R)-N-[7-chloro-6-[4-((3S,4S)-4-fluoro-3-methyl-tetrahydrofuran-3-yl)piperazin-1-yl]-3-isoquinolyl]-2-(1-methylpyrazol-3-yl)cyclopropanecarboxamide, (1S,2S)-N-[7-chloro-6-[4-((3R,4R)-4-fluoro-3-methyl-tetrahydrofuran-3-yl)piperazin-1-yl]-3-isoquinolyl]-2-(1-methylpyrazol-3-yl)cyclopropanecarboxamide, (1S,2S)-N-[7-chloro-6-[4-((3S,4S)-4-fluoro-3-methyl-tetrahydrofuran-3-yl)piperazin-1-yl]-3-isoquinolyl]-2-(1-methylpyrazol-3-yl)cyclopropanecarboxamide, N-[7-chloro-6-[4-(4-hydroxy-3-methyl-tetrahydrofuran-3-yl)piperazin-1-yl]-3-isoquinolyl]-2-(2-isobutylpyrazol-3-yl)cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-(2-isobutylpyrazol-3-yl)cyclopropanecarboxamide, (1R,2R)-N-[7-chloro-6-[4-((3S,4S)-4-hydroxy-3-methyl-tetrahydrofuran-3-yl)piperazin-1-yl]-3-isoquinolyl]-2-(2-isobutylpyrazol-3-yl)cyclopropanecarboxamide, (1S,2S)-N-[7-chloro-6-[4-((3R,4R)-4-hydroxy-3-methyl-tetrahydrofuran-3-yl)piperazin-1-yl]-3-isoquinolyl]-2-(2-isobutylpyrazol-3-yl)cyclopropanecarboxamide, (1S,2S)-N-[7-chloro-6-[4-((3S,4S)-4-hydroxy-3-methyl-tetrahydrofuran-3-yl)piperazin-1-yl]-3-isoquinolyl]-2-(2-isobutylpyrazol-3-yl)cyclopropanecarboxamide, N-[7-chloro-6-[4-(4-hydroxy-3-methyl-tetrahydrofuran-3-yl)piperazin-1-yl]-3-isoquinolyl]-2-(2-isopropylpyrazol-3-yl)cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-(2-isopropylpyrazol-3-yl)cyclopropanecarboxamide, (1R,2R)-N-[7-chloro-6-[4-((3S,4S)-4-hydroxy-3-methyl-tetrahydrofuran-3-yl)piperazin-1-yl]-3-isoquinolyl]-2-(2-isopropylpyrazol-3-yl)cyclopropanecarboxamide, (1S,2S)-N-[7-chloro-6-[4-((3R,4R)-4-hydroxy-3-methyl-tetrahydrofuran-3-yl)piperazin-1-yl]-3-isoquinolyl]-2-(2-isopropylpyrazol-3-yl)cyclopropanecarboxamide, (1S,2S)-N-[7-chloro-6-[4-((3S,4S)-4-hydroxy-3-methyl-tetrahydrofuran-3-yl)piperazin-1-yl]-3-isoquinolyl]-2-(2-isopropylpyrazol-3-yl)cyclopropanecarboxamide, N-[7-chloro-6-[4-(4-fluoro-3-methyl-tetrahydrofuran-3-yl)piperazin-1-yl]-3-isoquinolyl]-5-ethoxy-spiro[2.3]hexane-2-carboxamide, (1R,2R)-N-[7-chloro-6-[4-((3R,4R)-4-fluoro-3-methyl-tetrahydrofuran-3-yl)piperazin-1-yl]-3-isoquinolyl]-5-ethoxy-spiro[2.3]hexane-2-carboxamide, (1R,2R)-N-[7-chloro-6-[4-((3S,4S)-4-fluoro-3-methyl-tetrahydrofuran-3-yl)piperazin-1-yl]-3-isoquinolyl]-5-ethoxy-spiro[2.3]hexane-2-carboxamide, (1S,2S)-N-[7-chloro-6-[4-((3R,4R)-4-fluoro-3-methyl-tetrahydrofuran-3-yl)piperazin-1-yl]-3-isoquinolyl]-5-ethoxy-spiro[2.3]hexane-2-carboxamide, (1S,2S)-N-[7-chloro-6-[4-((3S,4S)-4-fluoro-3-methyl-tetrahydrofuran-3-yl)piperazin-1-yl]-3-isoquinolyl]-5-ethoxy-spiro[2.3]hexane-2-carboxamide, N-[7-chloro-6-[4-(3-methyltetrahydrofuran-3-yl)piperazin-4-ium-1-yl]-3-isoquinolyl]-2-[1-methyl-5-(trifluoromethyl) pyrazol-4-yl]cyclopropanecarboxamide, (1R,2R)-N-[7-chloro-6-[4-((R)-3-methyltetrahydrofuran-3-yl)piperazin-4-ium-1-yl]-3-isoquinolyl]-2-[1-methyl-5-(trifluoromethyl) pyrazol-4-yl]cyclopropanecarboxamide, (1R,2R)-N-[7-chloro-6-[4-((S)-3-methyltetrahydrofuran-3-yl)piperazin-4-ium-1-yl]-3-isoquinolyl]-2-[1-methyl-5-(trifluoromethyl) pyrazol-4-yl]cyclopropanecarboxamide, (1S,2S)-N-[7-chloro-6-[4-((R)-3-methyltetrahydrofuran-3-yl)piperazin-4-ium-1-yl]-3-isoquinolyl]-2-[1-methyl-5-(trifluoromethyl) pyrazol-4-yl]cyclopropanecarboxamide, (1S,2S)-N-[7-chloro-6-[4-((S)-3-methyltetrahydrofuran-3-yl)piperazin-4-ium-1-yl]-3-isoquinolyl]-2-[1-methyl-5-(trifluoromethyl) pyrazol-4-yl]cyclopropanecarboxamide, N-[7-chloro-6-[4-(4-hydroxy-3-methyl-tetrahydrofuran-3-yl)piperazin-1-yl]-3-isoquinolyl]-2-(2-furyl)cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-(2-furyl)cyclopropanecarboxamidE, (1R,2R)-N-[7-chloro-6-[4-((3S,4S)-4-hydroxy-3-methyl-tetrahydrofuran-3-yl)piperazin-1-yl]-3-isoquinolyl]-2-(2-furyl)cyclopropanecarboxamide, (1S,2S)-N-[7-chloro-6-[4-((3R,4R)-4-hydroxy-3-methyl-tetrahydrofuran-3-yl)piperazin-1-yl]-3-isoquinolyl]-2-(2-furyl)cyclopropanecarboxamide, (1S,2S)-N-[7-chloro-6-[4-((3S,4S)-4-hydroxy-3-methyl-tetrahydrofuran-3-yl)piperazin-1-yl]-3-isoquinolyl]-2-(2-furyl)cyclopropanecarboxamide, N-[7-chloro-6-[4-(4-hydroxy-3-methyl-tetrahydrofuran-3-yl)piperazin-1-yl]-3-isoquinolyl]-2-tetrahydropyran-4-yl-cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-tetrahydropyran-4-yl-cyclopropanecarboxamide, (1R,2R)-N-[7-chloro-6-[4-((3S,4S)-4-hydroxy-3-methyl-tetrahydrofuran-3-yl)piperazin-1-yl]-3-isoquinolyl]-2-tetrahydropyran-4-yl-cyclopropanecarboxamide, (1S,2S)-N-[7-chloro-6-[4-((3R,4R)-4-hydroxy-3-methyl-tetrahydrofuran-3-yl)piperazin-1-yl]-3-isoquinolyl]-2-tetrahydropyran-4-yl-cyclopropanecarboxamide, (1S,2S)-N-[7-chloro-6-[4-((3S,4S)-4-hydroxy-3-methyl-tetrahydrofuran-3-yl)piperazin-1-yl]-3-isoquinolyl]-2-tetrahydropyran-4-yl-cyclopropanecarboxamide, N-[7-methyl-6-[4-(3-methyltetrahydrofuran-3-yl)piperazin-1-yl]-3-isoquinolyl]-2-[1-methyl-5-(trifluoromethyl) pyrazol-4-yl]cyclopropanecarboxamide, (1R,2R)-N-[7-methyl-6-[4-((R)-3-methyltetrahydrofuran-3-yl)piperazin-1-yl]-3-isoquinolyl]-2-[1-methyl-5-(trifluoromethyl) pyrazol-4-yl]cyclopropanecarboxamide, (1R,2R)-N-[7-methyl-6-[4-((S)-3-methyltetrahydrofuran-3-yl)piperazin-1-yl]-3-isoquinolyl]-2-[1-methyl-5-(trifluoromethyl) pyrazol-4-yl]cyclopropanecarboxamide, (1S,2S)-N-[7-methyl-6-[4-((R)-3-methyltetrahydrofuran-3-yl)piperazin-1-yl]-3-isoquinolyl]-2-[1-methyl-5-(trifluoromethyl) pyrazol-4-yl]cyclopropanecarboxamide, (1S,2S)-N-[7-methyl-6-[4-((S)-3-methyltetrahydrofuran-3-yl)piperazin-1-yl]-3-isoquinolyl]-2-[1-methyl-5-(trifluoromethyl) pyrazol-4-yl]cyclopropanecarboxamide, 2-ethyl-N-[7-methyl-6-[4-(3-methyltetrahydrofuran-3-yl)piperazin-4-ium-1-yl]-3-isoquinolyl]-3-(1-methylpyrazol-4-yl)cyclopropanecarboxamide, (1R,2R,3R)-2-ethyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2R,3R)-2-ethyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1R,2S,3R)-2-ethyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1R,2S,3R)-2-ethyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1S,2R,3S)-2-ethyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1S,2R,3S)-2-ethyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, (1S,2S,3S)-2-ethyl-N-[7-methyl-6-[4-((R)-3-methyltetrahydrofuran-3-yl)piperazin-4-ium-1-yl]-3-isoquinolyl]-3-(1-methylpyrazol-4-yl)cyclopropanecarboxamide, (1S,2S,3S)-2-ethyl-N-[7-methyl-6-[4-((S)-3-methyltetrahydrofuran-3-yl)piperazin-4-ium-1-yl]-3-isoquinolyl]-3-(1-methylpyrazol-4-yl)cyclopropanecarboxamide, N-[7-chloro-6-[4-(4-hydroxy-3-methyl-tetrahydrofuran-3-yl)piperazin-1-yl]-3-isoquinolyl]-2-cyano-cyclobutanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-cyano-cyclobutanecarboxamide, (1R,2R)-N-[7-chloro-6-[4-((3S,4S)-4-hydroxy-3-methyltetrahydrofuran-3-yl)piperazin-1-yl]-3-isoquinolyl]-2-cyano-cyclobutanecarboxamide, (1S,2S)-N-[7-chloro-6-[4-((3R,4R)-4-hydroxy-3-methyltetrahydrofuran-3-yl)piperazin-1-yl]-3-isoquinolyl]-2-cyano-cyclobutanecarboxamide, (1S,2S)-N-[7-chloro-6-[4-((3S,4S)-4-hydroxy-3-methyltetrahydrofuran-3-yl)piperazin-1-yl]-3-isoquinolyl]-2-cyano-cyclobutanecarboxamide, 2,2-dimethyl-N-[7-methyl-6-[4-(3-methyltetrahydrofuran-3-yl)piperazin-1-yl]-3-isoquinolyl]tetrahydropyran-4-carboxamide, (4R)-2,2-dimethyl-N-[7-methyl-6-[4-((R)-3-methyltetrahydrofuran-3-yl)piperazin-1-yl]-3-isoquinolyl]tetrahydropyran-4-carboxamide, (4R)-2,2-dimethyl-N-[7-methyl-6-[4-((S)-3-methyltetrahydrofuran-3-yl)piperazin-1-yl]-3-isoquinolyl]tetrahydropyran-4-carboxamide, (4S)-2,2-dimethyl-N-[7-methyl-6-[4-((R)-3-methyltetrahydrofuran-3-yl)piperazin-1-yl]-3-isoquinolyl]tetrahydropyran-4-carboxamide, (4S)-2,2-dimethyl-N-[7-methyl-6-[4-((S)-3-methyltetrahydrofuran-3-yl)piperazin-1-yl]-3-isoquinolyl]tetrahydropyran-4-carboxamide, N-[7-methyl-6-[4-(3-methyltetrahydrofuran-3-yl)piperazin-1-yl]-3-isoquinolyl]-3-oxabicyclo[4.1.0]heptane-7-carboxamide, (1S,6R,7R)-N-(7-methyl-6-(4-((R)-3-methyltetrahydrofuran-3-yl)piperazin-1-yl)isoquinolin-3-yl)-3-oxabicyclo[4.1.0]heptane-7-carboxamide, (1S,6R,7R)-N-(7-methyl-6-(4-((S)-3-methyltetrahydrofuran-3-yl)piperazin-1-yl)isoquinolin-3-yl)-3-oxabicyclo[4.1.0]heptane-7-carboxamide, (1R,6S,7S)-N-(7-methyl-6-(4-((R)-3-methyltetrahydrofuran-3-yl)piperazin-1-yl)isoquinolin-3-yl)-3-oxabicyclo[4.1.0]heptane-7-carboxamide, (1R,6S,7S)-N-(7-methyl-6-(4-((S)-3-methyltetrahydrofuran-3-yl)piperazin-1-yl)isoquinolin-3-yl)-3-oxabicyclo[4.1.0]heptane-7-carboxamide, (1R,6R,7R)-N-(7-methyl-6-(4-((R)-3-methyltetrahydrofuran-3-yl)piperazin-1-yl)isoquinolin-3-yl)-3-oxabicyclo[4.1.0]heptane-7-carboxamide, (1R,6R,7R)-N-(7-methyl-6-(4-((S)-3-methyltetrahydrofuran-3-yl)piperazin-1-yl)isoquinolin-3-yl)-3-oxabicyclo[4.1.0]heptane-7-carboxamide, (1S,6S,7S)-N-(7-methyl-6-(4-((R)-3-methyltetrahydrofuran-3-yl)piperazin-1-yl)isoquinolin-3-yl)-3-oxabicyclo[4.1.0]heptane-7-carboxamide, (1S,6S,7S)-N-(7-methyl-6-(4-((S)-3-methyltetrahydrofuran-3-yl)piperazin-1-yl)isoquinolin-3-yl)-3-oxabicyclo[4.1.0]heptane-7-carboxamide, N-[7-chloro-6-[4-(4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R)-N-[7-chloro-6-[4-((3R,4R)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R)-N-[7-chloro-6-[4-((3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2S,3R)-N-[7-chloro-6-[4-((3R,4R)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1R,2S,3R)-N-[7-chloro-6-[4-((3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1S,2R,3S)-N-[7-chloro-6-[4-((3R,4R)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1S,2R,3S)-N-[7-chloro-6-[4-((3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1S,2S,3S)-N-[7-chloro-6-[4-((3R,4R)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, (1S,2S,3S)-N-[7-chloro-6-[4-((3S,4S)-4-fluoro-3-methyl-tetrahydrofuran-3-yl)piperazin-1-yl]-3-isoquinolyl]-2-ethyl-3-(1-methylpyrazol-3-yl)cyclopropanecarboxamide, N-[7-chloro-6-[4-(4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2S,3R)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2S,3R)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2R,3S)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2R,3S)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2S,3S)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2S,3S)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, N-[6-[4-(4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2R,3R)-N-[6-[4-((3R,4R)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2R,3R)-N-[6-[4-((3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2S,3R)-N-[6-[4-((3R,4R)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1R,2S,3R)-N-[6-[4-((3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1S,2R,3S)-N-[6-[4-((3R,4R)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1S,2R,3S)-N-[6-[4-((3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1S,2S,3S)-N-[6-[4-((3R,4R)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, (1S,2S,3S)-N-[6-[4-((3S,4S)-4-fluoro-3-methyl-tetrahydrofuran-3-yl)piperazin-1-yl]-7-methyl-3-isoquinolyl]-2-methyl-3-(1-methylpyrazol-4-yl)cyclopropanecarboxamide, N-[6-[4-(4-fluoro-3-methyl-tetrahydrofuran-3-yl)piperazin-1-yl]-7-methyl-3-isoquinolyl]-2-(1-methylpyrazol-3-yl)cyclopropanecarboxamide, (1R,2R)-N-[6-[4-((3R,4R)-4-fluoro-3-methyl-tetrahydrofuran-3-yl)piperazin-1-yl]-7-methyl-3-isoquinolyl]-2-(1-methylpyrazol-3-yl)cyclopropanecarboxamide, (1R,2R)-N-[6-[4-((3S,4S)-4-fluoro-3-methyl-tetrahydrofuran-3-yl)piperazin-1-yl]-7-methyl-3-isoquinolyl]-2-(1-methylpyrazol-3-yl)cyclopropanecarboxamide, (1S,2S)-N-[6-[4-((3R,4R)-4-fluoro-3-methyl-tetrahydrofuran-3-yl)piperazin-1-yl]-7-methyl-3-isoquinolyl]-2-(1-methylpyrazol-3-yl)cyclopropanecarboxamide, (1S,2S)-N-[6-[4-((3S,4S)-4-fluoro-3-methyl-tetrahydrofuran-3-yl)piperazin-1-yl]-7-methyl-3-isoquinolyl]-2-(1-methylpyrazol-3-yl)cyclopropanecarboxamide, N-[7-chloro-6-[4-(4-fluoro-3-methyl-tetrahydrofuran-3-yl)piperazin-4-ium-1-yl]-3-isoquinolyl]-2-[1-methyl-5-(trifluoromethyl) pyrazol-4-yl]cyclopropanecarboxamide, (1R,2R)-N-[7-chloro-6-[4-((3R,4R)-4-fluoro-3-methyl-tetrahydrofuran-3-yl)piperazin-4-ium-1-yl]-3-isoquinolyl]-2-[1-methyl-5-(trifluoromethyl) pyrazol-4-yl]cyclopropanecarboxamide, (1R,2R)-N-[7-chloro-6-[4-((3S,4S)-4-fluoro-3-methyl-tetrahydrofuran-3-yl)piperazin-4-ium-1-yl]-3-isoquinolyl]-2-[1-methyl-5-(trifluoromethyl) pyrazol-4-yl]cyclopropanecarboxamide, (1S,2S)-N-[7-chloro-6-[4-((3R,4R)-4-fluoro-3-methyl-tetrahydrofuran-3-yl)piperazin-4-ium-1-yl]-3-isoquinolyl]-2-[1-methyl-5-(trifluoromethyl) pyrazol-4-yl]cyclopropanecarboxamide, (1,2S)-N-[7-chloro-6-[4-((3S,4S)-4-fluoro-3-methyl-tetrahydrofuran-3-yl)piperazin-4-ium-1-yl]-3-isoquinolyl]-2-[1-methyl-5-(trifluoromethyl) pyrazol-4-yl]cyclopropanecarboxamide, N-[7-chloro-6-[4-(4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2R,3R)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2S,3R)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1R,2S,3R)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2R,3S)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2R,3S)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2S,3S)-N-[7-chloro-6-[4-((3R,4R)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, (1S,2S,3S)-N-[7-chloro-6-[4-((3S,4S)-4-hydroxy-3-methyl-tetrahydrofuran-3-yl)piperazin-1-yl]-3-isoquinolyl]-2-methyl-3-(1-methylpyrazol-3-yl)cyclopropanecarboxamide, N-[7-chloro-6-[4-(4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R)-N-[7-chloro-6-[4-((3R,4R)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2R,3R)-N-[7-chloro-6-[4-((3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2S,3R)-N-[7-chloro-6-[4-((3R,4R)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1R,2S,3R)-N-[7-chloro-6-[4-((3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1S,2R,3S)-N-[7-chloro-6-[4-((3R,4R)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, 1S,2R,3S)-N-[7-chloro-6-[4-((3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1S,2S,3S)-N-[7-chloro-6-[4-((3R,4R)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, (1S,2S,3S)-N-[7-chloro-6-[4-((3S,4S)-4-hydroxy-3-methyl-tetrahydrofuran-3-yl)piperazin-1-yl]-3-isoquinolyl]-2-ethyl-3-(1-methylpyrazol-3-yl)cyclopropanecarboxamide, N-[7-chloro-6-[4-(4-fluoro-3-methyl-tetrahydrofuran-3-yl)piperazin-1-yl]-3-isoquinolyl]-2-cyano-cyclobutanecarboxamide, (1R,2R)-N-[7-chloro-6-[4-((3R,4R)-4-fluoro-3-methyl-tetrahydrofuran-3-yl)piperazin-1-yl]-3-isoquinolyl]-2-cyano-cyclobutanecarboxamide, (1R,2R)-N-[7-chloro-6-[4-((3S,4S)-4-fluoro-3-methyl-tetrahydrofuran-3-yl)piperazin-1-yl]-3-isoquinolyl]-2-cyano-cyclobutanecarboxamide, (1S,2S)-N-[7-chloro-6-[4-((3R,4R)-4-fluoro-3-methyl-tetrahydrofuran-3-yl)piperazin-1-yl]-3-isoquinolyl]-2-cyano-cyclobutanecarboxamide, (1S,2S)-N-[7-chloro-6-[4-((3S,4S)-4-fluoro-3-methyl-tetrahydrofuran-3-yl)piperazin-1-yl]-3-isoquinolyl]-2-cyano-cyclobutanecarboxamide, N-[7-chloro-6-[4-(4-fluoro-3-methyl-tetrahydrofuran-3-yl)piperazin-1-yl]-3-isoquinolyl]-2-tetrahydropyran-4-yl-cyclopropanecarboxamide, (1R,2R)-N-[7-chloro-6-[4-((3R,4R)-4-fluoro-3-methyl-tetrahydrofuran-3-yl)piperazin-1-yl]-3-isoquinolyl]-2-tetrahydropyran-4-yl-cyclopropanecarboxamide, (1R,2R)-N-[7-chloro-6-[4-((3S,4S)-4-fluoro-3-methyl-tetrahydrofuran-3-yl)piperazin-1-yl]-3-isoquinolyl]-2-tetrahydropyran-4-yl-cyclopropanecarboxamide, (1S,2S)-N-[7-chloro-6-[4-((3R,4R)-4-fluoro-3-methyl-tetrahydrofuran-3-yl)piperazin-1-yl]-3-isoquinolyl]-2-tetrahydropyran-4-yl-cyclopropanecarboxamide, (1S,2S)-N-[7-chloro-6-[4-((3S,4S)-4-fluoro-3-methyl-tetrahydrofuran-3-yl)piperazin-1-yl]-3-isoquinolyl]-2-tetrahydropyran-4-yl-cyclopropanecarboxamide, N-[7-chloro-6-[4-(4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2R,3R)-N-[7-chloro-6-[4-((3R,4R)-4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2R,3R)-N-[7-chloro-6-[4-((3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2S,3R)-N-[7-chloro-6-[4-((3R,4R)-4-fluoro-3-methyl-tetrahydrofuran-3-yl)piperazin-4-ium-1-yl]-3-isoquinolyl]-2-methyl-3-(2-pyridyl)cyclopropanecarboxamide, (1R,2S,3R)-N-[7-chloro-6-[4-((3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide, (1S,2R,3S)-N-[7-chloro-6-[4-((3R,4R)-4-fluoro-3-methyl-tetrahydrofuran-3-yl)piperazin-4-ium-1-yl]-3-isoquinolyl]-2-methyl-3-(2-pyridyl)cyclopropanecarboxamide, (1S,2R,3S)-N-[7-chloro-6-[4-((3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide, (1S,2S,3S)-N-[7-chloro-6-[4-((3R,4R)-4-fluoro-3-methyl-tetrahydrofuran-3-yl)piperazin-4-ium-1-yl]-3-isoquinolyl]-2-methyl-3-(2-pyridyl)cyclopropanecarboxamide, (1S,2S,3S)-N-[7-chloro-6-[4-((3S,4S)-4-fluoro-3-methyl-tetrahydrofuran-3-yl)piperazin-4-ium-1-yl]-3-isoquinolyl]-2-methyl-3-(2-pyridyl)cyclopropanecarboxamide, N-[7-chloro-6-[4-(4-fluoro-3-methyl-tetrahydrofuran-3-yl)piperazin-1-yl]-3-isoquinolyl]-2-tetrahydropyran-4-yl-cyclopropanecarboxamide, (R)-N-[7-chloro-6-[4-((3R,4R)-4-fluoro-3-methyl-tetrahydrofuran-3-yl)piperazin-1-yl]-3-isoquinolyl]-2-tetrahydropyran-4-yl-cyclopropanecarboxamide, (R)-N-[7-chloro-6-[4-((3S,4S)-4-fluoro-3-methyl-tetrahydrofuran-3-yl)piperazin-1-yl]-3-isoquinolyl]-2-tetrahydropyran-4-yl-cyclopropanecarboxamide, (S)-N-[7-chloro-6-[4-((3R,4R)-4-fluoro-3-methyl-tetrahydrofuran-3-yl)piperazin-1-yl]-3-isoquinolyl]-2-tetrahydropyran-4-yl-cyclopropanecarboxamide, (S)-N-[7-chloro-6-[4-((3S,4S)-4-fluoro-3-methyl-tetrahydrofuran-3-yl)piperazin-1-yl]-3-isoquinolyl]-2-tetrahydropyran-4-yl-cyclopropanecarboxamide, N-[7-chloro-6-[4-(4-fluoro-3-methyl-tetrahydrofuran-3-yl)piperazin-1-yl]-3-isoquinolyl]-2-(difluoromethyl)cyclopropanecarboxamide, (1R,2R)-N-[7-chloro-6-[4-((3R,4R)-4-fluoro-3-methyl-tetrahydrofuran-3-yl)piperazin-1-yl]-3-isoquinolyl]-2-(difluoromethyl)cyclopropanecarboxamide, (1R,2R)-N-[7-chloro-6-[4-((3S,4S)-4-fluoro-3-methyl-tetrahydrofuran-3-yl)piperazin-1-yl]-3-isoquinolyl]-2-(difluoromethyl)cyclopropanecarboxamide, (1S,2S)-N-[7-chloro-6-[4-((3R,4R)-4-fluoro-3-methyl-tetrahydrofuran-3-yl)piperazin-1-yl]-3-isoquinolyl]-2-(difluoromethyl)cyclopropanecarboxamide, (1S,2S)-N-[7-chloro-6-[4-((3S,4S)-4-fluoro-3-methyl-tetrahydrofuran-3-yl)piperazin-1-yl]-3-isoquinolyl]-2-(difluoromethyl)cyclopropanecarboxamide, N-[7-chloro-6-[4-(4-fluoro-3-methyl-tetrahydrofuran-3-yl)piperazin-1-yl]-3-isoquinolyl]spiro[2.2]pentane-2-carboxamide, (R)-N-[7-chloro-6-[4-((3R,4R)-4-fluoro-3-methyl-tetrahydrofuran-3-yl)piperazin-1-yl]-3-isoquinolyl]spiro[2.2]pentane-2-carboxamide, (R)-N-[7-chloro-6-[4-((3S,4S)-4-fluoro-3-methyl-tetrahydrofuran-3-yl)piperazin-1-yl]-3-isoquinolyl]spiro[2.2]pentane-2-carboxamide, (S)-N-[7-chloro-6-[4-((3R,4R)-4-fluoro-3-methyl-tetrahydrofuran-3-yl)piperazin-1-yl]-3-isoquinolyl]spiro[2.2]pentane-2-carboxamide, (S)-N-[7-chloro-6-[4-((3S,4S)-4-fluoro-3-methyl-tetrahydrofuran-3-yl)piperazin-1-yl]-3-isoquinolyl]spiro[2.2]pentane-2-carboxamide, N-[7-chloro-6-[4-(4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R)-N-[7-chloro-6-[4-((3R,4R)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2R)-N-[7-chloro-6-[4-((3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2S)-N-[7-chloro-6-[4-((3R,4R)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1R,2S)-N-[7-chloro-6-[4-((3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1S,2R)-N-[7-chloro-6-[4-((3R,4R)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1S,2R)-N-[7-chloro-6-[4-((3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1S,2S)-N-[7-chloro-6-[4-((3R,4R)-4-hydroxy-3-methyl-tetrahydrofuran-3-yl)piperazin-1-yl]-3-isoquinolyl]-2-methyl-2-tetrahydrofuran-3-yl-cyclopropanecarboxamide, (1S,2S)-N-[7-chloro-6-[4-((3S,4S)-4-hydroxy-3-methyl-tetrahydrofuran-3-yl)piperazin-1-yl]-3-isoquinolyl]-2-methyl-2-tetrahydrofuran-3-yl-cyclopropanecarboxamide, N-[7-chloro-6-[4-(4-fluoro-3-methyl-tetrahydrofuran-3-yl)piperazin-1-yl]-3-isoquinolyl]-2-ethyl-3-(2-pyridyl)cyclopropanecarboxamide, (1R,2R,3R)-N-[7-chloro-6-[4-((3R,4R)-4-fluoro-3-methyl-tetrahydrofuran-3-yl)piperazin-1-yl]-3-isoquinolyl]-2-ethyl-3-(2-pyridyl)cyclopropanecarboxamide, (1R,2R,3R)-N-[7-chloro-6-[4-((3S,4S)-4-fluoro-3-methyl-tetrahydrofuran-3-yl)piperazin-1-yl]-3-isoquinolyl]-2-ethyl-3-(2-pyridyl)cyclopropanecarboxamide, (1R,2S,3R)-N-[7-chloro-6-[4-((3R,4R)-4-fluoro-3-methyl-tetrahydrofuran-3-yl)piperazin-1-yl]-3-isoquinolyl]-2-ethyl-3-(2-pyridyl)cyclopropanecarboxamide, (1R,2S,3R)-N-[7-chloro-6-[4-((3S,4S)-4-fluoro-3-methyl-tetrahydrofuran-3-yl)piperazin-1-yl]-3-isoquinolyl]-2-ethyl-3-(2-pyridyl)cyclopropanecarboxamide, (1S,2R,3S)-N-[7-chloro-6-[4-((3R,4R)-4-fluoro-3-methyl-tetrahydrofuran-3-yl)piperazin-1-yl]-3-isoquinolyl]-2-ethyl-3-(2-pyridyl)cyclopropanecarboxamide, (1S,2R,3S)-N-[7-chloro-6-[4-((3S,4S)-4-fluoro-3-methyl-tetrahydrofuran-3-yl)piperazin-1-yl]-3-isoquinolyl]-2-ethyl-3-(2-pyridyl)cyclopropanecarboxamide, (1S,2S,3S)-N-[7-chloro-6-[4-((3R,4R)-4-fluoro-3-methyl-tetrahydrofuran-3-yl)piperazin-1-yl]-3-isoquinolyl]-2-ethyl-3-(2-pyridyl)cyclopropanecarboxamide, (1S,2S,3S)-N-[7-chloro-6-[4-((3S,4S)-4-fluoro-3-methyl-tetrahydrofuran-3-yl)piperazin-1-yl]-3-isoquinolyl]-2-ethyl-3-(2-pyridyl)cyclopropanecarboxamide, N-[7-chloro-6-[4-(4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2R,3R)-N-[7-chloro-6-[4-((3R,4R)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2R,3R)-N-[7-chloro-6-[4-((3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2S,3R)-N-[7-chloro-6-[4-((3R,4R)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1R,2S,3R)-N-[7-chloro-6-[4-((3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1S,2R,3S)-N-[7-chloro-6-[4-((3R,4R)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1S,2R,3S)-N-[7-chloro-6-[4-((3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1S,2S,3S)-N-[7-chloro-6-[4-((3R,4R)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, (1S,2S,3S)-N-[7-chloro-6-[4-((3S,4S)-4-hydroxy-3-methyl-tetrahydrofuran-3-yl)piperazin-1-yl]-3-isoquinolyl]-2,2-dimethyl-3-tetrahydropyran-2-yl-cyclopropanecarboxamide, N-[6-[4-(4-fluoro-3-methyl-tetrahydrofuran-3-yl)piperazin-1-yl]-7-methyl-3-isoquinolyl]-5,5-dimethyl-tetrahydrofuran-3-carboxamide, (3R)-N-[6-[4-((3R,4R)-4-fluoro-3-methyl-tetrahydrofuran-3-yl)piperazin-1-yl]-7-methyl-3-isoquinolyl]-5,5-dimethyl-tetrahydrofuran-3-carboxamide, (3R)-N-[6-[4-((3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide, (3S)-N-[6-[4-((3R,4R)-4-fluoro-3-methyl-tetrahydrofuran-3-yl)piperazin-1-yl]-7-methyl-3-isoquinolyl]-5,5-dimethyl-tetrahydrofuran-3-carboxamide, (3S)-N-[6-[4-((3S,4S)-4-fluoro-3-methyl-tetrahydrofuran-3-yl)piperazin-1-yl]-7-methyl-3-isoquinolyl]-5,5-dimethyl-tetrahydrofuran-3-carboxamide, (1R,2R) (3R,4R)- or (1R,2S) (3R,4R)- or (1S,2R) (3R,4R)- or (1S,2S) (3R,4R)- or (1R,2R) (3S,4S)- or (1R,2S) (3S,4S)- or (1S,2R) (3S,4S)- or (1S,2S) (3S,4S)-N-(7-chloro-6-(4-(4-hydroxy-3-methyltetrahydrofuran-3-yl)piperazin-1-yl)isoquinolin-3-yl)-2-methyl-2-(pyridin-2-yl) cyclopropane-1-carboxamide, N-(7-chloro-6-(4-(4-hydroxy-3-methyltetrahydrofuran-3-yl)piperazin-1-yl)isoquinolin-3-yl)-2-methyl-3-(pyridin-2-yl) cyclopropane-1-carboxamide, (1R,2R,3R)-N-(7-chloro-6-(4-((3R,4R)-4-hydroxy-3-methyltetrahydrofuran-3-yl)piperazin-1-yl)isoquinolin-3-yl)-2-methyl-3-(pyridin-2-yl) cyclopropane-1-carboxamide, (1R,2R,3R)-N-(7-chloro-6-(4-((3S,4S)-4-hydroxy-3-methyltetrahydrofuran-3-yl)piperazin-1-yl)isoquinolin-3-yl)-2-methyl-3-(pyridin-2-yl) cyclopropane-1-carboxamide, (1R,2S,3R)-N-(7-chloro-6-(4-((3R,4R)-4-hydroxy-3-methyltetrahydrofuran-3-yl)piperazin-1-yl)isoquinolin-3-yl)-2-methyl-3-(pyridin-2-yl) cyclopropane-1-carboxamide, (1R,2S,3R)-N-(7-chloro-6-(4-((3S,4S)-4-hydroxy-3-methyltetrahydrofuran-3-yl)piperazin-1-yl)isoquinolin-3-yl)-2-methyl-3-(pyridin-2-yl) cyclopropane-1-carboxamide, (1S,2R,3S)-N-(7-chloro-6-(4-((3R,4R)-4-hydroxy-3-methyltetrahydrofuran-3-yl)piperazin-1-yl)isoquinolin-3-yl)-2-methyl-3-(pyridin-2-yl) cyclopropane-1-carboxamide, (1S,2R,3S)-N-(7-chloro-6-(4-((3S,4S)-4-hydroxy-3-methyltetrahydrofuran-3-yl)piperazin-1-yl)isoquinolin-3-yl)-2-methyl-3-(pyridin-2-yl) cyclopropane-1-carboxamide, (1S,2S,3S)-N-(7-chloro-6-(4-((3R,4R)-4-hydroxy-3-methyltetrahydrofuran-3-yl)piperazin-1-yl)isoquinolin-3-yl)-2-methyl-3-(pyridin-2-yl) cyclopropane-1-carboxamide, (1S,2S,3S)-N-(7-chloro-6-(4-((3S,4S)-4-hydroxy-3-methyltetrahydrofuran-3-yl)piperazin-1-yl)isoquinolin-3-yl)-2-methyl-3-(pyridin-2-yl) cyclopropane-1-carboxamide, N-(7-chloro-6-(4-(4-hydroxy-3-methyltetrahydrofuran-3-yl)piperazin-1-yl)isoquinolin-3-yl)-2-(pyridin-2-yl)cyclobutane-1-carboxamide, (1R,2R)-N-(7-chloro-6-(4-((3R,4R)-4-hydroxy-3-methyltetrahydrofuran-3-yl)piperazin-1-yl)isoquinolin-3-yl)-2-(pyridin-2-yl)cyclobutane-1-carboxamide, (1R,2R)-N-(7-chloro-6-(4-((3S,4S)-4-hydroxy-3-methyltetrahydrofuran-3-yl)piperazin-1-yl)isoquinolin-3-yl)-2-(pyridin-2-yl)cyclobutane-1-carboxamide, (1R,2S)-N-(7-chloro-6-(4-((3R,4R)-4-hydroxy-3-methyltetrahydrofuran-3-yl)piperazin-1-yl)isoquinolin-3-yl)-2-(pyridin-2-yl)cyclobutane-1-carboxamide, (1R,2S)-N-(7-chloro-6-(4-((3S,4S)-4-hydroxy-3-methyltetrahydrofuran-3-yl)piperazin-1-yl)isoquinolin-3-yl)-2-(pyridin-2-yl)cyclobutane-1-carboxamide, (1S,2R)-N-(7-chloro-6-(4-((3R,4R)-4-hydroxy-3-methyltetrahydrofuran-3-yl)piperazin-1-yl)isoquinolin-3-yl)-2-(pyridin-2-yl)cyclobutane-1-carboxamide, (1S,2R)-N-(7-chloro-6-(4-((3S,4S)-4-hydroxy-3-methyltetrahydrofuran-3-yl)piperazin-1-yl)isoquinolin-3-yl)-2-(pyridin-2-yl)cyclobutane-1-carboxamide, (1S,2S)-N-(7-chloro-6-(4-((3R,4R)-4-hydroxy-3-methyltetrahydrofuran-3-yl)piperazin-1-yl)isoquinolin-3-yl)-2-(pyridin-2-yl)cyclobutane-1-carboxamide, (1S,2S)-N-(7-chloro-6-(4-((3S,4S)-4-hydroxy-3-methyltetrahydrofuran-3-yl)piperazin-1-yl)isoquinolin-3-yl)-2-(pyridin-2-yl)cyclobutane-1-carboxamide, N-(7-ethyl-6-(4-(4-hydroxy-3-methyltetrahydrofuran-3-yl)piperazin-1-yl)isoquinolin-3-yl)-6-oxaspiro[2.5]octane-1-carboxamide, (R)-N-(7-ethyl-6-(4-(4-(3R,4R)-hydroxy-3-methyltetrahydrofuran-3-yl)piperazin-1-yl)isoquinolin-3-yl)-6-oxaspiro[2.5]octane-1-carboxamide, (R)-N-(7-ethyl-6-(4-(4-(3S,4S)-hydroxy-3-methyltetrahydrofuran-3-yl)piperazin-1-yl)isoquinolin-3-yl)-6-oxaspiro[2.5]octane-1-carboxamide, (S)-N-(7-ethyl-6-(4-(4-(3R,4R)-hydroxy-3-methyltetrahydrofuran-3-yl)piperazin-1-yl)isoquinolin-3-yl)-6-oxaspiro[2.5]octane-1-carboxamide, (S)-N-(7-ethyl-6-(4-(4-(3S,4S)-hydroxy-3-methyltetrahydrofuran-3-yl)piperazin-1-yl)isoquinolin-3-yl)-6-oxaspiro[2.5]octane-1-carboxamide, N-(6-(4-hydroxy-3-methyltetrahydrofuran-3-yl)piperazin-1-yl)-7-methoxyisoquinolin-3-yl)-6-oxaspiro[2.5]octane-1-carboxamide, (R)-N-(6-(4-(3R,4R)-hydroxy-3-methyltetrahydrofuran-3-yl)piperazin-1-yl)-7-methoxyisoquinolin-3-yl)-6-oxaspiro[2.5]octane-1-carboxamide, (R)-N-(6-(4-(3S,4S)-hydroxy-3-methyltetrahydrofuran-3-yl)piperazin-1-yl)-7-methoxyisoquinolin-3-yl)-6-oxaspiro[2.5]octane-1-carboxamide, (S)-N-(6-(4-(3R,4R)-hydroxy-3-methyltetrahydrofuran-3-yl)piperazin-1-yl)-7-methoxyisoquinolin-3-yl)-6-oxaspiro[2.5]octane-1-carboxamide, (S)-N-(6-(4-(3S,4S)-hydroxy-3-methyltetrahydrofuran-3-yl)piperazin-1-yl)-7-methoxyisoquinolin-3-yl)-6-oxaspiro[2.5]octane-1-carboxamide, N-(7-chloro-6-((2S)-4-(4-(3R,4R)-hydroxy-3-methyltetrahydrofuran-3-yl)-2-methylpiperazin-1-yl)isoquinolin-3-yl)-6-oxaspiro[2.5]octane-1-carboxamide, (R)-N-(7-chloro-6-((2S)-4-(4-(3R,4R)-hydroxy-3-methyltetrahydrofuran-3-yl)-2-methylpiperazin-1-yl)isoquinolin-3-yl)-6-oxaspiro[2.5]octane-1-carboxamide, (R)-N-(7-chloro-6-((2S)-4-(4-(3S,4S)-hydroxy-3-methyltetrahydrofuran-3-yl)-2-methylpiperazin-1-yl)isoquinolin-3-yl)-6-oxaspiro[2.5]octane-1-carboxamide, (S)-N-(7-chloro-6-((2S)-4-(4-(3R,4R)-hydroxy-3-methyltetrahydrofuran-3-yl)-2-methylpiperazin-1-yl)isoquinolin-3-yl)-6-oxaspiro[2.5]octane-1-carboxamide, (S)-N-(7-chloro-6-((2S)-4-(4-(3S,4S)-hydroxy-3-methyltetrahydrofuran-3-yl)-2-methylpiperazin-1-yl)isoquinolin-3-yl)-6-oxaspiro[2.5]octane-1-carboxamide, N-(6-((2S)-4-(4-hydroxy-3-methyltetrahydrofuran-3-yl)-2-methylpiperazin-1-yl)-7-methylisoquinolin-3-yl)-6-oxaspiro[2.5]octane-1-carboxamide, (R)-N-(6-((2S)-4-(4-(3R,4R)-hydroxy-3-methyltetrahydrofuran-3-yl)-2-methylpiperazin-1-yl)-7-methylisoquinolin-3-yl)-6-oxaspiro[2.5]octane-1-carboxamide, (R)-N-(6-((2S)-4-(4-(3S,4S)-hydroxy-3-methyltetrahydrofuran-3-yl)-2-methylpiperazin-1-yl)-7-methylisoquinolin-3-yl)-6-oxaspiro[2.5]octane-1-carboxamide, (S)-N-(6-((2S)-4-(4-(3R,4R)-hydroxy-3-methyltetrahydrofuran-3-yl)-2-methylpiperazin-1-yl)-7-methylisoquinolin-3-yl)-6-oxaspiro[2.5]octane-1-carboxamide, (S)-N-(6-((2S)-4-(4-(3S,4S)-hydroxy-3-methyltetrahydrofuran-3-yl)-2-methylpiperazin-1-yl)-7-methylisoquinolin-3-yl)-6-oxaspiro[2.5]octane-1-carboxamide, (1S,2R)-N-(N-(7-chloro-6-(4-(4-hydroxy-3-methyltetrahydrofuran-3-yl)piperazin-1-yl)isoquinolin-3-yl)-2-(2-methyl-2H-1,2,3-triazol-4-yl) cyclopropane-1-carboxamide, (1S,2S)-N-(N-(7-chloro-6-(4-(4-hydroxy-3-methyltetrahydrofuran-3-yl)piperazin-1-yl)isoquinolin-3-yl)-2-(2-methyl-2H-1,2,3-triazol-4-yl) cyclopropane-1-carboxamide, (R) or(S)-N-(7-chloro-6-((3R,4R) or (3S,4S)-4-(4-hydroxy-3,4-dimethyltetrahydrofuran-3-yl) piperazin-1-yl)isoquinolin-3-yl)-6-oxaspiro[2.5]octane-1-carboxamide, and rac-N-(7-chloro-6-(4-(4-cyano-3-methyltetrahydrofuran-3-yl)piperazin-1-yl)isoquinolin-3-yl)-6-oxaspiro[2.5] octane-1-carboxamide.

18. A pharmaceutical composition comprising a compound of claim 1, and a pharmaceutically acceptable carrier.

19. A method of treating Parkinson's Disease comprising administering an effective amount of a compound of claim 1, or a pharmaceutically acceptable salt thereof, to a person in need thereof.

20. A method for the treatment of an indication in which LRRK2 kinase is involved comprising administering to a subject in need thereof an effective amount of a compound according to claim 1, or a pharmaceutically acceptable salt thereof, said indication selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17, neuroinflammation associated with of microglial inflammatory responses associated with multiple sclerosis, HIV-induced dementia, ALS, ischemic stroke, traumatic brain injury and spinal cord injury, lymphomas, leukemias, multiple sclerosis, rheumatoid arthritis, systemic lupus erythematosus, autoimmune hemolytic anemia, pure red cell aplasia, idiopathic thrombocytopenia pupura (ITP), Evans Syndrome, vasculitis, bullous skin disorder, type I diabetes mellitus, Sjorgen's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

* * * * *